(12) United States Patent
Patterson et al.

(10) Patent No.: US 11,084,780 B1
(45) Date of Patent: Aug. 10, 2021

(54) CRYSTALLINE SOLIDS OF MEK INHIBITOR N-((R)-2,3-DIHYDROXYPROPOXY)-3,4-DIFLUORO-2-(2-FLUORO-4-IODO-PHENYLAMINO)-BENZAMIDE AND USES THEREOF

(71) Applicant: SpringWorks Therapeutics Inc., Stamford, CT (US)

(72) Inventors: Kristin Patterson, Stamford, CT (US); Jiping Liu, Stamford, CT (US); Ricky Wayne Couch, Durham, NC (US); Peter Gregory Varlashkin, Durham, NC (US); Mai Li, Greenville, SC (US); Yonghong Gan, Simpsonville, SC (US)

(73) Assignee: SpringWorks Therapeutics, Inc., Stamford, CT (US)

( * ) Notice: Subject to any disclaimer, the term of this patent is extended or adjusted under 35 U.S.C. 154(b) by 0 days.

(21) Appl. No.: 17/177,966

(22) Filed: Feb. 17, 2021

(51) Int. Cl.
| | |
|---|---|
| A61K 31/16 | (2006.01) |
| C07C 231/00 | (2006.01) |
| A61P 35/00 | (2006.01) |
| C07C 259/10 | (2006.01) |
| A61K 9/00 | (2006.01) |
| A61K 9/20 | (2006.01) |
| A61K 9/48 | (2006.01) |

(52) U.S. Cl.
CPC .......... *C07C 259/10* (2013.01); *A61K 9/0095* (2013.01); *A61K 9/2013* (2013.01); *A61K 9/2054* (2013.01); *A61K 9/4825* (2013.01); *A61K 9/4858* (2013.01); *A61K 9/4866* (2013.01); *C07B 2200/13* (2013.01)

(58) Field of Classification Search
CPC ........ A61K 31/16; C07C 231/00; A61P 35/00
USPC .......................................... 514/622; 564/163
See application file for complete search history.

(56) References Cited

U.S. PATENT DOCUMENTS

| | | | |
|---|---|---|---|
| 6,960,614 B2 | 11/2005 | Barrett et al. | |
| 7,060,856 B2 | 6/2006 | Macikenas et al. | |
| 7,411,001 B2 | 8/2008 | Barrett et al. | |
| 2014/0155372 A1* | 6/2014 | Lee .................. | A61K 45/06 514/210.18 |
| 2015/0275306 A1* | 10/2015 | Bernards .......... | G01N 33/57484 506/9 |
| 2016/0367539 A1* | 12/2016 | Saha .................. | A61K 31/4439 |

FOREIGN PATENT DOCUMENTS

| | | |
|---|---|---|
| WO | WO-2002006213 A2 | 1/2002 |
| WO | WO-2004045617 A1 | 6/2004 |
| WO | WO-2005040098 A1 | 5/2005 |
| WO | WO-2006061712 A2 | 6/2006 |
| WO | WO-2006134469 A1 | 12/2006 |
| WO | WO-2007042885 A2 | 4/2007 |

OTHER PUBLICATIONS

NCT00147550, "A Multicenter, Open-Label, Noncomparative Phase 1-2 Clinical and Pharmacokinetic Study of Oral PD 0325901 in Patients With Advanced Cancer," sponsored by Pfizer, first posted Sep. 7, 2005, accessed at https://clinicaltrials.gov/ct2/show/record/NCT00147550 on Feb. 22, 2021, 3 pages.

NCT00174369, "Phase 2 Study of the MEK Inhibitor PD-0325901 in Patients With Advanced Non-Small Cell Lung Cancer," sponsored by Pfizer, first posted Sep. 15, 2005, accessed at https://clinicaltrials.gov/ct2/show/record/NCT00174369 on Feb. 22, 2021, 3 pages.

NCT01347866, "A Multi-arm Phase 1 Dose Escalation Study of the Safety, Pharmacokinetics, and Pharmacodynamics of the Dual Pi3k/Mtor Inhibitors Pf-04691502 and Pf-05212384 in Combination With Experimental or Approved Anticancer Agents in Patients With Advanced Cancer," sponsored by Pfizer, first posted May 4, 2011, accessed at https://clinicaltrials.gov/ct2/show/record/NCT01347866 on Feb. 22, 2021, 6 pages.

NCT02022982, "Phase I/II Study of the CDK4/6 Inhibitor Palbociclib (PD-0332991) in Combination With the MEK Inhibitor PD-0325901 for Patients With KRAS Mutant Non-Small Cell Lung Cancer and Other Solid Tumors," sponsored by Dana-Farber Cancer Institute, first posted Dec. 30, 2013, accessed at https://clinicaltrials.gov/ct2/show/record/NCT02022982 on Feb. 22, 2021, 4 pages.

NCT02039336, "Phase I/II Study With the Combination of Dacomitinib and PD-0325901 in MEtastatic KRAS Mutation Positive Non-small Cell Lung Cancer," sponsored by The Netherlands Cancer Institute, first posted Jan. 17, 2014, accessed at https://clinicaltrials.gov/ct2/show/record/NCT02039336 on Feb. 22, 2021, 3 pages.

NCT02096471, "A Phase 2 Trial of the MEK Inhibitor PD-0325901 in Adolescents and Adults With NF1-Associated Morbid Plexiform Neurofibromas," sponsored by University of Alabama at Brimingham, first posted Mar. 26, 2014, accessed at https://clinicaltrials.gov/ct2/show/NCT02096471 on Feb. 22, 2021, 6 pages.

NCT02510001, "A Sequential Phase I Study of MEK1/2 Inhibitors PD-0325901 or Binimetinib Combined With cMET Inhibitor PF-02341066 in Patients With RAS Mutant and RAS Wild Type (With Aberrant c-MET) Colorectal Cancer," sponsored by University of Oxford, first posted Jul. 28, 2015, accessed at https://clinicaltrials.gov/ct2/show/record/NCT02510001 on Feb. 22, 2021, 11 pages.

(Continued)

*Primary Examiner* — Raymond J Henley, III
(74) *Attorney, Agent, or Firm* — Sterne, Kessler, Goldstein & Fox P.L.L.C.

(57) ABSTRACT

The present disclosure relates to a) crystalline forms of N—((R)-2,3-dihydroxypropoxy)-3,4-difluoro-2-(2-fluoro-4-iodo-phenylamino)-benzamide; b) pharmaceutical compositions comprising one or more crystalline forms of N—((R)-2,3-dihydroxypropoxy)-3,4-difluoro-2-(2-fluoro-4-iodo-phenylamino)-benzamide, and, optionally, one or more pharmaceutically acceptable carriers; c) methods of treating a tumor a cancer, or a Rasopathy disorder by administering one or more crystalline forms of N—((R)-2,3-dihydroxypropoxy)-3,4-difluoro-2-(2-fluoro-4-iodo-phenylamino)-benzamide to a subject in need thereof, and methods of producing essentially pure Form IV of N—((R)-2,3-dihydroxypropoxy)-3,4-difluoro-2-(2-fluoro-4-iodo-phenylamino)-benzamide.

15 Claims, 22 Drawing Sheets

(56) References Cited

OTHER PUBLICATIONS

NCT03170206, "Phase I/II Study of the CDK4/6 Inhibitor Palbociclib (PD-0332991) in Combination With the MEK Inhibitor Binimetinib (MEK162) for Patients With Advanced KRAS Mutant Non-Small Cell Lung Cancer," sponsored by Dana-Farber Cancer Institute, first posted May 30, 2017, accessed at https://clinicaltrials.gov/ct2/show/record/NCT03170206 on Feb. 22, 2021, 5 pages.

NCT03905148, "A Phase 1b, Open-Label, Dos-escalation and Expansion Study to Investigate the Safety, Pharmacokinetics and Antitumor Activities of a RAF Dimer Inhibitor BGB-283 in Combination With MEK Inhibitor PD-0325901 in Patients With Advanced or Refractory Solid Tumors," sponsored by BeiGene, first posted Apr. 5,2019, accessed at https://clinicaltrials.gov/ct2/show/record/NCT03905148 on Feb. 22, 2021, 4 pages.

NCT03962543, "A Phase 2b Trial of the MEK 1/2 Inhibitor (MEKi) in Adult and Pediatric Patients With Neurofibromatosis Type 1 (NF1)-Associated Inoperable Plexiform Neurofibromas (PNs) That Are Causing Significant Morbidity," sponsored by SpringWorks Therapeutics, Inc., first posted May 24, 2019 accessed at https://clinicaltrials.gov/ct2/show/NCT03962543 on Feb. 22, 2021, 4 pages.

The United States Pharmacopeia—National Formulary (NF18), "<941> X-Ray Diffraction," $23^{rd}$ Edition, pp. 1843-1844 (1995).

Co-pending Application, U.S. Appl. No. 17/177,999, inventors Patterson, K., et al., filed Feb. 17, 2021 (Not Yet Published).

Co-pending Application, U.S. Appl. No. 17/178,022, inventor Irdam, E., filed Feb. 17, 2021 (Not Yet Published).

\* cited by examiner

CRYSTALLINE SOLIDS OF MEK INHIBITOR N-((R)-2,3-DIHYDROXYPROPOXY)-3,4-DIFLUORO-2-(2-FLUORO-4-IODO-PHENYLAMINO)-BENZAMIDE AND USES THEREOF

FIELD OF THE INVENTION

The present disclosure relates to a) methods of synthesizing N—((R)-2,3-dihydroxypropoxy)-3,4-difluoro-2-(2-fluoro-4-iodo-phenylamino)-benzamide; b) crystalline forms of N—((R)-2,3-dihydroxypropoxy)-3,4-difluoro-2-(2-fluoro-4-iodo-phenylamino)-benzamide; c) pharmaceutical compositions comprising one or more crystalline forms of N—((R)-2,3-dihydroxypropoxy)-3,4-difluoro-2-(2-fluoro-4-iodo-phenylamino)-benzamide, and, optionally, one or more pharmaceutically acceptable carriers; and d) methods of treating a tumor, a cancer, or a Rasopathy disorder by administering one or more crystalline forms of N—((R)-2,3-dihydroxypropoxy)-3,4-difluoro-2-(2-fluoro-4-iodo-phenylamino)-benzamide to a subject in need thereof.

BACKGROUND

N—((R)-2,3-dihydroxypropoxy)-3,4-difluoro-2-(2-fluoro-4-iodo-phenylamino)-benzamide ("mirdametinib", or "PD-0325901") is a small molecule drug which has been designed to inhibit mitogen-activated protein kinase kinase 1 ("MEK1") and mitogen-activated protein kinase kinase 2 ("MEK2"). MEK1 and MEK2 are proteins that play key roles in the mitogen-activated protein kinase ("MAPK") signaling pathway. The MAPK pathway is critical for cell survival and proliferation, and overactivation of this pathway, has been shown to lead to tumor development and growth. Mirdametinib is a highly potent and specific allosteric non-ATP-competitive inhibitor of MEK1 and MEK2. By virtue of its mechanism of action, mirdametinib leads to significantly inhibited phosphorylation of the extracellular regulated MAP kinases ERK1 and ERK2, thereby leading to impaired growth of tumor cells both in vitro and in vivo. In addition, evidence indicates that inflammatory cytokine-induced increases in MEK/ERK activity contribute to the inflammation, pain, and tissue destruction associated with rheumatoid arthritis and other inflammatory diseases.

Crystal forms of N—((R)-2,3-dihydroxypropoxy)-3,4-difluoro-2-(2-fluoro-4-iodo-phenylamino)-benzamide have been described previously. WO2002/006213 describes crystalline Forms I and II. U.S. Pat. No. 7,060,856 ("the '856 patent") describes a method of producing Form IV. The '856 patent indicates that the material produced by this method was greater than 90% Form IV (The '856 patent, Example 1) The '856 patent also states that the differential scanning calorimetry ("DSC") of the material produced shows an onset of melting at 110° C. as well as a small peak with an onset at 117° C., consistent with the material being a mixture of two forms.

WO 2006/134469 ("the '469 PCT publication") also describes a method of synthesizing N—((R)-2,3-dihydroxypropoxy)-3,4-difluoro-2-(2-fluoro-4-iodo-phenylamino)-benzamide. The '469 PCT publication reports the method yields a product conforming to the polymorphic Form IV disclosed in U.S. patent application Ser. No. 10/969,681 which issued as the '856 patent.

Differences in the characteristics of different polymorphic forms can lead to differences in the effective dose or physical properties affecting processability of N—((R)-2,3-dihydroxypropoxy)-3,4-difluoro-2-(2-fluoro-4-iodo-phenylamino)-benzamide caused by differences in solubility or bioavailability. Thus, there is a need for compositions of polymorphic forms of N—((R)-2,3-dihydroxypropoxy)-3,4-difluoro-2-(2-fluoro-4-iodo-phenylamino)-benzamide, for use in treatment of a tumor, a cancer, or a Rasopathy disorder.

BRIEF SUMMARY OF THE INVENTION

Crystalline Forms and Amorphous Solids

Figure 1A:
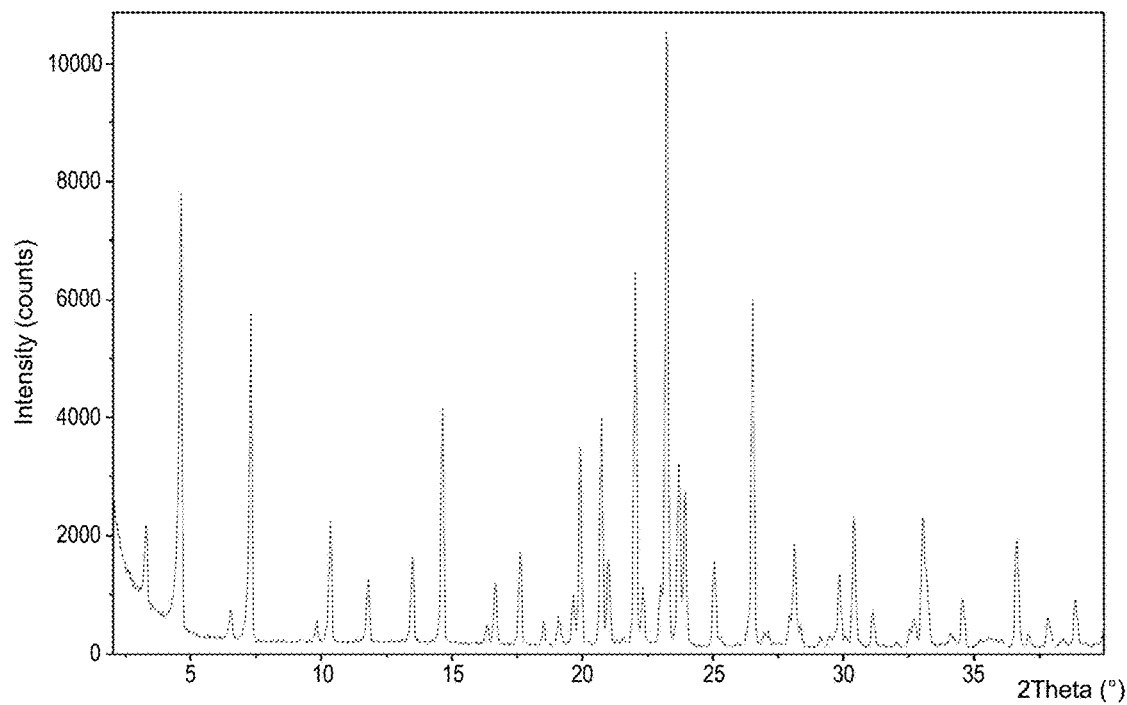
FIG. 1A is a X-ray powder diffraction pattern ("XRPD") corresponding to essentially pure crystalline Form IV of N—((R)-2,3-dihydroxypropoxy)-3,4-difluoro-2-(2-fluoro-4-iodo-phenylamino)-benzamide.

The present disclosure features useful compositions and methods to treat disorders whereby aberrant MEK1 or MEK2 activity is implicated, e.g., a cancer, a tumor, or a Rasopathy disorder, such as neurofibromatosis type 1, in a subject in need thereof. In some aspects, the present disclosure features novel polymorphic forms of N—((R)-2,3-dihydroxypropoxy)-3,4-difluoro-2-(2-fluoro-4-iodo-phenylamino)-benzamide and methods of producing them using pure Form IV, which is substantially free of contaminating forms, e.g., Form I.

In some aspects, the present disclosure features novel methods of synthesizing N—((R)-2,3-dihydroxypropoxy)-3,4-difluoro-2-(2-fluoro-4-iodo-phenylamino)-benzamide. In some aspects, the methods of synthesizing N—((R)-2,3-dihydroxypropoxy)-3,4-difluoro-2-(2-fluoro-4-iodo-phenylamino)-benzamide described herein are useful in producing pure Form IV of N—((R)-2,3-dihydroxypropoxy)-3,4-difluoro-2-(2-fluoro-4-iodo-phenylamino)-benzamide.

In some aspects, the methods and compositions described herein are useful in treating patients who struggle to swallow whole capsules or tablets, e.g., pediatric patients or subjects suffering from dysphagia, such as patients with esophageal cancer, Parkinson's disease, amyotrophic lateral sclerosis stroke, achalasia, or esophageal narrowing.

In some aspects, the present disclosure provides a crystalline form of N—((R)-2,3-dihydroxypropoxy)-3,4-difluoro-2-(2-fluoro-4-iodo-phenylamino)-benzamide of Formula (I)

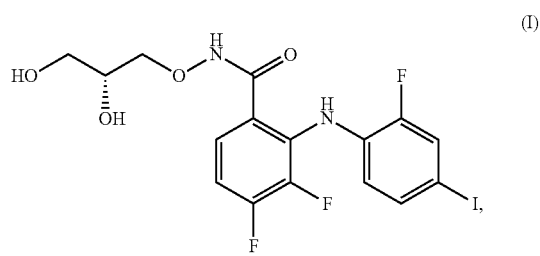 [SMILES: O=C(NOC[C@H](O)CO)c1ccc(F)c(F)c1Nc1ccc(I)cc1F]

selected from the group consisting of:
a) a crystalline form of N—((R)-2,3-dihydroxypropoxy)-3,4-difluoro-2-(2-fluoro-4-iodo-phenylamino)-benzamide characterized by an XRPD pattern having peaks at 5.4±0.2, 17.5±0.2, and 22.8±0.2 degrees two theta;

b) a crystalline form of N—((R)-2,3-dihydroxypropoxy)-3,4-difluoro-2-(2-fluoro-4-iodo-phenylamino)-benzamide characterized by an XRPD pattern having peaks at 5.9±0.2, 7.2±0.2, and 21.2±0.2 degrees two theta;

c) a crystalline form of N—((R)-2,3-dihydroxypropoxy)-3,4-difluoro-2-(2-fluoro-4-iodo-phenylamino)-benzamide characterized by an XRPD pattern having peaks at 5.3±0.2, 10.6±0.2, and 16.1±0.2 degrees two theta;

d) a crystalline form of N—((R)-2,3-dihydroxypropoxy)-3,4-difluoro-2-(2-fluoro-4-iodo-phenylamino)-benzamide characterized by an XRPD pattern having peaks at 5.4±0.2, 10.7±0.2, and 18.7±0.2 degrees two theta;

e) a crystalline form of N—((R)-2,3-dihydroxypropoxy)-3,4-difluoro-2-(2-fluoro-4-iodo-phenylamino)-benzamide characterized by an XRPD pattern having peaks at 6.7±0.2, 13.5±0.2, and 22.2±0.2 degrees two theta;

f) a crystalline form of N—((R)-2,3-dihydroxypropoxy)-3,4-difluoro-2-(2-fluoro-4-iodo-phenylamino)-benzamide characterized by an XRPD pattern having peaks at 10.6±0.2, 19.6±0.2, and 24.8±0.2 degrees two theta;

g) a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 6.9±0.2, and 10.1±0.2 degrees two theta;

h) a crystalline form of N—((R)-2,3-dihydroxypropoxy)-3,4-difluoro-2-(2-fluoro-4-iodo-phenylamino)-benzamide characterized by an XRPD pattern having peaks at 10.1±0.2, 17.3±0.2, and 22.6±0.2 degrees two theta;

i) a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 5.1±0.2, and 14.6±0.2 degrees two theta;

j) a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 23.4±0.2, and 25.2±0.2 degrees two theta;

k) a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 14.7±0.2, and 20.9±0.2 degrees two theta;

l) a crystalline form of N—((R)-2,3-dihydroxypropoxy)-3,4-difluoro-2-(2-fluoro-4-iodo-phenylamino)-benzamide characterized by an XRPD pattern having peaks at 6.0±0.2, 17.1±0.2, and 20.6±0.2 degrees two theta;

m) a crystalline form of N—((R)-2,3-dihydroxypropoxy)-3,4-difluoro-2-(2-fluoro-4-iodo-phenylamino)-benzamide characterized by an XRPD pattern having peaks at 5.9±0.2, 10.1±0.2, and 15.5±0.2 degrees two theta;

n) a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 10.7±0.2, and 15.9±0.2 degrees two theta;

o) a crystalline form of N—((R)-2,3-dihydroxypropoxy)-3,4-difluoro-2-(2-fluoro-4-iodo-phenylamino)-benzamide characterized by an XRPD pattern having peaks at 10.2±0.2, 11.6±0.2, and 20.0±0.2 degrees two theta;

p) a crystalline form of N—((R)-2,3-dihydroxypropoxy)-3,4-difluoro-2-(2-fluoro-4-iodo-phenylamino)-benzamide characterized by an XRPD pattern having peaks at 7.8±0.2, 14.0±0.2, and 17.1±0.2 degrees two theta;

q) a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 8.2±0.2, and 16.7±0.2 degrees two theta;

r) a crystalline form of N—((R)-2,3-dihydroxypropoxy)-3,4-difluoro-2-(2-fluoro-4-iodo-phenylamino)-benzamide characterized by an XRPD pattern having peaks at 7.2±0.2, 21.7±0.2, and 29.1±0.2 degrees two theta;

s) a crystalline form of N—((R)-2,3-dihydroxypropoxy)-3,4-difluoro-2-(2-fluoro-4-iodo-phenylamino)-benzamide characterized by an XRPD pattern having peaks at 5.4±0.2, 9.7±0.2, and 10.7±0.2 degrees two theta; and t) a crystalline form of N—((R)-2,3-dihydroxypropoxy)-3,4-difluoro-2-(2-fluoro-4-iodo-phenylamino)-benzamide characterized by an XRPD pattern having peaks at 7.2±0.2, 20.6±0.2, and 23.0±0.2 degrees two theta.

Figure 2A:
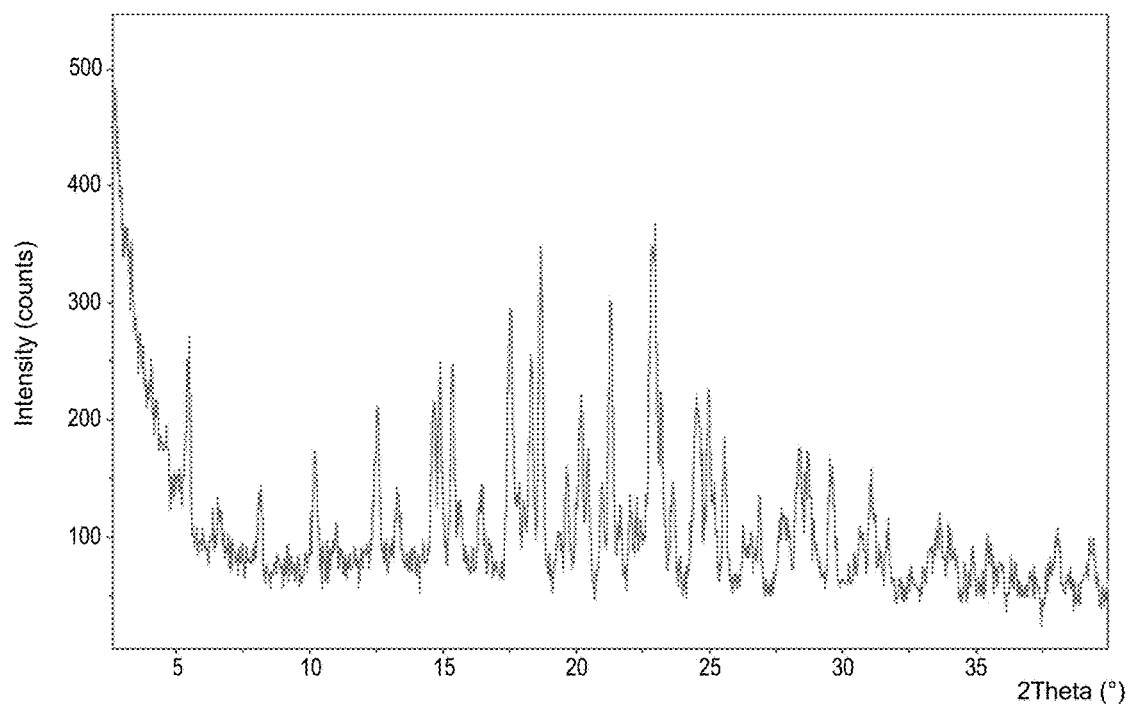
FIG. 2A is a X-ray powder diffraction pattern ("XRPD") corresponding to crystalline Form V.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks 5.4±0.2, 17.5±0.2, and 22.8±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks 5.4±0.2, 12.5±0.2, 17.5±0.2, and 22.8±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 2A.

Figure 2B:
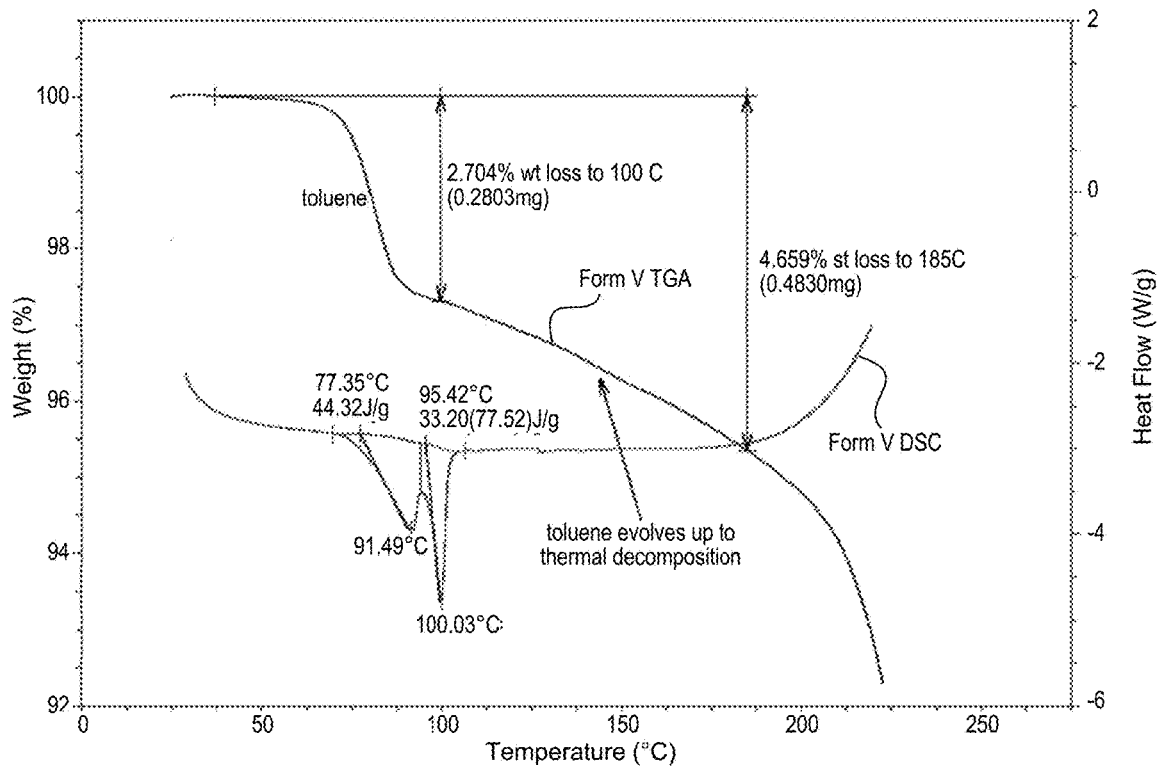
FIG. 2B is a thermogravimetric analysis thermogram ("TGA") and a differential scanning calorimetry thermogram ("DSC") corresponding to crystalline Form V.

In some aspects, the TGA exhibits that the crystalline form of N—((R)-2,3-dihydroxypropoxy)-3,4-difluoro-2-(2-fluoro-4-iodo-phenylamino)-benzamide loses about 2.7 wt % between about 35° C. and about 100° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 77° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 95° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 77° C. and a second endotherm onset at about 95° C. In some aspects, wherein the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 2B; and/or b) a DSC profile substantially as shown in FIG. 2B.

In some aspects, the crystalline form of N—((R)-2,3-dihydroxypropoxy)-3,4-difluoro-2-(2-fluoro-4-iodo-phenylamino)-benzamide is Form V.

Figure 3A:
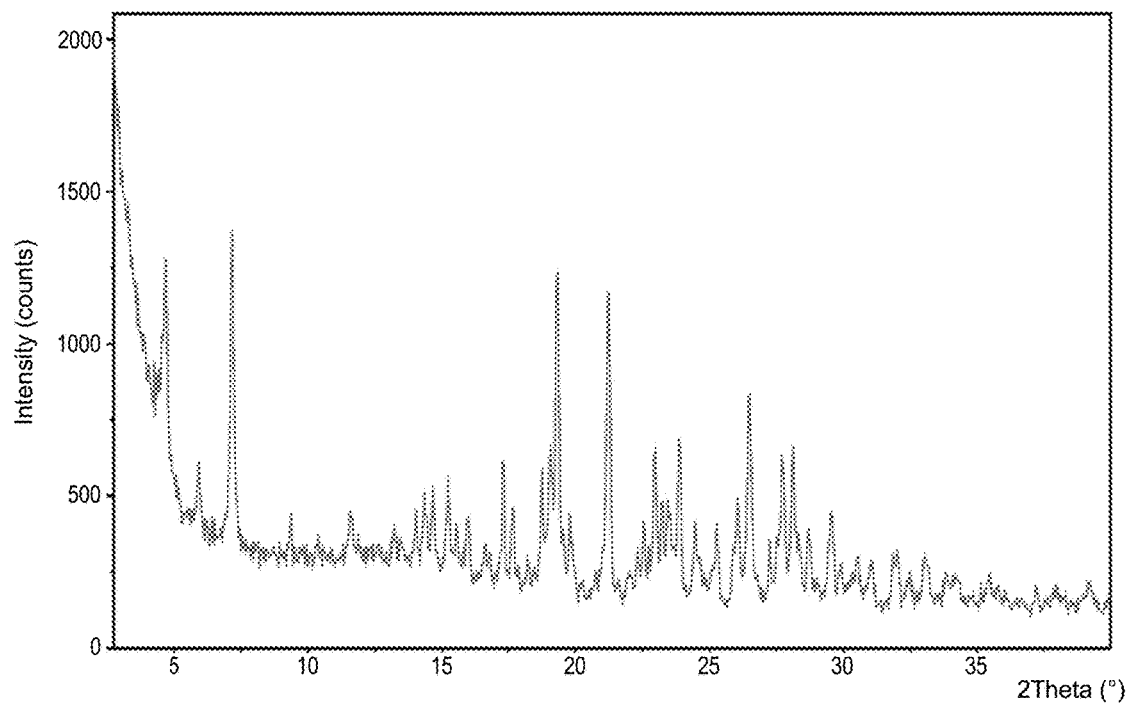
FIG. 3A is an XRPD corresponding to crystalline Form VI.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.9±0.2, 7.2±0.2, and 21.2±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.9±0.2, 7.2±0.2, 9.3±0.2, and 21.2±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 3A.

Figure 3B:
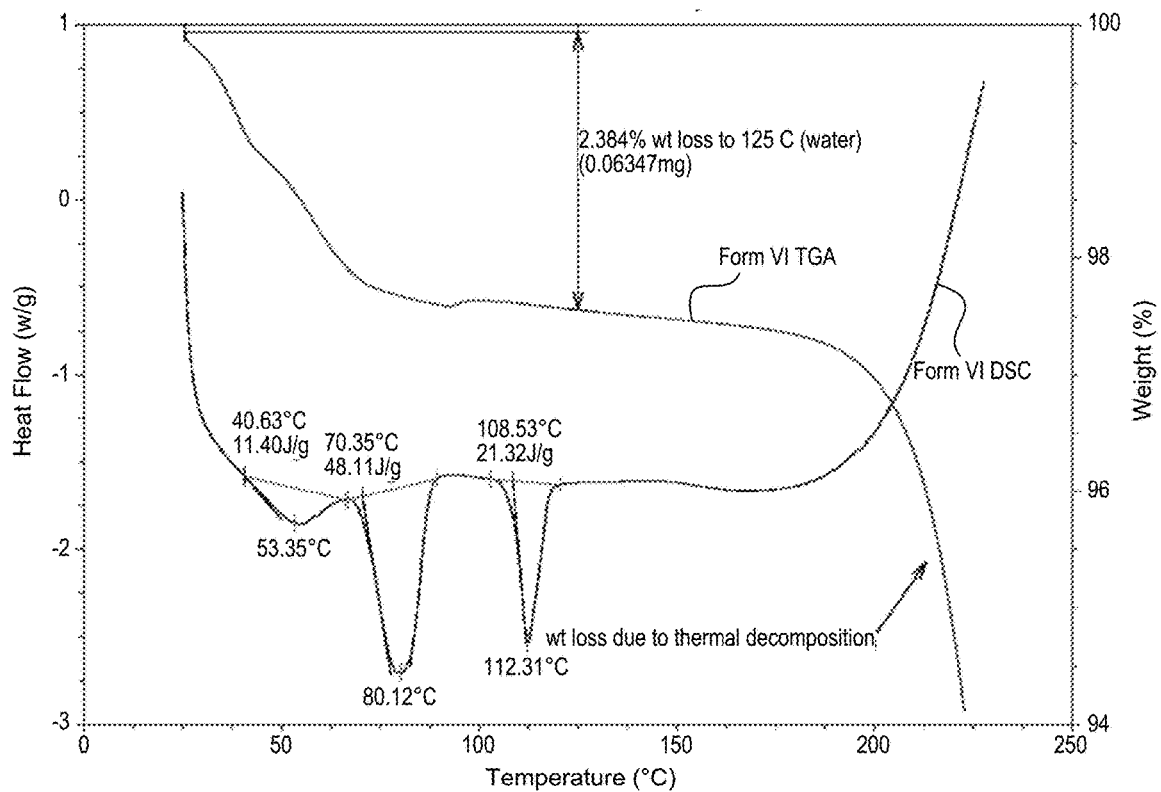
FIG. 3B is a DSC and a TGA corresponding to crystalline Form VI.

In some aspects, the TGA exhibits that the crystalline form of N—((R)-2,3-dihydroxypropoxy)-3,4-difluoro-2-(2-fluoro-4-iodo-phenylamino)-benzamide loses about 2.4 wt % between about 25° C. and about 125° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 41° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 70° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 109° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 41° C. and an endotherm onset at about 70° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 41° C. and an endotherm onset at about 109° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 70° C. and an endotherm onset at about 109° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 41° C., a second endotherm onset at about 70° C., and a third endotherm onset at about 109° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 3B; and/or b) a DSC profile substantially as shown in FIG. 3B.

In some aspects, the crystalline form of N—((R)-2,3-dihydroxypropoxy)-3,4-difluoro-2-(2-fluoro-4-iodo-phenylamino)-benzamide is Form VI.

Figure 4A:
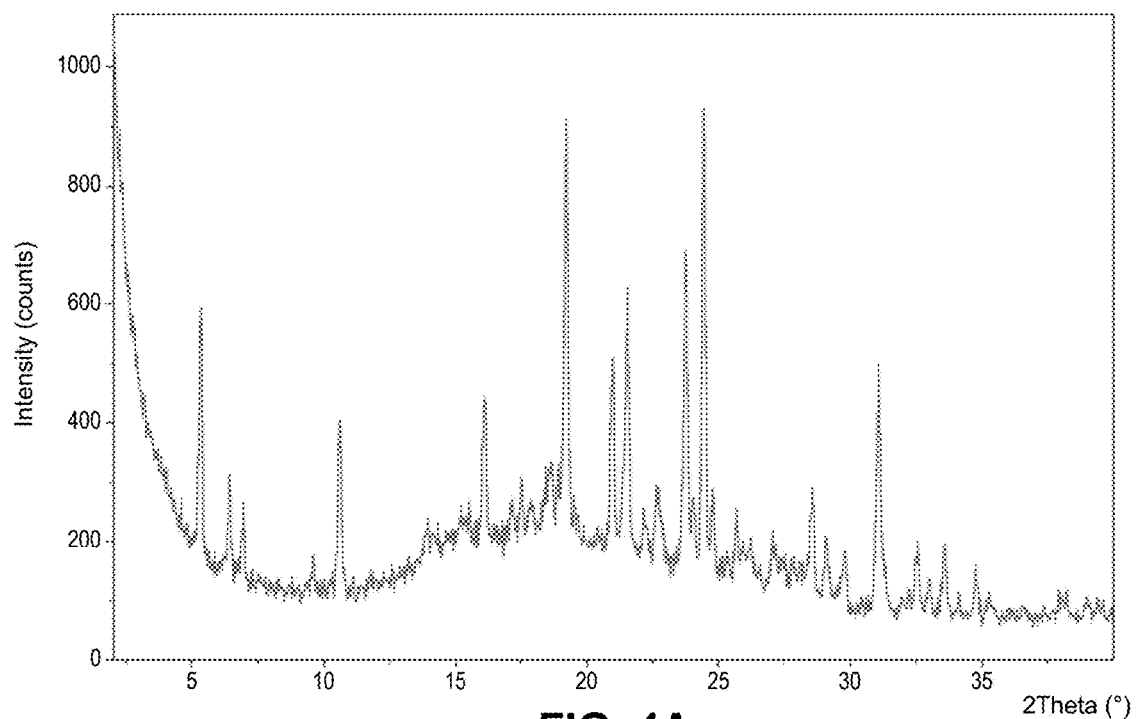
FIG. 4A is an XRPD corresponding to crystalline Form VII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.3±0.2, 10.6±0.2, and 16.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.3±0.2, 10.6±0.2, 13.9±0.2, and 16.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 4A.

Figure 4B:
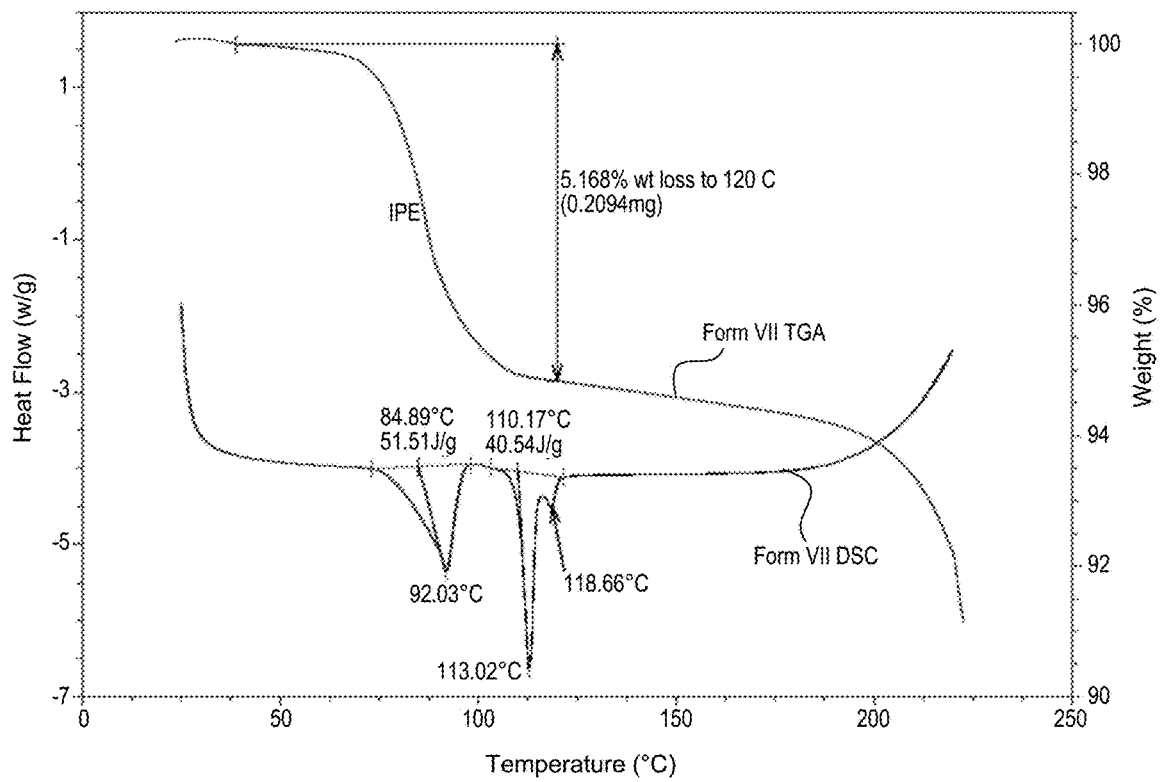
FIG. 4B is a DSC and a TGA corresponding to crystalline Form VII.

In some aspects, the TGA exhibits that the crystalline form of N—((R)-2,3-dihydroxypropoxy)-3,4-difluoro-2-(2-fluoro-4-iodo-phenylamino)-benzamide loses about 5.2 wt % between about 40° C. and about 120° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endothermic onset at about 85° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endothermic event at about 110° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 85° C. and a second endothermic event at about 110° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 4B; and/or b) a DSC profile substantially as shown in FIG. 4B.

In some aspects, the crystalline form of N—((R)-2,3-dihydroxypropoxy)-3,4-difluoro-2-(2-fluoro-4-iodo-phenylamino)-benzamide is Form VII.

Figure 5A:
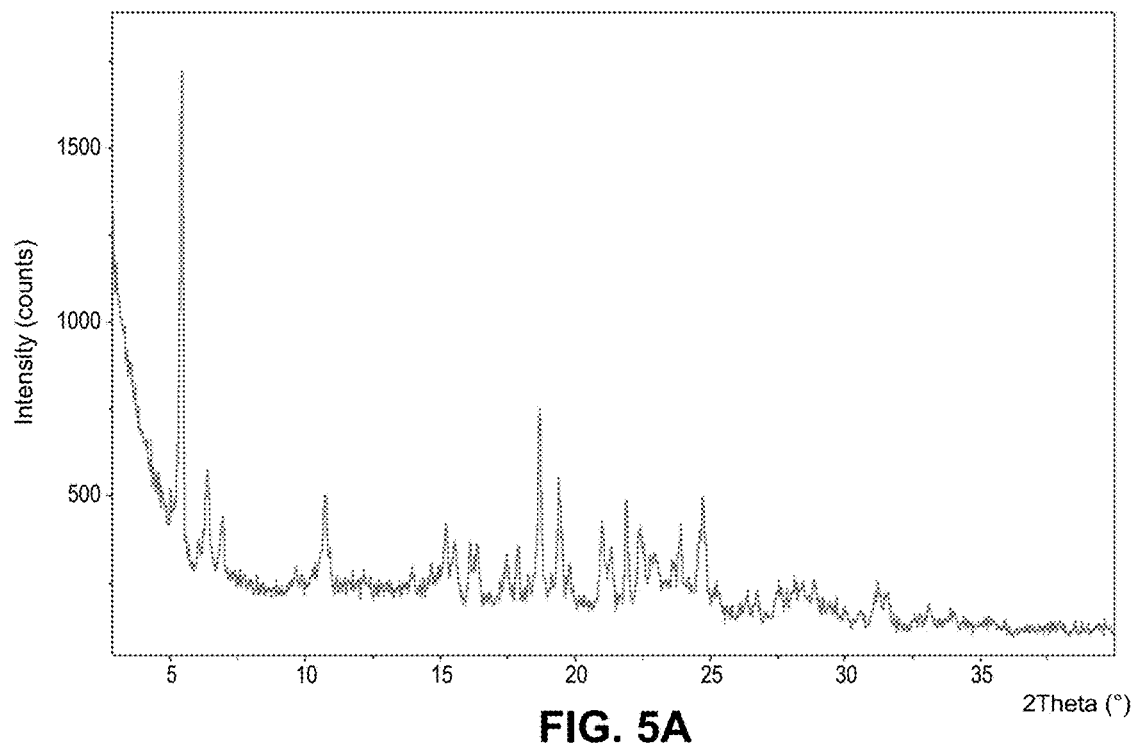
FIG. 5A is an XRPD corresponding to crystalline Form VIII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.4±0.2, 10.7±0.2, and 18.7±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.4±0.2, 10.7±0.2, 18.7±0.2, and 23.9±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 5A.

Figure 5B:
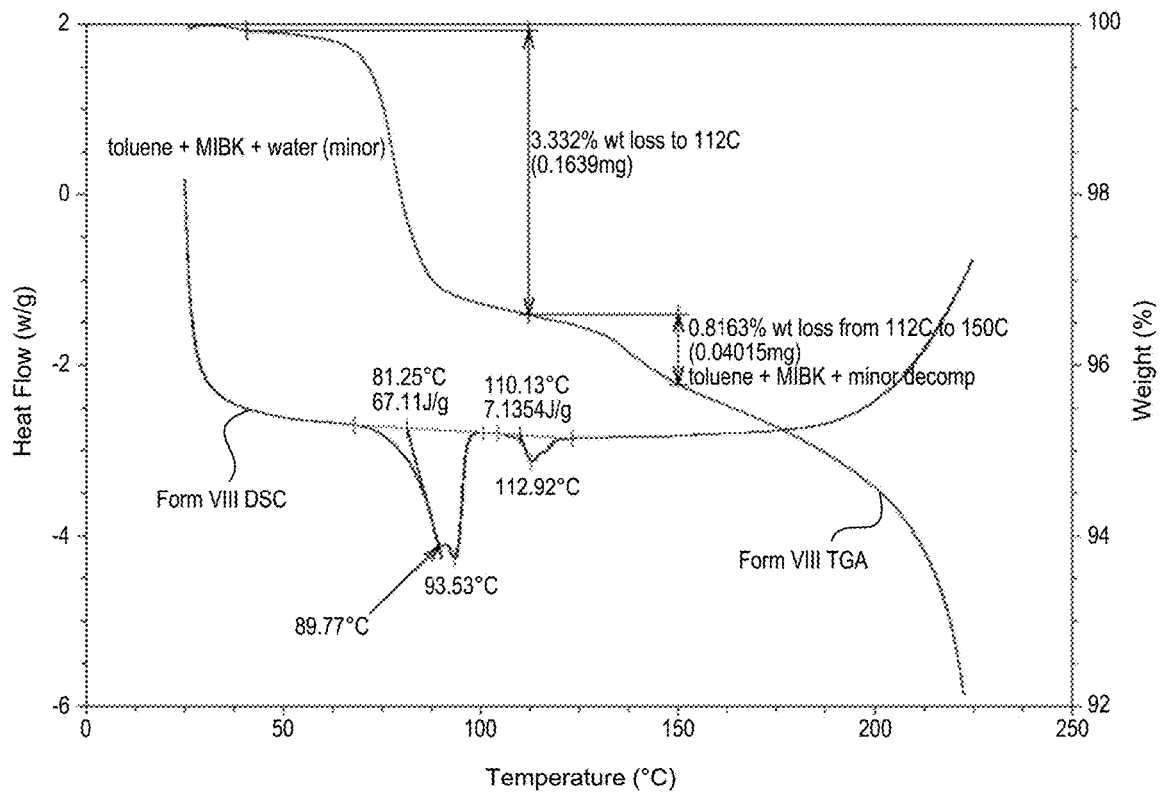
FIG. 5B is a DSC and a TGA corresponding to crystalline Form VIII.

In some aspects, the TGA exhibits that the crystalline form of N—((R)-2,3-dihydroxypropoxy)-3,4-difluoro-2-(2-fluoro-4-iodo-phenylamino)-benzamide loses about 3.3 wt % between about 40° C. and about 112° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 81° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 110° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 81° C. and a second endotherm onset at about 110° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 5B; and/or b) a DSC profile substantially as shown in FIG. 5B.

In some aspects, the crystalline form of N—((R)-2,3-dihydroxypropoxy)-3,4-difluoro-2-(2-fluoro-4-iodo-phenylamino)-benzamide is Form VIII.

Figure 6A:
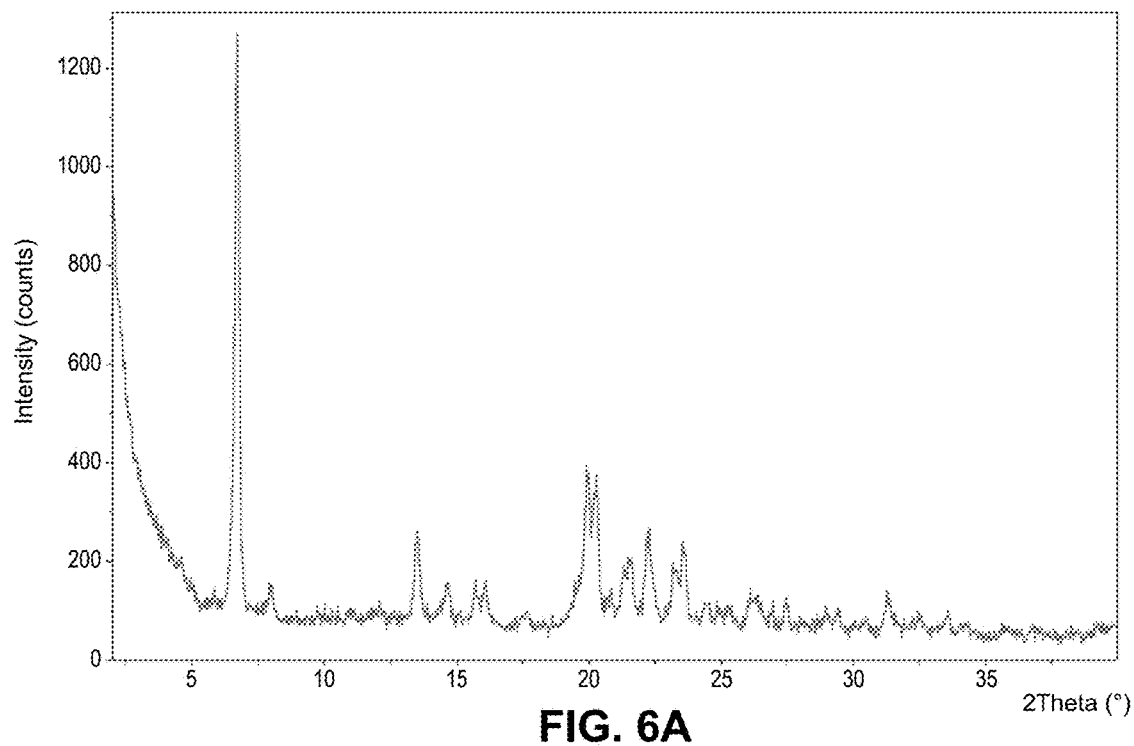
FIG. 6A is an XRPD corresponding to crystalline Form IX.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 6.7±0.2, 13.5±0.2, and 22.2±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 6.7±0.2, 8.0±0.2, 13.5±0.2, and 22.2±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 6A.

Figure 6B:
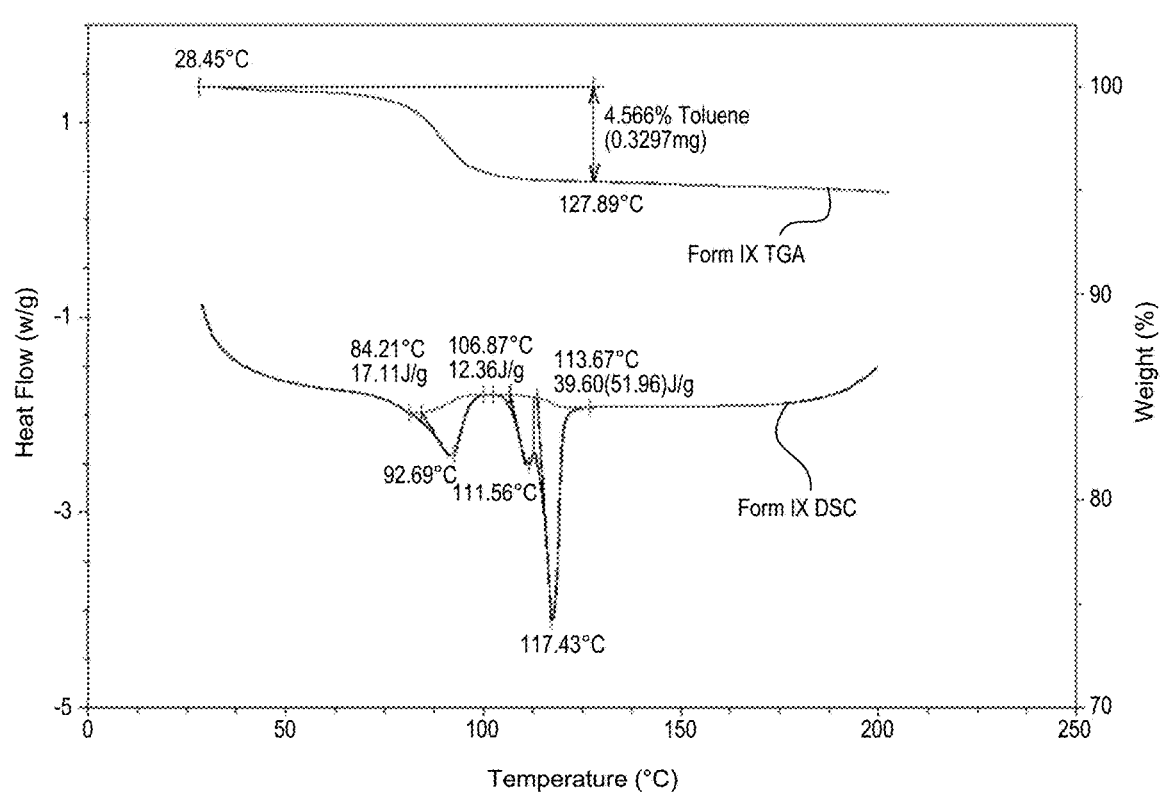
FIG. 6B is a DSC and a TGA corresponding to crystalline Form IX.

In some aspects, the TGA exhibits that the crystalline form of N—((R)-2,3-dihydroxypropoxy)-3,4-difluoro-2-(2-fluoro-4-iodo-phenylamino)-benzamide loses about 4.6 wt % between about 28° C. and about 128° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 84° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 107° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 114° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 84° C. and an endotherm onset at about 107° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 84° C. and an endotherm onset at about 114° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 107° C. and an endotherm onset at about 114° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 84° C., a second endotherm onset at about 107° C., and a third endotherm onset at about 114° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 6B; and/or b) a DSC profile substantially as shown in FIG. 6B.

In some aspects, the crystalline form of N—((R)-2,3-dihydroxypropoxy)-3,4-difluoro-2-(2-fluoro-4-iodo-phenylamino)-benzamide is Form IX.

Figure 7A:
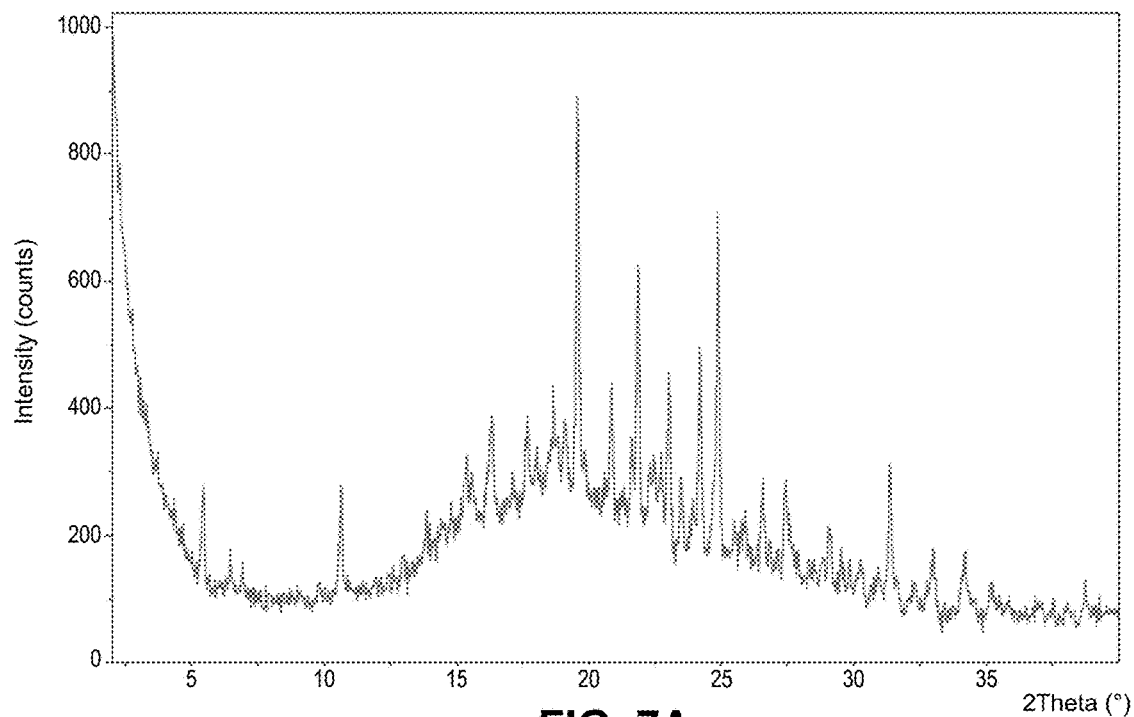
FIG. 7A is an XRPD corresponding to crystalline Form X.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 10.6±0.2, 19.6±0.2, and 24.8±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 10.6±0.2, 19.6±0.2, and 24.8±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 7A.

Figure 7B:
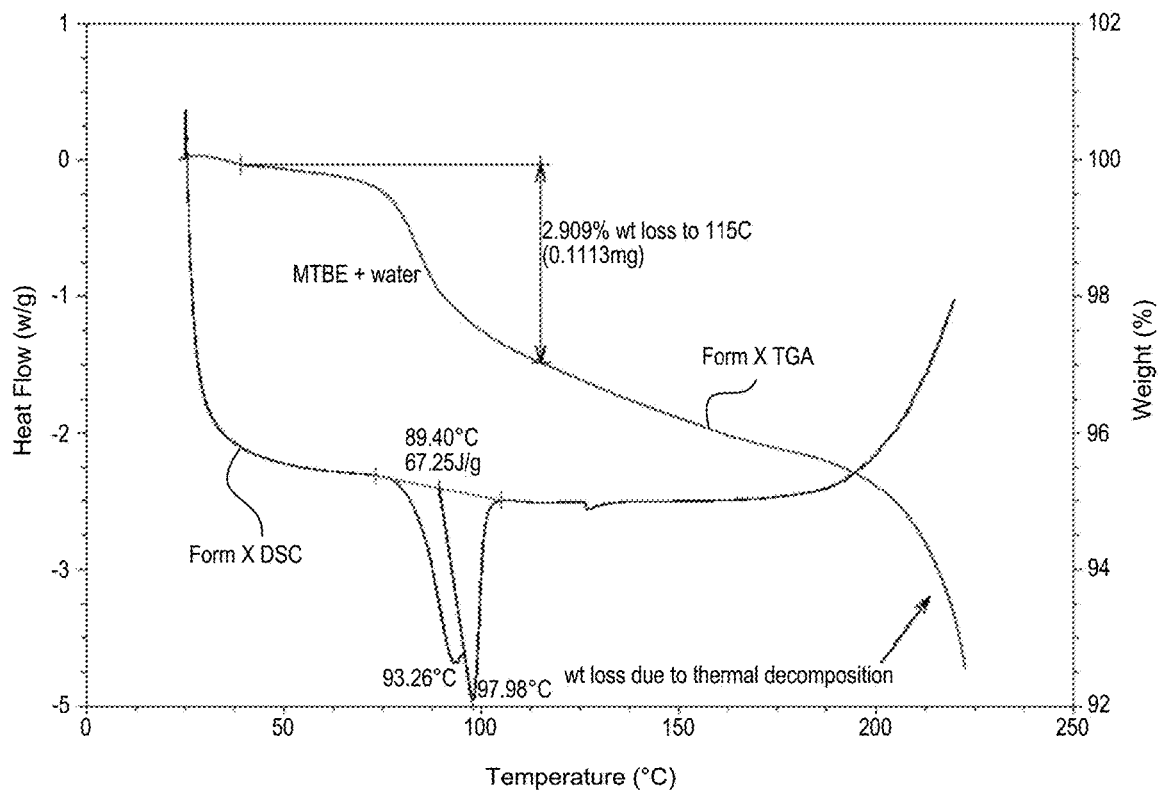
FIG. 7B is a DSC and a TGA corresponding to crystalline Form X.

In some aspects, the TGA exhibits that the crystalline form of N—((R)-2,3-dihydroxypropoxy)-3,4-difluoro-2-(2-fluoro-4-iodo-phenylamino)-benzamide loses about 2.9 wt % between about 40° C. and about 115° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 89° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 7B; and/or b) a DSC profile substantially as shown in FIG. 7B.

In some aspects, the crystalline form of N—((R)-2,3-dihydroxypropoxy)-3,4-difluoro-2-(2-fluoro-4-iodo-phenylamino)-benzamide is Form X.

Figure 8A:
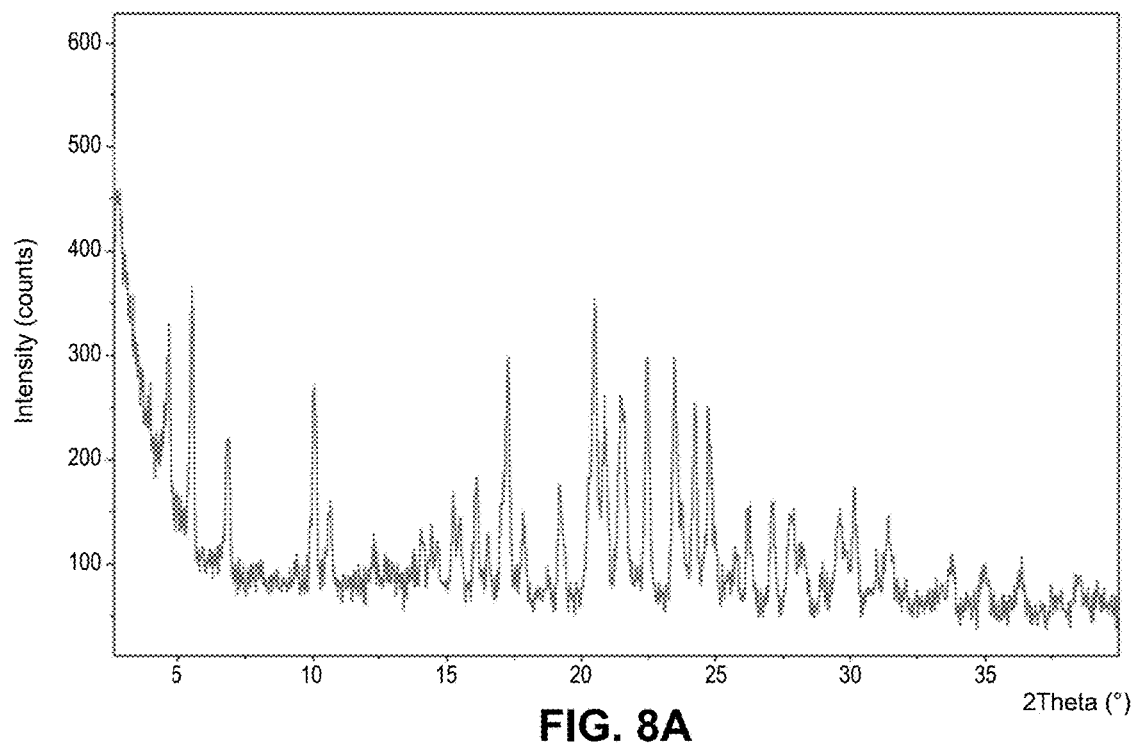
FIG. 8A is an XRPD corresponding to crystalline Form XI.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 6.9±0.2, and 10.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 6.9±0.2, 10.1±0.2, and 19.2±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 8A.

Figure 8B:
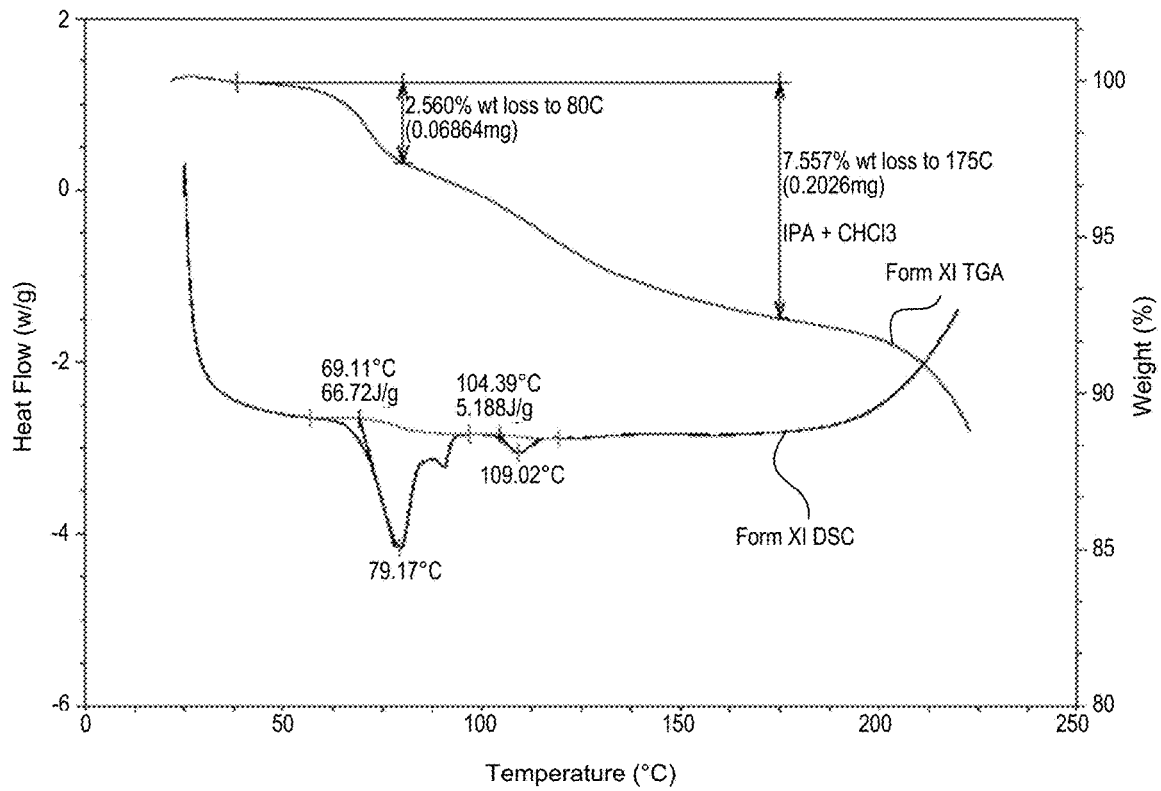
FIG. 8B is a DSC and a TGA corresponding to crystalline Form XI.

In some aspects, the TGA exhibits that the crystalline form of N—((R)-2,3-dihydroxypropoxy)-3,4-difluoro-2-(2-fluoro-4-iodo-phenylamino)-benzamide loses about 7.6 wt % between about 40° C. and about 175° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 69° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 104° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 69° C. and a second endotherm onset at about 104° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 8B; and/or b) a DSC profile substantially as shown in FIG. 8B.

In some aspects, the crystalline form of N—((R)-2,3-dihydroxypropoxy)-3,4-difluoro-2-(2-fluoro-4-iodo-phenylamino)-benzamide is Form XI.

Figure 9A:
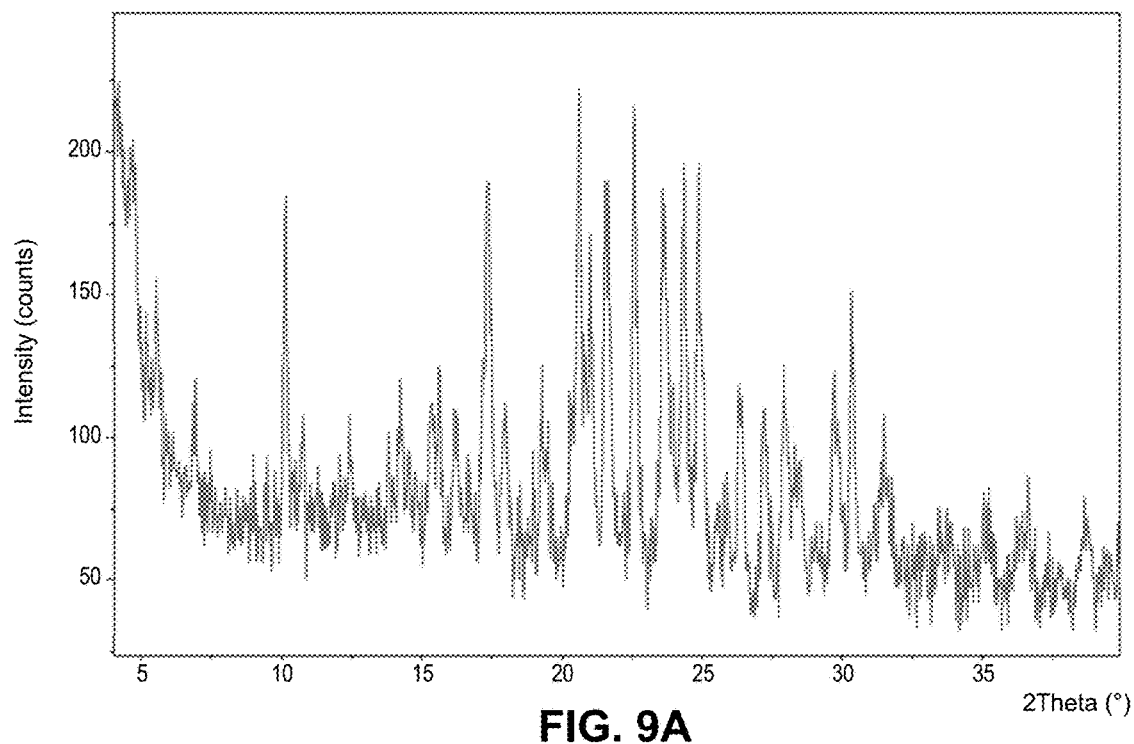
FIG. 9A is an XRPD corresponding to crystalline Form XII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 10.1±0.2, 17.3±0.2, and 22.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 10.1±0.2, 17.3±0.2, 21.5±0.2, and 22.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 9A.

Figure 9B:
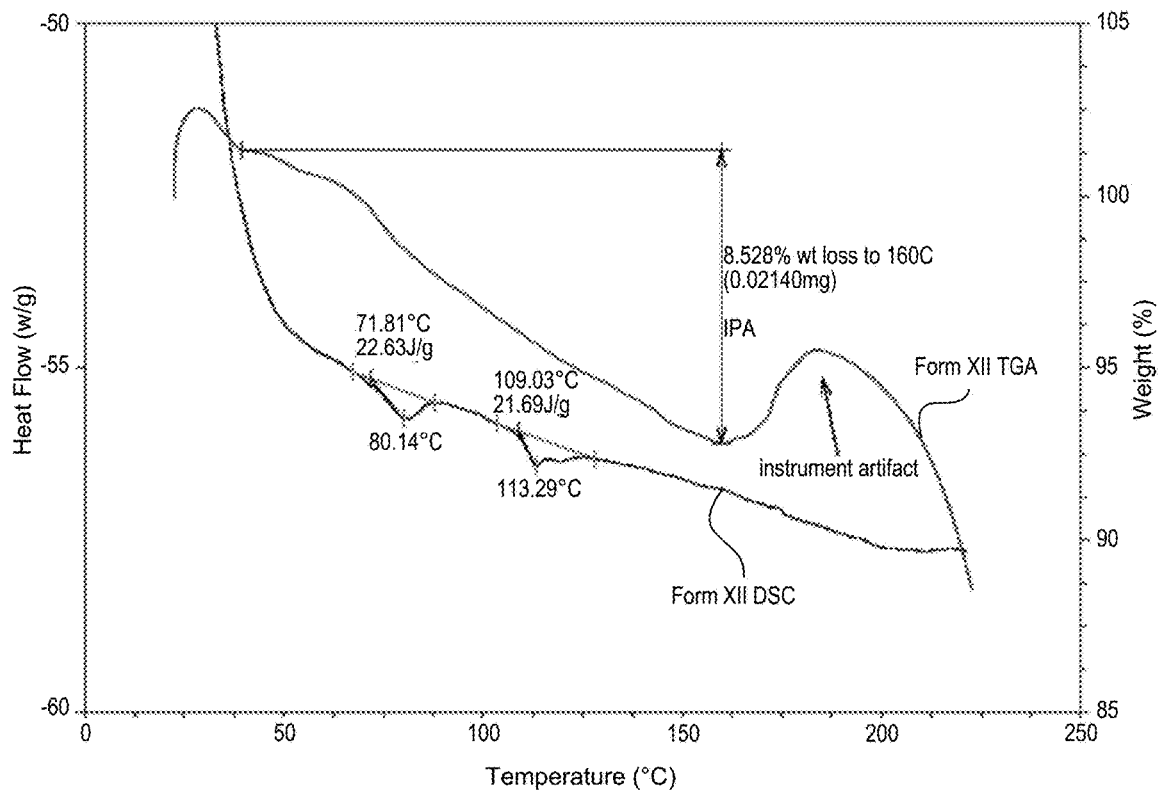
FIG. 9B is a DSC and a TGA corresponding to crystalline Form XII.

In some aspects, the TGA exhibits that the crystalline form of N—((R)-2,3-dihydroxypropoxy)-3,4-difluoro-2-(2-fluoro-4-iodo-phenylamino)-benzamide loses about 8.5 wt % between about 40° C. and about 160° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 72° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 109° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 72° C. and a second endotherm onset at about 109° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 9B; and/or b) a DSC profile substantially as shown in FIG. 9B.

In some aspects, the crystalline form of N—((R)-2,3-dihydroxypropoxy)-3,4-difluoro-2-(2-fluoro-4-iodo-phenylamino)-benzamide is Form XII.

Figure 10A:
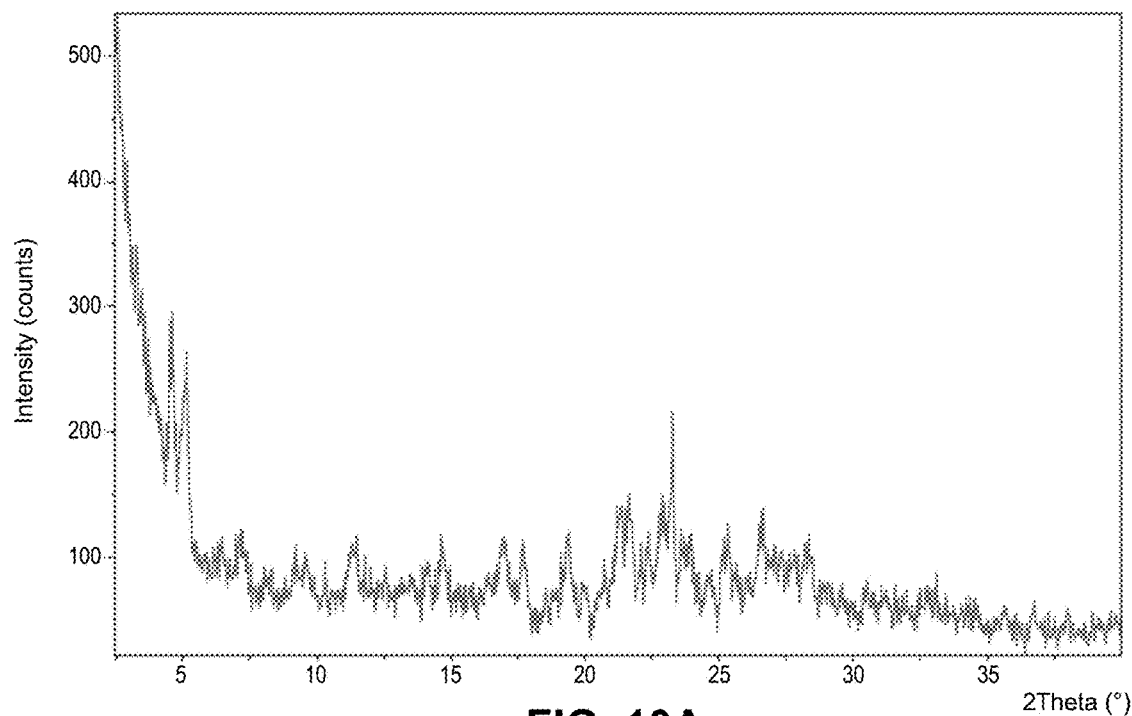
FIG. 10A is an XRPD corresponding to crystalline Form XIII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 5.1±0.2, and 14.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 5.1±0.2, 6.4±0.2, and 14.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 10A.

Figure 10B:
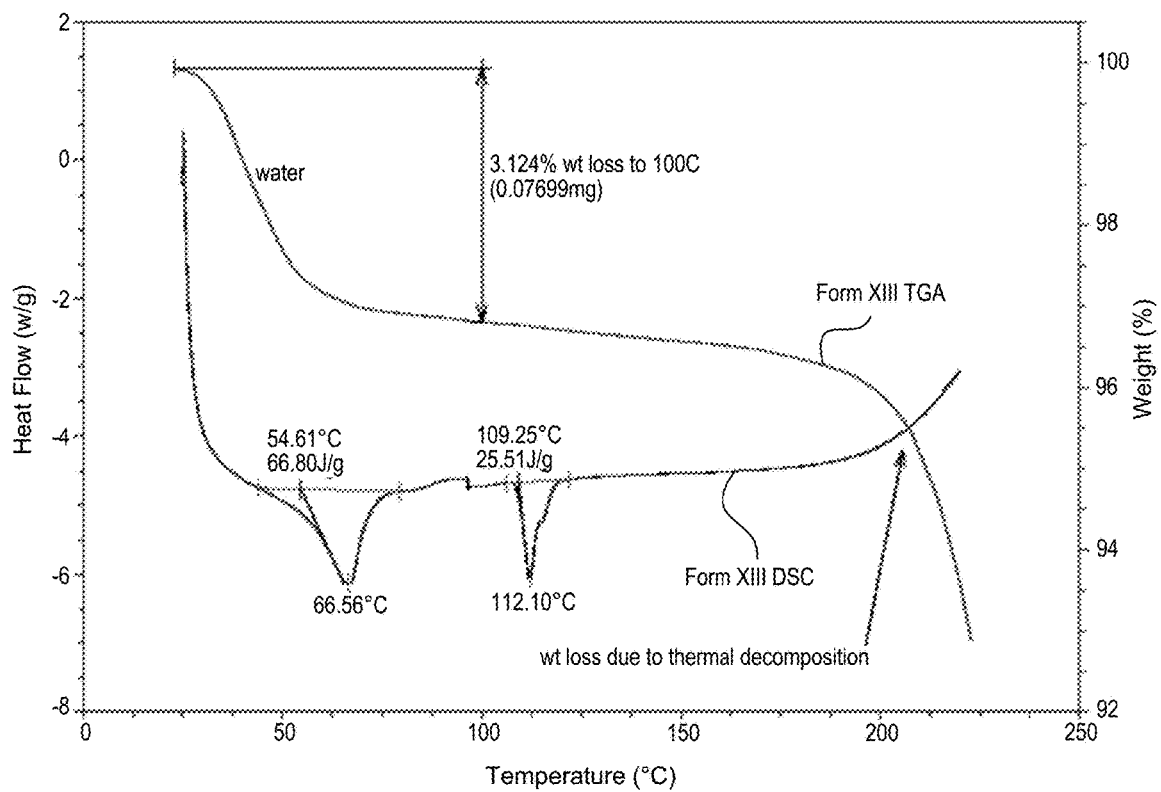
FIG. 10B is a DSC and a TGA corresponding to crystalline Form XIII.

In some aspects, the TGA exhibits that the crystalline form of N—((R)-2,3-dihydroxypropoxy)-3,4-difluoro-2-(2-fluoro-4-iodo-phenylamino)-benzamide loses about 3.1 wt % between about 20° C. and about 100° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 55° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 109° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 55° C. and a second endotherm onset at about 109° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 10B; and/or b) a DSC profile substantially as shown in FIG. 10B.

In some aspects, the crystalline form of N—((R)-2,3-dihydroxypropoxy)-3,4-difluoro-2-(2-fluoro-4-iodo-phenylamino)-benzamide is Form XIII.

Figure 11A:
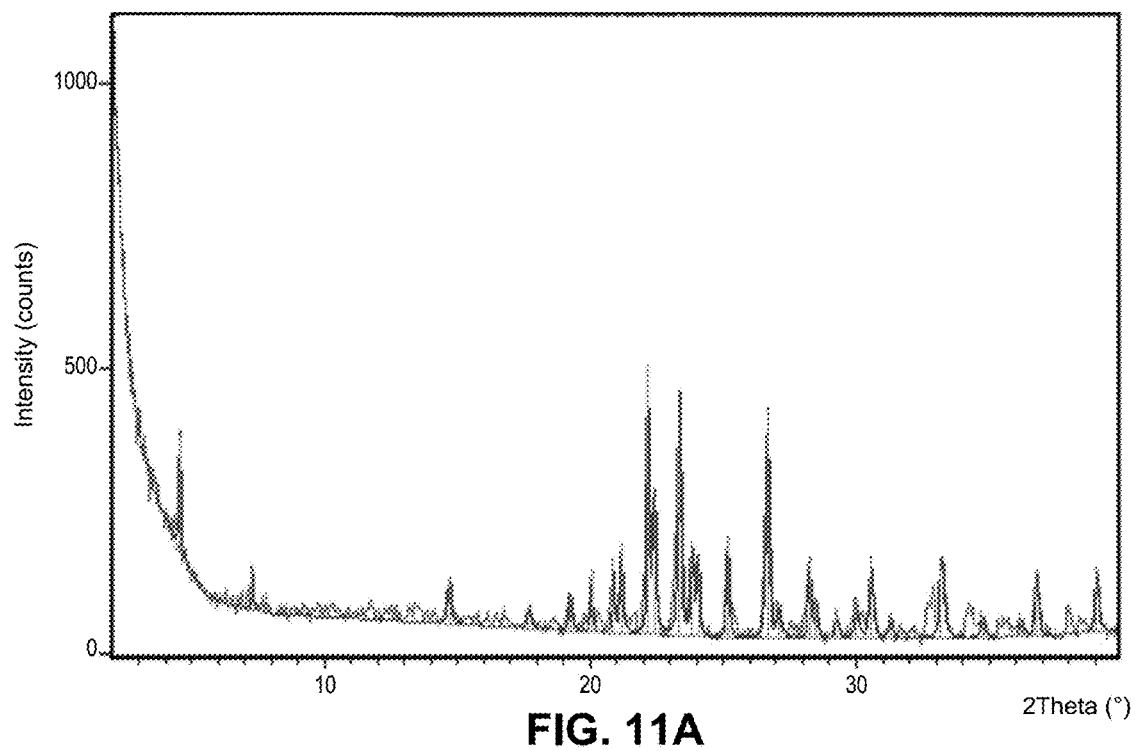
FIG. 11A is an XRPD corresponding to crystalline Form XIV overlaid with an XRPD corresponding to crystalline Form IV.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 23.4±0.2, and 25.2±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 23.4±0.2, 25.2±0.2, and 30.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 11A.

Figure 11B:
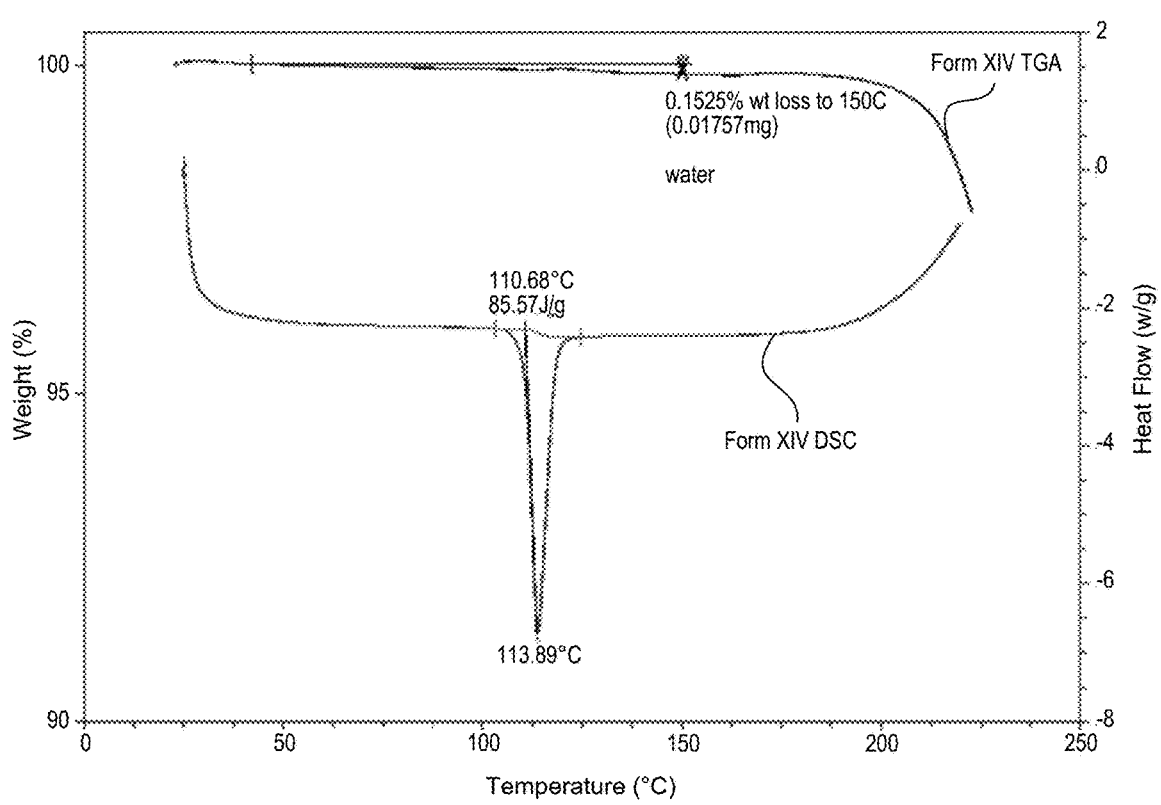
FIG. 11B is a DSC and a TGA corresponding to crystalline Form XIV.

In some aspects, the TGA exhibits that the crystalline form of N—((R)-2,3-dihydroxypropoxy)-3,4-difluoro-2-(2-fluoro-4-iodo-phenylamino)-benzamide loses about 0.15 wt % between about 40° C. and about 150° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 111° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 11B; and/or b) a DSC profile substantially as shown in FIG. 11B.

In some aspects, the crystalline form of N—((R)-2,3-dihydroxypropoxy)-3,4-difluoro-2-(2-fluoro-4-iodo-phenylamino)-benzamide is Form XIV.

Figure 12A:
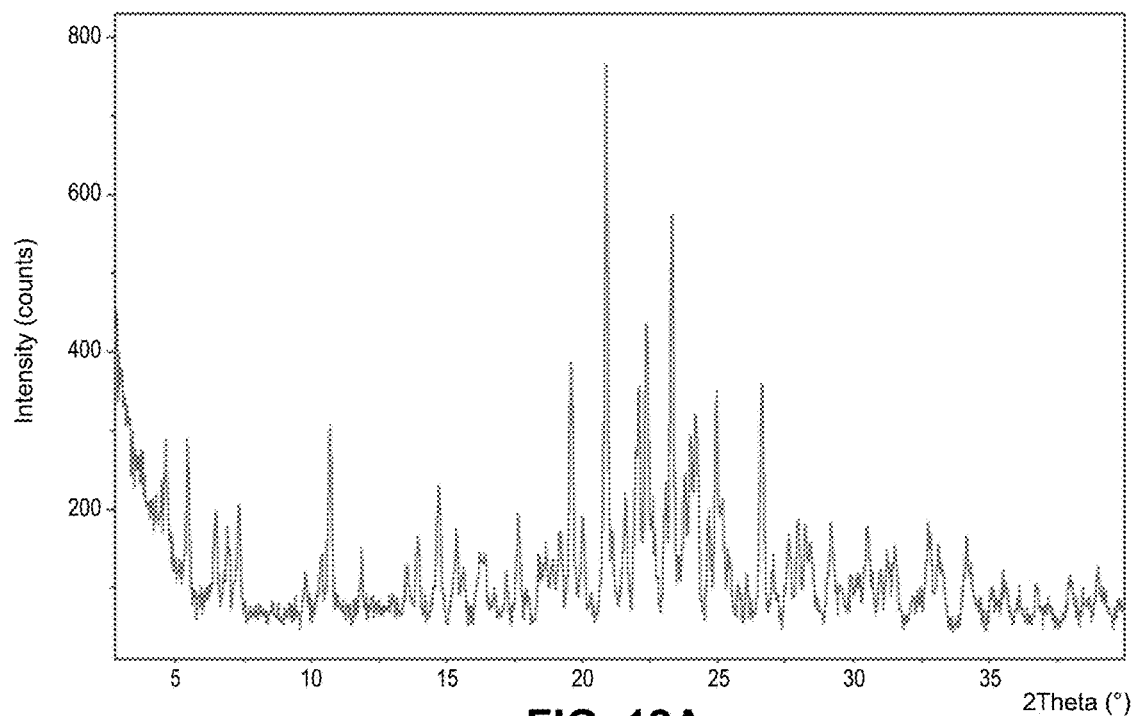
FIG. 12A is an XRPD corresponding to crystalline Form XV.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 14.7±0.2, and 20.9±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 14.7±0.2, 20.9±0.2, and 26.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 12A.

Figure 12B:
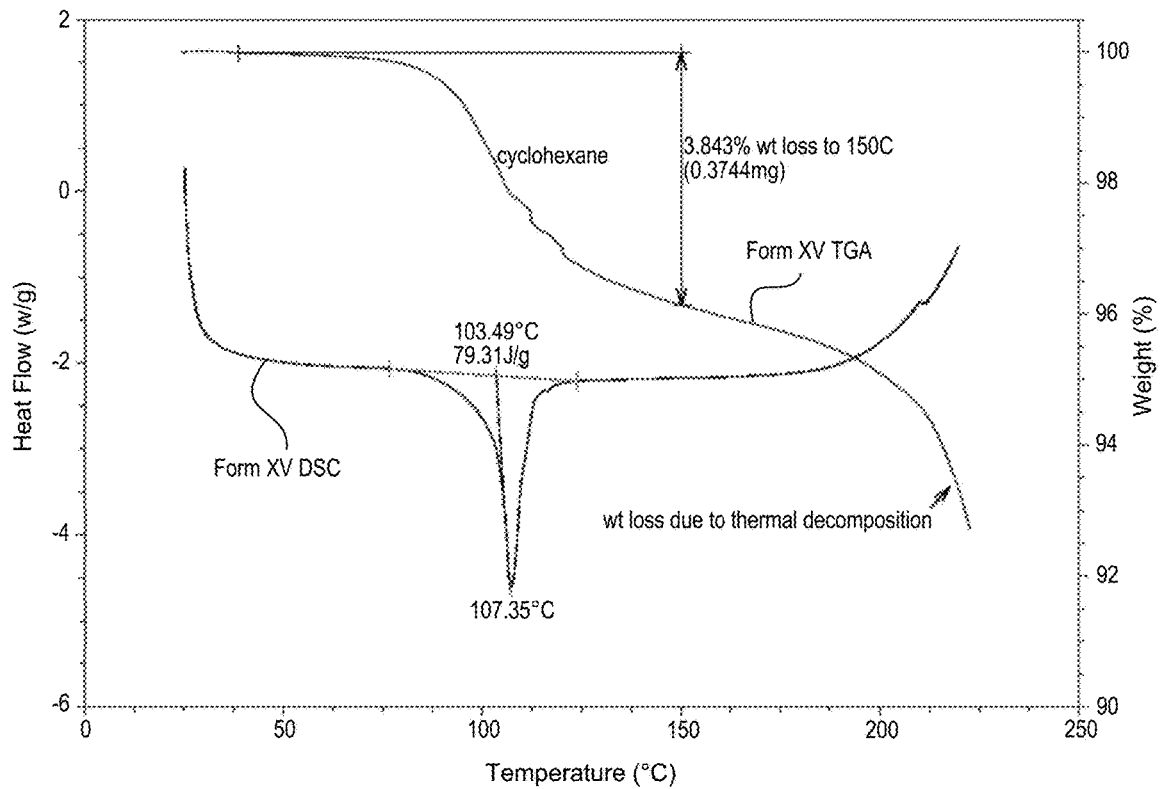
FIG. 12B is a DSC and a TGA corresponding to crystalline Form XV.

In some aspects, the TGA exhibits that the crystalline form of N—((R)-2,3-dihydroxypropoxy)-3,4-difluoro-2-(2-fluoro-4-iodo-phenylamino)-benzamide loses about 3.8 wt % between about 40° C. and about 150° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 104° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 12B; and/or b) a DSC profile substantially as shown in FIG. 12B.

In some aspects, the crystalline form of N—((R)-2,3-dihydroxypropoxy)-3,4-difluoro-2-(2-fluoro-4-iodo-phenylamino)-benzamide is Form XV.

Figure 13A:
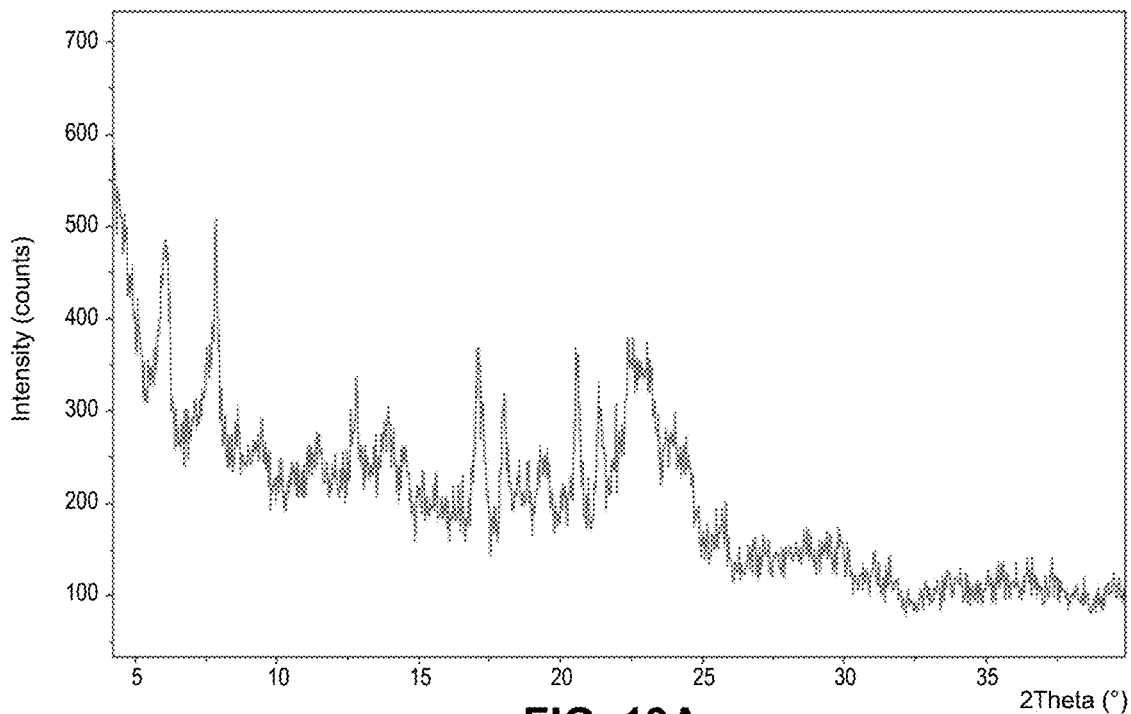
FIG. 13A is an XRPD corresponding to crystalline Form XVI.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 6.0±0.2, 17.1±0.2, and 20.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 6.0±0.2, 12.8±0.2, 17.1±0.2, and 20.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 13A.

Figure 13B:
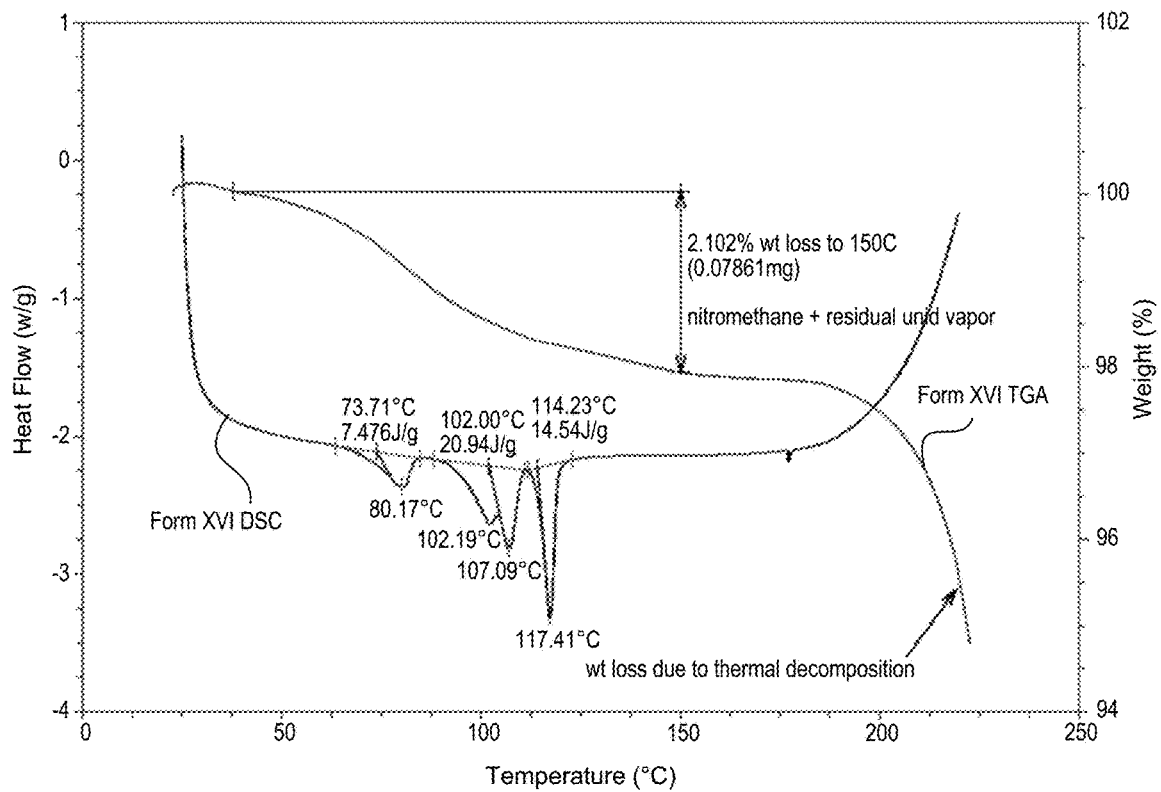
FIG. 13B is a DSC and a TGA corresponding to crystalline Form XVI.

In some aspects, the TGA exhibits that the crystalline form of N—((R)-2,3-dihydroxypropoxy)-3,4-difluoro-2-(2-fluoro-4-iodo-phenylamino)-benzamide loses about 2.1 wt % between about 40° C. and about 150° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 74° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 102° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 114° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 74° C. and an endotherm onset at about 102° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 74° C. and an endotherm onset at about 114° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 102° C. and an endotherm onset at about 114° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 74° C., a second endotherm onset at about 102° C., and a third endotherm onset at about 114° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 13B; and/or b) a DSC profile substantially as shown in FIG. 13B.

In some aspects, the crystalline form of N—((R)-2,3-dihydroxypropoxy)-3,4-difluoro-2-(2-fluoro-4-iodo-phenylamino)-benzamide is Form XVI.

Figure 14A:
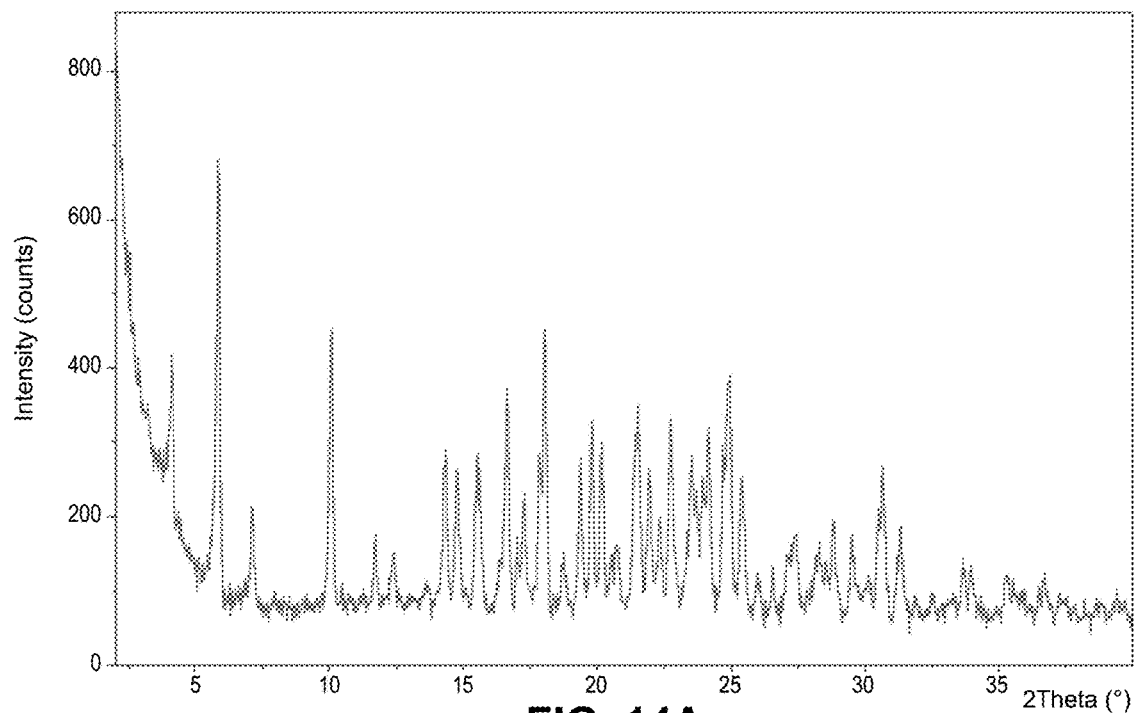
FIG. 14A is an XRPD corresponding to crystalline Form XVII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.9±0.2, 10.1±0.2, and 15.5±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.9±0.2, 10.1±0.2, 11.7±0.2, and 15.5±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 14A.

Figure 14B:
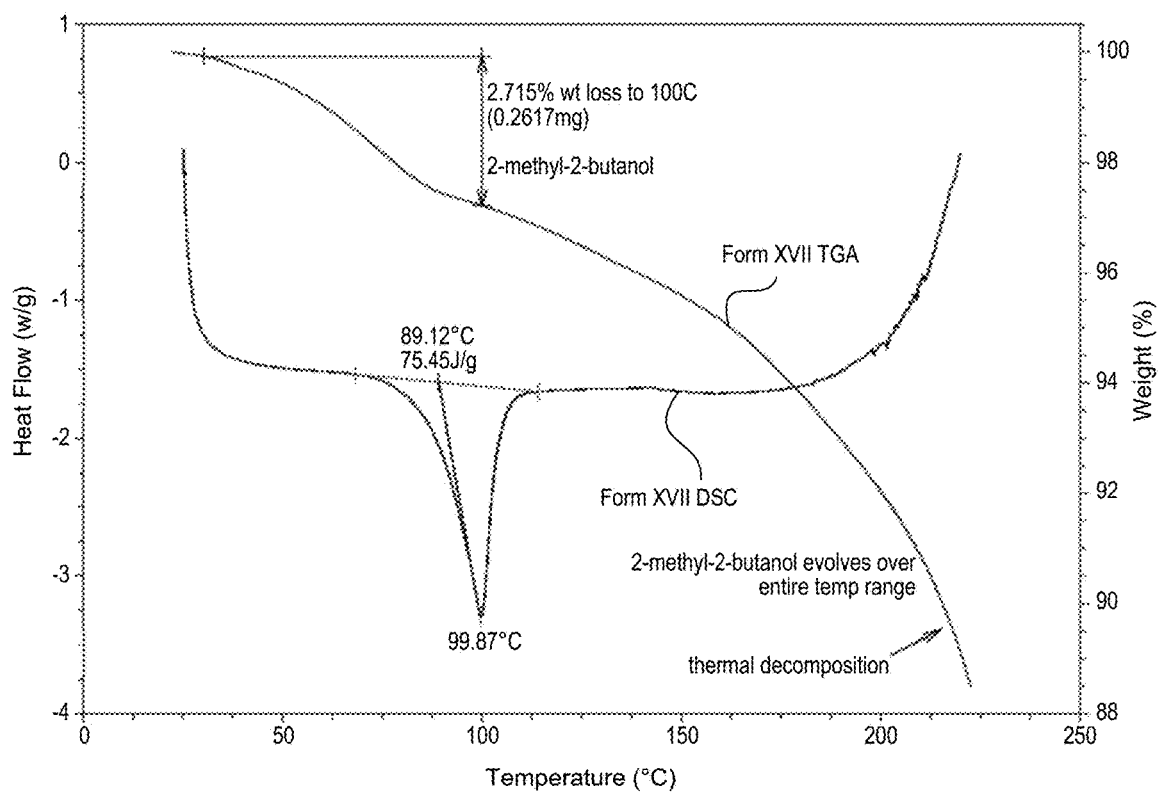
FIG. 14B is a DSC and a TGA corresponding to crystalline Form XVII.

In some aspects, the TGA exhibits that the crystalline form of N—((R)-2,3-dihydroxypropoxy)-3,4-difluoro-2-(2-fluoro-4-iodo-phenylamino)-benzamide loses about 2.7 wt % between about 40° C. and about 100° C. In some aspects, crystalline form of N—((R)-2,3-dihydroxypropoxy)-3,4-difluoro-2-(2-fluoro-4-iodo-phenylamino)-benzamide exhibits a DSC thermogram that has an endotherm onset at about 89° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 14B; and/or b) a DSC profile substantially as shown in FIG. 14B.

In some aspects, the crystalline form of N—((R)-2,3-dihydroxypropoxy)-3,4-difluoro-2-(2-fluoro-4-iodo-phenylamino)-benzamide is Form XVII.

Figure 15A:
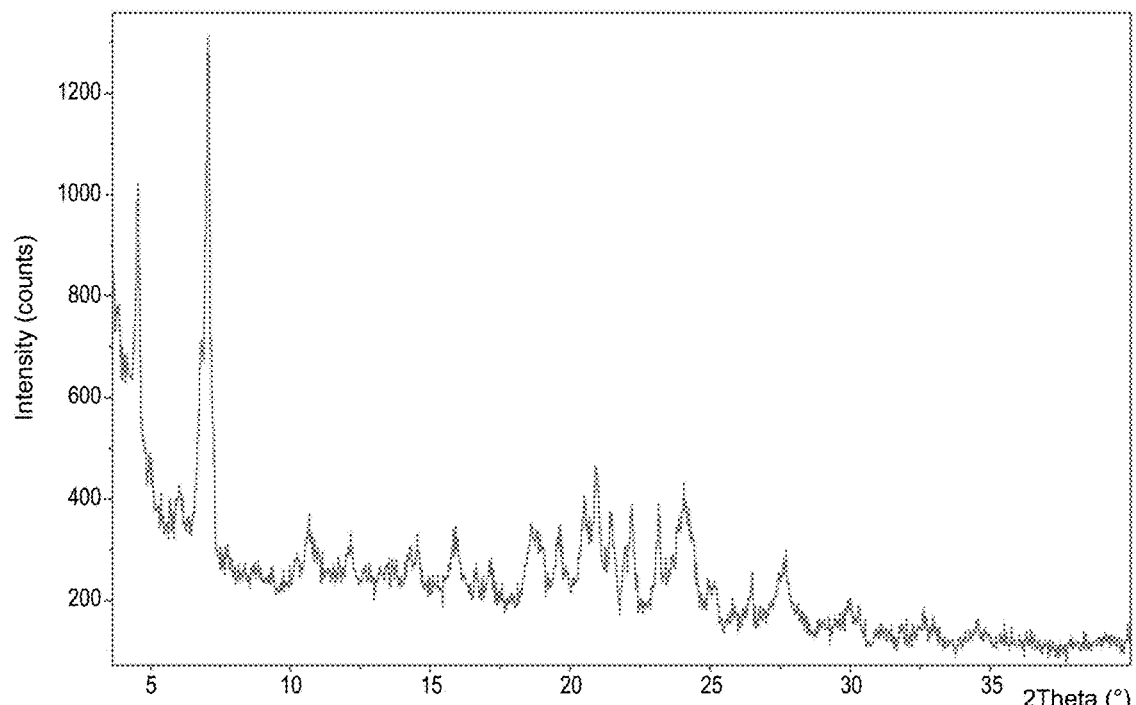
FIG. 15A is an XRPD corresponding to crystalline Form XVIII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 10.7±0.2, and 15.9±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 10.7±0.2, 15.9±0.2, and 19.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 15A.

Figure 15B:
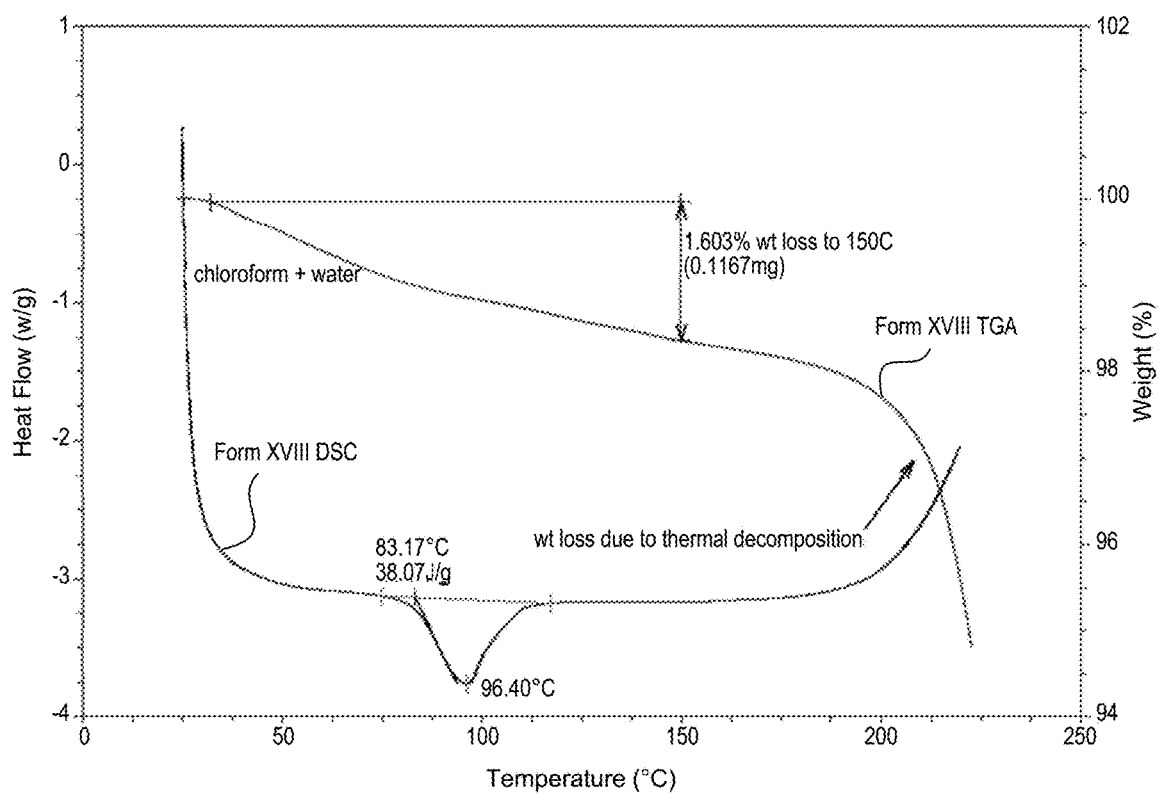
FIG. 15B is a DSC and a TGA corresponding to crystalline Form XVIII.

In some aspects, the TGA exhibits that the crystalline form of N—((R)-2,3-dihydroxypropoxy)-3,4-difluoro-2-(2-fluoro-4-iodo-phenylamino)-benzamide loses about 1.6 wt % between about 30° C. and about 150° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 83° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 15B; and/or b) a DSC profile substantially as shown in FIG. 15B.

In some aspects, the crystalline form of N—((R)-2,3-dihydroxypropoxy)-3,4-difluoro-2-(2-fluoro-4-iodo-phenylamino)-benzamide is Form XVIII.

Figure 16A:
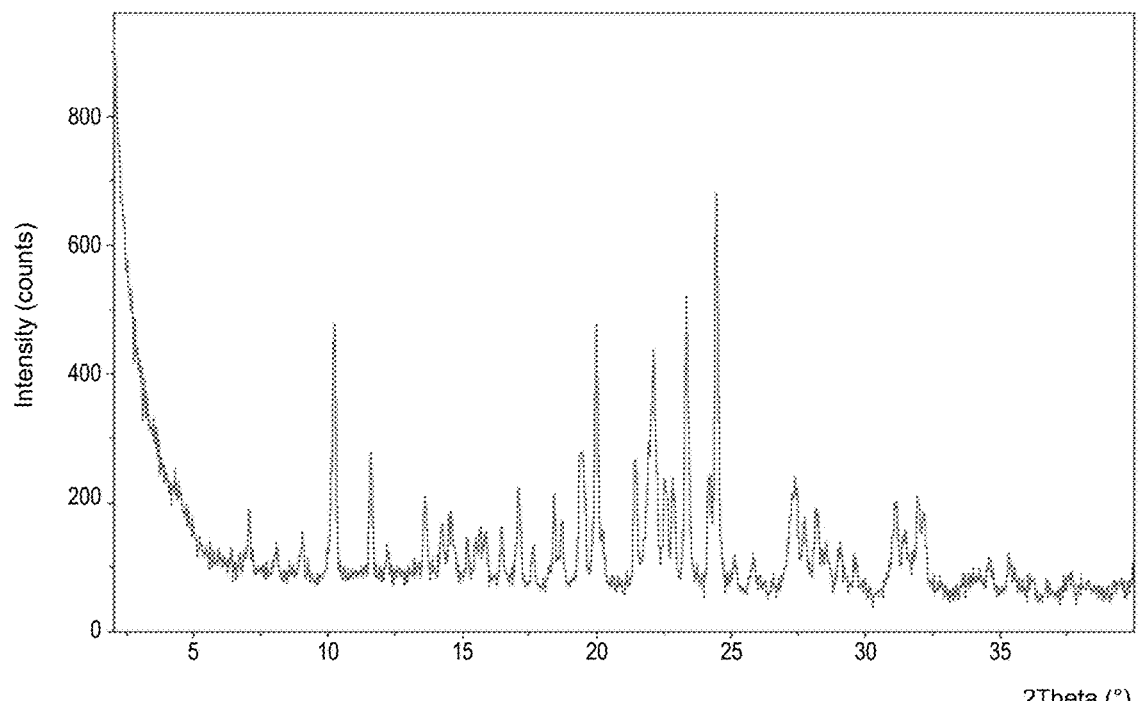
FIG. 16A is an XRPD corresponding to crystalline Form XIX.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 10.2±0.2, 11.6±0.2, and 20.0±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 10.2±0.2, 11.6±0.2, 17.1±0.2, and 20.0±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 16A.

Figure 16B:
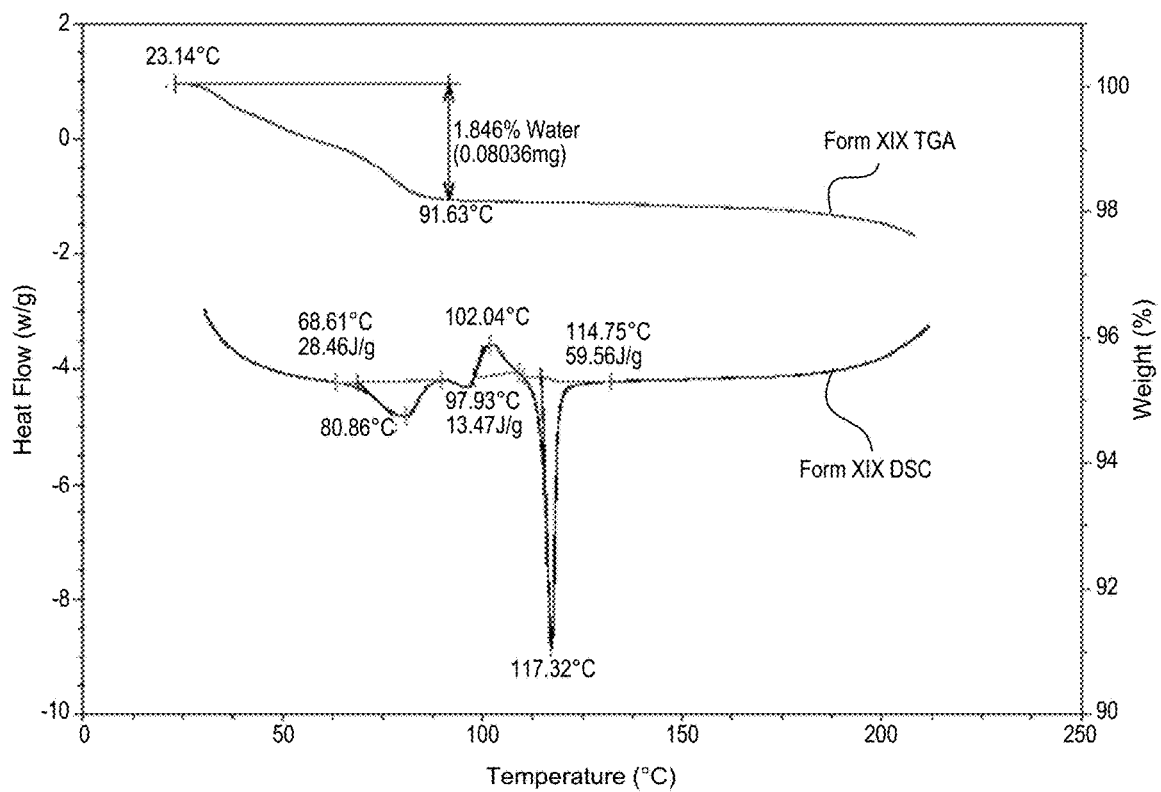
FIG. 16B is a DSC and a TGA corresponding to crystalline Form XIX.

In some aspects, the TGA exhibits that the crystalline form of N—((R)-2,3-dihydroxypropoxy)-3,4-difluoro-2-(2-fluoro-4-iodo-phenylamino)-benzamide loses about 1.85 wt % between about 23° C. and about 92° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 69° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 98° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 115° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 69° C. and an endotherm onset at about 98° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 69° C. and an endotherm onset at about 115° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 98° C. and an endotherm onset at about 115° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 69° C., a second endotherm onset at about 98° C., and a third endotherm onset at about 115° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 16B; and/or b) a DSC profile substantially as shown in FIG. 16B.

In some aspects, the crystalline form of N—((R)-2,3-dihydroxypropoxy)-3,4-difluoro-2-(2-fluoro-4-iodo-phenylamino)-benzamide is Form XIX.

Figure 17A:
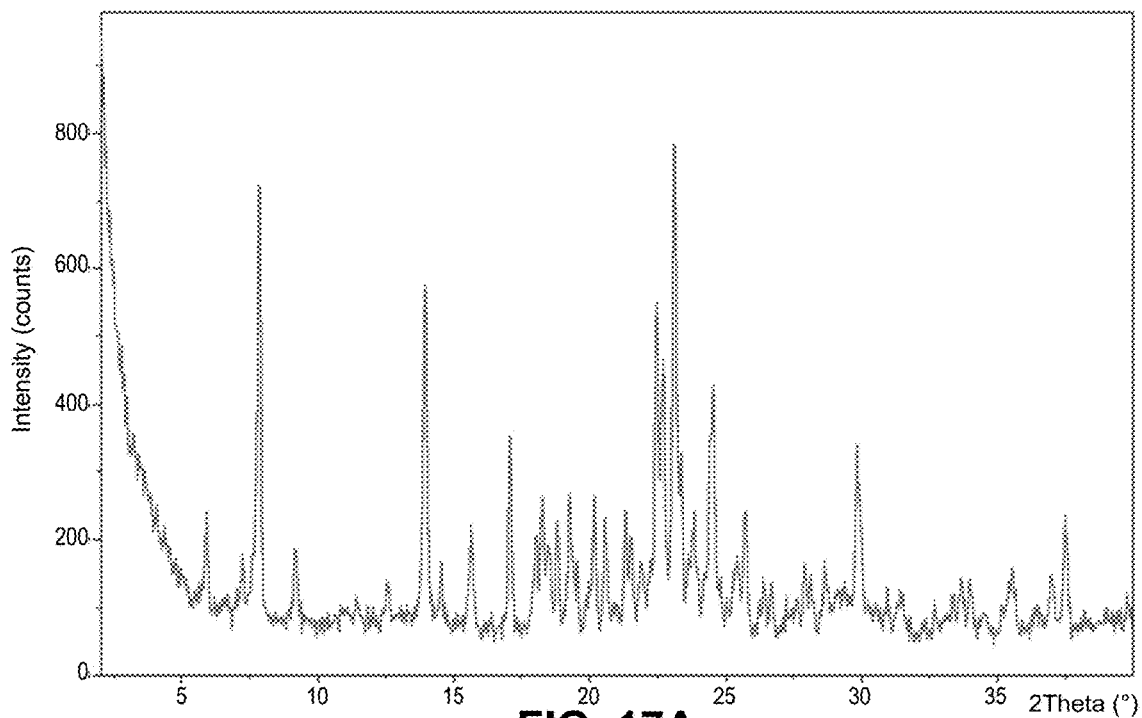
FIG. 17A is an XRPD corresponding to crystalline Form XX.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 7.8±0.2, 14.0±0.2, and 17.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 7.8±0.2, 14.0±0.2, 15.6±0.2, and 17.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 17A.

Figure 17B:
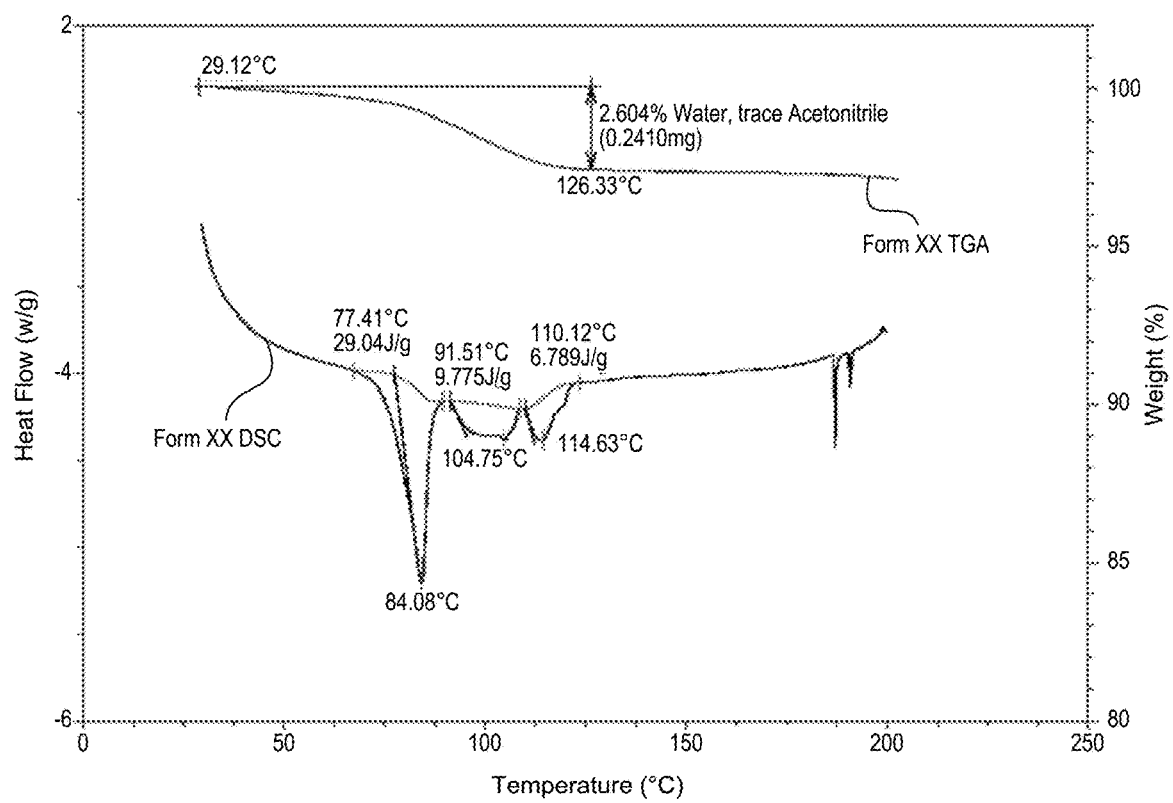
FIG. 17B is a DSC and a TGA corresponding to crystalline Form XX.

In some aspects, the TGA exhibits that the crystalline form of N—((R)-2,3-dihydroxypropoxy)-3,4-difluoro-2-(2-fluoro-4-iodo-phenylamino)-benzamide loses about 2.6 wt % between about 29° C. and about 126° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 77° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 92° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 110° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 77° C. and an endotherm onset at about 92° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 77° C. and an endotherm onset at about 110° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 92° C. and an endotherm onset at about 110° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 77° C., a second endotherm onset at about 92° C., and a third endotherm onset at about 110° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 17B; and/or b) a DSC profile substantially as shown in FIG. 17B.

In some aspects, the crystalline form of N—((R)-2,3-dihydroxypropoxy)-3,4-difluoro-2-(2-fluoro-4-iodo-phenylamino)-benzamide is Form XX.

Figure 18A:
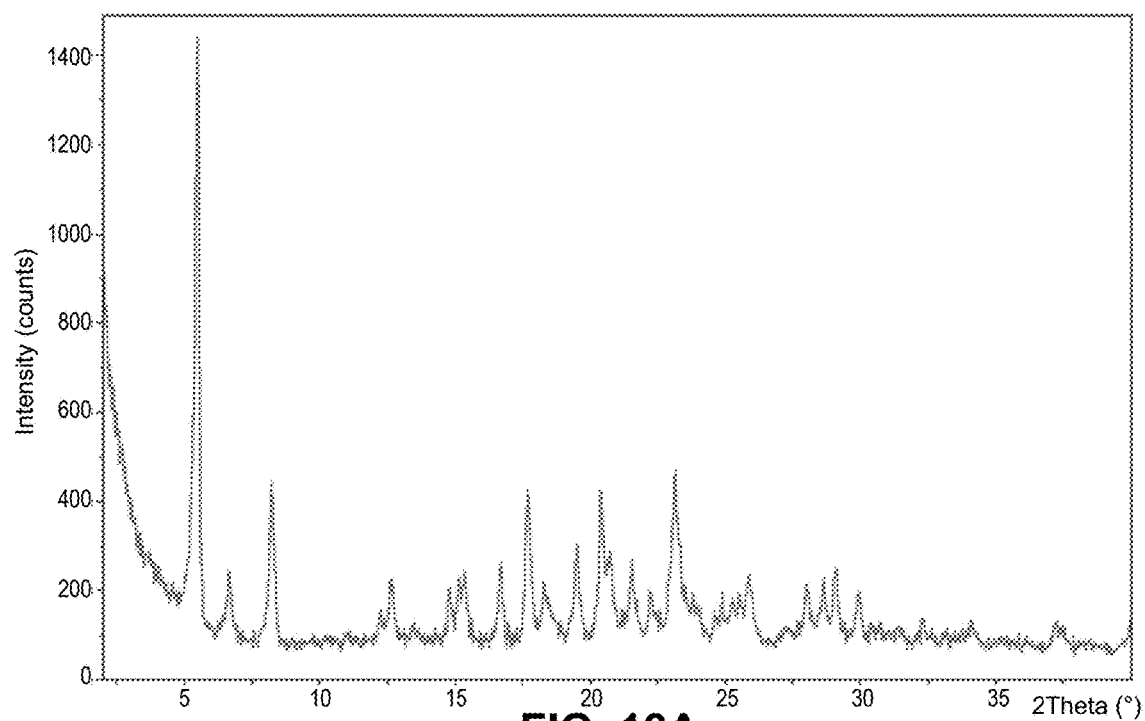
FIG. 18A is an XRPD corresponding to crystalline Form XXI.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 8.2±0.2, and 16.7±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 8.2±0.2, 16.7±0.2, and 17.7±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 18A.

Figure 18B:
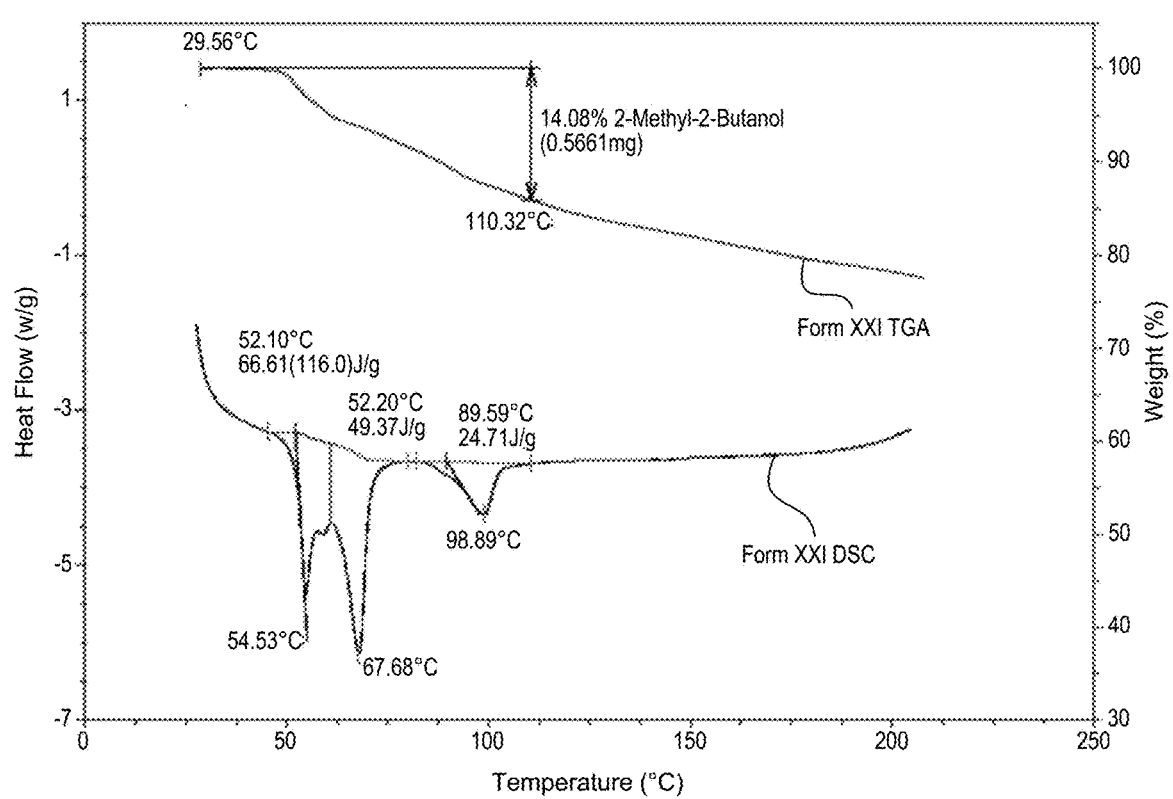
FIG. 18B is a DSC and a TGA corresponding to crystalline Form XXI.

In some aspects, the TGA exhibits that the crystalline form of N—((R)-2,3-dihydroxypropoxy)-3,4-difluoro-2-(2-fluoro-4-iodo-phenylamino)-benzamide loses about 14.1 wt % between about 30° C. and about 110° C. In some aspects, the crystalline form of N—((R)-2,3-dihydroxypropoxy)-3,4-difluoro-2-(2-fluoro-4-iodo-phenylamino)-benzamide exhibits a DSC thermogram has an endotherm onset at about 52° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 90° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 52° C. and a second endotherm onset at about 90° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 18B; and/or b) a DSC profile substantially as shown in FIG. 18B.

In some aspects, the crystalline form of N—((R)-2,3-dihydroxypropoxy)-3,4-difluoro-2-(2-fluoro-4-iodo-phenylamino)-benzamide is Form XXI.

Figure 19A:
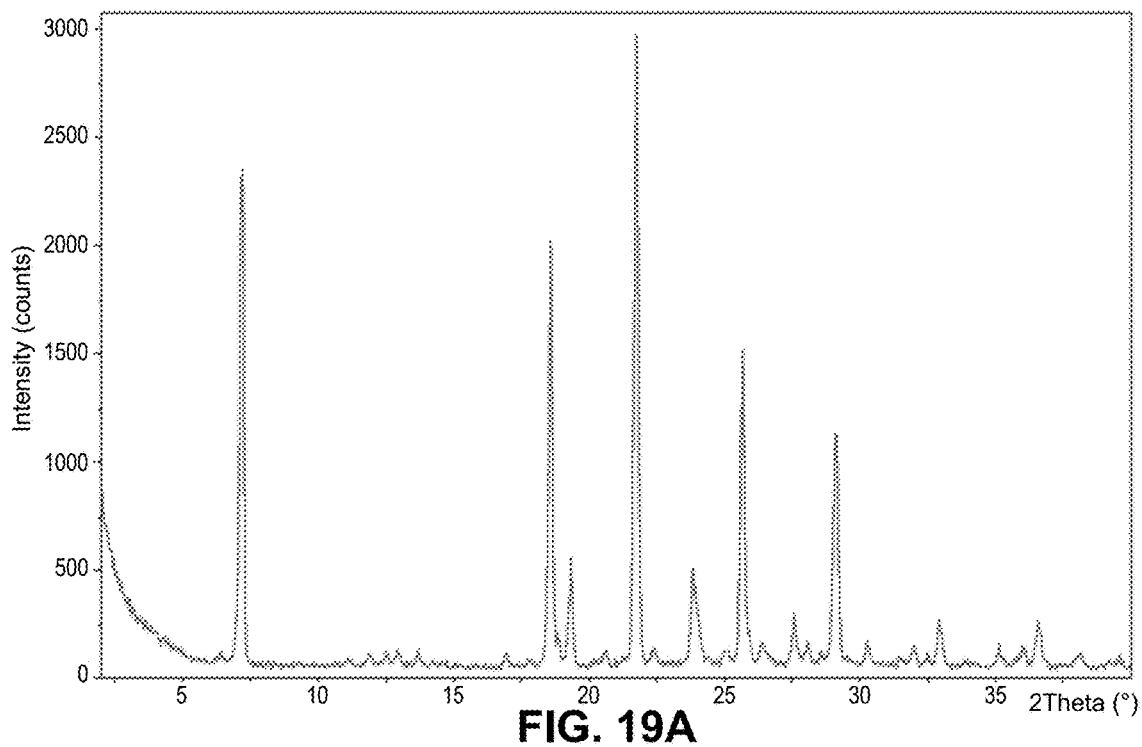
FIG. 19A is an XRPD corresponding to crystalline Form XXII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 7.2±0.2, 21.7±0.2, and 29.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 7.2±0.2, 18.6±0.2, 21.7±0.2, and 29.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 19A.

Figure 19B:
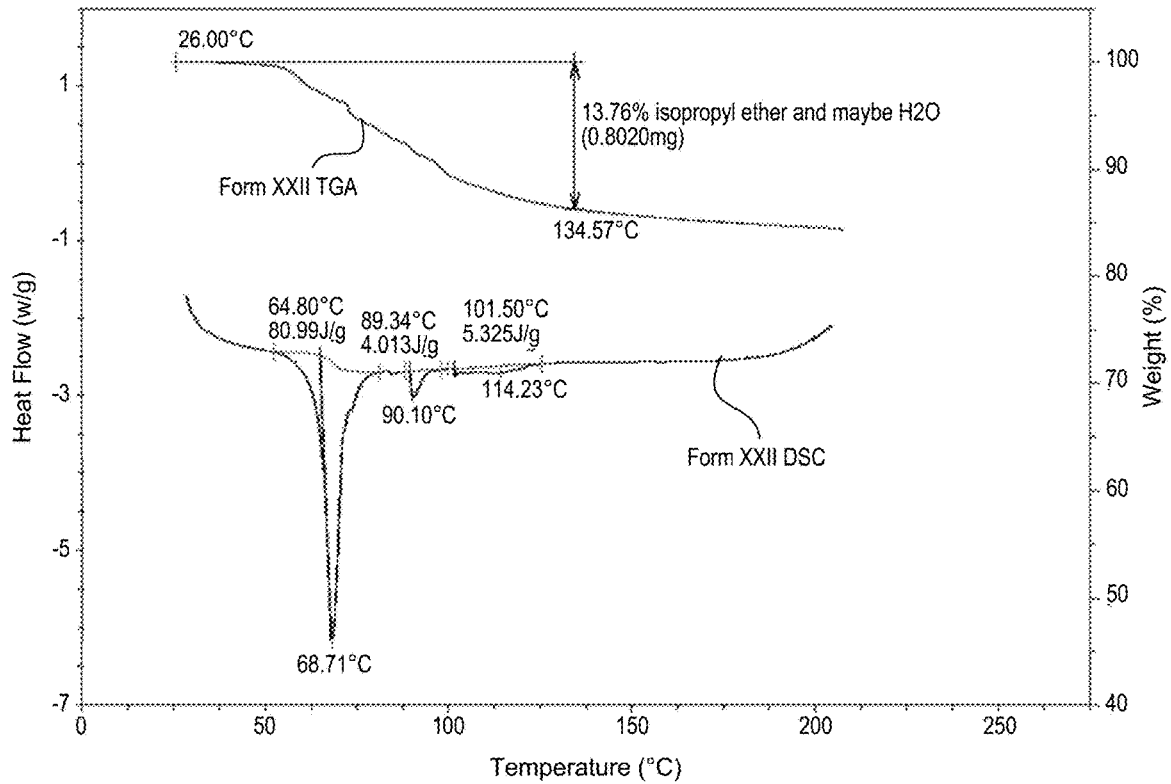
FIG. 19B is a DSC and a TGA corresponding to crystalline Form XXII.

In some aspects, the TGA exhibits that the crystalline form of N—((R)-2,3-dihydroxypropoxy)-3,4-difluoro-2-(2-fluoro-4-iodo-phenylamino)-benzamide loses about 13.8 wt % between about 26° C. and about 135° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 65° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 89° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 102° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 65° C. and an endotherm onset at about 89° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 65° C. and an endotherm onset at about 102° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 89° C. and an endotherm onset at about 102° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 65° C., a second endotherm onset at about 89° C., and a third endotherm onset at about 102° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 19B; and/or b) a DSC profile substantially as shown in FIG. 19B.

In some aspects, the crystalline form of N—((R)-2,3-dihydroxypropoxy)-3,4-difluoro-2-(2-fluoro-4-iodo-phenylamino)-benzamide is Form XXII.

Figure 20A:
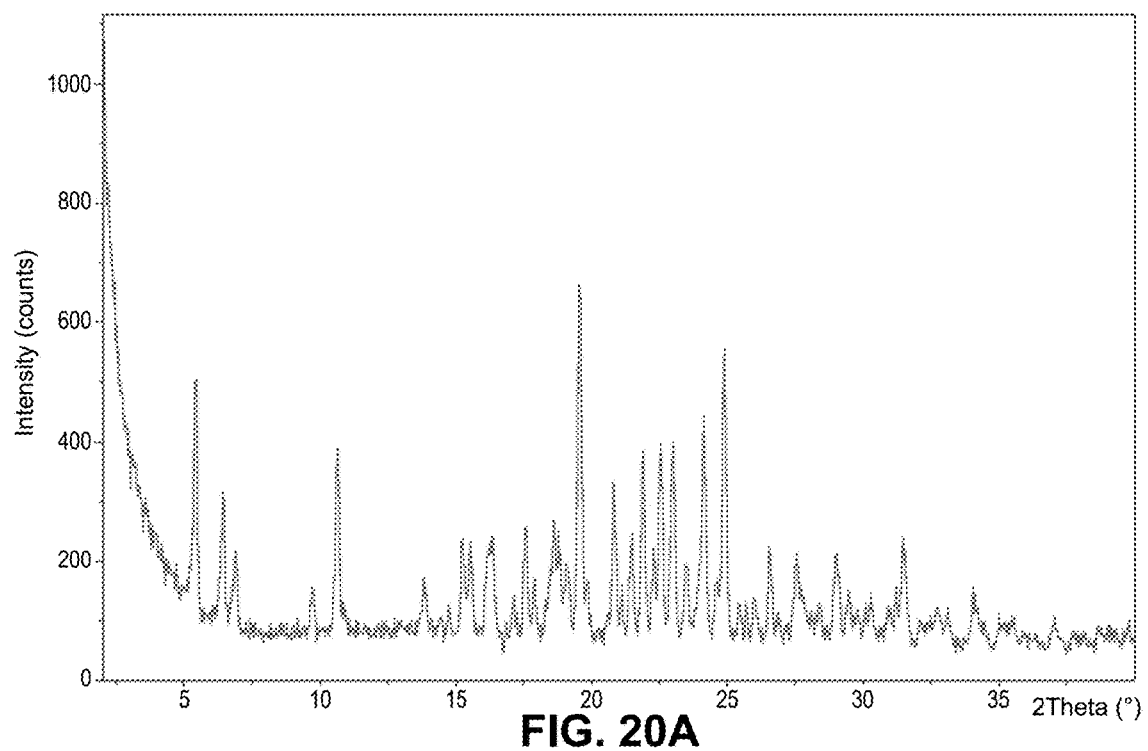
FIG. 20A is an XRPD corresponding to crystalline Form XXIII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.4±0.2, 9.7±0.2, and 10.7±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.4±0.2, 6.5±0.2, 9.7±0.2, and 10.7±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 20A.

Figure 20B:
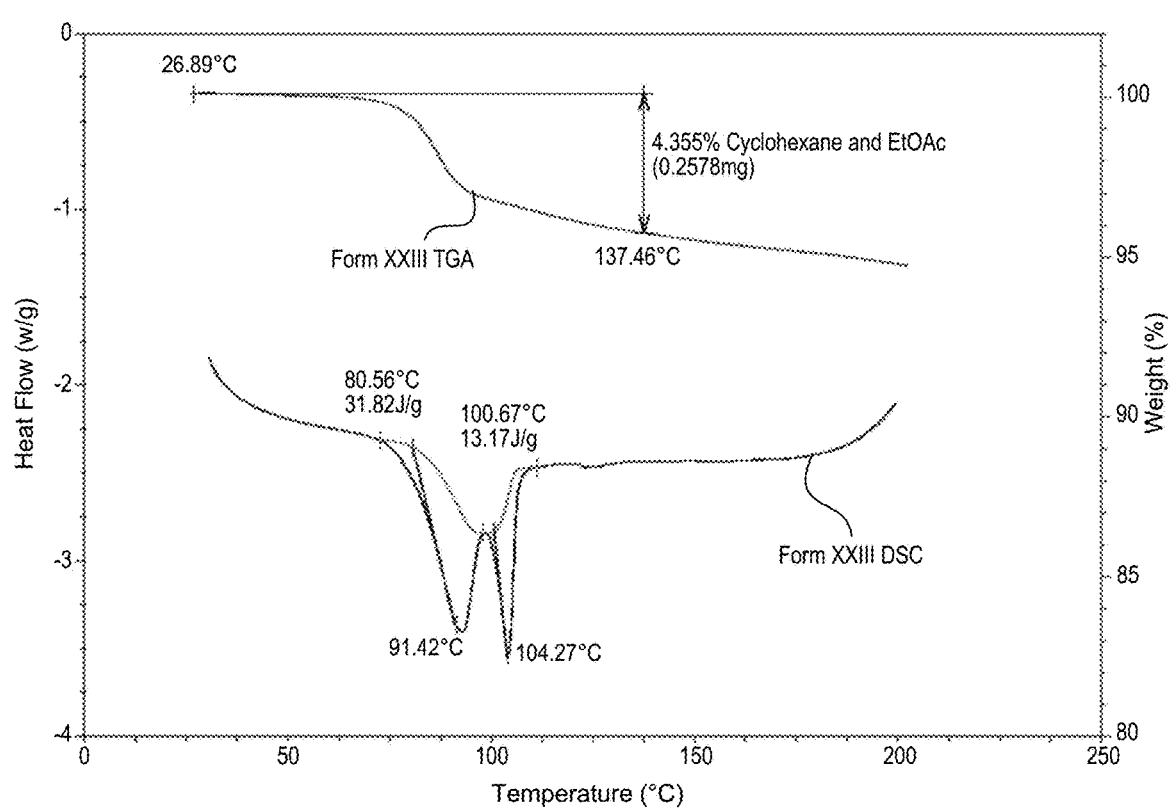
FIG. 20B is a DSC and a TGA corresponding to crystalline Form XXIII.

In some aspects, the TGA exhibits that the crystalline form of N—((R)-2,3-dihydroxypropoxy)-3,4-difluoro-2-(2-fluoro-4-iodo-phenylamino)-benzamide loses about 4.4 wt % between about 27° C. and about 137° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 81° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 101° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 81° C. and a second endotherm onset at about 101° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 20B; and/or b) a DSC profile substantially as shown in FIG. 20B.

In some aspects, the crystalline form of N—((R)-2,3-dihydroxypropoxy)-3,4-difluoro-2-(2-fluoro-4-iodo-phenylamino)-benzamide is Form XXIII.

Figure 21A:
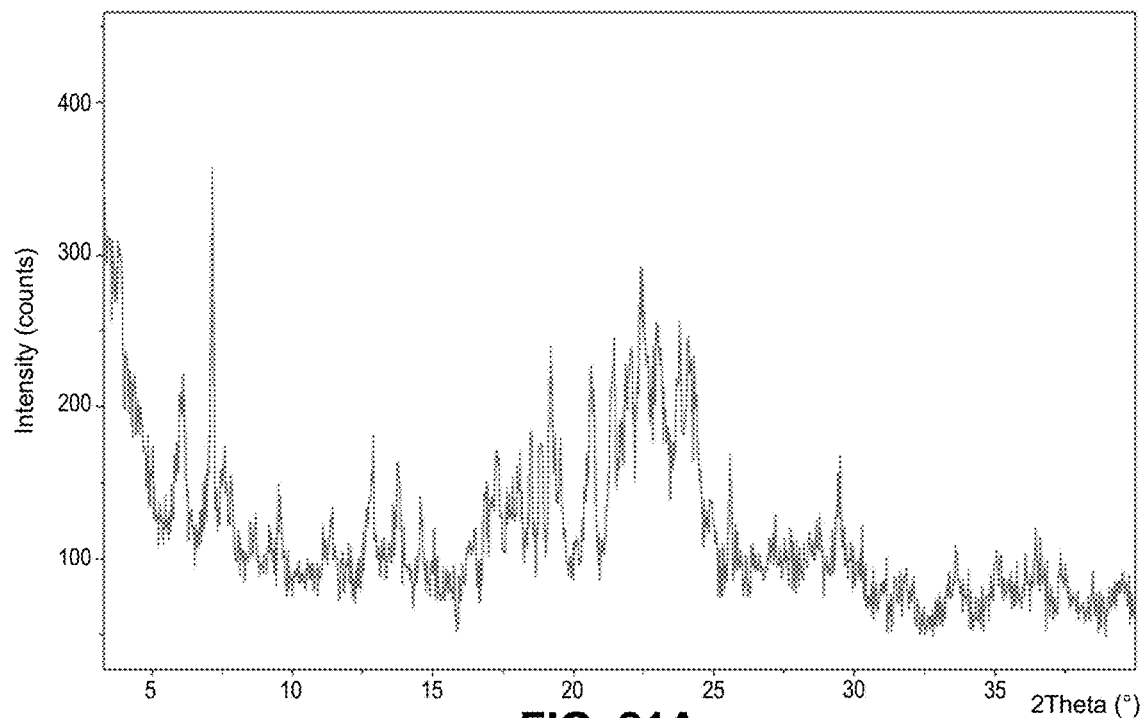
FIG. 21A is an XRPD corresponding to crystalline Form XXIV.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 7.2±0.2, 20.6±0.2, and 23.0±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 7.2±0.2, 9.5±0.2, 20.6±0.2, and 23.0±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 21A.

Figure 21B:
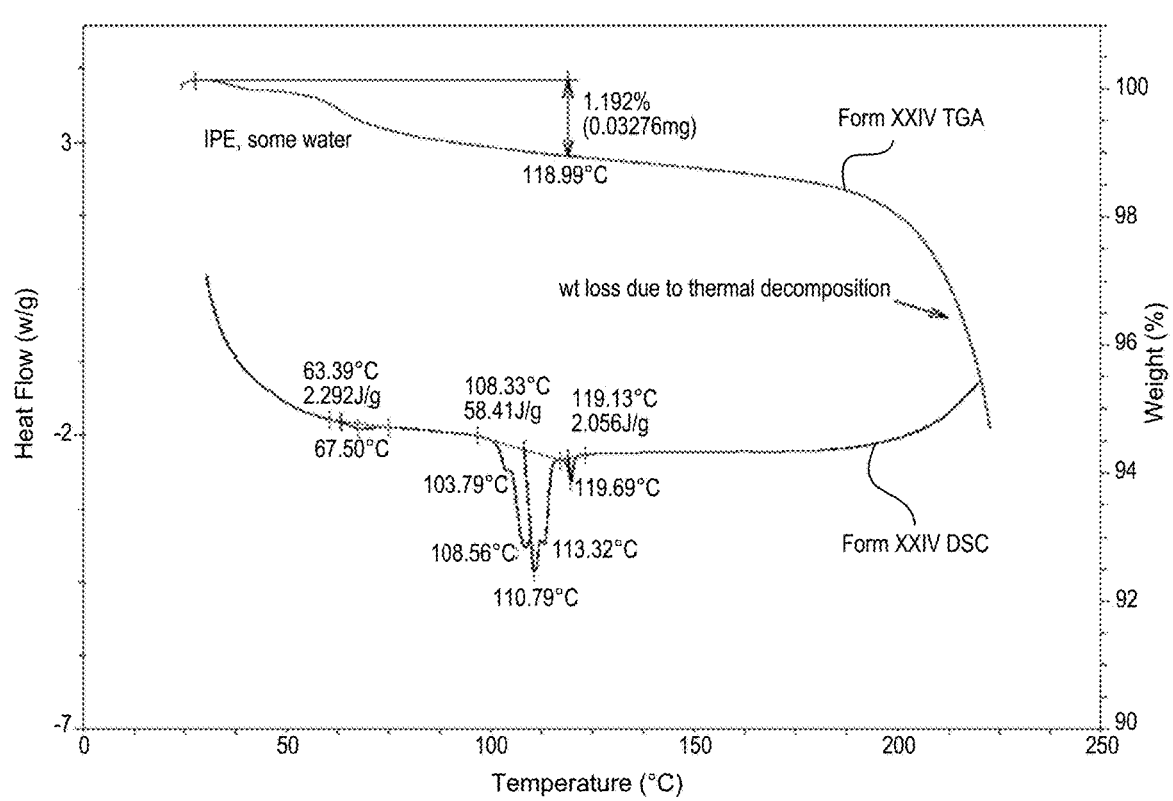
FIG. 21B is a DSC and a TGA corresponding to crystalline Form XXIV.

In some aspects, the TGA exhibits that the crystalline form of N—((R)-2,3-dihydroxypropoxy)-3,4-difluoro-2-(2-fluoro-4-iodo-phenylamino)-benzamide loses about 1.2 wt % between about 30° C. and about 119° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 104° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 21B; and/or b) a DSC profile substantially as shown in FIG. 21B.

In some aspects, the crystal form of N—((R)-2,3-dihydroxypropoxy)-3,4-difluoro-2-(2-fluoro-4-iodo-phenylamino)-benzamide is Form XXIV.

In some aspects, the present disclosure provides an amorphous form of N—((R)-2,3-dihydroxypropoxy)-3,4-difluoro-2-(2-fluoro-4-iodo-phenylamino)-benzamide of Formula (I)

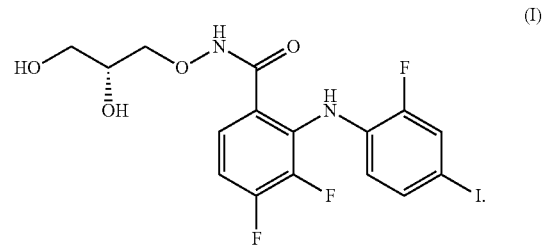 [SMILES: O=C(NOC[C@H](O)CO)c1ccc(F)c(F)c1Nc1ccc(I)cc1F]

Figure 22A:
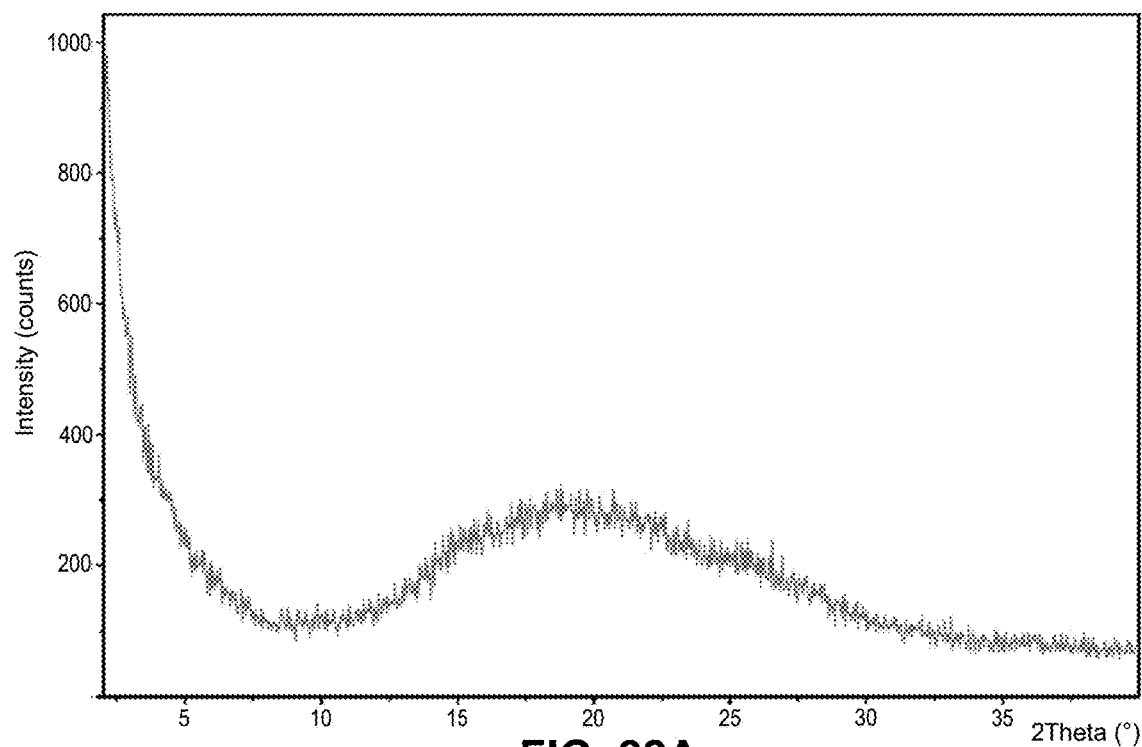
FIG. 22A is an XRPD corresponding to amorphous mirdametinib.

In some aspects, the amorphous form of N—((R)-2,3-dihydroxypropoxy)-3,4-difluoro-2-(2-fluoro-4-iodo-phenylamino)-benzamide is characterized by an XRPD pattern substantially as shown in FIG. 22A.

Figure 22B:
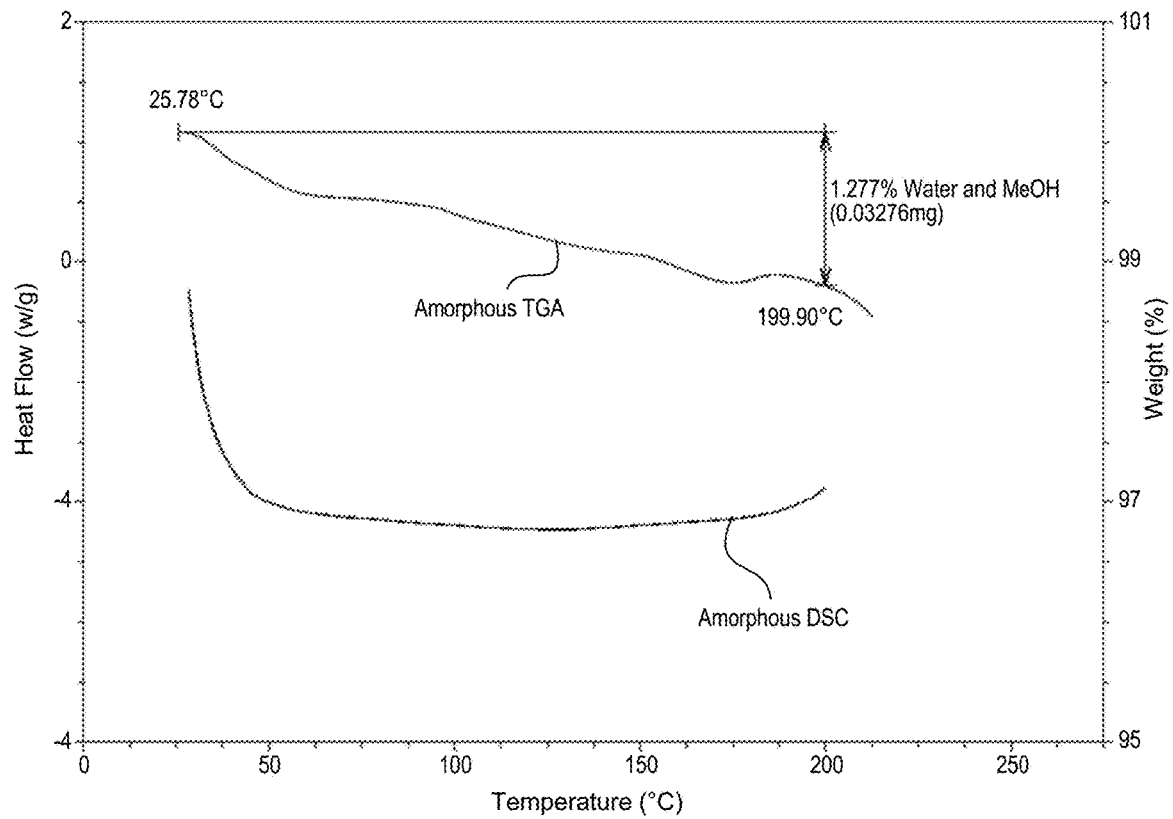
FIG. 22B is a DSC and a TGA corresponding to amorphous mirdametinib.

In some aspects, the amorphous form of N—((R)-2,3-dihydroxypropoxy)-3,4-difluoro-2-(2-fluoro-4-iodo-phenylamino)-benzamide is characterized by: a) a TGA profile substantially as shown in FIG. 22B; and/or b) a DSC profile substantially as shown in FIG. 22B.

In some aspects, the XRPD pattern is generated using a PANALYTICAL® X'Pert Pro diffractometer using Ni-filtered Cu Kα (45 kV/40 mA) radiation and a step size of 0.03° 2θ with a X'CELERATOR® Real Time Multi-Strip detector, configured (a) on the incidental beam side as follows: variable divergence slits (10 mm irradiated length), 0.04 rad Soller slits, fixed anti-scatter slit (0.50°), and 10 mm beam mask, and (b) on the diffracted beam side as follows: variable anti-scatter slit (10 mm observed length) and 0.04 rad Soller slit or a BRUKER® D8® ADVANCE™ system using Cu Kα (40 kV/40 mA) radiation and a step size of 0.03° 2θ with a LYNXEYE™ detector, configured (a) on the incidental beam side as follows: Goebel mirror, mirror exit slit (0.2 mm), 2.5° Soller slit, beam knife, and (b) on the diffracted beam side as follows: anti-scatter slit (8 mm) and 2.5° Soller slit; wherein samples are mounted flat on zero-background Si wafers. In some aspects, the DSC pattern is generated using a TA Instruments Q100 or Q2000 differential scanning calorimeter at a rate of temperature increase of about 15° C./min.

Pharmaceutical Composition

In some aspects, the present disclosure is directed to a pharmaceutical composition (e.g., capsule, tablet, powder, granules, minitablets, or pellets) comprising a crystalline form or amorphous solid of N—((R)-2,3-dihydroxypropoxy)-3,4-difluoro-2-(2-fluoro-4-iodo-phenylamino)-benzamide described herein and one or more pharmaceutically acceptable carriers.

In some aspects, the pharmaceutical composition is for oral administration. In some aspects, the pharmaceutical composition is a solid dosage form. In some aspects, the pharmaceutical composition is a capsule, tablet (e.g., dispersible tablet or orodispersible tablet), powder (e.g., dispersible powder), granules (e.g., dispersible granules), minitablets (e.g., dispersible minitablets), or pellets (e.g., dispersible pellets). In some aspects, the pharmaceutical composition is a tablet (e.g., dispersible tablet or orodispersible tablet) or a capsule.

In some aspects, the pharmaceutical composition is a capsule. In some aspects, the capsule comprises about 1 mg of N—((R)-2,3-dihydroxypropoxy)-3,4-difluoro-2-(2-fluoro-4-iodo-phenylamino)-benzamide, wherein each component of the capsule is as follows: (a) about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more lubricants; and (e) a gelatin capsule which encapsulates components (a)-(d). In some aspects, the capsule comprises about 1 mg of N—((R)-2,3-dihydroxypropoxy)-3,4-difluoro-2-(2-fluoro-4-iodo-phenylamino)-benzamide, wherein each component of the capsule is as follows: (a) about 0.25 wt/wt % to about 1.5 wt/wt % of the crystalline form or the amorphous solid of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) about 0.5 wt/wt % to about 2 wt/wt % of one or more lubricants; and (e) a gelatin capsule which encapsulates components (a)-(d).

In some aspects, the capsule comprises about 2 mg of N—((R)-2,3-dihydroxypropoxy)-3,4-difluoro-2-(2-fluoro-4-iodo-phenylamino)-benzamide, wherein each component of the capsule is as follows: (a) about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more lubricants; and (e) a gelatin capsule which encapsulates components (a)-(d). In some aspects, the capsule comprises about 2 mg of N—((R)-2,3-dihydroxypropoxy)-3,4-difluoro-2-(2-fluoro-4-iodo-phenylamino)-benzamide, wherein each component of the capsule is as follows: (a) about 0.25 wt/wt % to about 1.5 wt/wt % of the crystalline form or the amorphous solid of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) about 0.5 wt/wt % to about 2 wt/wt % of one or more lubricants; and (e) a gelatin capsule which encapsulates components (a)-(d).

In some aspects, the capsule comprises about 5 mg of N—((R)-2,3-dihydroxypropoxy)-3,4-difluoro-2-(2-fluoro-4-iodo-phenylamino)-benzamide, wherein each component of the capsule is as follows: (a) about 2.5 wt/wt % to about 7.0 wt/wt % of the crystalline form or the amorphous solid of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; and (d) a gelatin capsule which encapsulates components (a)-(c). In some aspects, the capsule comprises about 5 mg of N—((R)-2,3-dihydroxypropoxy)-3,4-difluoro-2-(2-fluoro-4-iodo-phenylamino)-benzamide, wherein each component of the capsule is as follows: (a) about 2.5 wt/wt % to about 7.0 wt/wt % of the crystalline form or the amorphous solid of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; and (d) a gelatin capsule which encapsulates components (a)-(c).

In some aspects, the pharmaceutical composition is a tablet. In some aspects, the tablet comprises about 1 mg of N—((R)-2,3-dihydroxypropoxy)-3,4-difluoro-2-(2-fluoro-4-iodo-phenylamino)-benzamide, wherein each component of the tablet is as follows: (a) about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; and (d) 0 wt/wt % to about 5 wt/wt % of one or more lubricants. In some aspects, the tablet comprises about 1 mg of N—((R)-2,3-dihydroxypropoxy)-3,4-difluoro-2-(2-fluoro-4-iodo-phenylamino)-benzamide, wherein each component of the tablet is as follows: (a) about 0.25 wt/wt % to about 1.5 wt/wt % of the crystalline form or the amorphous solid of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; and (d) about 0.5 wt/wt % to about 2 wt/wt % of one or more lubricants.

In some aspects, the tablet comprises about 2 mg of N—((R)-2,3-dihydroxypropoxy)-3,4-difluoro-2-(2-fluoro-4-iodo-phenylamino)-benzamide, wherein each component of the tablet is as follows: (a) about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; and (d) 0 wt/wt % to about 5 wt/wt % of one or more lubricants. In some aspects, the tablet comprises about 2 mg of N—((R)-2,3-dihydroxypropoxy)-3,4-difluoro-2-(2-fluoro-4-iodo-phenylamino)-benzamide, wherein each component of the tablet is as follows: (a) about 0.25 wt/wt % to about 1.5 wt/wt % of the crystalline form or the amorphous solid of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; and (d) about 0.5 wt/wt % to about 2 wt/wt % of one or more lubricants.

In some aspects, the tablet comprises about 5 mg of N—((R)-2,3-dihydroxypropoxy)-3,4-difluoro-2-(2-fluoro-4-iodo-phenylamino)-benzamide, wherein each component of the tablet is as follows: (a) about 2.5 wt/wt % to about 7.0 wt/wt % of the crystalline form or the amorphous solid of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; and (c) about 1 wt/wt % to about 10 wt/wt % of one or more disintegrants. In some aspects, the tablet comprises about 5 mg of N—((R)-2,3-dihydroxypropoxy)-3,4-difluoro-2-(2-fluoro-4-iodo-phenylamino)-benzamide, wherein each component of the tablet is as follows: (a) about 2.5 wt/wt % to about 7.0 wt/wt % of the crystalline form or the amorphous solid of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; and (c) about 3.5 wt/wt % to about 6 wt/wt % of one or more disintegrants.

In some aspects, the pharmaceutical composition is for oral administration. In some aspects, the pharmaceutical composition is dispersible orodispersible.

In some aspects, the pharmaceutical composition is a tablet, a powder, granules, minitablets, or pellets (also called beads).

In some aspects, the pharmaceutical composition is a powder. In some aspects, the pharmaceutical composition is a dispersible powder. In some aspects, a capsule or sachet comprises the dispersible powder.

In some aspects, the pharmaceutical composition is in the form of granules. In some aspects, the granules are dispersible granules. In some aspects, a capsule or sachet comprises the dispersible granules.

In some aspects, the pharmaceutical composition is in the form of minitablets. In some aspects, the minitablets are dispersible minitablets. In some aspects, a capsule or sachet comprises the dispersible minitablets.

In some aspects, the pharmaceutical composition is in the form of pellets. In some aspects, the pellets are dispersible pellets. In some aspects, a capsule or sachet comprises the dispersible pellets.

In some aspects, the pharmaceutical composition is a tablet. In some aspects, the tablet is a dispersible tablet. In some aspects, the tablet is an orodispersible tablet.

In some aspects, the pharmaceutical composition that is a dispersible tablet, dispersible powder, dispersible granules, dispersible minitablets, or dispersible pellets comprises about 0.1 mg to about 20 mg of N—((R)-2,3-dihydroxypropoxy)-3,4-difluoro-2-(2-fluoro-4-iodo-phenylamino)-benzamide, wherein each component of the pharmaceutical composition is as follows: (a) about 0.1 wt/wt % to about 7 wt/wt % of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the pharmaceutical composition that is a dispersible tablet, dispersible powder, dispersible granules, dispersible minitablets, or dispersible pellets comprises about 0.1 mg to about 20 mg of N—((R)-2,3-dihydroxypropoxy)-3,4-difluoro-2-(2-fluoro-4-iodo-phenylamino)-benzamide, wherein each component of the pharmaceutical composition is as follows: (a) about 0.2 wt/wt % to about 1.5 wt/wt % of N—((R)-2,3-dihydroxypropoxy)-3,4-difluoro-2-(2-fluoro-4-iodo-phenylamino)-benzamide; (b) about 75 wt/wt % to about 98 wt/wt % of one or more diluents; (c) about 3 wt/wt % to about 8 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the pharmaceutical composition that is a dispersible tablet, dispersible powder, dispersible granules, dispersible minitablets, or dispersible pellets comprises about 0.1 mg to about 20 mg of N—((R)-2,3-dihydroxypropoxy)-3,4-difluoro-2-(2-fluoro-4-iodo-phenylamino)-benzamide, wherein each component of the pharmaceutical composition is as follows: (a) about 0.5 wt/wt % to about 1.2 wt/wt % of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the pharmaceutical composition that is a dispersible tablet, dispersible powder, dispersible granules, dispersible minitablets, or dispersible pellets comprises about 0.5 mg of N—((R)-2,3-dihydroxypropoxy)-3,4-difluoro-2-(2-fluoro-4-iodo-phenylamino)-benzamide. In some aspects, the pharmaceutical composition comprises about 1 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 2 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 3 mg of N—((R)-2,3-dihydroxypropoxy)-3,4-difluoro-2-(2-fluoro-4-iodo-phenylamino)-benzamide. In some aspects, the pharmaceutical composition that is a dispersible tablet, dispersible powder, dispersible granules, dispersible minitablets, or dispersible pellets comprises about 4 mg of N—((R)-2,3-dihydroxypropoxy)-3,4-difluoro-2-(2-fluoro-4-iodo-phenylamino)-benzamide.

In some aspects, at least one of the diluents is selected from the group consisting of microcrystalline cellulose, lactose, mannitol, sorbitol, xylitol, sucrose, pregelatinized starch, calcium sulfate, calcium carbonate, starch, and dibasic calcium phosphate. In some aspects, at least one of the diluents is microcrystalline cellulose.

In some aspects, at least one of the disintegrants is selected from the group consisting of croscarmellose sodium, sodium starch glycolate, crospovidone, microcrystalline cellulose, starch, pregelatinized starch, low substituted hydroxypropyl cellulose, and alginic acid. In some aspects, at least one of the disintegrants is croscarmellose sodium.

In some aspects, at least one of the flavoring agents is selected from the group consisting of natural or synthetic flavors including but not limited to grape flavoring, bubble gum flavoring, caramel flavoring, orange flavoring, lemon flavoring, strawberry flavoring, raspberry flavoring, mint flavoring, peppermint flavoring, grapefruit flavoring, pineapple flavoring, pear flavoring, peach flavoring, vanilla flavoring, banana flavoring, or cherry flavoring. In some aspects, at least one of the flavoring agents is grape flavoring.

In some aspects, at least one of the sweeteners is selected from the group consisting of sucralose, acesulfame, saccharin, sucrose, xylitol, mannitol, sorbitol, glucose, fructose, and aspartame. In some aspects, at least one of the sweeteners is sucralose.

In some aspects, at least one of the lubricants is selected from the group consisting of magnesium stearate, sodium stearyl fumarate, glycerol dibehenate, stearic acid, hydrogenated vegetable oil, calcium stearate, zinc stearate, beeswax, colloidal silicon dioxide, and talc. In some aspects, at least one of the lubricants is magnesium stearate.

Methods of Treatment

In some aspects, the present disclosure provides a method of treating a tumor, a cancer, or a Rasopathy disorder comprising administering to a subject in need of such treatment a pharmaceutical composition (e.g., capsule, tablet, powder, granules, minitablets, or pellets) described herein.

In some aspects, the present disclosure provides use of a pharmaceutical composition (e.g., capsule, tablet, powder, granules, minitablets, or pellets) described herein for the manufacture of a medicament for treating a tumor, a cancer, or Rasopathy disorder.

In some aspects, the tumor is a neurofibroma. In some aspects, the tumor is a neurofibroma associated with Neurofibromatosis Type 1. In some aspects, the tumor is selected from the group consisting of cutaneous neurofibroma, plexiform neurofibroma, optic pathway glioma, low grade glioma, high grade glioma, or malignant peripheral nerve sheath tumor. In some aspects, the tumor is plexiform neurofibroma.

In some aspects, the subject has been diagnosed with a Rasopathy disorder selected from the group consisting of neurofibromatosis type 1, neurofibromatosis type 2, cardio-facio-cutaneous syndrome, Costello syndrome, Legius syndrome, Noonan syndrome, and Noonan syndrome with multiple lentigines.

In some aspects, the cancer is selected from the group consisting of skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum. In some aspects, the leukemia is selected from the group consisting of acute lymphocytic leukemia, acute myelogenous leukemia, chronic lymphocytic leukemia, and chronic myelogenous leukemia. In some aspects, the lymphoma is selected from the group consisting of B-cell lymphoma, T-cell lymphoma, Burkitt's lymphoma, follicular lymphoma, mantle cell lymphoma, primary mediastinal B cell lymphoma, small lymphocytic lymphoma, and Waldenstrom macroglobulinemia. In some aspects, the lung cancer is selected from the group consisting of lung adenocarcinoma, squamous non-small cell lung cancer, non-squamous non-small cell lung cancer, and small cell lung cancer.

In some aspects, the subject bears a mutation or other aberration in one or more genes for which the mutation or other aberration causes a gain or loss of function characteristic of certain cancers, wherein the mutation or other aberration in one or more genes is a mutation or other aberration in one or more of KRAS, NRAS, HRAS, BRAF, MEK1, MEK2, RASA1, MAP2K4, NF1, or NF2.

In some aspects, an individual dose of the N—((R)-2,3-dihydroxypropoxy)-3,4-difluoro-2-(2-fluoro-4-iodo-phenylamino)-benzamide is administered as more than one capsule, more than one tablet (e.g., dispersible tablet), more than one dose of powder (e.g., dispersible powder), more than one dose of granules (e.g., dispersible granules), more than one dose of minitablets (e.g., dispersible minitablets), more than one dose of pellets (e.g., dispersible pellets), or a combination thereof.

In some aspects, the pharmaceutical composition is a dispersible tablet, dispersible powder, dispersible granules, dispersible minitablets, or dispersible pellets, wherein the pharmaceutical composition is dispersed in a potable liquid prior to administration to the subject. For example, a dose of 3 mg of the N—((R)-2,3-dihydroxypropoxy)-3,4-difluoro-2-(2-fluoro-4-iodo-phenylamino)-benzamide can be administered as two dispersible tablets—one containing 2 mg and the other containing 1 mg or as three dispersible tablets each containing 1 mg. As another example, a dose of 1.5 mg of the N—((R)-2,3-dihydroxypropoxy)-3,4-difluoro-2-(2- fluoro-4-iodo-phenylamino)-benzamide can be administered as two dispersible dosage forms—one dispersible tablet containing 1 mg and a separate unit of dispersible powder containing 0.5 mg or as three units of dispersible powder each containing 0.5 mg.

In some aspects, the N—((R)-2,3-dihydroxypropoxy)-3,4-difluoro-2-(2-fluoro-4-iodo-phenylamino)-benzamide is administered in a total daily dose that does not exceed 20 mg. In some aspects, the N—((R)-2,3-dihydroxypropoxy)-3,4-difluoro-2-(2-fluoro-4-iodo-phenylamino)-benzamide is administered in a total daily dose that does not exceed 10 mg. In some aspects, the N—((R)-2,3-dihydroxypropoxy)-3,4-difluoro-2-(2-fluoro-4-iodo-phenylamino)-benzamide is administered in a total daily dose that does not exceed 8 mg. In some aspects, the N—((R)-2,3-dihydroxypropoxy)-3,4-difluoro-2-(2-fluoro-4-iodo-phenylamino)-benzamide is administered in a total daily dose that does not exceed 6 mg. In some aspects, the N—((R)-2,3-dihydroxypropoxy)-3,4-difluoro-2-(2-fluoro-4-iodo-phenylamino)-benzamide is administered in a total daily dose that does not exceed 2 mg. In some aspects, the N—((R)-2,3-dihydroxypropoxy)-3,4-difluoro-2-(2-fluoro-4-iodo-phenylamino)-benzamide is administered in a total daily dose that does not exceed 1 mg.

In some aspects, the total daily dose of the N—((R)-2,3-dihydroxypropoxy)-3,4-difluoro-2-(2-fluoro-4-iodo-phenylamino)-benzamide is about 0.1 mg to about 20 mg. In some aspects, the total daily dose of the N—((R)-2,3-dihydroxypropoxy)-3,4-difluoro-2-(2-fluoro-4-iodo-phenylamino)-benzamide is about 0.5 mg. In some aspects, the total daily dose of the N—((R)-2,3-dihydroxypropoxy)-3,4-difluoro-2-(2-fluoro-4-iodo-phenylamino)-benzamide is about 1 mg. In some aspects, the total daily dose of the N—((R)-2,3-dihydroxypropoxy)-3,4-difluoro-2-(2-fluoro-4-iodo-phenylamino)-benzamide is about 2 mg. In some aspects, the total daily dose of N—((R)-2,3-dihydroxypropoxy)-3,4-difluoro-2-(2-fluoro-4-iodo-phenylamino)-benzamide is about 4 mg. In some aspects, the total daily dose of the N—((R)-2,3-dihydroxypropoxy)-3,4-difluoro-2-(2-fluoro-4-iodo-phenylamino)-benzamide is about 6 mg. In some aspects, the total daily dose of the N—((R)-2,3-dihydroxypropoxy)-3,4-difluoro-2-(2-fluoro-4-iodo-phenylamino)-benzamide is about 8 mg. In some aspects, the total daily dose of the N—((R)-2,3-dihydroxypropoxy)-3,4-difluoro-2-(2-fluoro-4-iodo-phenylamino)-benzamide is administered about 20 mg.

In some aspects, the total daily dose of the N—((R)-2,3-dihydroxypropoxy)-3,4-difluoro-2-(2-fluoro-4-iodo-phenylamino)-benzamide is administered two times daily.

In some aspects, the total daily dose of the N—((R)-2,3-dihydroxypropoxy)-3,4-difluoro-2-(2-fluoro-4-iodo-phenylamino)-benzamide is administered two times daily at a dose of about 0.1 mg to about 10 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 0.5 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 1 mg each. In some aspects, the total daily dose of N—((R)-2,3-dihydroxypropoxy)-3,4-difluoro-2-(2-fluoro-4-iodo-phenylamino)-benzamide is administered two times daily at a dose of about 2 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 3 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 4 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 10 mg each.

In some aspects, the total daily dose of the N—((R)-2,3-dihydroxypropoxy)-3,4-difluoro-2-(2-fluoro-4-iodo-phenylamino)-benzamide is administered once daily. In some aspects, the total daily dose of the N—((R)-2,3-dihydroxypropoxy)-3,4-difluoro-2-(2-fluoro-4-iodo-phenylamino)-benzamide is administered once daily at a dose of about 0.1 mg to about 20 mg. In some aspects, the total daily dose of the N—((R)-2,3-dihydroxypropoxy)-3,4-difluoro-2-(2-fluoro-4-iodo-phenylamino)-benzamide is administered once daily at a dose of about 0.5 mg. In some aspects, the total daily dose of the N—((R)-2,3-dihydroxypropoxy)-3,4-difluoro-2-(2-fluoro-4-iodo-phenylamino)-benzamide is administered once daily at a dose of about 1 mg. In some aspects, the total daily dose of the N—((R)-2,3-dihydroxypropoxy)-3,4-difluoro-2-(2-fluoro-4-iodo-phenylamino)-benzamide is administered once daily at a dose of about 2 mg. In some aspects, the total daily dose of the N—((R)-2,3-dihydroxypropoxy)-3,4-difluoro-2-(2-fluoro-4-iodo-phenylamino)-benzamide is administered once daily at a dose of about 4 mg. In some aspects, the total daily dose of the N—((R)-2,3-dihydroxypropoxy)-3,4-difluoro-2-(2-fluoro-4-iodo-phenylamino)-benzamide is administered once daily at a dose of about 8 mg. In some aspects, the total daily dose of the N—((R)-2,3-dihydroxypropoxy)-3,4-difluoro-2-(2-fluoro-4-iodo-phenylamino)-benzamide is administered once daily at a dose of about 10 mg. In some aspects, the total daily dose of the N—((R)-2,3-dihydroxypropoxy)-3,4-difluoro-2-(2-fluoro-4-iodo-phenylamino)-benzamide is administered once daily at a dose of about 20 mg.

In some aspects, the N—((R)-2,3-dihydroxypropoxy)-3,4-difluoro-2-(2-fluoro-4-iodo-phenylamino)-benzamide is administered in a total daily dose that does not exceed 20 mg. In some aspects, the N—((R)-2,3-dihydroxypropoxy)-3,4-difluoro-2-(2-fluoro-4-iodo-phenylamino)-benzamide is administered in a total daily dose that does not exceed 10 mg. In some aspects, the N—((R)-2,3-dihydroxypropoxy)-3,4-difluoro-2-(2-fluoro-4-iodo-phenylamino)-benzamide is administered in a total daily dose that does not exceed 8 mg. In some aspects, the N—((R)-2,3-dihydroxypropoxy)-3,4-difluoro-2-(2-fluoro-4-iodo-phenylamino)-benzamide is administered in a total daily dose that does not exceed 6 mg. In some aspects, the N—((R)-2,3-dihydroxypropoxy)-3,4-difluoro-2-(2-fluoro-4-iodo-phenylamino)-benzamide is administered in a total daily dose that does not exceed 4 mg. In some aspects, the N—((R)-2,3-dihydroxypropoxy)-3,4-difluoro-2-(2-fluoro-4-iodo-phenylamino)-benzamide is administered in a total daily dose that does not exceed 2 mg.

In some aspects, the N—((R)-2,3-dihydroxypropoxy)-3,4-difluoro-2-(2-fluoro-4-iodo-phenylamino)-benzamide is administered in a total daily dose that does not exceed 1 mg.

In some aspects, the N—((R)-2,3-dihydroxypropoxy)-3,4-difluoro-2-(2-fluoro-4-iodo-phenylamino)-benzamide is administered on a 28-day dosing cycle comprising: (a) 21 days in which the total daily dose is administered; and (b) 7 days in which no N—((R)-2,3-dihydroxypropoxy)-3,4-difluoro-2-(2-fluoro-4-iodo-phenylamino)-benzamide is administered. In some aspects, the N—((R)-2,3-dihydroxypropoxy)-3,4-difluoro-2-(2-fluoro-4-iodo-phenylamino)-benzamide is administered on a 28-day dosing cycle comprising: (a) 21 consecutive days in which the total daily dose is administered; followed by (b) 7 consecutive days in which no N—((R)-2,3-dihydroxypropoxy)-3,4-difluoro-2-(2-fluoro-4-iodo-phenylamino)-benzamide is administered.

In some aspects, the N—((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 days in which the total daily dose is administered and (ii) 2 days in which no N—((R)-2,3-dihydroxypropoxy)-3,4-difluoro-2-(2-fluoro-4-iodo-phenylamino)-benzamide; and (b) 7 days in which no N—((R)-2,3-dihydroxypropoxy)-3,4-difluoro-2-(2-fluoro-4-iodo-phenylamino)-benzamide is administered. In some aspects, the N—((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 consecutive days in which the total daily dose is administered and (ii) 2 consecutive days in which no N—((R)-2,3-dihydroxypropoxy)-3,4-difluoro-2-(2-fluoro-4-iodo-phenylamino)-benzamide; followed by (b) 7 consecutive days in which no N—((R)-2,3-dihydroxypropoxy)-3,4-difluoro-2-(2-fluoro-4-iodo-phenylamino)-benzamide is administered.

In some aspects, the 28-day dosing cycle is repeated up to a total of 24 consecutive 28-day dosing cycles.

In some aspects, the N—((R)-2,3-dihydroxypropoxy)-3,4-difluoro-2-(2-fluoro-4-iodo-phenylamino)-benzamide is administered on a 28-day dosing cycle comprising 28 days in which the total daily dose is administered.

In some aspects, the subject experiences dysphagia. In some aspects, the subject experiences dysphagia caused by one or more of: disease of the nervous system, muscle weakening, developmental disability, stroke, injury, anatomical defect, cancer, treatment for cancer, allergic reaction, dementia, memory loss, or cognitive decline.

In some aspects, the subject is a pediatric subject.

Methods of Preparing N—((R)-2,3-dihydroxypropoxy)-3,4-difluoro-2-(2-fluoro-4-iodo-phenylamino)-benzamide and Essentially Pure Form IV Novel methods of producing N—((R)-2,3-dihydroxypropoxy)-3,4-difluoro-2-(2-fluoro-4-iodo-phenylamino)-benzamide of Formula (I)

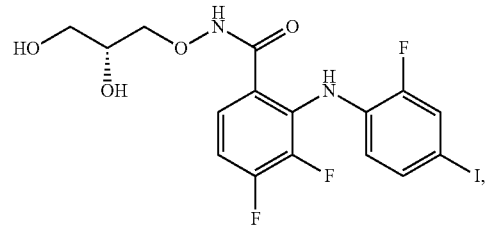

that comprise reacting PD-0315209 (FIPFA) and PD-0337792 (IPGA) with a coupling reagent that is 1-propylphosphonic anhydride ("T3P") to obtain 901 Acetonide, as shown in Scheme I below are disclosed herein.

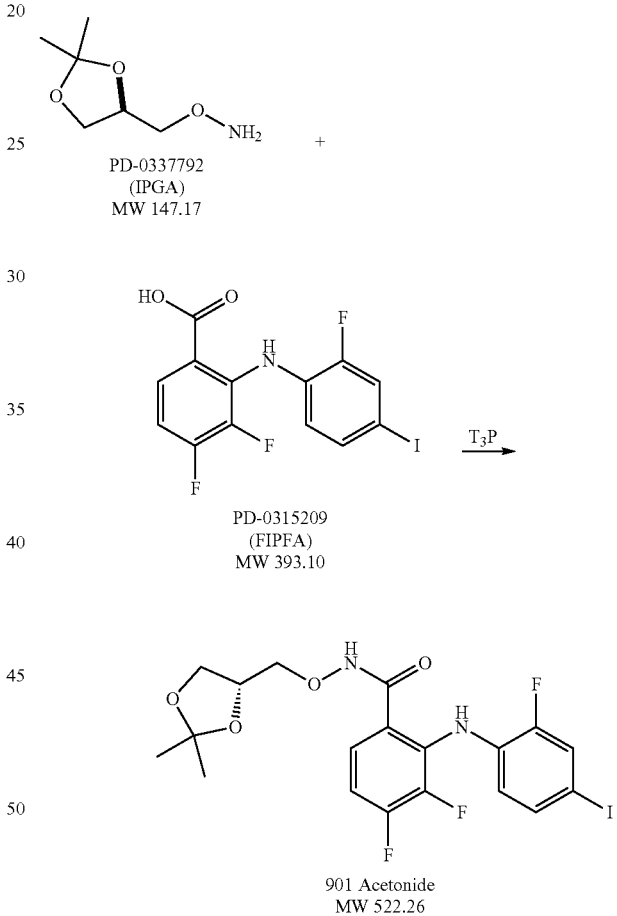

In some aspects, the T3P is in solution. In some aspects, T3P is provided as a solution in ethyl acetate.

In some aspects, the method of producing essentially pure Form IV N—((R)-2,3-dihydroxypropoxy)-3,4-difluoro-2-(2-fluoro-4-iodo-phenylamino)-benzamide of Formula (I) comprises (a) reacting PD-0315209 (FIPFA) and PD-0337792 (IPGA) with a coupling reagent that is T3P to obtain 901 Acetonide; and (b) treating 901 Acetonide with acid to form N—((R)-2,3-dihydroxypropoxy)-3,4-difluoro-2-(2-fluoro-4-iodo-phenylamino)-benzamide, as shown in Scheme II below.

Scheme II
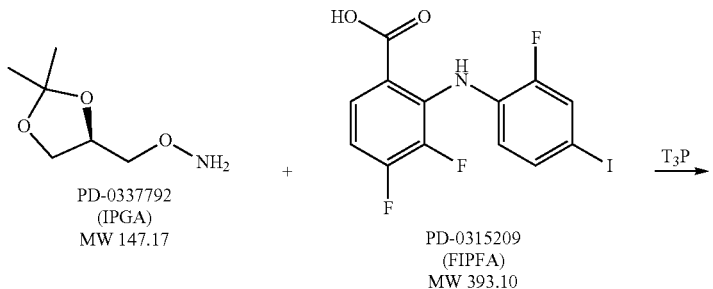
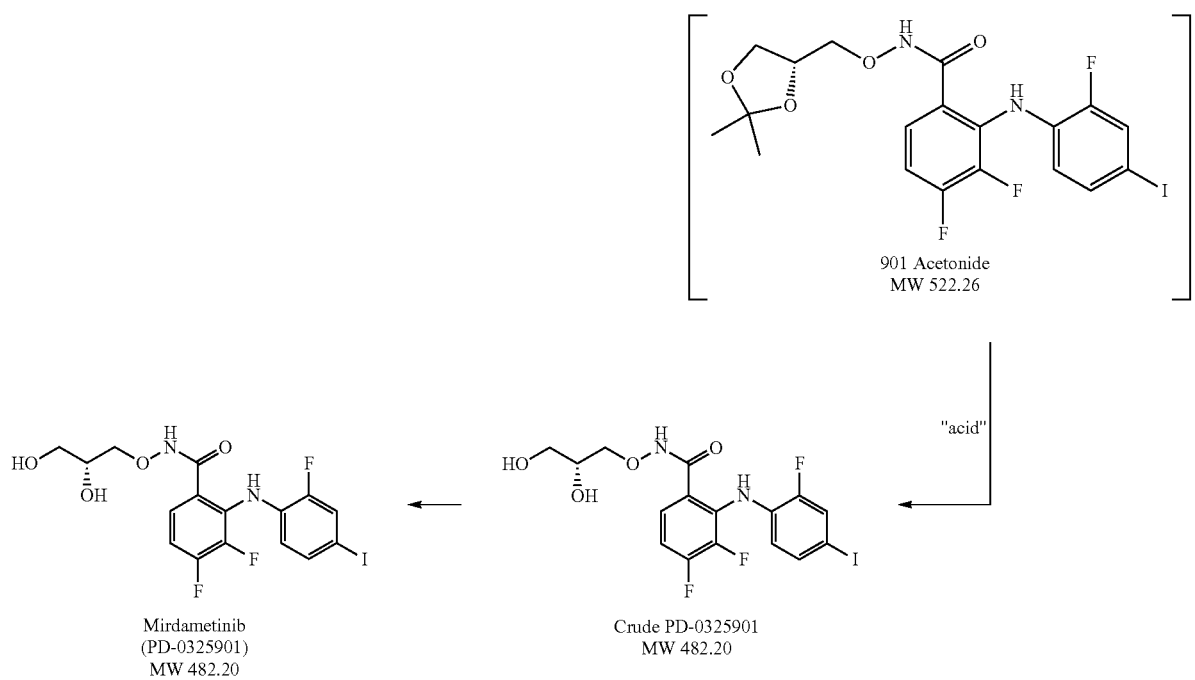
In some aspects, the synthesis for essentially pure crystalline Form IV of N—((R)-2,3-dihydroxypropoxy)-3,4-difluoro-2-(2-fluoro-4-iodo-phenylamino)-benzamide of Formula (I) comprises the reaction set forth according to Scheme III.
Scheme III
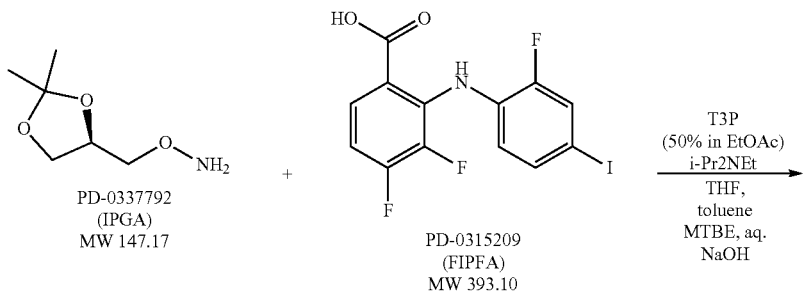

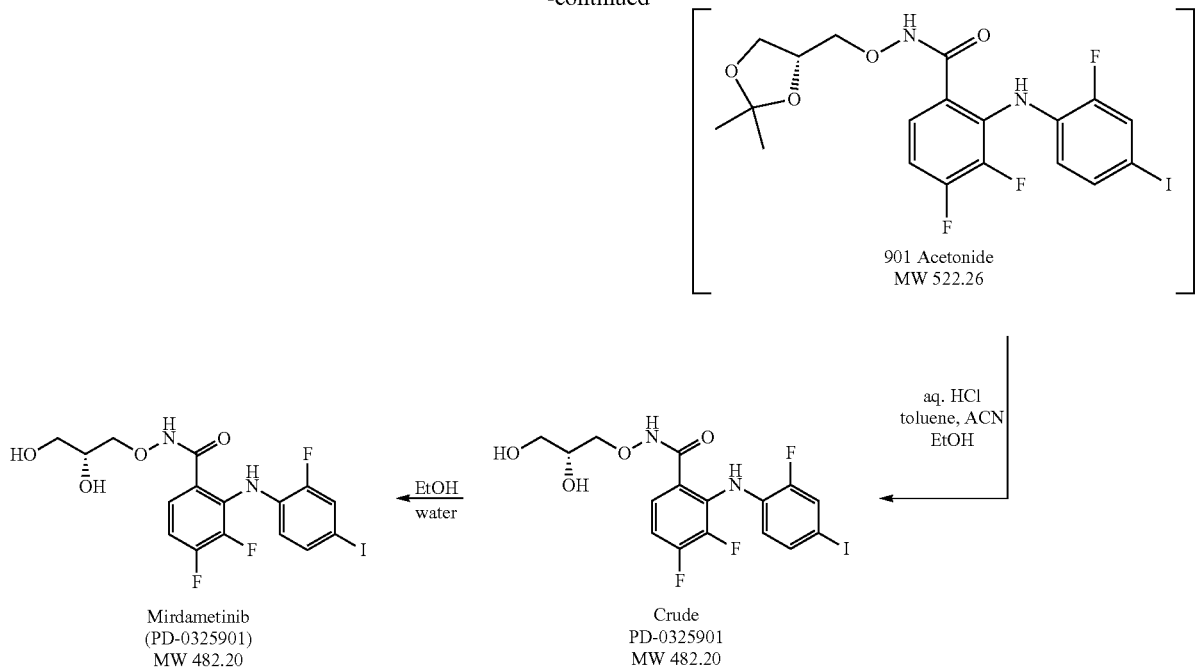
In some aspects, the synthesis for essentially pure Form IV of N—((R)-2,3-dihydroxypropoxy)-3,4-difluoro-2-(2-fluoro-4-iodo-phenylamino)-benzamide of Formula (I) is as shown below in Scheme IV.

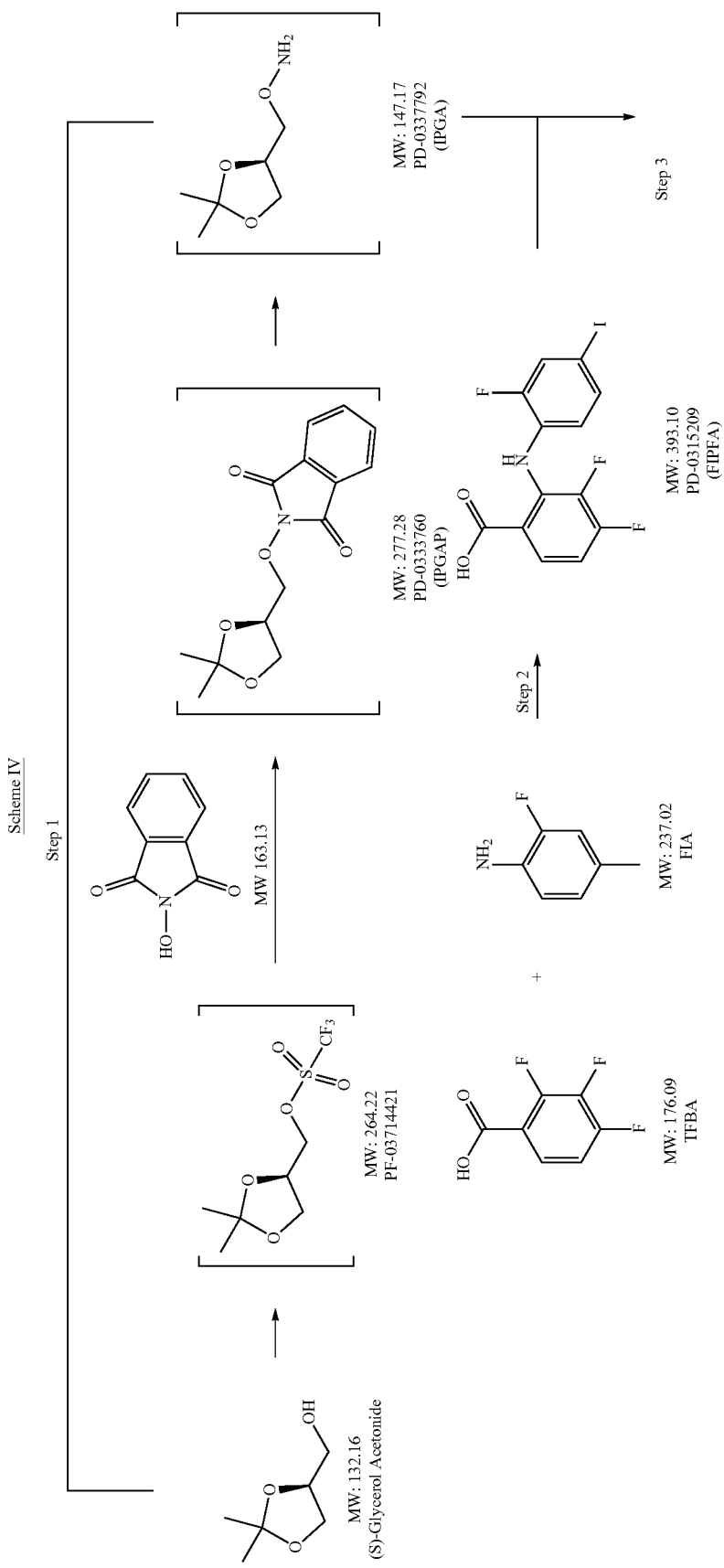

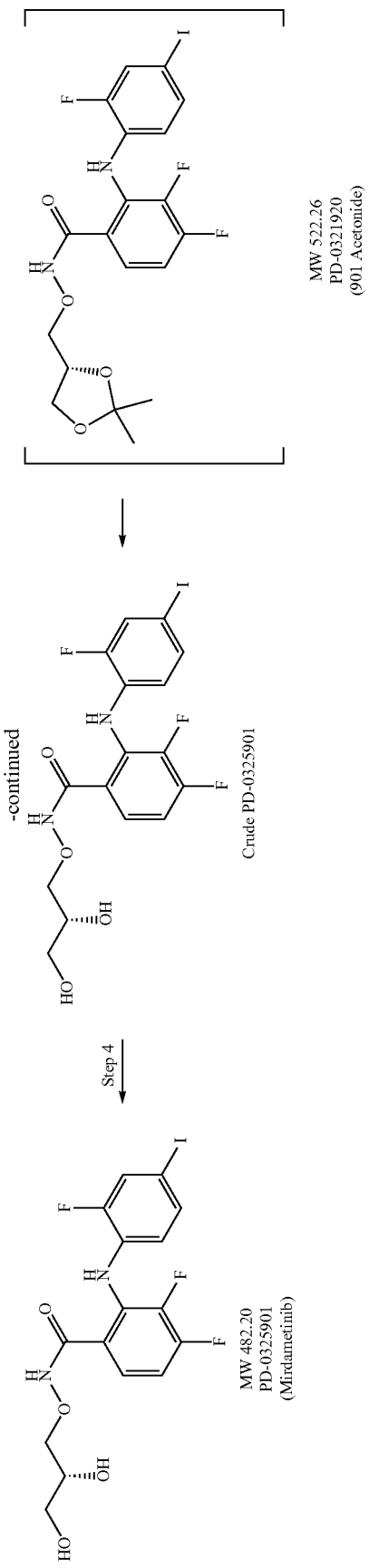

In some aspects, the methods provided herein provide a crystalline composition that is essentially pure Form IV of N—((R)-2,3-dihydroxypropoxy)-3,4-difluoro-2-(2-fluoro-4-iodo-phenylamino)-benzamide that contains ≤0.2% of dimeric impurity PF-00191189

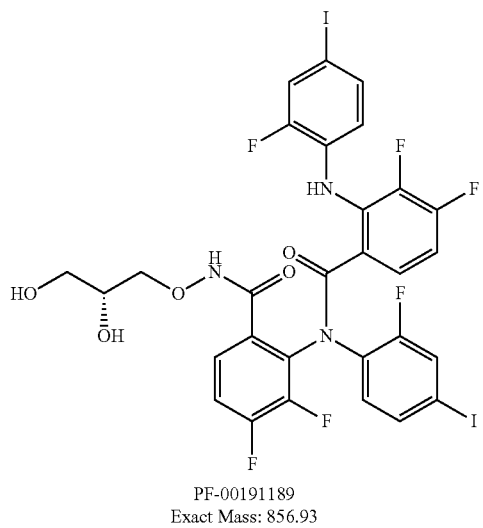 [SMILES: O=C(NOC[C@H](O)CO)c1ccc(F)c(F)c1N(C(=O)c1ccc(F)c(F)c1Nc1ccc(I)cc1F)c1ccc(I)cc1F]

PF-00191189
Exact Mass: 856.93

In some aspects, the crystalline composition contains about 0.05% to about 0.19% by weight of dimeric impurity PF-00191189. In some aspects, the crystalline composition contains no detectable amount of dimeric impurity PF-00191189.

Definitions

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "mirdametinib" and "PD-0325901" refer to the single enantiomer N—((R)-2,3-dihydroxypropoxy)-3,4-difluoro-2-(2-fluoro-4-iodo-phenylamino)-benzamide.

The term "subject" refers to an animal, including, but not limited to a primate (e.g., human), cow, sheep, goat, horse, dog, cat, rabbit, rat, or mouse. The terms "subject" and "patient" are used interchangeably herein in reference, for example, to a mammalian subject, such as a human subject.

The term "pediatric" refers to a human subject under the age of 21 years at the time of treatment. The term "pediatric" can be further divided into various subpopulations including: neonates (from birth through the first 28 days of life); infants (29 days of age to less than two years of age); children (two years of age to less than 12 years of age); and adolescents (12 years of age through 21 years of age (up to but not including, the twenty-second birthday)). See, e.g., Berhman R E, Kliegman R, Arvin A M, Nelson W E. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994. Younger pediatric patients in particular, such as neonates, infants and young children, can have difficulty swallowing whole capsules or tablets.

The term "dispersible" as used herein refers to a composition (e.g., a tablet, powder, granules, minitablets, or pellets (also known as "beads") which disintegrates and/or dissolves when combined with water or another potable liquid (e.g., a non-water beverage), or a subject's own saliva when placed in the subject's mouth, with or without the addition of agitation or temperature modification. In some aspects, the dispersible composition disintegrates or dissolves within 10 minutes, 9 minutes, 8 minutes, 7 minutes, 6 minutes, 5 minutes, 4 minutes, 3 minutes, 2 minutes, or 1 minute after being combined with water or another potable liquid. Such disintegration or dissolution need not be complete. For example, a dispersible tablet may dissolve almost entirely, but some undissolved particulate matter may remain.

The term "orodispersible" refers to a composition which is capable of dissolving or disintegrating in a subject's mouth (i.e., dissolving or disintegrating in a subject's saliva) if administered orally, without a requirement of first dissolving or disintegrating in a separate container.

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Thus, those in need of treatment include those already diagnosed with or suspected of having the disorder. Beneficial or desired clinical results include, but are not limited to alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. The term "therapeutically effective amount" is meant to include the amount of a compound that, when administered, is sufficient to prevent development of, or alleviate to some extent, one or more of the symptoms of a disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

In certain aspects, a subject is successfully "treated" for a tumor, according to the methods described herein if the patient shows one or more of the following: a reduction in the size of the tumor; relief of one or more symptoms associated with the specific tumor; a reduction in the volume of the tumor; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given tumor can be used to determine whether an effective amount of mirdametinib meets any of these particular endpoints (e.g., CR, PFS, PR).

In certain aspects, a subject is successfully "treated" for cancer, e.g., lung cancer or ovarian cancer, according to the methods disclosed herein if the patient shows one or more of the following: a reduction in the number of or complete absence of cancer cells; relief of one or more symptoms associated with the specific cancer; reduced morbidity and mortality; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given cancer can be used to determine whether an effective amount of mirdametinib meets any of these particular endpoints (e.g., CR, PFS, PR).

The terms "pharmaceutically acceptable carrier," "pharmaceutically acceptable excipient," "physiologically acceptable carrier," or "physiologically acceptable excipient" refer to a pharmaceutically acceptable material, composition, or vehicle, such as a liquid or solid excipient, solvent, or encapsulating material. In one aspect, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See *Remington: The Science and Practice of Pharmacy*, 21$^{st}$ Edition, Lippincott Williams & Wilkins: Philadelphia, Pa. 2005; *Handbook of Pharmaceutical Excipients*, 5$^{th}$ Edition, Rowe et al., Eds., The Pharmaceutical Press and the American Pharmaceutical Association: 2005; and *Handbook of Pharmaceutical Additives*, 3$^{rd}$ Edition, Ash and Ash Eds., Gower Publishing Company: 2007; Pharmaceutical Preformulation and Formulation, Gibson Ed., CRC Press LLC: Boca Raton, Fla. 2004 (incorporated herein by reference). Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to butylated hydroxytoluene (BHT), calcium carbonate, calcium phosphate (dibasic), calcium stearate, calcium sulfate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The term "pharmaceutical composition," as used herein, represents a composition containing a compound described herein formulated with one or more pharmaceutically acceptable excipients (carriers), and can be manufactured or sold with the approval of a governmental regulatory agency as part of a therapeutic regimen for the treatment of disease in a mammal. Pharmaceutical compositions can be formulated, for example, for oral administration in unit dosage form (e.g., a tablet (e.g., dispersible tablet), powder (e.g., dispersible powder) capsule, granules, minitablets, pellets, caplet, gelcap, or syrup).

The terms "about" or "approximately" means within a range of an acceptable error for a particular value as determined by one of ordinary skill in the art, which depends in part on how the value is measured or determined. In some aspects, the term "about" or "approximately" means within 1, 2, 3, or 4 standard deviations. In some aspects, the term "about" or "approximately" means a quantity, level, value, number, frequency, percentage, dimension, size, amount, weight or length that varies by as much as 30, 25, 20, 15, 10, 9, 8, 7, 6, 5, 4, 3, 2, or 1% to a reference quantity, level, value, number, frequency, percentage, dimension, size, amount, weight or length.

As used herein, the term "administration" refers to the administration of a composition (e.g., a compound or a preparation that includes a compound as described herein) to a subject or system. Administration to an animal subject (e.g., to a human) can be by any appropriate route, such as one described herein.

The term "solvate" refers to a compound provided herein or a salt thereof, which further includes a stoichiometric or non-stoichiometric amount of solvent bound by non-covalent intermolecular forces. Where the solvent is water, the solvate is a hydrate. Where the solvent includes ethanol, the compound can be an ethanol solvate.

The term "crystalline," as used herein, refers to a solid-state form which consists of orderly arrangement of structural units. Different crystalline forms of the same compound, or a salt, hydrate, or solvate thereof, arise from different packing of the molecules in the solid-state, which results in different crystal symmetries and/or unit cell parameter. Different crystalline forms usually have different X-ray diffraction patterns, infrared spectra, melting points, density, hardness, crystal shape, optical and electrical properties, stability, and solubility. See, e.g., *Remington's Pharmaceutical Sciences*, 18$^{th}$ ed., Mack Publishing, Easton Pa. 173 (1990); *The United States Pharmacopeia*, 23$^{rd}$ ed., 1843-1844 (1995) (incorporated herein by reference).

Crystalline forms are commonly characterized by X-ray powder diffraction (XRPD). An XRPD pattern of reflections (peaks, typically expressed in degrees 2-theta) is commonly considered a fingerprint of a particular crystalline form. The relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings. In some instances, any particular peak in an XRPD pattern may appear as a singlet, doublet, triplet, quartet, or multiplet, depending on the type of instrument or the settings, the sensitivity of the instrument, measuring conditions, and/or purity of the crystalline form. In some instances, any particular peak in an XRPD may appear in a symmetric shape or in an asymmetric shape, e.g., having a shoulder. Moreover, instrument variation and other factors can affect the 2-theta values. A skilled artisan understanding these variations is capable of discriminating or ascertaining the defining features or characteristics of a particular crystal form using XRPD, as well as using other known physicochemical techniques.

The term "anhydrate" as applied to a compound refers to a crystalline form wherein the compound contains no structural water within the crystal lattice.

As used herein, the term "essentially pure" with respect to Form IV means that the composition comprising Form IV contains no detectable amount of another polymorphic form (e.g., Form I or Form II), as determined by observing no detectable differences in an XRPD and/or DSC pattern between a single Form IV crystal and the crystalline composition of N—((R)-2,3-dihydroxypropoxy)-3,4-difluoro-2-(2-fluoro-4-iodo-phenylamino)-benzamide. However, "essentially pure" Form IV of N—((R)-2,3-dihydroxypropoxy)-3,4-difluoro-2-(2-fluoro-4-iodo-phenylamino)-benzamide can include impurities, such as, but not limited to, synthetic reactants or by-products generated during the chemical synthesis.

As used herein, the term "aberration" as applied to a gene refers to a mutation, chromosomal loss or fusion, epigenetic chemical modification, or other event which alters the sequence, level of expression, or processed mRNA sequence associated with a gene relative to the sequence, level of expression, or processed mRNA sequence associated with the wild-type gene.

It is understood that wherever aspects are described herein with the language "comprising," otherwise analogous aspects described in terms of "consisting of" and/or "consisting essentially of" are also provided.

The details of one or more aspects are set forth in the description below. Other features, objects, and advantages will be apparent from the description and from the claims.

DETAILED DESCRIPTION OF THE INVENTION

Novel crystalline forms and amorphous solids of N—((R)-2,3-dihydroxypropoxy)-3,4-difluoro-2-(2-fluoro-4-iodo-phenylamino)-benzamide are described herein. Pharmaceutical compositions (e.g., capsules, tablets, dispersible and non-dispersible dosage forms) and methods to treat a patient in need of therapeutic administration of N—((R)-2,3-dihydroxypropoxy)-3,4-difluoro-2-(2-fluoro-4-iodo-phenylamino)-benzamide are also described herein. Additionally, a novel method of producing a pure composition of crystalline Form IV of N—((R)-2,3-dihydroxypropoxy)-3,4-difluoro-2-(2-fluoro-4-iodo-phenylamino)-benzamide is described herein.

Crystalline Forms and Amorphous Solids

The present disclosure relates in part to novel crystalline forms of N—((R)-2,3-dihydroxypropoxy)-3,4-difluoro-2-(2-fluoro-4-iodo-phenylamino)-benzamide. As with all pharmaceutical compounds and compositions, the chemical and physical properties of N—((R)-2,3-dihydroxypropoxy)-3,4-difluoro-2-(2-fluoro-4-iodo-phenylamino)-benzamide are important in its commercial development. These properties include, but are not limited to (1) packing properties such as molar volume, bulk density and hygroscopicity, (2) thermodynamic properties such as melting temperature, vapor pressure and solubility, (3) kinetic properties such as dissolution rate and stability (including stability at ambient conditions, especially to moisture and under storage conditions), (4) surface properties such as surface area, wettability, interfacial tension and shape, (5) mechanical properties such as hardness, tensile strength, compactability, handling, flow and blend; and (6) filtration properties. These properties can affect, for example, the processing and storage of the compound and pharmaceutical compositions comprising the compound.

In some aspects, the present disclosure provides a crystalline form of N—((R)-2,3-dihydroxypropoxy)-3,4-difluoro-2-(2-fluoro-4-iodo-phenylamino)-benzamide of Formula (I)

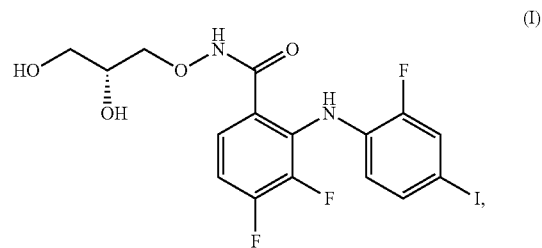 [SMILES: O=C(NOC[C@H](O)CO)c1ccc(F)c(F)c1Nc1ccc(I)cc1F]

selected from the group consisting of:

a) a crystalline form of N—((R)-2,3-dihydroxypropoxy)-3,4-difluoro-2-(2-fluoro-4-iodo-phenylamino)-benzamide characterized by an XRPD pattern having peaks at 5.4±0.2, 17.5±0.2, and 22.8±0.2 degrees two theta;

b) a crystalline form of N—((R)-2,3-dihydroxypropoxy)-3,4-difluoro-2-(2-fluoro-4-iodo-phenylamino)-benzamide characterized by an XRPD pattern having peaks at 5.9±0.2, 7.2±0.2, and 21.2±0.2 degrees two theta;

c) a crystalline form of N—((R)-2,3-dihydroxypropoxy)-3,4-difluoro-2-(2-fluoro-4-iodo-phenylamino)-benzamide characterized by an XRPD pattern having peaks at 5.3±0.2, 10.6±0.2, and 16.1±0.2 degrees two theta;

d) a crystalline form of N—((R)-2,3-dihydroxypropoxy)-3,4-difluoro-2-(2-fluoro-4-iodo-phenylamino)-benzamide characterized by an XRPD pattern having peaks at 5.4±0.2, 10.7±0.2, and 18.7±0.2 degrees two theta;

e) a crystalline form of N—((R)-2,3-dihydroxypropoxy)-3,4-difluoro-2-(2-fluoro-4-iodo-phenylamino)-benzamide characterized by an XRPD pattern having peaks at 6.7±0.2, 13.5±0.2, and 22.2±0.2 degrees two theta;

f) a crystalline form of N—((R)-2,3-dihydroxypropoxy)-3,4-difluoro-2-(2-fluoro-4-iodo-phenylamino)-benzamide characterized by an XRPD pattern having peaks at 10.6±0.2, 19.6±0.2, and 24.8±0.2 degrees two theta;

g) a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 6.9±0.2, and 10.1±0.2 degrees two theta;

h) a crystalline form of N—((R)-2,3-dihydroxypropoxy)-3,4-difluoro-2-(2-fluoro-4-iodo-phenylamino)-benzamide characterized by an XRPD pattern having peaks at 10.1±0.2, 17.3±0.2, and 22.6±0.2 degrees two theta;

i) a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 5.1±0.2, and 14.6±0.2 degrees two theta;

j) a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 23.4±0.2, and 25.2±0.2 degrees two theta;

k) a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 14.7±0.2, and 20.9±0.2 degrees two theta;

l) a crystalline form of N—((R)-2,3-dihydroxypropoxy)-3,4-difluoro-2-(2-fluoro-4-iodo-phenylamino)-benzamide characterized by an XRPD pattern having peaks at 6.0±0.2, 17.1±0.2, and 20.6±0.2 degrees two theta;

m) a crystalline form of N—((R)-2,3-dihydroxypropoxy)-3,4-difluoro-2-(2-fluoro-4-iodo-phenylamino)-benzamide characterized by an XRPD pattern having peaks at 5.9±0.2, 10.1±0.2, and 15.5±0.2 degrees two theta;

n) a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 10.7±0.2, and 15.9±0.2 degrees two theta;

o) a crystalline form of N—((R)-2,3-dihydroxypropoxy)-3,4-difluoro-2-(2-fluoro-4-iodo-phenylamino)-benzamide characterized by an XRPD pattern having peaks at 10.2±0.2, 11.6±0.2, and 20.0±0.2 degrees two theta;

p) a crystalline form of N—((R)-2,3-dihydroxypropoxy)-3,4-difluoro-2-(2-fluoro-4-iodo-phenylamino)-benzamide characterized by an XRPD pattern having peaks at 7.8±0.2, 14.0±0.2, and 17.1±0.2 degrees two theta;

q) a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 8.2±0.2, and 16.7±0.2 degrees two theta;

r) a crystalline form of N—((R)-2,3-dihydroxypropoxy)-3,4-difluoro-2-(2-fluoro-4-iodo-phenylamino)-benzamide characterized by an XRPD pattern having peaks at 7.2±0.2, 21.7±0.2, and 29.1±0.2 degrees two theta;

s) a crystalline form of N—((R)-2,3-dihydroxypropoxy)-3,4-difluoro-2-(2-fluoro-4-iodo-phenylamino)-benzamide characterized by an XRPD pattern having peaks at 5.4±0.2, 9.7±0.2, and 10.7±0.2 degrees two theta; and t) a crystalline form of N—((R)-2,3-dihydroxypropoxy)-3,4-difluoro-2-(2-fluoro-4-iodo-phenylamino)-benzamide characterized by an XRPD pattern having peaks at 7.2±0.2, 20.6±0.2, and 23.0±0.2 degrees two theta.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks 5.4±0.2, 17.5±0.2, and 22.8±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks 5.4±0.2, 12.5±0.2, 17.5±0.2, and 22.8±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 2A.

In some aspects, the TGA exhibits that the crystalline form of N—((R)-2,3-dihydroxypropoxy)-3,4-difluoro-2-(2-fluoro-4-iodo-phenylamino)-benzamide loses about 2.7 wt % between about 35° C. and about 100° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 77° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 95° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 77° C. and a second endotherm onset at about 95° C. In some aspects, wherein the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 2B; and/or b) a DSC profile substantially as shown in FIG. 2B.

In some aspects, the crystalline form of N—((R)-2,3-dihydroxypropoxy)-3,4-difluoro-2-(2-fluoro-4-iodo-phenylamino)-benzamide is Form V.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.9±0.2, 7.2±0.2, and 21.2±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.9±0.2, 7.2±0.2, 9.3±0.2, and 21.2±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 3A.

In some aspects, the TGA exhibits that the crystalline form of N—((R)-2,3-dihydroxypropoxy)-3,4-difluoro-2-(2-fluoro-4-iodo-phenylamino)-benzamide loses about 2.4 wt % between about 25° C. and about 125° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 41° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 70° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 109° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 41° C. and an endotherm onset at about 70° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 41° C. and an endotherm onset at about 109° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 70° C. and an endotherm onset at about 109° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 41° C., a second endotherm onset at about 70° C., and a third endotherm onset at about 109° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 3B; and/or b) a DSC profile substantially as shown in FIG. 3B.

In some aspects, the crystalline form of N—((R)-2,3-dihydroxypropoxy)-3,4-difluoro-2-(2-fluoro-4-iodo-phenylamino)-benzamide is Form VI.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.3±0.2, 10.6±0.2, and 16.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.3±0.2, 10.6±0.2, 13.9±0.2, and 16.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 4A.

In some aspects, the TGA exhibits that the crystalline form of N—((R)-2,3-dihydroxypropoxy)-3,4-difluoro-2-(2-fluoro-4-iodo-phenylamino)-benzamide loses about 5.2 wt % between about 40° C. and about 120° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 85° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endothermic event at about 110° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 85° C. and a second endothermic event at about 110° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 4B; and/or b) a DSC profile substantially as shown in FIG. 4B.

In some aspects, the crystalline form of N—((R)-2,3-dihydroxypropoxy)-3,4-difluoro-2-(2-fluoro-4-iodo-phenylamino)-benzamide is Form VII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.4±0.2, 10.7±0.2, and 18.7±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.4±0.2, 10.7±0.2, 18.7±0.2 and 23.9±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 5A.

In some aspects, the TGA exhibits that the crystalline form of N—((R)-2,3-dihydroxypropoxy)-3,4-difluoro-2-(2-fluoro-4-iodo-phenylamino)-benzamide loses about 3.3 wt % between about 40° C. and about 112° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 81° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 110° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 81° C. and a second endotherm onset at about 110° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 5B; and/or b) a DSC profile substantially as shown in FIG. 5B.

In some aspects, the crystalline form of N—((R)-2,3-dihydroxypropoxy)-3,4-difluoro-2-(2-fluoro-4-iodo-phenylamino)-benzamide is Form VIII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 6.7±0.2, 13.5±0.2, and 22.2±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 6.7±0.2, 8.0±0.2, 13.5±0.2, and 22.2±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 6A.

In some aspects, the TGA exhibits that the crystalline form of N—((R)-2,3-dihydroxypropoxy)-3,4-difluoro-2-(2-fluoro-4-iodo-phenylamino)-benzamide loses about 4.6 wt % between about 28° C. and about 128° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 84° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 107° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 114° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 84° C. and an endotherm onset at about 107° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 84° C. and an endotherm onset at about 114° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 107° C. and an endotherm onset at about 114° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 84° C., a second endotherm onset at about 107° C., and a third endotherm onset at about 114° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 6B; and/or b) a DSC profile substantially as shown in FIG. 6B.

In some aspects, the crystalline form of N—((R)-2,3-dihydroxypropoxy)-3,4-difluoro-2-(2-fluoro-4-iodo-phenylamino)-benzamide is Form IX.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 10.6±0.2, 19.6±0.2, and 24.8±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 10.6±0.2, 19.6±0.2, and 24.8±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 7A.

In some aspects, the TGA exhibits that the crystalline form of N—((R)-2,3-dihydroxypropoxy)-3,4-difluoro-2-(2-fluoro-4-iodo-phenylamino)-benzamide loses about 2.9 wt % between about 40° C. and about 115° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 89° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 7B; and/or b) a DSC profile substantially as shown in FIG. 7B.

In some aspects, the crystalline form of N—((R)-2,3-dihydroxypropoxy)-3,4-difluoro-2-(2-fluoro-4-iodo-phenylamino)-benzamide is Form X.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 6.9±0.2, and 10.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 6.9±0.2, 10.1±0.2, and 19.2±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 8A.

In some aspects, the TGA exhibits that the crystalline form of N—((R)-2,3-dihydroxypropoxy)-3,4-difluoro-2-(2-fluoro-4-iodo-phenylamino)-benzamide loses about 7.6 wt % between about 40° C. and about 175° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 69° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 104° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 69° C. and a second endotherm onset at about 104° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 8B; and/or b) a DSC profile substantially as shown in FIG. 8B.

In some aspects, the crystalline form of N—((R)-2,3-dihydroxypropoxy)-3,4-difluoro-2-(2-fluoro-4-iodo-phenylamino)-benzamide is Form XI.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 10.1±0.2, 17.3±0.2, and 22.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 10.1±0.2, 17.3±0.2, 21.5±0.2, and 22.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 9A.

In some aspects, the TGA exhibits that the crystalline form of N—((R)-2,3-dihydroxypropoxy)-3,4-difluoro-2-(2-fluoro-4-iodo-phenylamino)-benzamide loses about 8.5 wt % between about 40° C. and about 160° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 72° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 109° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 72° C. and a second endotherm onset at about 109° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 9B; and/or b) a DSC profile substantially as shown in FIG. 9B.

In some aspects, the crystalline form of N—((R)-2,3-dihydroxypropoxy)-3,4-difluoro-2-(2-fluoro-4-iodo-phenylamino)-benzamide is Form XII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 5.1±0.2, and 14.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 5.1±0.2, 6.4±0.2, and 14.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 10A.

In some aspects, the TGA exhibits that the crystalline form of N—((R)-2,3-dihydroxypropoxy)-3,4-difluoro-2-(2-fluoro-4-iodo-phenylamino)-benzamide loses about 3.1 wt % between about 20° C. and about 100° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 55° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 109° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 55° C. and a second endotherm onset at about 109° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 10B; and/or b) a DSC profile substantially as shown in FIG. 10B.

In some aspects, the crystalline form of N—((R)-2,3-dihydroxypropoxy)-3,4-difluoro-2-(2-fluoro-4-iodo-phenylamino)-benzamide is Form XIII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 23.4±0.2, and 25.2±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 23.4±0.2, 25.2±0.2, and 30.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 11A.

In some aspects, the TGA exhibits that the crystalline form of N—((R)-2,3-dihydroxypropoxy)-3,4-difluoro-2-(2-fluoro-4-iodo-phenylamino)-benzamide loses about 0.15 wt % between about 40° C. and about 150° C. In some aspects, the crystalline form of N—((R)-2,3-dihydroxypropoxy)-3, 4-difluoro-2-(2-fluoro-4-iodo-phenylamino)-benzamide exhibits a DSC thermogram that has an endotherm onset at about 111° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 11B; and/or b) a DSC profile substantially as shown in FIG. 11B.

In some aspects, the crystalline form of N—((R)-2,3-dihydroxypropoxy)-3,4-difluoro-2-(2-fluoro-4-iodo-phenylamino)-benzamide is Form XIV.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 14.7±0.2, and 20.9±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 14.7±0.2, 20.9±0.2, and 26.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 12A.

In some aspects, the TGA exhibits that the crystalline form of N—((R)-2,3-dihydroxypropoxy)-3,4-difluoro-2-(2-fluoro-4-iodo-phenylamino)-benzamide loses about 3.8 wt % between about 40° C. and about 150° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 104° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 12B; and/or b) a DSC profile substantially as shown in FIG. 12B.

In some aspects, the crystalline form of N—((R)-2,3-dihydroxypropoxy)-3,4-difluoro-2-(2-fluoro-4-iodo-phenylamino)-benzamide is Form XV.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 6.0±0.2, 17.1±0.2, and 20.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 6.0±0.2, 12.8±0.2, 17.1±0.2, and 20.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 13A.

In some aspects, the TGA exhibits that the crystalline form of N—((R)-2,3-dihydroxypropoxy)-3,4-difluoro-2-(2-fluoro-4-iodo-phenylamino)-benzamide loses about 2.1 wt % between about 40° C. and about 150° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 74° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 102° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 114° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 74° C. and an endotherm onset at about 102° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 74° C. and an endotherm onset at about 114° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 102° C. and an endotherm onset at about 114° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 74° C., a second endotherm onset at about 102° C., and a third endotherm onset at about 114° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 13B; and/or b) a DSC profile substantially as shown in FIG. 13B.

In some aspects, the crystalline form of N—((R)-2,3-dihydroxypropoxy)-3,4-difluoro-2-(2-fluoro-4-iodo-phenylamino)-benzamide is Form XVI.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.9±0.2, 10.1±0.2, and 15.5±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.9±0.2, 10.1±0.2, 11.7±0.2, and 15.5±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 14A.

In some aspects, the TGA exhibits that the crystalline form of N—((R)-2,3-dihydroxypropoxy)-3,4-difluoro-2-(2-fluoro-4-iodo-phenylamino)-benzamide loses about 2.7 wt % between about 40° C. and about 100° C. In some aspects, crystalline form of N—((R)-2,3-dihydroxypropoxy)-3,4-difluoro-2-(2-fluoro-4-iodo-phenylamino)-benzamide exhibits a DSC thermogram that has an endotherm onset at about 89° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 14B; and/or b) a DSC profile substantially as shown in FIG. 14B.

In some aspects, the crystalline form of N—((R)-2,3-dihydroxypropoxy)-3,4-difluoro-2-(2-fluoro-4-iodo-phenylamino)-benzamide is Form XVII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 10.7±0.2, and 15.9±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 10.7±0.2, 15.9±0.2, and 19.6±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 15A.

In some aspects, the TGA exhibits that the crystalline form of N—((R)-2,3-dihydroxypropoxy)-3,4-difluoro-2-(2-fluoro-4-iodo-phenylamino)-benzamide loses about 1.6 wt % between about 30° C. and about 150° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 83° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 15B; and/or b) a DSC profile substantially as shown in FIG. 15B.

In some aspects, the crystalline form of N—((R)-2,3-dihydroxypropoxy)-3,4-difluoro-2-(2-fluoro-4-iodo-phenylamino)-benzamide is Form XVIII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 10.2±0.2, 11.6±0.2, and 20.0±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 10.2±0.2, 11.6±0.2, 17.1±0.2, and 20.0±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 16A.

In some aspects, the TGA exhibits that the crystalline form of N—((R)-2,3-dihydroxypropoxy)-3,4-difluoro-2-(2-fluoro-4-iodo-phenylamino)-benzamide loses about 1.85 wt % between about 23° C. and about 92° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 69° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 98° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 115° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 69° C. and an endotherm onset at about 98° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 69° C. and an endotherm onset at about 115° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 98° C. and an endotherm onset at about 115° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 69° C., a second endotherm onset at about 98° C., and a third endotherm onset at about 115° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 16B; and/or b) a DSC profile substantially as shown in FIG. 16B.

In some aspects, the crystalline form of N—((R)-2,3-dihydroxypropoxy)-3,4-difluoro-2-(2-fluoro-4-iodo-phenylamino)-benzamide is Form XIX.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 7.8±0.2, 14.0±0.2, and 17.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 7.8±0.2, 14.0±0.2, 15.6±0.2, and 17.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 17A.

In some aspects, the TGA exhibits that the crystalline form of N—((R)-2,3-dihydroxypropoxy)-3,4-difluoro-2-(2-fluoro-4-iodo-phenylamino)-benzamide loses about 2.6 wt % between about 29° C. and about 126° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 77° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 92° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 110° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 77° C. and an endotherm onset at about 92° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 77° C. and an endotherm onset at about 110° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 92° C. and an endotherm onset at about 110° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 77° C., a second endotherm onset at about 92° C., and a third endotherm onset at about 110° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 17B; and/or b) a DSC profile substantially as shown in FIG. 17B.

In some aspects, the crystalline form of N—((R)-2,3-dihydroxypropoxy)-3,4-difluoro-2-(2-fluoro-4-iodo-phenylamino)-benzamide is Form XX.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 8.2±0.2, and 16.7±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 8.2±0.2, 16.7±0.2, and 17.7±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 18A.

In some aspects, the TGA exhibits that the crystalline form of N—((R)-2,3-dihydroxypropoxy)-3,4-difluoro-2-(2-fluoro-4-iodo-phenylamino)-benzamide loses about 14.1 wt % between about 30° C. and about 110° C. In some aspects, the crystalline form of N—((R)-2,3-dihydroxypropoxy)-3,4-difluoro-2-(2-fluoro-4-iodo-phenylamino)-benzamide exhibits a DSC thermogram has an endotherm onset at about 52° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 90° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 52° C. and a second endotherm onset at about 90° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 18B; and/or b) a DSC profile substantially as shown in FIG. 18B.

In some aspects, the crystalline form of N—((R)-2,3-dihydroxypropoxy)-3,4-difluoro-2-(2-fluoro-4-iodo-phenylamino)-benzamide is Form XXI.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 7.2±0.2, 21.7±0.2, and 29.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 7.2±0.2, 18.6±0.2, 21.7±0.2, and 29.1±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 19A.

In some aspects, the TGA exhibits that the crystalline form of N—((R)-2,3-dihydroxypropoxy)-3,4-difluoro-2-(2-fluoro-4-iodo-phenylamino)-benzamide loses about 13.8 wt % between about 26° C. and about 135° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 65° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 89° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 102° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 65° C. and an endotherm onset at about 89° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 65° C. and an endotherm onset at about 102° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 89° C. and an endotherm onset at about 102° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 65° C., a second endotherm onset at about 89° C., and a third endotherm onset at about 102° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 19B; and/or b) a DSC profile substantially as shown in FIG. 19B.

In some aspects, the crystalline form of N—((R)-2,3-dihydroxypropoxy)-3,4-difluoro-2-(2-fluoro-4-iodo-phenylamino)-benzamide is Form XXII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.4±0.2, 9.7±0.2, and 10.7±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 5.4±0.2, 6.5±0.2, 9.7±0.2, and 10.7±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 20A.

In some aspects, the TGA exhibits that the crystalline form of N—((R)-2,3-dihydroxypropoxy)-3,4-difluoro-2-(2-fluoro-4-iodo-phenylamino)-benzamide loses about 4.4 wt % between about 27° C. and about 137° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 81° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 101° C. In some aspects, the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 81° C. and a second endotherm onset at about 101° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 20B; and/or b) a DSC profile substantially as shown in FIG. 20B.

In some aspects, the crystalline form of N—((R)-2,3-dihydroxypropoxy)-3,4-difluoro-2-(2-fluoro-4-iodo-phenylamino)-benzamide is Form XXIII.

In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 7.2±0.2, 20.6±0.2, and 23.0±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern having peaks at 7.2±0.2, 9.5±0.2, 20.6±0.2, and 23.0±0.2 degrees two theta. In some aspects, the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 21A.

In some aspects, the TGA exhibits that the crystalline form of N—((R)-2,3-dihydroxypropoxy)-3,4-difluoro-2-(2-fluoro-4-iodo-phenylamino)-benzamide loses about 1.2 wt % between about 30° C. and about 119° C. In some aspects, the crystalline form of N—((R)-2,3-dihydroxypropoxy)-3,4-difluoro-2-(2-fluoro-4-iodo-phenylamino)-benzamide exhibits a DSC thermogram that has an endotherm onset at about 104° C. In some aspects, the crystalline form of N—((R)-2,3-dihydroxypropoxy)-3,4-difluoro-2-(2-fluoro-4-iodo-phenylamino)-benzamide is characterized by: a) a TGA profile substantially as shown in FIG. 21B; and/or b) a DSC profile substantially as shown in FIG. 21B.

In some aspects, the crystal form of N—((R)-2,3-dihydroxypropoxy)-3,4-difluoro-2-(2-fluoro-4-iodo-phenylamino)-benzamide is Form XXIV.

In some aspects, the present disclosure provides an amorphous form of N—((R)-2,3-dihydroxypropoxy)-3,4-difluoro-2-(2-fluoro-4-iodo-phenylamino)-benzamide of Formula (I)

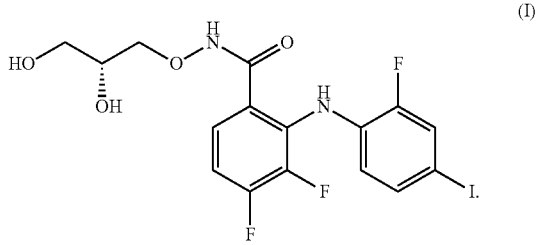 [SMILES: O=C(NOC[C@H](O)CO)c1ccc(F)c(F)c1Nc1ccc(I)cc1F]

(I)

In some aspects, the amorphous form of N—((R)-2,3-dihydroxypropoxy)-3,4-difluoro-2-(2-fluoro-4-iodo-phenylamino)-benzamide is characterized by an XRPD pattern substantially as shown in FIG. 22A.

In some aspects, the amorphous form of N—((R)-2,3-dihydroxypropoxy)-3,4-difluoro-2-(2-fluoro-4-iodo-phenylamino)-benzamide is characterized by: a) a TGA profile substantially as shown in FIG. 22B; and/or b) a DSC profile substantially as shown in FIG. 22B.

In some aspects, the XRPD pattern is generated using a PANALYTICAL® X'Pert Pro diffractometer using Ni-filtered Cu Kα (45 kV/40 mA) radiation and a step size of 0.03° 2θ with a X'CELERATOR® Real Time Multi-Strip detector, configured (a) on the incidental beam side as follows: variable divergence slits (10 mm irradiated length), 0.04 rad Soller slits, fixed anti-scatter slit (0.50°), and 10 mm beam mask, and (b) on the diffracted beam side as follows: variable anti-scatter slit (10 mm observed length) and 0.04 rad Soller slit or a BRUKER® D8® ADVANCE™ system using Cu Kα (40 kV/40 mA) radiation and a step size of 0.03° 2θ with a LYNXEYE™ detector, configured (a) on the incidental beam side as follows: Goebel mirror, mirror exit slit (0.2 mm), 2.5° Soller slit, beam knife, and (b) on the diffracted beam side as follows: anti-scatter slit (8 mm) and 2.5° Soller slit; wherein samples are mounted flat on zero-background Si wafers. In some aspects, the DSC pattern is generated using a TA Instruments Q100 or Q2000 differential scanning calorimeter at a rate of temperature increase of about 15° C./min.

Pharmaceutical Compositions

In some aspects, the present disclosure provides a pharmaceutical composition comprising a crystalline form or amorphous solid of N—((R)-2,3-dihydroxypropoxy)-3,4-difluoro-2-(2-fluoro-iodo-phenylamino)-benzamide described herein and one or more pharmaceutically acceptable carriers.

In some aspects, the desired crystalline form or amorphous solid comprises less than 10% by weight total of one or more other crystalline forms and/or amorphous solid. In some aspects, the desired crystalline form or amorphous solid comprises less than 9% by weight total of one or more other crystalline forms and/or amorphous solid. In some aspects, the desired crystalline form or amorphous solid comprises less than 8% by weight total of one or more other crystalline forms and/or amorphous solid. In some aspects, the desired crystalline form or amorphous solid comprises less than 7% by weight total of one or more other crystalline forms and/or amorphous solid. In some aspects, the desired crystalline form or amorphous solid comprises less than 6% by weight total of one or more other crystalline forms and/or amorphous solid. In some aspects, the desired crystalline form or amorphous solid comprises less than 5% by weight total of one or more other crystalline forms and/or amorphous solid. In some aspects, the desired crystalline form or amorphous solid comprises less than 4% by weight total of one or more other crystalline forms and/or amorphous solid. In some aspects, the desired crystalline form or amorphous solid comprises less than 3% by weight total of one or more other crystalline forms and/or amorphous solid. In some aspects, the desired crystalline form or amorphous solid comprises less than 2% by weight total of one or more other crystalline forms and/or amorphous solid. In some aspects, the desired crystalline form or amorphous solid comprises less than 1% by weight total of one or more other crystalline forms and/or amorphous solid. In some aspects, the desired crystalline form or amorphous solid comprises less than 0.5% by weight total of one or more other crystalline forms and/or amorphous solid. In some aspects, the desired crystalline form or amorphous solid comprises less than 0.4% by weight total of one or more other crystalline forms and/or amorphous solid. In some aspects, the desired crystalline form or amorphous form is essentially pure of other crystalline forms and/or amorphous solid.

In some aspects, the pharmaceutical composition is for oral administration. In some aspects, the pharmaceutical composition is a solid dosage form. In some aspects, the pharmaceutical composition is a capsule, tablet (e.g., dispersible tablet), powder (e.g., dispersible powder), granules (e.g., dispersible granules), minitablets (e.g., dispersible minitablets), or pellets (e.g., dispersible pellets). In some aspects, the pharmaceutical composition (e.g., a dispersible tablet, dispersible powder, dispersible granules, dispersible minitablets, or dispersible pellets) further comprises one or more pharmaceutically acceptable carriers. In some aspects, the pharmaceutical composition is for oral administration. In some aspects, the pharmaceutical composition is orodispersible.

In some aspects, the potable liquid is water, milk or a juice (e.g., orange juice or apple juice). In some aspects, the potable liquid is water. In some aspects, the potable liquid is a juice.

In some aspects, the pharmaceutical composition is a tablet, a powder, granules, minitablets, or pellets.

In some aspects, the pharmaceutical composition is a powder. In some aspects, the powder is a dispersible powder. In some aspects, a capsule or sachet comprises the dispersible powder.

In some aspects, the pharmaceutical composition is in the form of granules. In some aspects, the granules are dispersible granules. In some aspects, a capsule or sachet comprises the dispersible granules.

In some aspects, the pharmaceutical composition is in the form of minitablets. In some aspects, the minitablets are dispersible minitablets. In some aspects, a capsule or sachet comprises the dispersible minitablets.

In some aspects, the pharmaceutical composition is in the form of pellets. In some aspects, the pellets are dispersible pellets. In some aspects, a capsule or sachet comprises the dispersible pellets.

In some aspects, the pharmaceutical composition is a tablet. In some aspects, the tablet is a dispersible tablet. In some aspects, the dispersible tablet is an orodispersible tablet.

In some aspects, the pharmaceutical composition comprises about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, or about 10 mg of one or more crystalline or amorphous forms of N—((R)-2,3-dihydroxypropoxy)-3,4- difluoro-2-(2-fluoro-4-iodo-phenylamino)-benzamide. In some aspects, the pharmaceutical composition comprises about 0.5 mg of one or more crystalline or amorphous forms of N—((R)-2,3-dihydroxypropoxy)-3,4-difluoro-2-(2-fluoro-4-iodo-phenylamino)-benzamide. In some aspects, the pharmaceutical composition comprises about 1 mg of one or more crystalline or amorphous forms of N—((R)-2,3-dihydroxypropoxy)-3,4-difluoro-2-(2-fluoro-4-iodo-phenylamino)-benzamide. In some aspects, the pharmaceutical composition comprises about 2 mg of one or more crystalline or amorphous forms of N—((R)-2,3-dihydroxypropoxy)-3,4-difluoro-2-(2-fluoro-4-iodo-phenylamino)-benzamide. In some aspects, the pharmaceutical composition comprises about 3 mg of one or more crystalline or amorphous forms of N—((R)-2,3-dihydroxypropoxy)-3,4-difluoro-2-(2-fluoro-4-iodo-phenylamino)-benzamide. In some aspects, the pharmaceutical composition comprises about 4 mg of one or more crystalline or amorphous forms of N—((R)-2,3-dihydroxypropoxy)-3,4-difluoro-2-(2-fluoro-4-iodo-phenylamino)-benzamide. In some aspects, the pharmaceutical composition comprises about 5 mg of the crystalline composition of N—((R)-2,3-dihydroxypropoxy)-3,4-difluoro-2-(2-fluoro-4-iodo-phenylamino)-benzamide.

In some aspects, the pharmaceutical composition comprises about 0.1 wt/wt % to about 7 wt/wt % of one or more crystalline or amorphous forms of N—((R)-2,3-dihydroxypropoxy)-3,4-difluoro-2-(2-fluoro-4-iodo-phenylamino)-benzamide. In some aspects, the pharmaceutical composition comprises about 0.1 wt/wt % to about 5 wt/wt % of one or more crystalline or amorphous forms of N—((R)-2,3-dihydroxypropoxy)-3,4-difluoro-2-(2-fluoro-4-iodo-phenylamino)-benzamide. In some aspects, the pharmaceutical composition comprises about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, about 5 wt/wt %, about 5.1 wt/wt %, about 5.2 wt/wt %, about 5.3 wt/wt %, about 5.4 wt/wt %, about 5.5 wt/wt %, about 5.6 wt/wt %, about 5.7 wt/wt %, about 5.8 wt/wt %, about 5.9 wt/wt %, about 6 wt/wt %, about 6.1 wt/wt %, about 6.2 wt/wt %, about 6.3 wt/wt %, about 6.4 wt/wt %, about 6.5 wt/wt %, about 6.6 wt/wt %, about 6.7 wt/wt %, about 6.8 wt/wt %, about 6.9 wt/wt %, or about 7 wt/wt % of one or more crystalline or amorphous forms of N—((R)-2,3-dihydroxypropoxy)-3,4-difluoro-2-(2-fluoro-4-iodo-phenylamino)-benzamide. In some aspects, the pharmaceutical composition comprises about 0.5 wt/wt % of one or more crystalline or amorphous forms of N—((R)-2,3-dihydroxypropoxy)-3,4-difluoro-2-(2-fluoro-4-iodo-phenylamino)-benzamide. In some aspects, the pharmaceutical composition comprises about 0.8 wt/wt % of one or more crystalline or amorphous forms of N—((R)-2,3-dihydroxypropoxy)-3,4-difluoro-2-(2-fluoro-4-iodo-phenylamino)-benzamide.

In some aspects, the pharmaceutical composition comprises one or more diluents. In some aspects, the pharmaceutical composition comprises about 50 wt/wt % to about 98 wt/wt % of one or more diluents. In some aspects, the pharmaceutical composition comprises about 70 wt/wt % to about 98 wt/wt % of one or more diluent. In some aspects, the pharmaceutical composition comprises about 85 wt/wt % to about 95 wt/wt % of one or more diluents. In some aspects, the pharmaceutical composition comprises about 50 wt/wt %, about 51 wt/wt %, about 52 wt/wt %, about 53 wt/wt %, about 54 wt/wt %, about 55 wt/wt %, about 56 wt/wt %, about 57 wt/wt %, about 58 wt/wt %, about 59 wt/wt %, about 60 wt/wt %, about 61 wt/wt %, about 62 wt/wt %, about 63 wt/wt %, about 64 wt/wt %, about 65 wt/wt %, about 66 wt/wt %, about 67 wt/wt %, about 68 wt/wt %, about 69 wt/wt %, about 70 wt/wt %, about 71 wt/wt %, about 72 wt/wt %, about 73 wt/wt %, about 74 wt/wt %, about 75 wt/wt %, about 76 wt/wt %, about 77 wt/wt %, about 78 wt/wt %, about 79 wt/wt %, about 80 wt/wt %, about 81 wt/wt %, about 82 wt/wt %, about 83 wt/wt %, about 84 wt/wt %, about 85 wt/wt %, about 86 wt/wt %, about 87 wt/wt %, about 88 wt/wt %, about 89 wt/wt %, about 90 wt/wt %, about 91 wt/wt %, about 92 wt/wt %, about 93 wt/wt %, about 94 wt/wt %, about 95 wt/wt %, about 96 wt/wt %, about 97 wt/wt %, or about 98 wt/wt % of one or more diluents. In some aspects, the pharmaceutical composition comprises about 90 wt/wt % of one or more diluents. In some aspects, the pharmaceutical composition comprises about 93 wt/wt % of one or more diluents.

In some aspects, at least one of the diluents is selected from the group consisting of microcrystalline cellulose, lactose, mannitol, sorbitol, xylitol, sucrose, pregelatinized starch, calcium sulfate, calcium carbonate, starch, and dibasic calcium phosphate. In some aspects, at least one of the diluents is microcrystalline cellulose.

In some aspects, the pharmaceutical composition comprises about 50 wt/wt % to about 98 wt/wt % microcrystalline cellulose. In some aspects, the pharmaceutical composition comprises about 70 wt/wt % to about 95 wt/wt % microcrystalline cellulose. In some aspects, the pharmaceutical composition comprises about 85 wt/wt % to about 95 wt/wt % microcrystalline cellulose. In some aspects, the pharmaceutical composition comprises about 50 wt/wt %, about 51 wt/wt %, about 52 wt/wt %, about 53 wt/wt %, about 54 wt/wt %, about 55 wt/wt %, about 56 wt/wt %, about 57 wt/wt %, about 58 wt/wt %, about 59 wt/wt %, about 60 wt/wt %, about 61 wt/wt %, about 62 wt/wt %, about 63 wt/wt %, about 64 wt/wt %, about 65 wt/wt %, about 66 wt/wt %, about 67 wt/wt %, about 68 wt/wt %, about 69 wt/wt %, about 70 wt/wt %, about 71 wt/wt %, about 72 wt/wt %, about 73 wt/wt %, about 74 wt/wt %, about 75 wt/wt %, about 76 wt/wt %, about 77 wt/wt %, about 78 wt/wt %, about 79 wt/wt %, about 80 wt/wt %, about 81 wt/wt %, about 82 wt/wt %, about 83 wt/wt %, about 84 wt/wt %, about 85 wt/wt %, about 86 wt/wt %, about 87 wt/wt %, about 88 wt/wt %, about 89 wt/wt %, about 90 wt/wt %, about 91 wt/wt %, about 92 wt/wt %, about 93 wt/wt %, about 94 wt/wt %, about 95%, about 96 wt/wt %, about 97 wt/wt %, or about 98 wt/wt % microcrystalline cellulose. In some aspects, the pharmaceutical composition comprises about 90 wt/wt % microcrystalline cellulose. In some aspects, the pharmaceutical composition comprises about 93 wt/wt % microcrystalline cellulose.

In some aspects, the pharmaceutical composition comprises about 1 wt/wt % to about 10 wt/wt % of one or more disintegrants. In some aspects, the pharmaceutical composition comprises about 3.5 wt/wt % to about 6 wt/wt % of one or more disintegrants. In some aspects, the pharmaceutical composition comprises about 1.0 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, about 2.0 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, about 5.0 wt/wt %, about 5.1 wt/wt %, about 5.2 wt/wt %, about 5.3 wt/wt %, about 5.4 wt/wt %, about 5.5 wt/wt %, about 5.6 wt/wt %, about 5.7 wt/wt %, about 5.8 wt/wt %, about 5.9 wt/wt %, about 6.0 wt/wt %, about 6.1 wt/wt %, about 6.2 wt/wt %, about 6.3 wt/wt %, about 6.4 wt/wt %, about 6.5 wt/wt %, about 6.6 wt/wt %, about 6.7 wt/wt %, about 6.8 wt/wt %, about 6.9 wt/wt %, about 7.0 wt/wt %, about 7.1 wt/wt %, about 7.2 wt/wt %, about 7.3 wt/wt %, about 7.4 wt/wt %, about 7.5 wt/wt %, about 7.6 wt/wt %, about 7.7 wt/wt %, about 7.8 wt/wt %, about 7.9 wt/wt %, about 8.0 wt/wt %, about 8.1 wt/wt %, about 8.2 wt/wt %, about 8.3 wt/wt %, about 8.4 wt/wt %, about 8.5 wt/wt %, about 8.6 wt/wt %, about 8.7 wt/wt %, about 8.8 wt/wt %, about 8.9 wt/wt %, about 9.0 wt/wt %, about 9.1 wt/wt %, about 9.2 wt/wt %, about 9.3 wt/wt %, about 9.4 wt/wt %, about 9.5 wt/wt %, about 9.6 wt/wt %, about 9.7 wt/wt %, about 9.8 wt/wt %, about 9.9 wt/wt %, or about 10.0 wt/wt % of one or more disintegrants. In some aspects, the pharmaceutical composition comprises about 5 wt/wt % of one or more disintegrants.

In some aspects, at least one of the disintegrants is selected from the group consisting of croscarmellose sodium, sodium starch glycolate, crospovidone, microcrystalline cellulose, starch, pregelatinized starch, low substituted hydroxypropyl cellulose, and alginic acid. In some aspects, at least one of the disintegrants is croscarmellose sodium. In some aspects, the disintegrant is croscarmellose sodium. In some aspects, the pharmaceutical composition comprises about 1 wt/wt % to about 10 wt/wt % croscarmellose sodium. In some aspects, the pharmaceutical composition comprises about 3.5 wt/wt % to about 6 wt/wt % croscarmellose sodium. In some aspects, the pharmaceutical composition comprises about 1.0 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, about 2.0 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, about 5 wt/wt %, about 5.1 wt/wt %, about 5.2 wt/wt %, about 5.3 wt/wt %, about 5.4 wt/wt %, about 5.5 wt/wt %, about 5.6 wt/wt %, about 5.7 wt/wt %, about 5.8 wt/wt %, about 5.9 wt/wt %, about 6.0 wt/wt %, about 6.1 wt/wt %, about 6.2 wt/wt %, about 6.3 wt/wt %, about 6.4 wt/wt %, about 6.5 wt/wt %, about 6.6 wt/wt %, about 6.7 wt/wt %, about 6.8 wt/wt %, about 6.9 wt/wt %, about 7.0 wt/wt %, about 7.1 wt/wt %, about 7.2 wt/wt %, about 7.3 wt/wt %, about 7.4 wt/wt %, about 7.5 wt/wt %, about 7.6 wt/wt %, about 7.7 wt/wt %, about 7.8 wt/wt %, about 7.9 wt/wt %, about 8.0 wt/wt %, about 8.1 wt/wt %, about 8.2 wt/wt %, about 8.3 wt/wt %, about 8.4 wt/wt %, about 8.5 wt/wt %, about 8.6 wt/wt %, about 8.7 wt/wt %, about 8.8 wt/wt %, about 8.9 wt/wt %, about 9.0 wt/wt %, about 9.1 wt/wt %, about 9.2 wt/wt %, about 9.3 wt/wt %, about 9.4 wt/wt %, about 9.5 wt/wt %, about 9.6 wt/wt %, about 9.7 wt/wt %, about 9.8 wt/wt %, about 9.9 wt/wt %, or about 10.0 wt/wt % croscarmellose sodium. In some aspects, the pharmaceutical composition comprises about 5 wt/wt % croscarmellose sodium.

In some aspects, the pharmaceutical composition comprises 0 wt/wt % to about 5 wt/wt % of one or more lubricants. In some aspects, the pharmaceutical composition comprises about 0.1 wt/wt % to about 5 wt/wt % of one or more lubricants. In some aspects, the pharmaceutical composition comprises 0 wt/wt % to about 2 wt/wt % of one or more lubricants. In some aspects, the pharmaceutical composition comprises about 0.1 wt/wt % to about 2 wt/wt % of one or more lubricants. In some aspects, the pharmaceutical composition comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, or about 5.0 wt/wt % of one or more lubricants. In some aspects, the pharmaceutical composition comprises about 1 wt/wt % of one or more lubricants.

In some aspects, at least one of the lubricants is selected from the group consisting of magnesium stearate, sodium stearyl fumarate, glycerol dibehenate, stearic acid, hydrogenated vegetable oil, calcium stearate, zinc stearate, beeswax, colloidal silicon dioxide, and talc. In some aspects, at least one of the lubricants is magnesium stearate. In some aspects, the lubricant is magnesium stearate. In some aspects, the pharmaceutical composition comprises 0 wt/wt % to about 5 wt/wt % of magnesium stearate. In some aspects, the pharmaceutical composition comprises about 0.1 wt/wt % to about 5 wt/wt % of magnesium stearate. In some aspects, the pharmaceutical composition comprises 0 wt/wt % to about 2 wt/wt % of magnesium stearate. In some aspects, the pharmaceutical composition comprises about 0.1 wt/wt % to about 2 wt/wt % of magnesium stearate. In some aspects, the pharmaceutical composition comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, or about 5.0 wt/wt % magnesium stearate. In some aspects, the pharmaceutical composition comprises 0 wt/wt % magnesium stearate. In some aspects, the pharmaceutical composition comprises about 0.1 wt/wt % magnesium stearate. In some aspects, the pharmaceutical composition comprises about 1 wt/wt % magnesium stearate.

In some aspects, the pharmaceutical composition comprises 0 wt/wt % to about 5 wt/wt % of one or more flavoring agents. In some aspects, the pharmaceutical composition comprises 0 wt/wt % to about 2.5 wt/wt % of one or more flavoring agents. In some aspects, the pharmaceutical composition comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 w/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, or about 5.0 wt/wt % of one or more flavoring agents. In some aspects, the pharmaceutical composition comprises about 2 wt/wt % of one or more flavoring agents.

In some aspects, at least one of the flavoring agents is selected from the group consisting of natural or synthetic flavors including but not limited to grape flavoring, bubble gum flavoring, caramel flavoring, orange flavoring, lemon flavoring, strawberry flavoring, raspberry flavoring, mint flavoring, peppermint flavoring, grapefruit flavoring, pineapple flavoring, pear flavoring, peach flavoring, vanilla flavoring, banana flavoring, or cherry flavoring. In some aspects, at least one of the flavoring agents is grape flavoring. In some aspects, the pharmaceutical composition comprises 0 wt/wt % to about 5.0 wt/wt % grape flavoring. In some aspects, the pharmaceutical composition comprises 0 wt/wt % to about 2.5 wt/wt % grape flavoring. In some aspects, the pharmaceutical composition comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, or about 5.0 wt/wt % grape flavoring. In some aspects, the pharmaceutical composition comprises about 2 wt/wt % grape flavoring.

In some aspects, the pharmaceutical composition comprises 0 wt/wt % to about 5 wt/wt % of one or more sweeteners. In some aspects, the pharmaceutical composition comprises 0 wt/wt % to about 2 wt/wt % of one or more sweeteners. In some aspects, the pharmaceutical composition comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, about 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, or about 5.0 wt/wt % of one or more sweeteners. In some aspects, the pharmaceutical composition comprises about 1 wt/wt % of one or more sweeteners.

In some aspects, at least one of the sweeteners is selected from the group consisting of sucralose, acesulfame, saccharin, sucrose, xylitol, mannitol, sorbitol, glucose, fructose, and aspartame. In some aspects, at least one of the sweeteners is sucralose. In some aspects, the sweetener is sucralose. In some aspects, the pharmaceutical composition comprises 0 wt/wt % to about 5 wt/wt % sucralose. In some aspects, the pharmaceutical composition comprises 0 wt/wt % to about 2 wt/wt % sucralose. In some aspects, the pharmaceutical composition comprises 0 wt/wt %, about 0.1 wt/wt %, about 0.2 wt/wt %, about 0.3 wt/wt %, about 0.4 wt/wt %, about 0.5 wt/wt %, about 0.6 wt/wt %, about 0.7 wt/wt %, about 0.8 wt/wt %, about 0.9 wt/wt %, about 1 wt/wt %, about 1.1 wt/wt %, about 1.2 wt/wt %, about 1.3 wt/wt %, about 1.4 wt/wt %, about 1.5 wt/wt %, 1.6 wt/wt %, about 1.7 wt/wt %, about 1.8 wt/wt %, about 1.9 wt/wt %, about 2 wt/wt %, about 2.1 wt/wt %, about 2.2 wt/wt %, about 2.3 wt/wt %, about 2.4 wt/wt %, about 2.5 wt/wt %, about 2.6 wt/wt %, about 2.7 wt/wt %, about 2.8 wt/wt %, about 2.9 wt/wt %, about 3.0 wt/wt %, about 3.1 wt/wt %, about 3.2 wt/wt %, about 3.3 wt/wt %, about 3.4 wt/wt %, about 3.5 wt/wt %, about 3.6 wt/wt %, about 3.7 wt/wt %, about 3.8 wt/wt %, about 3.9 wt/wt %, about 4.0 wt/wt %, about 4.1 wt/wt %, about 4.2 wt/wt %, about 4.3 wt/wt %, about 4.4 wt/wt %, about 4.5 wt/wt %, about 4.6 wt/wt %, about 4.7 wt/wt %, about 4.8 wt/wt %, about 4.9 wt/wt %, or about 5.0 wt/wt % sucralose. In some aspects, the pharmaceutical composition comprises about 1 wt/wt % sucralose.

In some aspects, the pharmaceutical composition is a capsule. In some aspects, the capsule comprises about 1 mg of one or more crystalline or amorphous forms of N—((R)-2,3-dihydroxypropoxy)-3,4-difluoro-2-(2-fluoro-4-iodo-phenylamino)-benzamide, wherein each component of the capsule is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more lubricants; and (e) a gelatin capsule which encapsulates components (a)-(d).

In some aspects, the capsule comprises about 1 mg of one or more crystalline or amorphous forms of N—((R)-2,3-dihydroxypropoxy)-3,4-difluoro-2-(2-fluoro-4-iodo-phenylamino)-benzamide, wherein each component of the capsule is as follows: (a) about 0.25 wt/wt % to about 1.5 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) about 0.5 wt/wt % to about 2 wt/wt % of one or more lubricants; and (e) a gelatin capsule which encapsulates components (a)-(d).

In some aspects, the capsule comprises about 2 mg of one or more crystalline or amorphous forms of N—((R)-2,3-dihydroxypropoxy)-3,4-difluoro-2-(2-fluoro-4-iodo-phenylamino)-benzamide, wherein each component of the capsule is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more lubricants; and (e) a gelatin capsule which encapsulates components (a)-(d).

In some aspects, the capsule comprises about 2 mg of one or more crystalline or amorphous forms of N—((R)-2,3-dihydroxypropoxy)-3,4-difluoro-2-(2-fluoro-4-iodo-phenylamino)-benzamide, wherein each component of the capsule is as follows: (a) about 0.25 wt/wt % to about 1.5 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) about 0.5 wt/wt % to about 2 wt/wt % of one or more lubricants; and (e) a gelatin capsule which encapsulates components (a)-(d). In some aspects, the capsule comprises about 3 mg of one or more crystalline or amorphous forms of N—((R)-2,3-dihydroxypropoxy)-3,4-difluoro-2-(2-fluoro-4-iodo-phenylamino)-benzamide described herein, wherein each component of the capsule is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more lubricants; and (e) a gelatin capsule which encapsulates components (a)-(d).

In some aspects, the capsule comprises about 3 mg of one or more crystalline or amorphous forms of N—((R)-2,3-dihydroxypropoxy)-3,4-difluoro-2-(2-fluoro-4-iodo-phenylamino)-benzamide described herein, wherein each component of the capsule is as follows: (a) about 0.25 wt/wt % to about 1.5 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) about 0.5 wt/wt % to about 2 wt/wt % of one or more lubricants; and (e) a gelatin capsule which encapsulates components (a)-(d). In some aspects, the capsule comprises about 4 mg of one or more crystalline or amorphous forms of N—((R)-2,3-dihydroxypropoxy)-3,4-difluoro-2-(2-fluoro-4-iodo-phenylamino)-benzamide, wherein each component of the capsule is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more lubricants; and (e) a gelatin capsule which encapsulates components (a)-(d).

In some aspects, the capsule comprises about 4 mg of one or more crystalline or amorphous forms of N—((R)-2,3-dihydroxypropoxy)-3,4-difluoro-2-(2-fluoro-4-iodo-phenylamino)-benzamide, wherein each component of the capsule is as follows: (a) about 0.25 wt/wt % to about 1.5 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) about 0.5 wt/wt % to about 2 wt/wt % of one or more lubricants; and (e) a gelatin capsule which encapsulates components (a)-(d).

In some aspects, the capsule comprises about 5 mg of one or more crystalline or amorphous forms of N—((R)-2,3-dihydroxypropoxy)-3,4-difluoro-2-(2-fluoro-4-iodo-phenylamino)-benzamide, wherein each component of the capsule is as follows: (a) about 2.5 wt/wt % to about 7.0 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; and (d) a gelatin capsule which encapsulates components (a)-(c).

In some aspects, the capsule comprises about 5 mg of one or more crystalline or amorphous forms of N—((R)-2,3-dihydroxypropoxy)-3,4-difluoro-2-(2-fluoro-4-iodo-phenylamino)-benzamide, wherein each component of the capsule is as follows: (a) about 2.5 wt/wt % to about 7.0 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; and (d) a gelatin capsule which encapsulates components (a)-(c).

In some aspects, the pharmaceutical composition is a tablet (e.g., dispersible tablet). In some aspects, the tablet is a dispersible tablet. In some aspects, the tablet (e.g., dispersible tablet) comprises about 0.5 mg of a crystalline or amorphous form of N—((R)-2,3-dihydroxypropoxy)-3,4-difluoro-2-(2-fluoro-4-iodo-phenylamino)-benzamide described herein, and wherein each component of the tablet (e.g., dispersible tablet) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the tablet (e.g., dispersible tablet) comprises about 0.5 mg of a crystalline or amorphous form of N—((R)-2,3-dihydroxypropoxy)-3,4-difluoro-2-(2-fluoro-4-iodo-phenylamino)-benzamide described herein, and wherein each component of the tablet (e.g., dispersible tablet) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c)

about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the tablet (e.g., dispersible tablet) comprises about 1 mg of a crystalline or amorphous form of N—((R)-2,3-dihydroxypropoxy)-3,4-difluoro-2-(2-fluoro-4-iodo-phenylamino)-benzamide described herein, and wherein each component of the tablet (e.g., dispersible tablet) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the tablet (e.g., dispersible tablet) comprises about 1 mg of a crystalline or amorphous form of N—((R)-2,3-dihydroxypropoxy)-3,4-difluoro-2-(2-fluoro-4-iodo-phenylamino)-benzamide described herein, and wherein each component of the tablet (e.g., dispersible tablet) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the tablet (e.g, dispersible tablet) comprises about 2 mg of a crystalline or amorphous form of N—((R)-2,3-dihydroxypropoxy)-3,4-difluoro-2-(2-fluoro-4-iodo-phenylamino)-benzamide described herein, and wherein each component of the tablet (e.g., dispersible tablet) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the tablet (e.g, dispersible tablet) comprises about 2 mg of a crystalline or amorphous form of N—((R)-2,3-dihydroxypropoxy)-3,4-difluoro-2-(2-fluoro-4-iodo-phenylamino)-benzamide described herein, and wherein each component of the tablet (e.g., dispersible tablet) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the tablet (e.g., dispersible tablet) comprises about 3 mg of a crystalline or amorphous form of N—((R)-2,3-dihydroxypropoxy)-3,4-difluoro-2-(2-fluoro-4-iodo-phenylamino)-benzamide described herein, and wherein each component of the tablet (e.g., dispersible tablet) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the tablet (e.g., dispersible tablet) comprises about 3 mg of a crystalline or amorphous form of N—((R)-2,3-dihydroxypropoxy)-3,4-difluoro-2-(2-fluoro-4-iodo-phenylamino)-benzamide described herein, and wherein each component of the tablet (e.g., dispersible tablet) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the tablet (e.g., dispersible tablet) comprises about 4 mg of a crystalline or amorphous form of N—((R)-2,3-dihydroxypropoxy)-3,4-difluoro-2-(2-fluoro-4-iodo-phenylamino)-benzamide described herein, and wherein each component of the tablet (e.g, dispersible tablet) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the tablet (e.g., dispersible tablet) comprises about 4 mg of a crystalline or amorphous form of N—((R)-2,3-dihydroxypropoxy)-3,4-difluoro-2-(2-fluoro-4-iodo-phenylamino)-benzamide described herein, and wherein each component of the tablet (e.g, dispersible tablet) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the tablet (e.g., dispersible tablet) comprises about 5 mg of a crystalline or amorphous form of N—((R)-2,3-dihydroxypropoxy)-3,4-difluoro-2-(2-fluoro-4-iodo-phenylamino)-benzamide described herein, and wherein each component of the tablet (e.g., dispersible tablet) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the tablet (e.g., dispersible tablet) comprises about 5 mg of a crystalline or amorphous form of N—((R)-2,3-dihydroxypropoxy)-3,4-difluoro-2-(2-fluoro- 4-iodo-phenylamino)-benzamide described herein, and wherein each component of the tablet (e.g., dispersible tablet) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the tablet (e.g., dispersible tablet) comprises about 0.1 mg to about 5 mg of N—((R)-2,3-dihydroxypropoxy)-3,4-difluoro-2-(2-fluoro-4-iodo-phenylamino)-benzamide; wherein the pharmaceutical composition is dispersible in a potable liquid; and wherein each component of the pharmaceutical composition is as follows: (a) about 0.1 wt/wt % to about 7 wt/wt % of a crystalline form of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the tablet (e.g., dispersible tablet) comprises about 0.1 mg to about 5 mg of N—((R)-2,3-dihydroxypropoxy)-3,4-difluoro-2-(2-fluoro-4-iodo-phenylamino)-benzamide; wherein the pharmaceutical composition is dispersible in a potable liquid; and wherein each component of the pharmaceutical composition is as follows: (a) about 0.5 wt/wt % to about 1.2 wt/wt % of a crystalline form of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the tablet (e.g., dispersible tablet) is dissolved in a potable liquid before administration. In some aspects, the potable liquid is water, milk or a juice (e.g., orange juice or apple juice). In some aspects, the potable liquid is water. In some aspects, the potable liquid is a juice. In some aspects, the tablet is orodispersible in a subject's saliva.

In some aspects, the pharmaceutical composition is a powder (e.g., dispersible powder). In some aspects, the powder (e.g., dispersible powder) is a dispersible powder. In some aspects, a capsule or sachet comprises the dispersible powder. In some aspects, the powder (e.g., dispersible powder) comprises about 0.5 mg of a crystalline or amorphous form of N—((R)-2,3-dihydroxypropoxy)-3,4-difluoro-2-(2-fluoro-4-iodo-phenylamino)-benzamide described herein, and wherein each component of the powder (e.g., dispersible powder) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the powder (e.g., dispersible powder) comprises about 0.5 mg of a crystalline or amorphous form of N—((R)-2,3-dihydroxypropoxy)-3,4-difluoro-2-(2-fluoro-4-iodo-phenylamino)-benzamide described herein, and wherein each component of the powder (e.g., dispersible powder) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the powder (e.g., dispersible powder) comprises about 1 mg of a crystalline or amorphous form of N—((R)-2,3-dihydroxypropoxy)-3,4-difluoro-2-(2-fluoro-4-iodo-phenylamino)-benzamide described herein, and wherein each component of the powder (e.g., dispersible powder) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the powder (e.g., dispersible powder) comprises about 1 mg of a crystalline or amorphous form of N—((R)-2,3-dihydroxypropoxy)-3,4-difluoro-2-(2-fluoro-4-iodo-phenylamino)-benzamide described herein, and wherein each component of the powder (e.g., dispersible powder) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the powder (e.g, dispersible powder) comprises about 2 mg of a crystalline or amorphous form of N—((R)-2,3-dihydroxypropoxy)-3,4-difluoro-2-(2-fluoro-4-iodo-phenylamino)-benzamide described herein, and wherein each component of the powder (e.g., dispersible powder) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the powder (e.g, dispersible powder) comprises about 2 mg of a crystalline or amorphous form of N—((R)-2,3-dihydroxypropoxy)-3,4-difluoro-2-(2-fluoro-4-iodo-phenylamino)-benzamide described herein, and wherein each component of the powder (e.g., dispersible powder) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the powder (e.g., dispersible powder) comprises about 3 mg of a crystalline or amorphous form of N—((R)-2,3-dihydroxypropoxy)-3,4-difluoro-2-(2-fluoro-4-iodo-phenylamino)-benzamide described herein, and wherein each component of the powder (e.g., dispersible powder) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the powder (e.g., dispersible powder) comprises about 3 mg of a crystalline or amorphous form of N—((R)-2,3-dihydroxypropoxy)-3,4-difluoro-2-(2-fluoro-4-iodo-phenylamino)-benzamide described herein, and wherein each component of the powder (e.g., dispersible powder) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the powder (e.g., dispersible powder) comprises about 4 mg of a crystalline or amorphous form of N—((R)-2,3-dihydroxypropoxy)-3,4-difluoro-2-(2-fluoro-4-iodo-phenylamino)-benzamide described herein, and wherein each component of the powder (e.g, dispersible powder) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the powder (e.g., dispersible powder) comprises about 4 mg of a crystalline or amorphous form of N—((R)-2,3-dihydroxypropoxy)-3,4-difluoro-2-(2-fluoro-4-iodo-phenylamino)-benzamide described herein, and wherein each component of the powder (e.g, dispersible powder) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the powder (e.g., dispersible powder) comprises about 5 mg of a crystalline or amorphous form of N—((R)-2,3-dihydroxypropoxy)-3,4-difluoro-2-(2-fluoro-4-iodo-phenylamino)-benzamide described herein, and wherein each component of the powder (e.g., dispersible powder) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the powder (e.g., dispersible powder) comprises about 5 mg of a crystalline or amorphous form of N—((R)-2,3-dihydroxypropoxy)-3,4-difluoro-2-(2-fluoro-4-iodo-phenylamino)-benzamide described herein, and wherein each component of the powder (e.g., dispersible powder) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the powder (e.g., dispersible powder) comprises about 0.1 mg to about 5 mg of N—((R)-2,3-dihydroxypropoxy)-3,4-difluoro-2-(2-fluoro-4-iodo-phenylamino)-benzamide; wherein the pharmaceutical composition is dispersible in a potable liquid; and wherein each component of the pharmaceutical composition is as follows: (a) about 0.1 wt/wt % to about 7 wt/wt % of a crystalline form of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the powder (e.g., dispersible powder) comprises about 0.1 mg to about 5 mg of N—((R)-2,3-dihydroxypropoxy)-3,4-difluoro-2-(2-fluoro-4-iodo-phenylamino)-benzamide; wherein the pharmaceutical composition is dispersible in a potable liquid; and wherein each component of the pharmaceutical composition is as follows: (a) about 0.5 wt/wt % to about 1.2 wt/wt % of a crystalline form of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the powder (e.g., dispersible powder) is dissolved in a potable liquid before administration. In some aspects, the potable liquid is water, milk or a juice (e.g., orange juice or apple juice). In some aspects, the potable liquid is water. In some aspects, the potable liquid is a juice. In some aspects, the powder is orodispersible in a subject's saliva.

In some aspects, the pharmaceutical composition is in the form of granules (e.g., dispersible granules). In some aspects, the granules (e.g., dispersible granules) are dispersible granules. In some aspects, a capsule or sachet comprises the dispersible granules. In some aspects, the granules (e.g., dispersible granules) comprise about 0.5 mg of a crystalline or amorphous form of N—((R)-2,3-dihydroxypropoxy)-3,4-difluoro-2-(2-fluoro-4-iodo-phenylamino)-benzamide described herein, and wherein each component of the granules (e.g., dispersible granules) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the granules (e.g., dispersible granules) comprise about 0.5 mg of a crystalline or amorphous form of N—((R)-2,3-dihydroxypropoxy)-3,4-difluoro-2-(2-fluoro-4-iodo-phenylamino)-benzamide described herein, and wherein each component of the granules (e.g., dispersible granules) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the granules (e.g., dispersible granules) comprise about 1 mg of a crystalline or amorphous form of N—((R)-2,3-dihydroxypropoxy)-3,4-difluoro-2-(2-fluoro-4-iodo-phenylamino)-benzamide described herein, and wherein each component of the granules (e.g., dispersible granules) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the granules (e.g., dispersible granules) comprise about 1 mg of a crystalline or amorphous form of N—((R)-2,3-dihydroxypropoxy)-3,4-difluoro-2-(2-fluoro-4-iodo-phenylamino)-benzamide described herein, and wherein each component of the granules (e.g., dispersible granules) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the granules (e.g, dispersible granules) comprise about 2 mg of a crystalline or amorphous form of N—((R)-2,3-dihydroxypropoxy)-3,4-difluoro-2-(2-fluoro-4-iodo-phenylamino)-benzamide described herein, and wherein each component of the granules (e.g., dispersible granules) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the granules (e.g, dispersible granules) comprise about 2 mg of a crystalline or amorphous form of N—((R)-2,3-dihydroxypropoxy)-3,4-difluoro-2-(2-fluoro-4-iodo-phenylamino)-benzamide described herein, and wherein each component of the granules (e.g., dispersible granules) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the granules (e.g., dispersible granules) comprise about 3 mg of a crystalline or amorphous form of N—((R)-2,3-dihydroxypropoxy)-3,4-difluoro-2-(2-fluoro-4-iodo-phenylamino)-benzamide described herein, and wherein each component of the granules (e.g., dispersible granules) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the granules (e.g., dispersible granules) comprise about 3 mg of a crystalline or amorphous form of N—((R)-2,3-dihydroxypropoxy)-3,4-difluoro-2-(2-fluoro-4-iodo-phenylamino)-benzamide described herein, and wherein each component of the granules (e.g., dispersible granules) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the granules (e.g., dispersible granules) comprise about 4 mg of a crystalline or amorphous form of N—((R)-2,3-dihydroxypropoxy)-3,4-difluoro-2-(2-fluoro-4-iodo-phenylamino)-benzamide described herein, and wherein each component of the granules (e.g, dispersible granules) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the granules (e.g., dispersible granules) comprise about 4 mg of a crystalline or amorphous form of N—((R)-2,3-dihydroxypropoxy)-3,4-difluoro-2-(2-fluoro-4-iodo-phenylamino)-benzamide described herein, and wherein each component of the granules (e.g, dispersible granules) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the granules (e.g., dispersible granules) comprise about 5 mg of a crystalline or amorphous form of N—((R)-2,3-dihydroxypropoxy)-3,4-difluoro-2-(2-fluoro-4-iodo-phenylamino)-benzamide described herein, and wherein each component of the granules (e.g., dispersible granules) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the granules (e.g., dispersible granules) comprise about 5 mg of a crystalline or amorphous form of N—((R)-2,3-dihydroxypropoxy)-3,4-difluoro-2-(2-fluoro-4-iodo-phenylamino)-benzamide described herein, and wherein each component of the granules (e.g., dispersible granules) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the granules (e.g., dispersible granules) comprise about 0.1 mg to about 5 mg of N—((R)-2,3-dihydroxypropoxy)-3,4-difluoro-2-(2-fluoro-4-iodo-phenylamino)-benzamide; wherein the pharmaceutical composition is dispersible in a potable liquid; and wherein each component of the pharmaceutical composition is as follows: (a) about 0.1 wt/wt % to about 7 wt/wt % of a crystalline form of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the granules (e.g., dispersible granules) comprise about 0.1 mg to about 5 mg of N—((R)-2,3-dihydroxypropoxy)-3,4-difluoro-2-(2-fluoro-4-iodo-phenylamino)-benzamide; wherein the pharmaceutical composition is dispersible in a potable liquid; and wherein each component of the pharmaceutical composition is as follows: (a) about 0.5 wt/wt % to about 1.2 wt/wt % of a crystalline form of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the granules (e.g., dispersible granules) are dissolved in a potable liquid before administration. In some aspects, the potable liquid is water, milk or a juice (e.g., orange juice or apple juice). In some aspects, the potable liquid is water. In some aspects, the potable liquid is a juice. In some aspects, the granules are orodispersible in a subject's saliva.

In some aspects, the pharmaceutical composition is in the form of minitablets (e.g., dispersible minitablets). In some aspects, the minitablets are dispersible minitablets. In some aspects, the minitablets (e.g., dispersible minitablets) comprise about 0.5 mg of a crystalline or amorphous form of N—((R)-2,3-dihydroxypropoxy)-3,4-difluoro-2-(2-fluoro-4-iodo-phenylamino)-benzamide described herein, and wherein each component of the minitablets (e.g., dispersible minitablets) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the minitablets (e.g., dispersible minitablets) comprise about 0.5 mg of a crystalline or amorphous form of N—((R)-2,3-dihydroxypropoxy)-3,4-difluoro-2-(2-fluoro-4-iodo-phenylamino)-benzamide described herein, and wherein each component of the minitablets (e.g., dispersible minitablets) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the minitablets (e.g., dispersible minitablets) comprise about 1 mg of a crystalline or amorphous form of N—((R)-2,3-dihydroxypropoxy)-3,4-difluoro-2-(2-fluoro-4-iodo-phenylamino)-benzamide described herein, and wherein each component of the minitablets (e.g., dispersible minitablets) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the minitablets (e.g., dispersible minitablets) comprise about 1 mg of a crystalline or amorphous form of N—((R)-2,3-dihydroxypropoxy)-3,4-difluoro-2-(2-fluoro-4-iodo-phenylamino)-benzamide described herein, and wherein each component of the minitablets (e.g., dispersible minitablets) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the minitablets (e.g, dispersible minitablets) comprise about 2 mg of a crystalline or amorphous form of N—((R)-2,3-dihydroxypropoxy)-3,4-difluoro-2-(2-fluoro-4-iodo-phenylamino)-benzamide described herein, and wherein each component of the minitablets (e.g., dispersible minitablets) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the minitablets (e.g, dispersible minitablets) comprise about 2 mg of a crystalline or amorphous form of N—((R)-2,3-dihydroxypropoxy)-3,4-difluoro-2-(2-fluoro-4-iodo-phenylamino)-benzamide described herein, and wherein each component of the minitablets (e.g., dispersible minitablets) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the minitablets (e.g., dispersible minitablets) comprise about 3 mg of a crystalline or amorphous form of N—((R)-2,3-dihydroxypropoxy)-3,4-difluoro-2-(2-fluoro-4-iodo-phenylamino)-benzamide described herein, and wherein each component of the minitablets (e.g., dispersible minitablets) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the minitablets (e.g., dispersible minitablets) comprise about 3 mg of a crystalline or amorphous form of N—((R)-2,3-dihydroxypropoxy)-3,4-difluoro-2-(2-fluoro-4-iodo-phenylamino)-benzamide described herein, and wherein each component of the minitablets (e.g., dispersible minitablets) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the minitablets (e.g., dispersible minitablets) comprise about 4 mg of a crystalline or amorphous form of N—((R)-2,3-dihydroxypropoxy)-3,4-difluoro-2-(2-fluoro-4-iodo-phenylamino)-benzamide described herein, and wherein each component of the minitablets (e.g, dispersible minitablets) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the minitablets (e.g., dispersible minitablets) comprise about 4 mg of a crystalline or amorphous form of N—((R)-2,3-dihydroxypropoxy)-3,4-difluoro-2-(2-fluoro-4-iodo-phenylamino)-benzamide described herein, and wherein each component of the minitablets (e.g, dispersible minitablets) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the minitablets (e.g., dispersible minitablets) comprise about 5 mg of a crystalline or amorphous form of N—((R)-2,3-dihydroxypropoxy)-3,4-difluoro-2-(2-fluoro-4-iodo-phenylamino)-benzamide described herein, and wherein each component of the minitablets (e.g., dispersible minitablets) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the minitablets (e.g., dispersible minitablets) comprise about 5 mg of a crystalline or amorphous form of N—((R)-2,3-dihydroxypropoxy)-3,4-difluoro-2-(2-fluoro-4-iodo-phenylamino)-benzamide described herein, and wherein each component of the minitablets (e.g., dispersible minitablets) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the minitablets (e.g., dispersible minitablets) comprise about 0.1 mg to about 5 mg of N—((R)-2,3-dihydroxypropoxy)-3,4-difluoro-2-(2-fluoro-4-iodo-phenylamino)-benzamide; wherein the pharmaceutical composition is dispersible in a potable liquid; and wherein each component of the pharmaceutical composition is as follows: (a) about 0.1 wt/wt % to about 7 wt/wt % of a crystalline form of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the minitablets (e.g., dispersible minitablets) comprise about 0.1 mg to about 5 mg of N—((R)-2,3-dihydroxypropoxy)-3,4-difluoro-2-(2-fluoro-4-iodo-phenylamino)-benzamide; wherein the pharmaceutical composition is dispersible in a potable liquid; and wherein each component of the pharmaceutical composition is as follows: (a) about 0.5 wt/wt % to about 1.2 wt/wt % of a crystalline form of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the minitablets (e.g., dispersible minitablets) are dissolved in a potable liquid before administration. In some aspects, the potable liquid is water, milk or a juice (e.g., orange juice or apple juice). In some aspects, the potable liquid is water. In some aspects, the potable liquid is a juice. In some aspects, the minitablets are orodispersible in a subject's saliva.

In some aspects, the pharmaceutical composition is in the form of pellets (e.g., dispersible pellet). In some aspects, the pellets are dispersible pellets. In some aspects, the pellets (e.g., dispersible pellets) comprise about 0.5 mg of a crystalline or amorphous form of N—((R)-2,3-dihydroxypropoxy)-3,4-difluoro-2-(2-fluoro-4-iodo-phenylamino)-benzamide described herein, and wherein each component of the pellets (e.g., dispersible pellets) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the pellets (e.g., dispersible pellets) comprise about 0.5 mg of a crystalline or amorphous form of N—((R)-2,3-dihydroxypropoxy)-3,4-difluoro-2-(2-fluoro-4-iodo-phenylamino)-benzamide described herein, and wherein each component of the pellets (e.g., dispersible pellets) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the pellets (e.g., dispersible pellets) comprise about 1 mg of a crystalline or amorphous form of N—((R)-2,3-dihydroxypropoxy)-3,4-difluoro-2-(2-fluoro-4-iodo-phenylamino)-benzamide described herein, and wherein each component of the pellets (e.g., dispersible pellets) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the pellets (e.g., dispersible pellets) comprise about 1 mg of a crystalline or amorphous form of N—((R)-2,3-dihydroxypropoxy)-3,4-difluoro-2-(2-fluoro-4-iodo-phenylamino)-benzamide described herein, and wherein each component of the pellets (e.g., dispersible pellets) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the pellets (e.g, dispersible pellets) comprise about 2 mg of a crystalline or amorphous form of N—((R)-2,3-dihydroxypropoxy)-3,4-difluoro-2-(2-fluoro-4-iodo-phenylamino)-benzamide described herein, and wherein each component of the pellets (e.g., dispersible pellets) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the pellets (e.g, dispersible pellets) comprise about 2 mg of a crystalline or amorphous form of N—((R)-2,3-dihydroxypropoxy)-3,4-difluoro-2-(2-fluoro-4-iodo-phenylamino)-benzamide described herein, and wherein each component of the pellets (e.g., dispersible pellets) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the pellets (e.g., dispersible pellets) comprise about 3 mg of a crystalline or amorphous form of N—((R)-2,3-dihydroxypropoxy)-3,4-difluoro-2-(2-fluoro-4-iodo-phenylamino)-benzamide described herein, and wherein each component of the pellets (e.g., dispersible pellets) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the pellets (e.g., dispersible pellets) comprise about 3 mg of a crystalline or amorphous form of N—((R)-2,3-dihydroxypropoxy)-3,4-difluoro-2-(2-fluoro-4-iodo-phenylamino)-benzamide described herein, and wherein each component of the pellets (e.g., dispersible pellets) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the pellets (e.g., dispersible pellets) comprise about 4 mg of a crystalline or amorphous form of N—((R)-2,3-dihydroxypropoxy)-3,4-difluoro-2-(2-fluoro-4-iodo-phenylamino)-benzamide described herein, and wherein each component of the pellets (e.g, dispersible pellets) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the pellets (e.g., dispersible pellets) comprise about 4 mg of a crystalline or amorphous form of N—((R)-2,3-dihydroxypropoxy)-3,4-difluoro-2-(2-fluoro-4-iodo-phenylamino)-benzamide described herein, and wherein each component of the pellets (e.g, dispersible pellets) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the pellets (e.g., dispersible pellets) comprise about 5 mg of a crystalline or amorphous form of N—((R)-2,3-dihydroxypropoxy)-3,4-difluoro-2-(2-fluoro-4-iodo-phenylamino)-benzamide described herein, and wherein each component of the pellets (e.g., dispersible pellets) is as follows: (a) about 0.1 wt/wt % to about 7 wt/wt % of the N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the pellets (e.g., dispersible pellets) comprise about 5 mg of a crystalline or amorphous form of N—((R)-2,3-dihydroxypropoxy)-3,4-difluoro-2-(2-fluoro-4-iodo-phenylamino)-benzamide described herein, and wherein each component of the pellets (e.g., dispersible pellets) is as follows: (a) about 0.5 wt/wt % to about 1.2 wt/wt % of the N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the pellets (e.g., dispersible pellets) comprise about 0.1 mg to about 5 mg of N—((R)-2,3-dihydroxypropoxy)-3,4-difluoro-2-(2-fluoro-4-iodo-phenylamino)-benzamide; wherein the pharmaceutical composition is dispersible in a potable liquid; and wherein each component of the pharmaceutical composition is as follows: (a) about 0.1 wt/wt % to about 7 wt/wt % of a crystalline form of N—((R)-2,3-dihydroxypropoxy)-3,4-difluoro-2-(2-fluoro-4-iodo-phenylamino)-benzamide; (b) about 50 wt/wt % to about 98 wt/wt % of one or more diluents; (c) about 1 wt/wt % to about 10 wt/wt % of one or more disintegrants; (d) 0 wt/wt % to about 5 wt/wt % of one or more flavoring agents; (e) 0 wt/wt % to about 5 wt/wt % of one or more sweeteners; and (f) 0 wt/wt % to about 5 wt/wt % of one or more lubricants.

In some aspects, the pellets (e.g., dispersible pellets) comprise about 0.1 mg to about 5 mg of N—((R)-2,3-dihydroxypropoxy)-3,4-difluoro-2-(2-fluoro-4-iodo-phenylamino)-benzamide; wherein the pharmaceutical composition is dispersible in a potable liquid; and wherein each component of the pharmaceutical composition is as follows: (a) about 0.5 wt/wt % to about 1.2 wt/wt % of a crystalline form of N—((R)-2,3-dihydroxypropoxy)-3,4-difluoro-2-(2-fluoro-4-iodo-phenylamino)-benzamide; (b) about 85 wt/wt % to about 95 wt/wt % of one or more diluents; (c) about 3.5 wt/wt % to about 6 wt/wt % of one or more disintegrants; (d) 0 wt/wt % to about 2.5 wt/wt % of one or more flavoring agents; (e) 0 wt/wt % to about 2 wt/wt % of one or more sweeteners; and (f) about 0.5 wt/wt % to about 2 wt/wt % of one or more lubricants.

In some aspects, the pellets (e.g., dispersible pellets) are dissolved in a potable liquid before administration. In some aspects, the potable liquid is water, milk or a juice (e.g., orange juice or apple juice). In some aspects, the potable liquid is water. In some aspects, the potable liquid is a juice. In some aspects, the pellets are orodispersible in a subject's saliva.

Methods of Treatment

In some aspects, the present disclosure provides a method of treating a tumor, a cancer, or a Rasopathy disorder comprising administering to a subject in need of such treatment a pharmaceutical composition described herein.

In some aspects, the tumor is a neurofibroma. In some aspects, the tumor is a neurofibroma associated with Neurofibromatosis Type 1. In some aspects, the tumor is selected from the group consisting of cutaneous neurofibroma, plexiform neurofibroma, optic pathway glioma, low grade glioma, high grade glioma, or malignant peripheral nerve sheath tumor. In some aspects, the tumor is plexiform neurofibroma.

In some aspects, the subject has been diagnosed with a Rasopathy disorder selected from the group consisting of neurofibromatosis type 1, neurofibromatosis type 2, cardio-facio-cutaneous syndrome, Costello syndrome, Legius syndrome, Noonan syndrome, and Noonan syndrome with multiple lentigines.

In some aspects, the cancer is selected from the group consisting of skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum. In some aspects, the leukemia is selected from the group consisting of acute lymphocytic leukemia, acute myelogenous leukemia, chronic lymphocytic leukemia, and chronic myelogenous leukemia. In some aspects, the lymphoma is selected from the group consisting of B-cell lymphoma, T-cell lymphoma, Burkitt's lymphoma, follicular lymphoma, mantle cell lymphoma, primary mediastinal B cell lymphoma, small lymphocytic lymphoma, and Waldenstrom macroglobulinemia. In some aspects, the lung cancer is selected from the group consisting of lung adenocarcinoma, squamous non-small cell lung cancer, non-squamous non-small cell lung cancer, and small cell lung cancer.

In some aspects, the subject bears a mutation or other aberration in one or more genes for which the mutation or other aberration causes a gain or loss of function characteristic of certain cancers, wherein the mutation or other aberration in one or more genes is a mutation or other aberration in one or more of KRAS, NRAS, HRAS, BRAF, MEK1, MEK2, RASA1, MAP2K4, NF1, or NF2.

In some aspects, an individual dose of the N—((R)-2,3-dihydroxypropoxy)-3,4-difluoro-2-(2-fluoro-4-iodo-phenylamino)-benzamide is administered as more than one capsule, tablet (e.g., dispersible tablet), dose of powder (e.g, dispersible powder), dose of granules (e.g., dispersible granules), dose of minitablets (e.g., dispersible minitablets), dose of pellets (e.g., dispersible pellets), or a combination thereof. For example, a dose of 3 mg of the N—((R)-2,3-dihydroxypropoxy)-3,4-difluoro-2-(2-fluoro-4-iodo-phenylamino)-benzamide can be administered as two capsules—one containing 2 mg and the other containing 1 mg or as three capsules each containing 1 mg. As another example, a dose of 1.5 mg of the N—((R)-2,3-dihydroxypropoxy)-3,4-difluoro-2-(2-fluoro-4-iodo-phenylamino)-benzamide can be administered as two dispersible dosage forms—one dispersible tablet containing 1 mg and a separate unit of dispersible powder containing 0.5 mg or as three units of dispersible powder each containing 0.5 mg.

In some aspects, if the N—((R)-2,3-dihydroxypropoxy)-3,4-difluoro-2-(2-fluoro-4-iodo-phenylamino)-benzamide is to be administered more than one time a day, the total daily dose of the N—((R)-2,3-dihydroxypropoxy)-3,4-difluoro-2-(2-fluoro-4-iodo-phenylamino)-benzamide can be divided so the patient receives different doses at each administration. For example, if the total daily dose of the N—((R)-2,3-dihydroxypropoxy)-3,4-difluoro-2-(2-fluoro-4-iodo-phenylamino)-benzamide is to be 2 mg administered two times per day, the patient can receive 0.5 mg (e.g., as one 0.5 mg tablet (e.g., dispersible tablet)) in the morning and 1.5 mg (e.g., as one 0.5 mg dose of powder (e.g., dispersible powder) and one 1 mg capsule) in the evening.

In some aspects, the N—((R)-2,3-dihydroxypropoxy)-3,4-difluoro-2-(2-fluoro-4-iodo-phenylamino)-benzamide is provided in an amount of about 0.1 mg to about 20 mg per dose of the pharmaceutical compositions described herein. In some aspects, one or more crystalline or amorphous forms of N—((R)-2,3-dihydroxypropoxy)-3,4-difluoro-2-(2-fluoro-4-iodo-phenylamino)-benzamide is provided in an amount of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg per dose. In some aspects, one or more crystalline or amorphous forms of N—((R)-2,3-dihydroxypropoxy)-3,4-difluoro-2-(2-fluoro-4-iodo-phenylamino)-benzamide is provided in an amount of about 0.5 mg per dose. In some aspects, one or more crystalline or amorphous forms of N—((R)-2,3-dihydroxypropoxy)-3,4-difluoro-2-(2-fluoro-4-iodo-phenylamino)-benzamide is provided in an amount of about 1 mg per dose. In some aspects, one or more crystalline or amorphous forms of N—((R)-2,3-dihydroxypropoxy)-3,4-difluoro-2-(2-fluoro-4-iodo-phenylamino)-benzamide is provided in an amount of about 2 mg per dose. In some aspects, one or more crystalline or amorphous forms of N—((R)-2,3-dihydroxypropoxy)-3,4-difluoro-2-(2-fluoro-4-iodo-phenylamino)-benzamide is provided in an amount of about 3 mg per dose. In some aspects, one or more crystalline or amorphous forms of N—((R)-2,3-dihydroxypropoxy)-3,4-difluoro-2-(2-fluoro-4-iodo-phenylamino)-benzamide is provided in an amount of about 4 mg per dose. In some aspects, one or more crystalline or amorphous forms of N—((R)-2,3-dihydroxypropoxy)-3,4-difluoro-2-(2-fluoro-4-iodo-phenylamino)-benzamide is provided in an amount of about 5 mg per dose. In some aspects, one or more crystalline or amorphous forms of N—((R)-2,3-dihydroxypropoxy)-3,4-difluoro-2-(2-fluoro-4-iodo-phenylamino)-benzamide is provided in an amount of about 10 mg per dose. In some aspects, one or more crystalline or amorphous forms of N—((R)-2,3-dihydroxypropoxy)-3,4-difluoro-2-(2-fluoro-4-iodo-phenylamino)-benzamide is provided in an amount of about 20 mg per dose.

In some aspects, the pharmaceutical composition comprising one or more crystalline or amorphous forms of N—((R)-2,3-dihydroxypropoxy)-3,4-difluoro-2-(2-fluoro-4-iodo-phenylamino)-benzamide is administered one time, two times, three times, or four times per day. In some aspects, the total daily dose of the N—((R)-2,3-dihydroxypropoxy)-3,4-difluoro-2-(2-fluoro-4-iodo-phenylamino)-benzamide is administered two times per day.

In some aspects, the present disclosure provides a method of treating a tumor, a cancer, or a Rasopathy disorder comprising administering to a patient in need of such treatment a pharmaceutical composition described herein, wherein the total daily dose of the N—((R)-2,3-dihydroxypropoxy)-3,4-difluoro-2-(2-fluoro-4-iodo-phenylamino)-benzamide is administered two times daily of about 0.1 mg to about 10 mg each.

In some aspects, the N—((R)-2,3-dihydroxypropoxy)-3,4-difluoro-2-(2-fluoro-4-iodo-phenylamino)-benzamide is administered via a pharmaceutical composition described herein, wherein the N—((R)-2,3-dihydroxypropoxy)-3,4-difluoro-2-(2-fluoro-4-iodo-phenylamino)-benzamide is provided at a total daily dose that does not exceed 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg. In some aspects, the N—((R)-2,3-dihydroxypropoxy)-3,4-difluoro-2-(2-fluoro-4-iodo-phenylamino)-benzamide is administered in a total daily dose that does not exceed 20 mg. In some aspects, the N—((R)-2,3-dihydroxypropoxy)-3,4-difluoro-2-(2-fluoro-4-iodo-phenylamino)-benzamide is administered in a total daily dose that does not exceed 15 mg. In some aspects, the N—((R)-2,3-dihydroxypropoxy)-3,4-difluoro-2-(2-fluoro-4-iodo-phenylamino)-benzamide is administered in a total daily dose that does not exceed 12 mg. In some aspects, the N—((R)-2,3-dihydroxypropoxy)-3,4-difluoro-2-(2-fluoro-4-iodo-phenylamino)-benzamide is administered in a total daily dose that does not exceed 10 mg. In some aspects, the N—((R)-2,3-dihydroxypropoxy)-3,4-difluoro-2-(2-fluoro-4-iodo-phenylamino)-benzamide is administered in a total daily dose that does not exceed 8 mg. In some aspects, the N—((R)-2,3-dihydroxypropoxy)-3,4-difluoro-2-(2-fluoro-4-iodo-phenylamino)-benzamide is administered in a total daily dose that does not exceed 6 mg. In some aspects, the N—((R)-2,3-dihydroxypropoxy)-3,4-difluoro-2-(2-fluoro-4-iodo-phenylamino)-benzamide is administered in a total daily dose that does not exceed 4 mg. In some aspects, the N—((R)-2,3-dihydroxypropoxy)-3,4-difluoro-2-(2-fluoro-4-iodo-phenylamino)-benzamide is administered in a total daily dose that does not exceed 2 mg. In some aspects, the N—((R)-2,3-dihydroxypropoxy)-3,4-difluoro-2-(2-fluoro-4-iodo-phenylamino)-benzamide is administered in a total daily dose that does not exceed 1 mg.

In some aspects, the present disclosure provides a method of treating a tumor, a cancer, or a Rasopathy disorder comprising administering to a patient in need of such treatment a pharmaceutical composition described herein, wherein the total daily dose of the N—((R)-2,3-dihydroxypropoxy)-3,4-difluoro-2-(2-fluoro-4-iodo-phenylamino)-benzamide is administered once daily at a dose of about 0.1 mg to about 20 mg.

In some aspects, the total daily dose of the N—((R)-2,3-dihydroxypropoxy)-3,4-difluoro-2-(2-fluoro-4-iodo-phenylamino)-benzamide is administered once daily. In some aspects, the total daily dose of the N—((R)-2,3-dihydroxypropoxy)-3,4-difluoro-2-(2-fluoro-4-iodo-phenylamino)- benzamide is administered once daily at a dose of about 0.1 mg to about 20 mg. In some aspects, the total daily dose of the N—((R)-2,3-dihydroxypropoxy)-3,4-difluoro-2-(2-fluoro-4-iodo-phenylamino)-benzamide is administered once daily at a dose of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg. In some aspects, the total daily dose of the N—((R)-2,3-dihydroxypropoxy)-3,4-difluoro-2-(2-fluoro-4-iodo-phenylamino)-benzamide is administered once daily at a dose of about 0.5 mg. In some aspects, the total daily dose of the N—((R)-2,3-dihydroxypropoxy)-3,4-difluoro-2-(2-fluoro-4-iodo-phenylamino)-benzamide is administered once daily at a dose of about 1 mg. In some aspects, the total daily dose of the N—((R)-2,3-dihydroxypropoxy)-3,4-difluoro-2-(2-fluoro-4-iodo-phenylamino)-benzamide is administered once daily at a dose of about 2 mg. In some aspects, the total daily dose of the N—((R)-2,3-dihydroxypropoxy)-3,4-difluoro-2-(2-fluoro-4-iodo-phenylamino)-benzamide is administered once daily at a dose of about 3 mg. In some aspects, the total daily dose of N—((R)-2,3-dihydroxypropoxy)-3,4-difluoro-2-(2-fluoro-4-iodo-phenylamino)-benzamide is administered once daily at a dose of about 4 mg. In some aspects, the total daily dose of the N—((R)-2,3-dihydroxypropoxy)-3,4-difluoro-2-(2-fluoro-4-iodo-phenylamino)-benzamide is administered once daily at a dose of about 5 mg. In some aspects, the total daily dose of the N—((R)-2,3-dihydroxypropoxy)-3,4-difluoro-2-(2-fluoro-4-iodo-phenylamino)-benzamide is administered once daily at a dose of about 6 mg. In some aspects, the total daily dose of the N—((R)-2,3-dihydroxypropoxy)-3,4-difluoro-2-(2-fluoro-4-iodo-phenylamino)-benzamide is administered once daily at a dose of about 7 mg. In some aspects, the total daily dose of the N—((R)-2,3-dihydroxypropoxy)-3,4-difluoro-2-(2-fluoro-4-iodo-phenylamino)-benzamide is administered once daily at a dose of about 8 mg. In some aspects, the total daily dose of the N—((R)-2,3-dihydroxypropoxy)-3,4-difluoro-2-(2-fluoro-4-iodo-phenylamino)-benzamide is administered once daily at a dose of about 9 mg. In some aspects, the total daily dose of the N—((R)-2,3-dihydroxypropoxy)-3,4-difluoro-2-(2-fluoro-4-iodo-phenylamino)-benzamide is administered once daily at a dose of about 10 mg. In some aspects, the total daily dose of the N—((R)-2,3-dihydroxypropoxy)-3,4-difluoro-2-(2-fluoro-4-iodo-phenylamino)-benzamide is administered once daily at a dose of about 11 mg. In some aspects, the total daily dose of the N—((R)-2,3-dihydroxypropoxy)-3,4-difluoro-2-(2-fluoro-4-iodo-phenylamino)-benzamide is administered once daily at a dose of about 12 mg. In some aspects, the total daily dose of the N—((R)-2,3-dihydroxypropoxy)-3,4-difluoro-2-(2-fluoro-4-iodo-phenylamino)-benzamide is administered once daily at a dose of about 13 mg. In some aspects, the total daily dose of the N—((R)-2,3-dihydroxypropoxy)-3,4-difluoro-2-(2-fluoro-4-iodo-phenylamino)-benzamide is administered once daily at a dose of about 14 mg. In some aspects, the total daily dose of the N—((R)-2,3-dihydroxypropoxy)-3,4-difluoro-2-(2-fluoro-4-iodo-phenylamino)-benzamide is administered once daily at a dose of about 15 mg. In some aspects, the total daily dose of the N—((R)-2,3-dihydroxypropoxy)-3,4-difluoro-2-(2-fluoro-4-iodo-phenylamino)-benzamide is administered once daily at a dose of about 16 mg. In some aspects, the total daily dose of the N—((R)-2,3-dihydroxypropoxy)-3,4-difluoro-2-(2-fluoro-4-iodo-phenylamino)-benzamide is administered once daily at a dose of about 17 mg. In some aspects, the total daily dose of the N—((R)-2,3-dihydroxypropoxy)-3,4-difluoro-2-(2-fluoro-4-iodo-phenylamino)-benzamide is administered once daily at a dose of about 18 mg. In some aspects, the total daily dose of the N—((R)-2,3-dihydroxypropoxy)-3,4-difluoro-2-(2-fluoro-4-iodo-phenylamino)-benzamide is administered once daily at a dose of about 19 mg. In some aspects, the total daily dose of the N—((R)-2,3-dihydroxypropoxy)-3,4-difluoro-2-(2-fluoro-4-iodo-phenylamino)-benzamide is administered once daily at a dose of about 20 mg.

In some aspects, the total daily dose of the N—((R)-2,3-dihydroxypropoxy)-3,4-difluoro-2-(2-fluoro-4-iodo-phenylamino)-benzamide is administered two times daily. In some aspects, the total daily dose of the N—((R)-2,3-dihydroxypropoxy)-3,4-difluoro-2-(2-fluoro-4-iodo-phenylamino)-benzamide is administered two times daily at a dose of about 0.1 mg to about 10 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, or about 10 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 0.25 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 0.5 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 1 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 2 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 3 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 4 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 5 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 6 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 7 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 8 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 9 mg each. In some aspects, the total daily dose of the N—((R)-2,3-dihydroxypropoxy)-3,4-difluoro-2-(2-fluoro-4-iodo-phenylamino)-benzamide is administered two times daily at a dose of about 10 mg each.

In some aspects, the N—((R)-2,3-dihydroxypropoxy)-3,4-difluoro-2-(2-fluoro-4-iodo-phenylamino)-benzamide is administered on a 28-day dosing cycle comprising: (a) 21 days in which the total daily dose is administered; and (b) 7 days in which no N—((R)-2,3-dihydroxypropoxy)-3,4-difluoro-2-(2-fluoro-4-iodo-phenylamino)-benzamide is administered. In some aspects, the N—((R)-2,3-dihydroxypropoxy)-3,4-difluoro-2-(2-fluoro-4-iodo-phenylamino)-benzamide is administered on a 28-day dosing cycle comprising: (a) 21 consecutive days in which the total daily dose is administered; followed by (b) 7 consecutive days in which no N—((R)-2,3-dihydroxypropoxy)-3,4-difluoro-2-(2-fluoro-4-iodo-phenylamino)-benzamide is administered.

In some aspects, the N—((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 days in which the total daily dose is administered and (ii) 2 days in which no N—((R)-2,3-dihydroxypropoxy)-3,4-difluoro-2-(2-fluoro-4-iodo-phenylamino)-benzamide; and (b) 7 days in which no N—((R)-2,3-dihydroxypropoxy)-3,4-difluoro-2-(2-fluoro-4-iodo-phenylamino)-benzamide is administered. In some aspects, the N—((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 consecutive days in which the total daily dose is administered and (ii) 2 consecutive days in which no N—((R)-2,3-dihydroxypropoxy)-3,4-difluoro-2-(2-fluoro-4-iodo-phenylamino)-benzamide; followed by (b) 7 consecutive days in which no N—((R)-2,3-dihydroxypropoxy)-3,4-difluoro-2-(2-fluoro-4-iodo-phenylamino)-benzamide is administered.

In some aspects, the N—((R)-2,3-dihydroxypropoxy)-3,4-difluoro-2-(2-fluoro-4-iodo-phenylamino)-benzamide is administered on a 28-day dosing cycle comprising 28 days in which the total daily dose is administered.

In some aspects, the 28-day dosing cycle is repeated up to a total of 24 consecutive 28-day dosing cycles.

In some aspects, the pharmaceutical composition is a dispersible tablet, dispersible powder, dispersible granules, dispersible minitablets, or dispersible pellets, and wherein the pharmaceutical composition is dispersed in a potable liquid (e.g., water or a juice (e.g., orange juice or apple juice)) prior to administration to the subject.

In some aspects, the composition is an orodispersible dosage form (e.g., dispersible tablet, dispersible powder, dispersible granules, dispersible minitablets, or dispersible pellets) which is administered to the subject without first dissolving the dosage form in a separate container.

In some aspects, the subject experiences dysphagia. In some aspects, the subject experiences dysphagia caused by one or more of: disease of the nervous system, muscle weakening, developmental disability, stroke, injury, anatomical defect, cancer, treatment for cancer, allergic reaction, dementia, memory loss, or cognitive decline. In some aspects, the subject has been diagnosed with an autism spectrum disorder. In some aspects, the subject has been diagnosed with a craniofacial disorder. In some aspects, the subject has been diagnosed with myasthenia gravis. In some aspects, the subject has been diagnosed with tardive dyskinesia.

In some aspects, the subject is a pediatric subject. In some aspects, the subject is less than 18 years old, less than 17 years old, less than 16 years old, less than 15 years old, less than 14 years old, less than 13 years old, less than 12 years old, less than 11 years old, less than 10 years old, less than 9 years old, less than 8 years old, less than 7 years old, less than 6 years old, less than 5 years old, less than 4 years old, less than 3 years old, less than 2 years old, or less than 1 year old. In some aspects, the subject is 1 year old, 2 years old, 3 years old, 4 years old, 5 years old, 6 years old, 7 years old, 8 years old, 9 years old, 10 years old, 11 years old, 12 years old, 13 years old, 14 years old, 15 years old, 16 years old, or 17 years old. In some aspects, the subject is less than 13 years old. In some aspects, the subject is less than 12 years old. In some aspects, the subject is less than 11 years old. In some aspects, the subject is less than 10 years old. In some aspects, the subject is less than 9 years old. In some aspects, the subject is less than 8 years old. In some aspects, the subject is less than 7 years old. In some aspects, the subject is less than 6 years old. In some aspects, the subject is less than 5 years old. In some aspects, the subject is less than 4 years old. In some aspects, the subject is less than 3 years old. In some aspects, the subject is less than 2 years old. In some aspects, the subject is less than 1 year old. In some aspects, the subject is about 2 to about 18 years old. In some aspects, the subject is about 3 to about 17 years old. In some aspects, the subject is about 4 to about 16 years old. In some aspects, the subject is about 5 to about 15 years old. In some aspects, the subject is about 6 to about 14 years old. In some aspects, the subject is about 7 to about 13 years old. In some aspects, the subject is about 8 to about 12 years old.

In some aspects, the subject is a geriatric subject. In some aspects, the subject is more than 30 years old, more than 35 years old, more than 40 years old, more than 45 years old, more than 50 years old, more than 55 years old, more than 60 years old, more than 65 years old, more than 70 years old, more than 75 years old, more than 80 years old, more than 85 years old, more than 90 years old, more than 95 years old, or more than 100 year old. In some aspects, the subject is more than 50 years old. In some aspects, the subject is more than 60 years old. In some aspects, the subject is more than 70 years old. In some aspects, the subject is more than 80 years old. In some aspects, the subject is more than 90 years old. In some aspects, the subject is more than 100 years old.

In some aspects, the present disclosure provides use of a pharmaceutical composition described herein for the manufacture of a medicament for treating a cancer, a tumor, or a Rasopathy disorder.

Methods of Preparing N—((R)-2,3-dihydroxypropoxy)-3,4-difluoro-2-(2-fluoro-4-iodo-phenylamino)-benzamide and Essentially Pure Form IV Novel methods of producing N—((R)-2,3-dihydroxypropoxy)-3,4-difluoro-2-(2-fluoro-4-iodo-phenylamino)-benzamide of Formula (I)

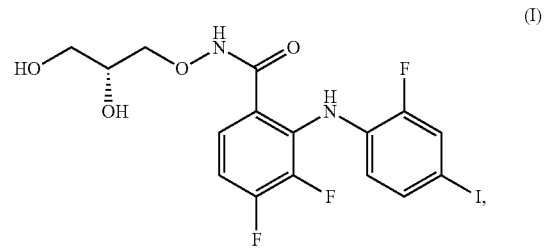 [SMILES: O=C(NOC[C@H](O)CO)c1ccc(F)c(F)c1Nc1ccc(I)cc1F]

that comprise reacting PD-0315209 (FIPFA) and PD-0337792 (IPGA) with a coupling reagent that is 1-propylphosphonic anhydride ("T3P") to obtain 901 Acetonide, as shown in Scheme I below, are disclosed herein.

85

Scheme 1

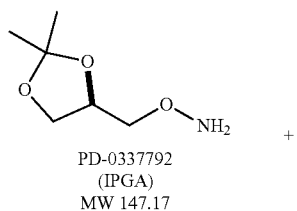

PD-0337792
(IPGA)
MW 147.17

+

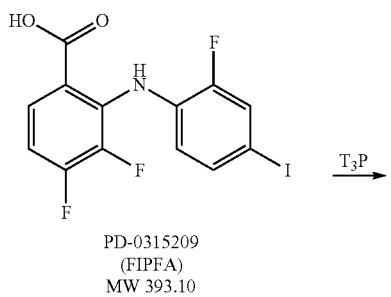

PD-0315209
(FIPFA)
MW 393.10

→ T₃P

86

-continued

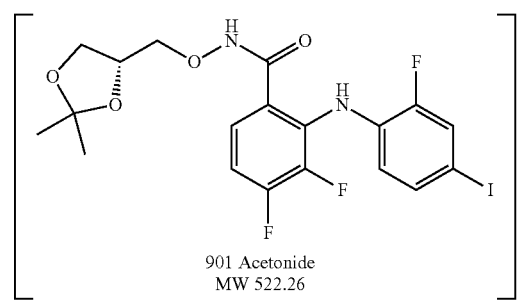

901 Acetonide
MW 522.26

In some aspects, the T3P is in solution. In some aspects, T3P is provided as a solution in ethyl acetate.

In some aspects, the method of producing essentially pure Form IV N—((R)-2,3-dihydroxypropoxy)-3,4-difluoro-2-(2-fluoro-4-iodo-phenylamino)-benzamide of Formula (I) comprises (a) reacting PD-0315209 (FIPFA) and PD-0337792 (IPGA) with a coupling reagent that is T3P to obtain 901 Acetonide; and (b) treating 901 Acetonide with acid to form N—((R)-2,3-dihydroxypropoxy)-3,4-difluoro-2-(2-fluoro-4-iodo-phenylamino)-benzamide, as shown in Scheme II below.

Scheme II

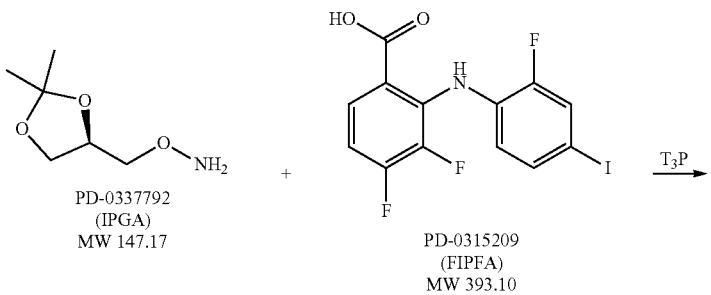

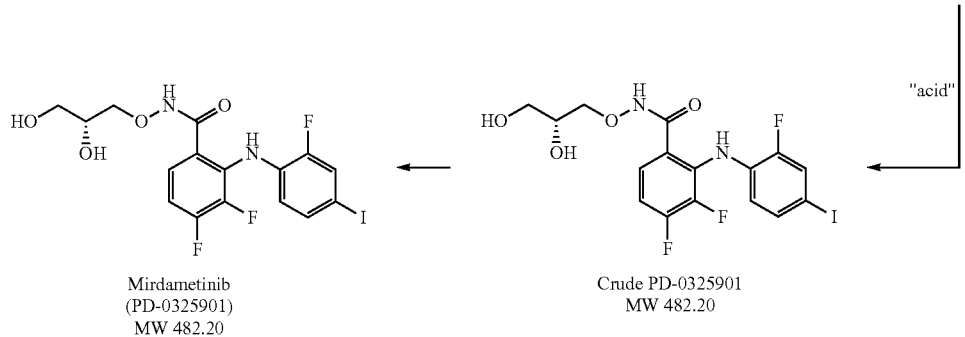

In some aspects, the synthesis for essentially pure crystalline Form IV of N—((R)-2,3-dihydroxypropoxy)-3,4-difluoro-2-(2-fluoro-4-iodo-phenylamino)-benzamide of Formula (I) comprises the reaction set forth according to Scheme III.

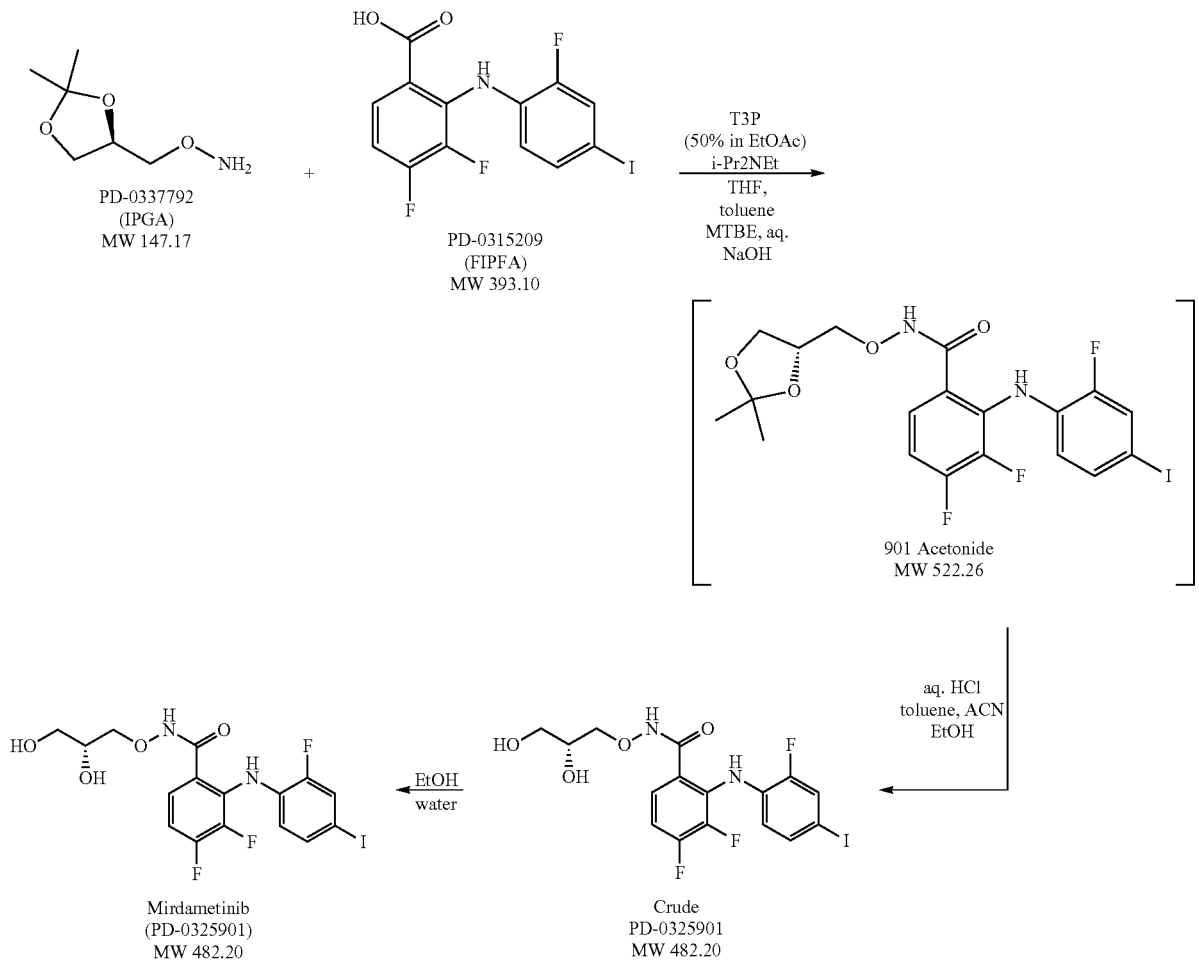

In some aspects, the synthesis for essentially pure Form IV of N—((R)-2,3-dihydroxypropoxy)-3,4-difluoro-2-(2-fluoro-4-iodo-phenylamino)-benzamide of Formula (I) is as shown below in Scheme IV.

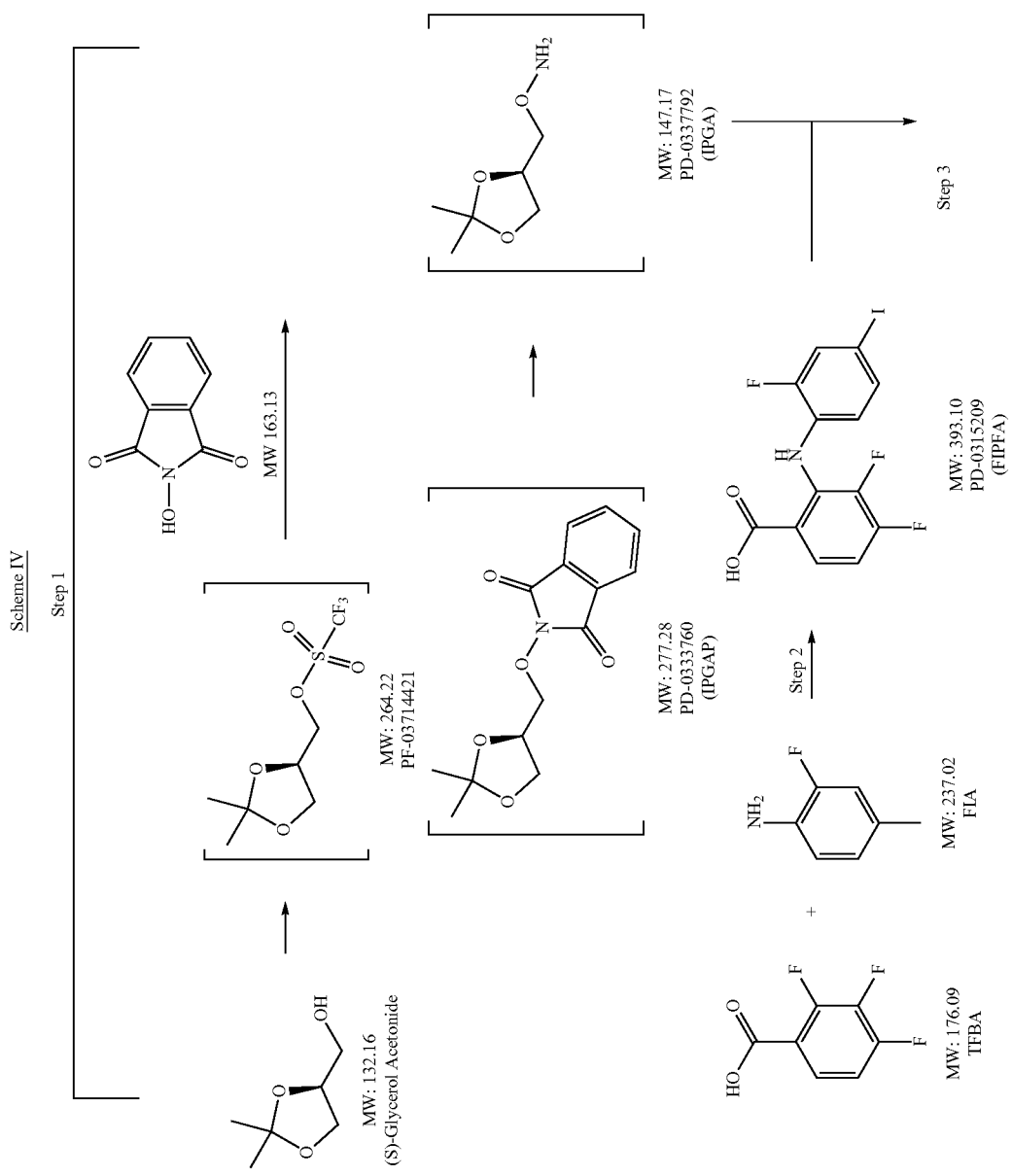

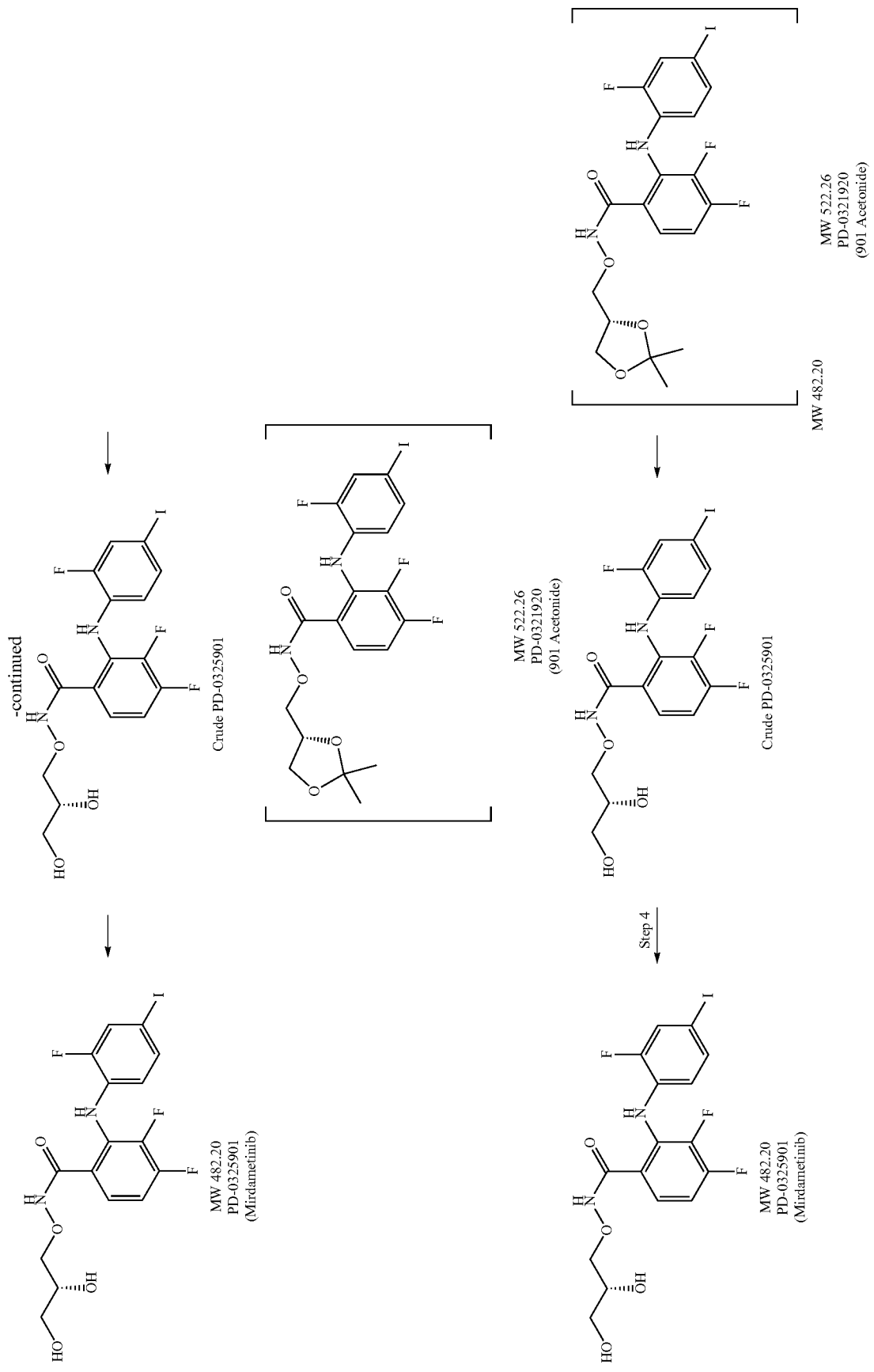

In some aspects, the methods of preparing N—((R)-2,3-dihydroxypropoxy)-3,4-difluoro-2-(2-fluoro-4-iodo-phenylamino)-benzamide yields a crystalline composition that is essentially pure Form IV of N—((R)-2,3-dihydroxypropoxy)-3,4-difluoro-2-(2-fluoro-4-iodo-phenylamino)-benzamide.

In some aspects, the essentially pure Form IV crystalline composition contains ≤0.2% of dimeric impurity PF-00191189

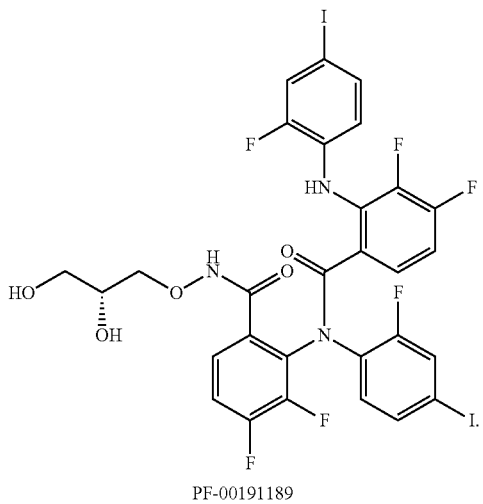

PF-00191189
Exact Mass: 856.93

In some aspects, the essentially pure Form IV crystalline composition contains about 0.05% to about 0.19% by weight of dimeric impurity PF-00191189. In some aspects, the essentially pure Form IV crystalline composition contains about 0.05% to about 0.15% by weight of dimeric impurity PF-00191189. In some aspects, the essentially pure Form IV crystalline composition contains about 0.05% to about 0.10% by weight of dimeric impurity PF-00191189. In some aspects, the essentially pure Form IV crystalline composition contains no detectable amount of dimeric impurity PF-00191189.

In some aspects, the amount of dimeric impurity PF-00191189 is determined using High Performance Liquid Chromatography ("HPLC"). In some aspects, reversed-phase liquid chromatography using an ultraviolet detector at 275 nm is used.

EXAMPLES

Abbreviations and Acronyms

| ACN | Acetonitrile |
| --- | --- |
| CC | Controlled cooling |
| DCM | Dichloromethane |
| DMF | N,N-Dimethyl formamide |
| DMSO | Dimethyl sulfoxide |
| DSC | Differential scanning calorimetry |
| EtOAc | Ethyl acetate |
| EtOH | Ethanol |
| Exp | Experiment |
| FEV | Fast evaporation |
| FIA | 2-fluoro-4-idodoaniline |
| FT | Fourier Transform |
| GVS | Gravimetric Vapor Sorption |
| HCl | Hydrochloric acid |
| HOAc | Acetic acid |
| i-Pr$_2$NEt | N,N-diisopropylethylamine |
| IPA | 2-Propanol |
| IPE | Isopropyl ether |
| LiNH2 | Lithium amide |
| MeCN | Acetonitrile |
| MeOH | Methanol |
| MIBK | 4-Methyl-2-pentanone |
| min | Minutes |
| MTBE | Methyl t-butyl ether |
| n/a | Not Applicable |
| NaOH | Sodium hydroxide |
| NH$_4$OH | Ammonium hydroxide |
| NHP | N-hydroxyphthalimide |
| PLM | Polarized light microscopy |
| PXRD | Powder X-ray diffraction (also known as XRPD (X-ray powder diffraction) |
| RC | Rapid cooling |
| RT | Room temperature |
| SAS | Solvent-antisolvent |
| SEV | Slow evaporation |
| SGA | (S)-(+)-2,2-dimethyl-1,3-dioxolane-4-methanol |
| SU | Scale Up |
| t-BuOH | Tert-butanol |
| TC | Temperature cycling |
| T3P | 1-propylphosphonic anhydride solution |
| TEA | triethylamine |
| Tf$_2$O | Trifluoromethanesulfonic anhydride |
| TFBA | 2,3,4-trifluorobenzoic acid |
| TFE | 2,2,2-Trifluoroethanol |
| TGA | Thermogravimetric analyzer |
| TGA-IR | Thermogravimetric analysis interfaced with infrared spectrophotometer |
| THF | Tetrahydrofuran |
| v/v | Volume/volume |

Example 1: Production of Seed Crystals of Form IV

Step 1: Preparation of "Side Chain", PD-0337792

14.4 kg alcohol (chemical purity 99.4%, optical purity 99.6% enantiomeric excess) was converted to 97.5 kg 9.7% w/w PD-0337792 (IPGA) solution in toluene (overall yield 60%). The triflate activation was performed in the 200 L reactor by maintaining temperatures under −20° C. during triflic anhydride addition. The resulting activated alcohol was then transferred to a 400 L reactor containing solid N-hydroxypthalimide (NHP) and the reaction was allowed to occur at ambient temperature to completion. The final base de-protection was performed by adding aqueous ammonia (~28% soln, 5 equiv., 34 kg). After reaction completion, water was removed by distillation from toluene, and the resulting solid side product was filtered out to yield the product solution.

Step 2: Preparation of PD-0315209

The process yielded 21.4 kg (99.4% w/w assay), which is 80% of theoretical from starting materials 2,3,4-trifluorobenzoic acid (12 kg, 1 eq.) and 2-fluoro-4-iodoaniline (16.4 kg, 1.02 eq.) with lithium amide base (5 kg, 3.2 eq.). The reaction was initiated by adding 5% of total solution of TFBA and FIA into lithium amide slurry at 50° C. This reaction demonstrated a minimal initiation period of ~10 minutes, which was observed by color change and slight exotherm. The remaining TFBA/FIA solution in THE was slowly added through a pressure can in an hour while maintaining the reaction temperatures within 45-55° C. There was no appreciable pressure rise (due to ammonia gas release) observed during the entire operation.

Step 3: Preparation of PD-0325901

A modification was made to the CDI charging to mitigate potential gas generation. Two equal portions of CDI were added into solid FIPFA before and after solvent addition (through a shot loader). The timing between the two solid CDI additions (4.6 kg each) should not exceed 30 minutes. Then two intermediate filter cakes were dissolved with ethanol. The excess ethanol was distilled and replaced with toluene to approximately 5% v/v ethanol prior to PD-0325901 recrystallization. Lab studies suggested that the crystallization from toluene and acetonitrile and recrystallization from ethanol in toluene would not be able to reduce impurities which is essential for the polymorph transformation. The presence of a dimeric impurity (PF-00191189) at a level greater than 0.2% has been known to result in the formation of undesired polymorph.

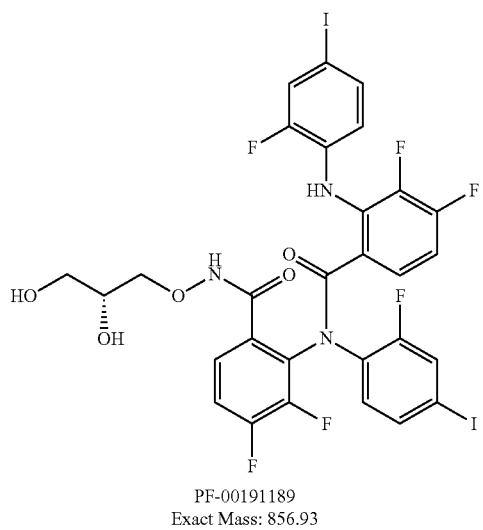 [SMILES: O=C(NOC[C@H](O)CO)c1ccc(F)c(F)c1N(C(=O)c1ccc(F)c(F)c1Nc1ccc(I)cc1F)c1ccc(I)cc1F]

PF-00191189
Exact Mass: 856.93

The crude crystallization from the final reaction mixture reduced dimeric impurity PF-00191189 to approximately 1.9% and the subsequent recrystallization further reduced it to approximately 0.4%. As a consequence, undesired polymorphs were produced. The DSC patterns indicated two different melting points ~80° C. (low melt Form II) and ~117° C. (Form I). Also during the processing, the solids crystallized at a much lower temperature than expected (actual ~10° C., expected ~40° C.). It is suspected that the unsuccessful recrystallization is due to a change in the solvent composition as a result of incomplete drying of the crude. Drying of the crude wet cake prior to ethanol dissolution was stopped after about 36 hours when the crude product was ~28 kg (26 kg theoretical).

Polymorph Transformation

Approximately 7.4 kg of PD-0325901 (mixed polymorphs) from the final EtOH/Water crystallization and precipitated materials from the earlier EtOH/Toluene filtrate were taken forward to the polymorph transformation. Both crops were separately dried in the filter until constant weights and each was dissolved in EtOH. The combined EtOH solution was analyzed by HPLC and resulted in an estimated amount of 16.4 kg PD-0325901. The recrystallization was started after removing EtOH via vacuum distillation and adjusting the solvent composition to about 5% EtOH in Toluene at 65° C. (i.e., EtOH is added dropwise at 65° C. until complete solids dissolution).

A slow 4-hour cooling ramp to 5° C. followed by 12 h stirring was performed to ensure satisfactory results. The resulting slurry was filtered and again it was completely dried in the filter until constant weight (approximately 3 days). The purified solid showed 99.8% pure PD-0325901 with not detected level of dimeric impurity PF-00191189.

The dried solid (15.4 kg) was re-dissolved in exactly 4 volumes of EtOH (62 L) off of the filter, transferred to the reactor and precipitated by a slow (~3 h) water addition (308 L) at 30-35° C., cooled to 20° C. and stirred for 12 h. The DSC analysis of a slurry sample taken at 2 h shows the solids to be completely Form IV (desired polymorph).

21.4 kg PD-0315209, 9.7 kg CDI (1.05 equiv.), 91 kg solution of 9.7% PD-0337792 in Toluene (1.1 equiv.) were used and resulted in 12.74 kg of PD-0325901 (assay 99.4%, 100% Form IV, Yield 48%).

Example 2: Assay/Impurities and Identification of PD-0325901

PD-0325901 is separated from process impurities and degradants by reversed-phase liquid chromatography with UV detection at 275 nm. Identification of PD-0325901 is performed by obtaining either an infrared or proton NMR spectrum, in addition to the HPLC retention time. For purity evaluation, process impurities and degradants are identified by their characteristic relative retention times and quantitated by area normalization.

Chromatographic Conditions: Agilent Zorbax SB C18, 5 µm, 4.6×250 mm (or equivalent); flow rate is 1.0 mL/min; column temperature is 30° C.; detector wavelength is 275 nm; diluent is 50/50 acetonitrile/water; mobile phase A is 0.1% trifluoroacetic acid (TFA) in water; mobile phase B is methanol; and the gradient conditions below. The assay is determined against a reference standard and reported on an anhydrous, solvent free basis. Quantification of specified and unspecified impurities is reported by area percent. Total impurities is the sum of all impurities present above the reporting threshold of 0.05%.

| | Time (minutes) | | | | |
| --- | --- | --- | --- | --- | --- |
| | 0 | 15 | 40 | 45 | 46 |
| % mobile phase B | 70 | 70 | 100 | 100 | 70 |

Example 3: Improved Process for Preparation of Form IV

As described in Example 1, synthetic methods of producing mirdametinib as Form IV produced Form IV with dimeric impurity PF-00191189, and further steps were required to transform the product into essentially pure Form IV without undesired polymorphs Form I and Form II. Therefore, it was necessary to develop a method of producing essentially pure Form IV without additional processing steps.

Mirdametinib Manufacturing Process

The route is a convergent four step synthesis with six chemical steps overall, using the proposed starting materials (S)-(+)-2,2-dimethyl-1,3-dioxolane-4-methanol (SGA), 2,3,4-trifluorobenzoic acid (TFBA), 2-fluoro-4-idodoaniline (FIA), and N-hydroxyphthalimide (NHP). The final step (Step 4) provides essentially pure Form IV of mirdametinib.

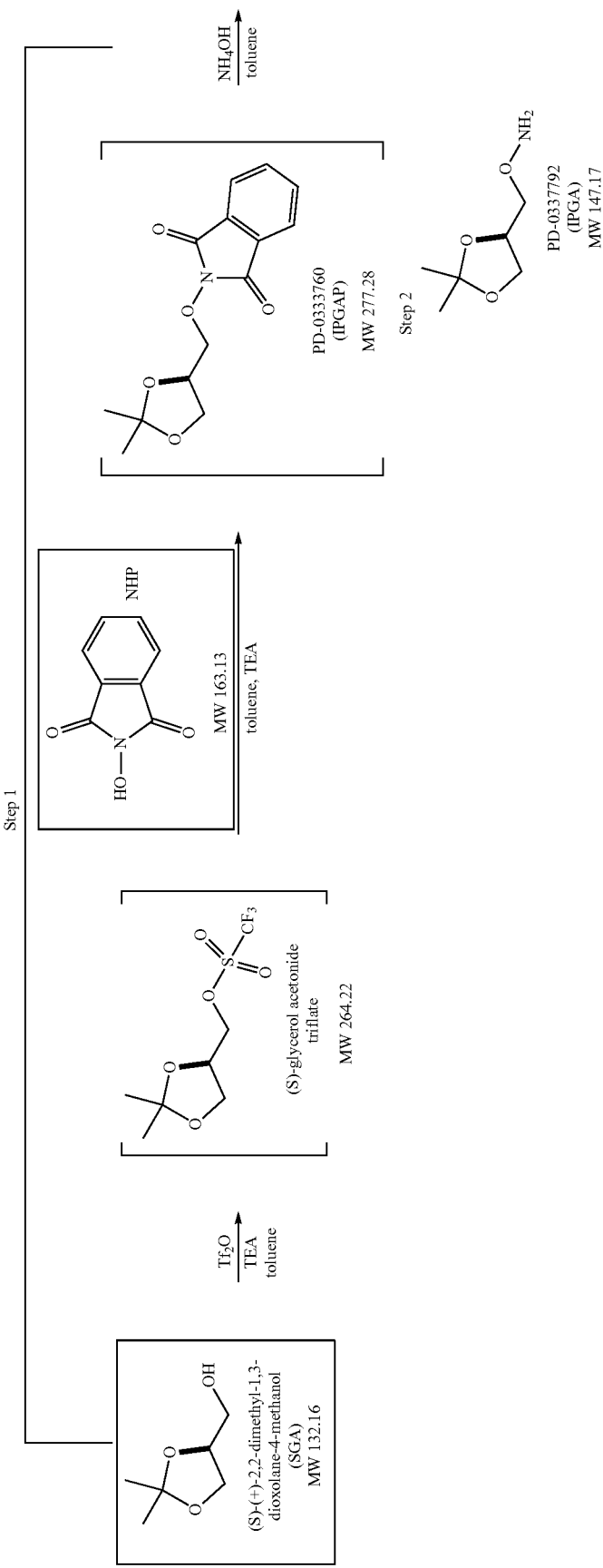

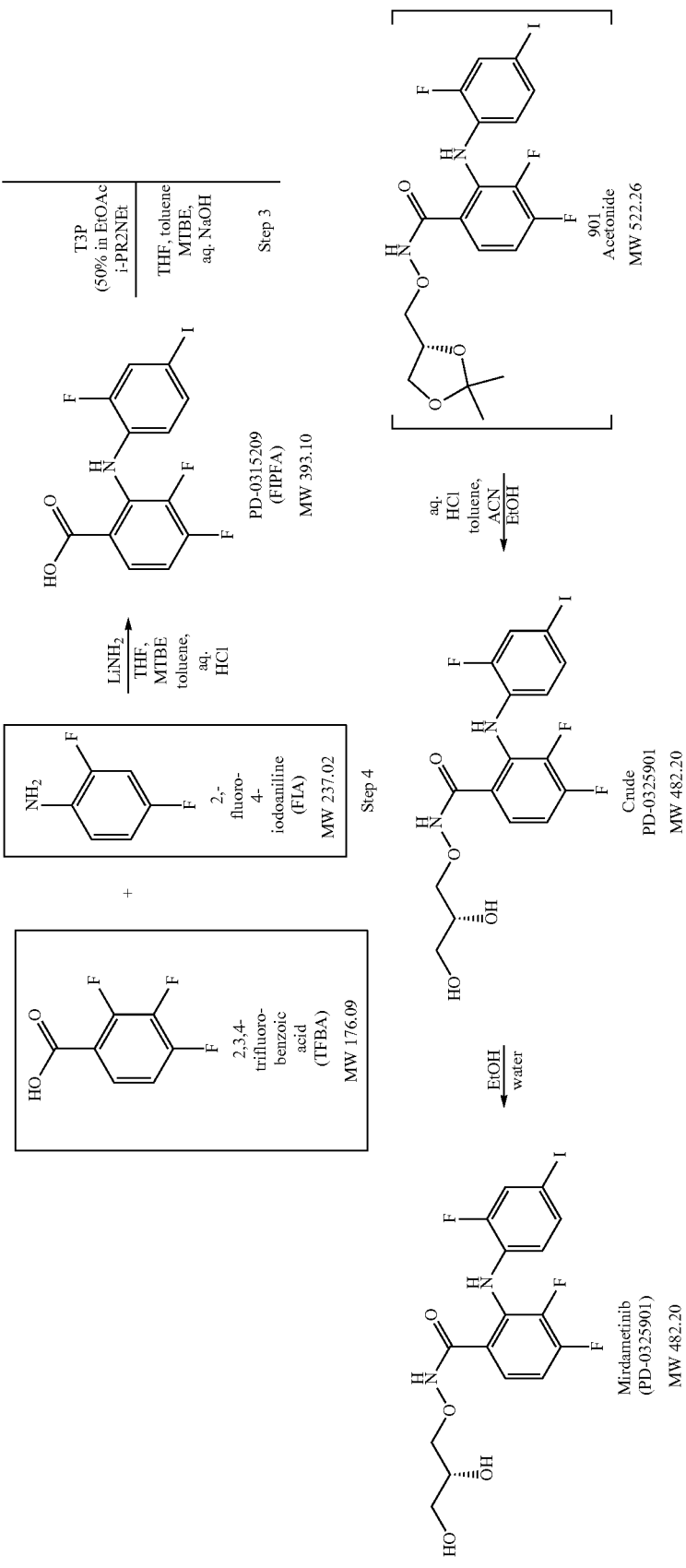

Step 1 (Preparation of PD-0337792 (IPGA)): A clean, dry 100-gallon reactor was charged with toluene (139.3 kg, 8 volumes) and (S)-(+)-2,2-Dimethyl-1,3-dioxolane-4-methanol (SGA; 20.0 kg, 1.0 equivalents). Triethylamine (18.8 kg, 1.22 equivalents) was charged to the reactor. The reactor contents were agitated and cooled to −10±10° C. Trifluoromethanesulfonic anhydride (43.5 kg, 1.02 equivalents) was added to a clean 50-L round bottom flask under nitrogen then cooled to a temperature of ≤−10° C. The cooled trifluoromethanesulfonic anhydride was slowly transferred to the 100-gallon reactor while maintaining the internal temperature at −10±10° C. The reaction mixture was agitated at −10±10° C. for 30 minutes. Reaction monitoring by TLC indicated the conversion to be complete. While maintaining the internal temperature at −10±10° C., anhydrous toluene (99.8 kg, 5.75 volumes) was charged to the reactor followed by N-hydroxyphthalimide (26.4 kg, 1.07 equivalents). The contents were warmed to 20±5° C. then agitated at this temperature for at least 5 hours, until the triflate intermediate was not detectable by TLC. The reaction mixture was split into two equal portions. Each toluene solution was quenched with USP purified water (66 kg, 6.7 volumes). The toluene solution was then washed twice with USP purified water (66 kg, 6.7 volumes).

The toluene solutions were recombined in a 100-gallon reactor. The organic solution was treated with 28% ammonium hydroxide solution (41.5 kg, 7.8 equivalents). The contents were heated to 35±5° C. then agitated for not less than ("NLT") 12 hours. Upon reaction completion, the lower, aqueous phase was removed. The toluene solution was dried via azeotropic distillation of toluene. The toluene solution was then concentrated to minimum stir volume. The concentrated solution was filtered to remove by-product solids. The cake was washed with toluene and the filtrates were combined. Assay of the toluene solution indicated 8.6 kg (36.7% yield) of PD-0337792 (IPGA) was present.

Step 2 (Preparation of PD-0315209): A clean, dry 100-gallon reactor was purged with nitrogen then charged with lithium amide (LiNH2, 8.8 kg, 3.4 equivalents) followed by tetrahydrofuran (THF, 56.8 kg, 3.2 volumes). The mixture was cooled to 10±10° C. then additional THE (15.1 kg, 0.85 volumes) was charged to the reactor, followed by a solution of 2,3,4-trifluorobenzoic acid (TFBA, 20.0 kg, 1.0 equivalent) in THE (26.4 kg, 1.5 volumes). The reaction mixture was heated to NMT ("not more than") 50° C. A solution of 2-fluoro-4-iodoaniline (FIA, 27.5 kg, 1.02 equivalents) in THE (17.8 kg, 1 volumes) was added portion wise to the reactor, maintaining the batch temperature at NMT 50° C. and stirring for 1 hour between additions. After completing the additions, the reaction mixture stirred for an additional 3 hours at 50±10° C. Upon reaction completion, the mixture was cooled to NMT 10° C. then quenched with USP purified water (120.3 kg, 6 volumes). The reaction mixture was distilled to approximately 30 gallons after which methyl t-butyl ether (MTBE, 118.6 kg, 8 volumes) was added. The MTBE solution was then quenched with 2M hydrochloric acid solution (89.5 kg) to a pH=7. The aqueous phase was then removed. The MTBE solution was filtered through celite then washed twice with 5% brine solution (104.1 kg, 5.2 volumes) followed by 1M hydrochloric acid solution (77.4 kg). The MTBE solution was solvent swapped with toluene followed by volume adjustment to approximately 50 gallons. This mixture was heated to 75±5° C. for 1 hour then cooled to 20±5° C. and stirred for 1 hour. The product was filtered, washed with toluene (68.1 kg, ~4 volumes), then dried under vacuum at 40° C. to obtain 25.2 kg of PD-0315209 (56.4% yield).

Step 3 (Preparation of crude PD-0325901): A clean, dry 100-gallon reactor was purged with nitrogen then charged with PD-0315209 (18.0 kg, 1 equivalent) and THE (113.0 kg, 7 volumes). The mixture was cooled to 5±5° C. N,N-diisopropylethylamine (15.1 kg, 2.55 equivalents) was charged maintaining the temperature NMT 25° C. The mixture was cooled to 5±5° C. then stirred for 10 minutes. PD-0337792 solution in toluene (121.7 kg total, 1.3 equivalents) was charged to the reactor at 5±5° C., followed by 50% T3P in ethyl acetate (42.0 kg, 1.45 equivalents). The reaction mixture stirred at 10±5° C. for NLT 3 hours. An additional charge of N,N-diisopropylethylamine (1.9 kg, 0.3 equivalents) and 50% T3P in ethyl acetate (4.1 kg, 0.15 equivalents) were made to advance the coupling to completion. The reaction was reverse quenched into a 5% sodium hydroxide solution (50 kg), followed by washing with 5% brine (55.4 kg). The organic solution was concentrated then solvent swapped with toluene. Acetonitrile (43.0 kg, 2.4 volumes) was added to the reactor followed by 2M hydrochloric acid (117.6 kg, 5.1 equivalents). The mixture stirred at 5° C. until reaction completion after 16 hours. The bottom aqueous was removed then the reaction mixture was washed with 5% brine (75.2 kg). The organic phase was concentrated then solvent swapped with toluene to an appropriate volume. The mixture was then heated to 75±5° C. for 30 minutes then slowly cooled to 20° C. The solids were filtered then washed with toluene (31.1 kg, 1.7 volumes)

The crude solids were charged back to the 100-gallon reactor, followed by 5% ethanol in toluene (170.0 kg). The mixture was heated to 75±5° C. for 60 minutes to achieve a solution then slowly cooled to 20° C. The solids were filtered then washed twice with toluene (31 kg, 1.7 volumes). The wet cake was dried under vacuum at 45° C. to obtain 8.2 kg of crude PD-0325901 (37.1% yield).

Step 4 (Preparation of Essentially Pure Form IV Mirdametinib): A clean, dry 100-gallon reactor was purged with nitrogen then charged with USP Purified Water (164.1 kg, 20 volumes) followed by ethanol (200 proof, 20.8 kg, 3.25 volumes). The solution was heated to 35±5° C. In a separate vessel, crude PD-0325901 (8.1 kg, 1 equivalent) was dissolved in ethanol (200 proof, 40.5 kg, 6.3 volumes). A portion of this solution (14.4 kg) was added to the 100-gallon reactor over 60 minutes. PD-0325901 Form IV seeds as prepared in Example 1 (82.6 g, 1% wt) was added to the reactor to facilitate precipitation. The remainder of the crude PD-0325901/ethanol solution (34.3 kg) was added to the reactor over 90 minutes as the mixture stirred at 35±5° C. The reactor contents continued to stir at 35±5° C. for 5.5 hours then were slowly cooled to 20° C. The solids were then filtered, washed with USP purified water (16.5 kg, 2 volumes), then dried under vacuum at 45° C. for 16 hours. The dried solids were screened through a 10-mesh sieve to obtain 5.7 kg PD-0325901 Form IV (70.4% yield).

Figure 1B:
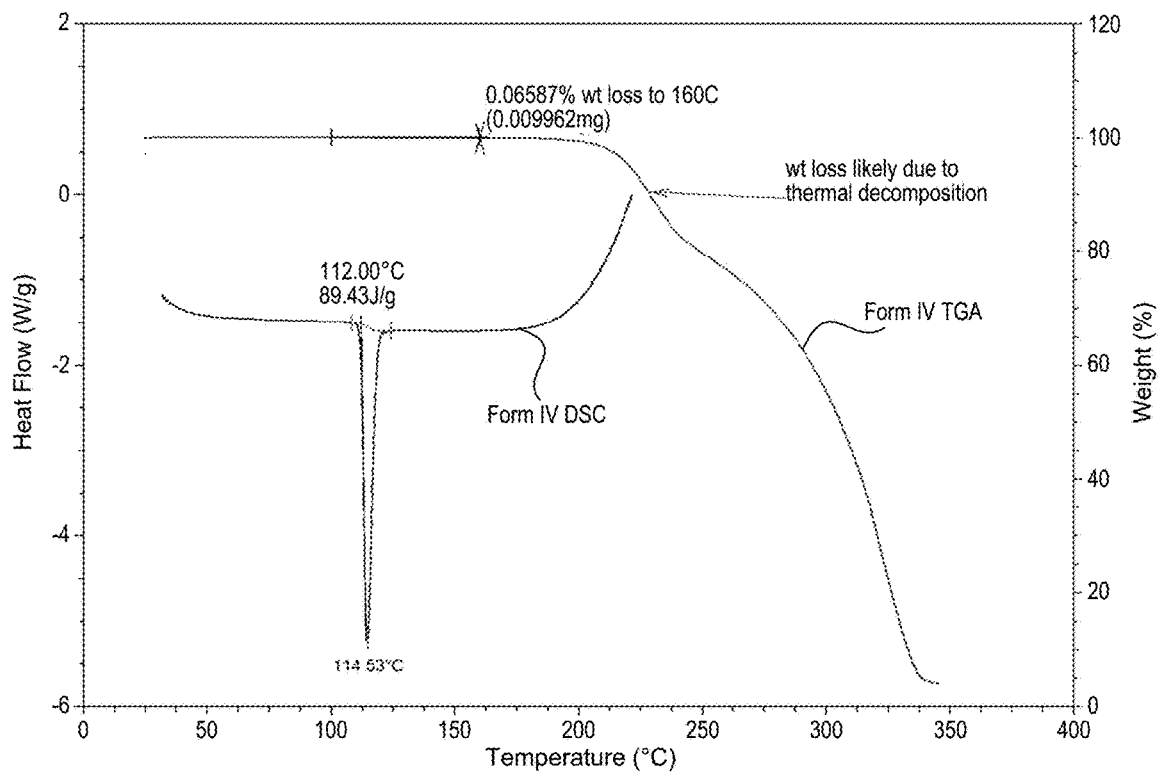
FIG. 1B is a thermogravimetric analysis thermogram ("TGA") and a differential scanning calorimetry thermogram ("DSC") corresponding to essentially pure crystalline Form IV of N—((R)-2,3-dihydroxypropoxy)-3,4-difluoro-2-(2-fluoro-4-iodo-phenylamino)-benzamide.

An XRPD pattern for essentially pure Form IV used herein is shown in FIG. 1A. TGA and DSC analysis of essentially pure Form IV used herein are shown in FIG. 1B.

Example 4: Approximate Kinetic Solubility

Solubility of mirdametinib prepared by Example 3 was assessed in 30 solvents. The solubility was visually estimated at room temperature (RT; ~23° C.) by dosing small aliquots of solvent into a fixed amount of solid (~10 mg) until the dissolution point or a maximum volume (1.8 mL) was reached. Samples that contained undissolved solids at RT were heated to 40° C. for 1 hour and the dissolution was assessed visually. The solubility data are shown below in Table 1.

TABLE 1

| # | Solvent (v/v) | Solubility (mg/mL) at RT (23° C.) | Solubility (mg/mL) at 40° C. |
|---|---|---|---|
| 1 | Ethanol/Water (9:1 v/v) | >424 | n/a |
| 2 | MeCN/water (8:2 v/v) | >412 | n/a |
| 3 | MeCN/Water (7:3 v:v) | >408 | n/a |
| 4 | Dioxane | >408 | n/a |
| 5 | DMF (dimethylformamide) | >408 | n/a |
| 6 | 2-Propanol:water (9:1 v/v) | >400 | n/a |
| 7 | Acetone | >400 | n/a |
| 8 | Tetrahydrofuran (THF) | >396 | n/a |
| 9 | Acetic acid (HOAc) | >388 | n/a |
| 10 | Dimethyl sulfoxide (DMSO) | >388 | n/a |
| 11 | Methanol (MeOH) | >380 | n/a |
| 12 | Ethanol/Toluene (9:1) | 210-420 | n/a |
| 13 | Ethanol | 208-416 | n/a |
| 14 | 1-Propanol | 101-202 | n/a |
| 15 | 2-Propanol (IPA) | 98-196 | n/a |
| 16 | 2-Methyl-2-Butanol | 97-194 | n/a |
| 17 | Ethyl Acetate (EtOAc) | 48-95 | n/a |
| 18 | MIBK (4-methyl-2-pentanone) | 48-95 | n/a |
| 19 | Acetonitrile (MeCN) | 19-49 | n/a |
| 20 | Nitromethane | 10-20 | n/a |
| 21 | Dimethylcarbonate (DMC) | 10-19 | n/a |
| 22 | Trifluoroethanol (TFE) | 7-12 | n/a |
| 23 | Tert-butanol (t-BuOH) | 6-10* | n/a |
| 24 | MTBE (methyl-t-butyl ether) | <6 | >6 |
| 25 | Dichloromethane (DCM) | <6 | >6 |
| 26 | Cyclohexane | <6 | <6 |
| 27 | Chloroform | <6 | <6 |
| 28 | Isopropyl ether (IPE) | <6 | <6 |
| 29 | Toluene | <6 | <6 |
| 30 | Water | <6 | <6 | n/a - not applicable
*solubility determined at 30° C.

Example 5: Comprehensive Crystal-Form Screening

About 450 crystallization experiments were performed using the mirdametinib prepared in Example 3 to identify novel polymorphs and solvates/hydrates of mirdametinib. The description of crystallization methods and solid-state forms of the input materials are described here.

Crystallization Modes

Four main types of crystallization modes were employed in the screening study:

Slurry equilibration:
　Isothermal at 5, 25, and 50° C. for 48-72 hours
　Thermocycling between 40-5° C. (in one-hour periods) for 48 hours Rapid and controlled cooling of clarified solutions of mirdametinib:
　Controlled cooling from 50° C. to 5° C. at a rate of 0.1° C./min with one hour hold every 5° C. followed by hold at 5° C. for 5 days, followed by hold at −20° C. (for remaining solutions) for 6 to 9 days
　Rapid cooling from 50° C. to −20° C. at an uncontrolled rate followed by hold at −20° C. for 4 to 14 days Rapid and slow evaporation of clarified solutions of mirdametinib:
　Slow evaporation over up to 30 days at ambient conditions
　Rapid evaporation for up to 3 days at reduced pressure at ambient temperature Addition of antisolvent to saturated and clarified mirdametinib solutions at room temperature:
　Rapid antisolvent addition and stirring at ambient temperature for up to 11 days

| Crystallization Mode | Experimental Mode | # Exps. | Description | Input Forms |
|---|---|---|---|---|
| Slurry | Thermo-cycled | 48 | Slurry of mirdametinib stirred while cycling temperature between 5-40° C. for 48 hours | Amorphous |
| | Isothermal at Elevated Temperature | 48 | Slurry of excess mirdametinib stirred at 50° C. for 48 hours | Amorphous |
| | Isothermal at Ambient Temperature | 48 | Slurry of excess mirdametinib stirred at 25° C. for >48 hours | Amorphous |
| | Isothermal at Low Temperature | 48 | Slurry of excess mirdametinib stirred at 5° C. for 72 hours | Amorphous |
| Solution Cooling | Controlled Cooling | 48 | Mirdametinib solution equilibrated at ~50° C., filtered, cooled at 0.1° C./min to 5° C. with 1 hour hold every 5° C. and hold 5 days at 5° C., followed by −20° C. storage for 6-9 days for remaining solutions | Form IV |
| | Rapid Cooling | 48 | Mirdametinib solution equilibrated at ~50° C., filtered crash cooled to −20° C. and hold 4-14 days at −20° C. | Form IV |
| Solution Evaporation | Fast Evaporation | 48 | Solution of mirdametinib equilibrated at ambient is filtered and rapidly evaporated under reduced pressure at ambient temperature | Form IV |
| | Slow Evaporation | 48 | Solution of mirdametinib equilibrated at ambient is slowly evaporated over up to 30 days at ambient conditions | Form IV |

-continued

| Crystallization Mode | Experimental Mode | # Exps. | Description | Input Forms |
|---|---|---|---|---|
| Solution Antisolvent Addition | Rapid (but dropwise) Addition | 48 | Precipitation of the mirdametinib from saturated solution induced by the addition of an antisolvent. | Form IV |
| Focused Experiments | Process Solvent Experiments to Evaluate Solvate Risk, Vacuum-Oven Drying, Desolvation/ Dehydration by Heating Experiments | 11 | Slurry of Toluene Solvate in Water/Ethanol Spiked with Toluene to Evaluate Solvate Risk in Mirdametinib Process. Vacuum-Oven Drying of Important Solvates and Hydrates to Determine Stability. Desolvation/Dehydration by Heating of Important Solvates and Hydrates to Investigate Potential New Non-Solvated Forms | Various |
| | Total | 443 | | |

Example 6: Amorphous Material Preparation and Experiments

Amorphous mirdametinib was prepared on a 100 mg scale by rapid evaporation under reduced pressure (Genevac® vacuum centrifuge) of 100 mg/mL solutions of the mirdametinib in methanol and THE (A-1 and A-2, respectfully).

Solutions of mirdametinib (100 mg/mL) were prepared in methanol and THF, and each solution was divided into three equal parts to be used for 1) open at RT stability evaluation, 2) closed at RT stability evaluation, and 3) closed at −20° C. stability evaluation. Observations after rapid evaporation revealed that the samples from methanol were mostly dry, glassy materials, and the samples from THE were mostly sticky, dark amber gums.

PXRD analyses of all six samples (three from both methanol and THF) following rapid evaporation indicated an amorphous state. Other analyses (e.g. PLM, TGA-R, DSC) were performed on one sample from each solvent. Following initial analyses, one sample from each solvent was stored at RT in an open vial, at RT in a capped vial, and at −20° C. in a capped vial.

PXRD and PLM analyses after one day showed no crystallization in A-1a (open at RT), and A-1b (capped at RT) from methanol. A-1c (capped at −20° C.) was not analyzed.

PXRD and PLM analyses after one day showed crystallization to Form IV in A-2a (open at RT) from THF. A-2b (capped at RT) and A-2c (capped at −20° C.) were not analyzed.

Since amorphous mirdametinib (A-1) was successfully prepared at 100 mg scale by rapid evaporation at reduced pressure from a methanol solution, this method was used to prepare vials containing amorphous material for use as the input material for slurry-ripening experiments in the screen.

| | Amorphous Mirdametinib Experiments | |
|---|---|---|
| Experiment | Procedure | Results |
| A-1 | A-1: Combined 299.8 mg of mirdametinib with 3 mL of methanol and stirred for 1 hour yielding a solution. Filtered the solution through 2 μm PTFE filter to clarify. Pipetted 900 μL of A-1 above into 3 separate 2 mL vials: A-1a, A-1b, and A-1c. Rapidly evaporated the solvent under reduced pressure in a vacuum centrifuge (GeneVac ®) for 20 hours. Products were mostly glassy with a thin film of dark amber on bottom. PXRD and PLM analyses of all 3 samples indicated they were initially amorphous. Analyzed A-1a by PLM, TGA-IR, and DSC. DSC data was consistent with an amorphous state. TGA-IR showed 1.3% wt. water and MeOH evolved upon heating to 200° C. PXRD and PLM analyses of A-1a, after one day open at RT indicated an amorphous state. | Amorphous (after 1 day at ambient) |
| A-2 | A-2: Combined 298.9 mg of mirdametinib with 3 mL of THF and stirred for 1 hour yielding a solution. Filtered the solution through 2 μm PTFE filter to clarify. Pipetted 900 μL of A-2 above into 3 separate 2 mL vials: A-2a, A-2b, and A-2c. Rapidly evaporated the solvent under reduced pressure in a vacuum centrifuge (GeneVacg) for 20 hours. Product was a dark amber clear gum with some glassy material on top. PXRD and PLM analyses of all three samples indicated they were initially amorphous. Analyzed A-2a by PLM and TGA-IR. TGA-IR showed 7.8% wt. water and THF evolved upon heating to 200° C.. PXRD and PLM analyses of A-2a after one day open at RT showed crystallization to the supplied Form IV. | Form IV (after 1 day at ambient) |

Characterization of Amorphous Material (A-1)

PXRD and PLM analyses indicated the material was non-crystalline. DSC analysis showed no melting endotherm up to 200° C., which is consistent with an amorphous phase. TGA-IR analysis showed about 1.3% wt. loss of water and methanol upon heating from 26-200° C. Amorphous mirdametinib was physically stable in both open and closed vials for at least 24 hours at RT.

Example 7: Results of Crystal-Form Screen

The crystal-form screen consisted of about 450 crystallization experiments covering crystalline and amorphous input materials, and various crystallization modes, solvents, and temperatures.

Four hydrates (designated Forms VI, XIII, XIX and XX) were observed and appear to be novel forms. Water activity experiments conducted between non-solvated Form IV and two stable hydrates (Forms VI and XIX) indicated that Form IV is more stable at water activities (aw) 0.6-0.99 than hydrate Forms VI and XIX.

Fifteen solvates (designated Forms V, VII-XII, XV-XVIII, and XXI-XXIV) observed included process-related toluene (Form V), toluene/MIBK (Form VIII), and unstable toluene (Form IX) solvates.

Mirdametinib/process solvent conversion studies involving stirring the toluene solvate (Form V) in 1.1/0.5 (v/v) water/ethanol at RT with varying amounts of added toluene indicated that if crude mirdametinib from toluene/ethanol was the pure toluene solvate, controlling toluene levels going into the final crystallization could be critical. However, if the crude API is mostly Form IV with lesser amounts of the toluene solvate, it may not be as critical to monitor toluene levels in the crude mirdametinib.

Summary of Slurry-Ripening and Evaporative Screening Results

| # | Solvent | Amorph 5C | Amorph 25C | Amorph TC | Amorph 50C | Solvent | Fast Evap | Slow Evap |
|---|---|---|---|---|---|---|---|---|
| 1 | water | C | C | A  R | A | Ethanol | A | A |
| 2 | water:ethanol (80:20 v/v) | A | A | A | A | ethanol:water (95:5 v/v) | A | C |
| 3 | water:ethanol (90:10 v/v) | A | A | A | A | ethanol:water (90:10 v/v) | A | C |
| 4 | water:ethanol (95:5 v/v) | A | A | A | A | ethanol:water (80:20 v/v) | A | C |
| 5 | water:methanol (95:5 v/v) | A | A | A |   | ethanol:toluene (90:10 v/v) | A | A |
| 6 | water:THF (95:5 v/v) | A | A | A | A | ethanol:toluene (50:50 v/v) | A | A |
| 7 | water:dimethylformamide (95:5 v/v) | A | A | A | A | ethanol:TFE (90:10 v/v) | A | A |
| 8 | water:dioxane (95:5) | A | A | A | A | ethanol:DMF (80:20 v/v) | A | A |
| 9 | water:acetone (95:5 v/v) | A | A | A | A | ethanol:dimethylcarbonate (70:30 v/v) | A | A |
| 10 | water:2-propanol (99:1 v/v) | C | C | R  A | A | Acetone | A | A |
| 11 | cyclohexane | A | A | A | A | acetone:water (95:5 v/v) | A | A |
| 12 | chloroform | A | A | A | A | acetone:water (90:10 v/v) | A | C |
| 13 | isopropyl ether (IPE) | D | D | D  A | D | acetone:water (80:20 v/v) | A | A |
| 14 | toluene | X | B | F | B | acetone:dichloromethane (90:10 v/v) | X | A |
| 15 | toluene:ethanol (95:5 v/v) |   | B | B | B | acetone:chloroform (90:10 v/v) | X |   |
| 16 | toluene:ethanol (85:15 v/v) |   | B | B | B | acetone:isopropyl ether (90:10 v/v) | X | A |
| 17 | toluene:acetone (80:20 v/v) | A | B | B | B | acetone:tetrahydrofuran (50:50 v/v) | A | A |
| 18 | toluene:4-methyl-2-pentanone (80:20 v/v) | E | F | B | B | acetone:nitromethane (70:30 v/v) | N | A |
| 19 | toluene:ethyl acetate (80:20 v/v) | B | B | F | B | acetone:methyl-t-butyl ether (90:10 v/v) | A | A |
| 20 | toluene:2-propanol (80:20 v/v) |   | F | B | A | acetone:DMF (80:20 v/v) | A | 2 |
| 21 | dimethylcarbonate:ethanol (95:5 v/v) |   | A | A | A | Acetonitrile | A | A |
| 22 | trifluoroethanol (TFE) |   | A | A | A | acetonitrile:water (90:10 v/v) | A | A |
| 23 | MTBE (methyl-t-butyl ether) |   | G | A | G | acetonitrile:water (80:20 v/v) | A | C |
| 24 | acetonitrile |   | A | A | A | acetonitrile:water (70:30 v/v) |   | C |
| 25 | acetonitrile:toluene (50:50 v/v) | B | B | B | B | acetonitrile:DMSO (80:20 v/v) |   | 2 |
| 26 | acetontrile:isopropyl ether (50:50 v/v) |   | A | A | A | acetonitrile:DMF (80:20 v/v) | A | 2 |
| 27 | acetontrile:dichloromethane (50:50 v/v) |   |   | A | A | Methanol | A | A |
| 28 | dichloromethane:methanol (80:20 v/v) |   |   | A | A | methanol:nitromethane (80:20 v/v) | A | C |
| 29 | dichloromethane:tetrahydrofuran (80:20 v/v) |   |   | A | A | methanol:methyl acetate (50:50 v/v) | A | C |
| 30 | dichloromethane:ethanol (80:20 v/v) |   |   |   | J | 2-propanol | A | A |
| 31 | isopropyl ether:methanol (80:20 v/v) |   |   | A | J | 2-propanol:toluene (90:10 v/v) | A | A |
| 32 | isopropyl ether:tetrahydrofuran (80:20 v/v) |   |   |   | J | 2-propanol:cyclohexane (90:10 v/v) | A | A |
| 33 | chloroform:2-propanol (60:40 v/v) |   |   |   | J | 2-propanol:dichloromethane (90:10 v/v) | A | A |
| 34 | chloroform:dimethylformamide (90:10 v/v) |   |   | A | J | 2-propanol:chloroform (90:10 v/v) | A | A |
| 35 | dichloromethane:2-propanol (60:40 v/v) |   |   |   | J | 2-methyl-2-butanol | O | O |
| 36 | dichloromethane:DMSO (90:10 v/v) |   |   | A | A | ethyl acetate:dimethyl formamide (70:30 v/v) | A | 2 |
| 37 | heptane |   | A | A | A | ethyl acetate | A | A |
| 38 | heptane:ethyl acetate (50:50 v/v) | A | A | A | A | methyl acetate | A | A |
| 39 |   | A | A | A | A | 4-methyl-e-pentanone (MIBK) | A | Q |
| 40 |   | A | A | A | A  J | tetrahydrofuran (THF) | A |   |
| 41 |   | A | A | A | A | tetrahydrofuran:water (90:10 v/v) | A | A |
| 42 |   | A | A | A | A | tetrahydrofuran:2-butanol (90:10 v/v) | A | A |
| 43 |   | A | A | A | M | tetrahydrofuran:cyclohexane (90:10 v/v) | A | A |
| 44 |   |   | A | J | J | dioxane:water (90:10 v/v) | A | A |
| 45 |   |   | A | J | A | dioxane:toluene (90:10 v/v) | A | A |
| 46 |   |   | A | A | A | dioxane:toluene (80:20 v/v) | A | A |
| 47 |   |   | A | A | A | dioxane:dichloromethane (90:10 v/v) | A | A |
| 48 |   |   |   | A | A | dioxane:cyclohexane (90:10 v/v) | A | A |

| | | |
|---|---|---|
| A | Form IV | Non-solvated Form IV |
| B | Form V | Toluene solvate |
| C | Form VI | Hydrate |
| D | Form VII | IPE or IPE/Water solvate |

| | | |
|---|---|---|
| E | Form VIII | Toluene/MIBK solvate |
| F | Form IX | Unstable Toluene solvate |
| G | Form X | MTBE/Water solvate |
| H | Form XI | Chloroform/IPA solvate |
| I | Form XII | IPA solvate (isostructural to Form XI) |
| J | Form I | Non-solvated Form I |
| K | Form XIII | Hydrate |
| L | Form XIV | Transient Non-solv. form (similar to Form IV) |
| M | Form XV | Cyclohexane solvate |
| N | Form XVI | Poorly crystalline Nitromethane solvate |
| O | Form XVII | 2-Methyl-2-Butanol solvate |
| P | Form XVIII | Chloroform/Water solvate |
| Q | Form II | Non-solvated Form II |
| R | Form XIX | Hydrate |
| S | Form XX | Hydrate (unstable) |
| T | Form XXI | 2-Methyl-2-Butanol solvate 2 (unstable) |
| U | Form XXII | IPE or IPE/Water solvate 2 |
| V | Form XXIII | Cyclohexane/EtOAc solvate |
| W | Form XIV | IPE Solvate (unstable to desolvation) |
| X | Amorphous | |
| | No Solid | |

Notes:
1. Some extra peaks of unknown transient form observed. Some conversion to Form IV observed at ambient conditions.
2. Sample was a solution after 30 days of evaporation.
3. Sample was a solution after 11 days mixing.

Summary of Slurry-Ripening and Evaporative Screening Results

| # | Solvent | RC | CC | # | Solvent | Anti-Solvent | SAS |
|---|---|---|---|---|---|---|---|
| 1 | water:ethanol (60:40 v/v)water | C A | C | 1 | ethanol | water | A |
| 2 | water:ethanol (50:50 v/v) | A | | 2 | ethanol | toluene | 3 |
| 3 | water:ethanol (40:60 v/v) | | | 3 | ethanol | cyclohexane | 3 |
| 4 | water:Methanol (40:60 v/v) | R | A | 4 | ethanol | chloroform | 3 |
| 5 | water:THF (95:5 v/v) | C | | 5 | ethanol | IPE | 3 |
| 6 | water:dimethylformamide (50:50 v/v) | | | 6 | MIBK | toluene | F |
| 7 | water:dioxane (50:50) | | | 7 | MIBK | cyclohexane | A |
| 8 | water:acetone (50:50 v/v) | | | 8 | MIBK | chloroform | 3 |
| 9 | 2-propanol | I | I | 9 | MIBK | IPE | 3 |
| 10 | cyclohexane | | | 10 | MeCN | water | A |
| 11 | chloroform | | | 11 | MeCN | toluene | 3 |
| 12 | isopropyl ether (IPE) | | | 12 | MeCN | cyclohexane | 3 |
| 13 | toluene | | | 13 | MeCN | chloroform | 3 |
| 14 | toluene:ethanol (70:30 v/v) | B | | 14 | MeCN | DCM | 3 |
| 15 | toluene:ethanol (80:20 v/v) | B | B | 15 | MeCN | IPF | 3 |
| 16 | toluene:ethanol (90:10 v/v) | B | B | 16 | EtOAc | toluene | A |
| 17 | toluene:acetone (70:30 v/v) | | | 17 | EtOAc | cyclohexane | V |
| 18 | toluene:4-methyl-2-pentanone (50:50 v/v) | | E | 18 | EtOAc | chloroform | A |
| 19 | toluene:ethyl acetate (50:50 v/v) | | | 19 | EtOAc | IPE | D |
| 20 | toluene:2-propanol (50:50 v/v) | | | 20 | EtOAc | DCM | 3 |
| 21 | dimethylcarbonate:ethanol (70:30 v/v) | A | | | | | |
| 22 | trifluoroethanol (TFE): ethanol (70:30 v/v) | A | A | | | | |
| 23 | MTBE (methyl-t-butyl ether): 2-propanol (50:50 v/v) | | | | | | |
| 24 | acetonitrile | S | S | | | | |
| 25 | acetonitrile:toluene (50:50 v/v) | | | | | | |
| 26 | acetontrile:isopropyl ether (50:50 v/v) | A D | W | | | | |
| 27 | acetontrile:dichloromethane (50:50 v/v) | | S | | | | |
| 28 | dichloromethane:methanol (80:20 v/v) | | | | | | |
| 29 | dichloromethane:tetrahydrofuran (80:20 v/v) | | | | | | |
| 30 | dichloromethane:ethanol (80:20 v/v) | | | | | | |
| 31 | isopropyl ether:methanol (80:20 v/v) | U | | | | | |
| 32 | isopropyl ether:tetrahydrofuran (80:20 v/v) | | | | | | |
| 33 | chloroform:2-propanol (60:40 v/v) | H | H | | | | |
| 34 | chloroform:dimethylformamide (90:10 v/v) | | | | | | |
| 35 | dichloromethane:2-propanol (40:60 v/v) | | | | | | |
| 36 | dichloromethane:dimethyl sulfoxide (50:50 v/v) | | | | | | |
| 37 | methyl acetate | | | | | | |
| 38 | heptane:ethyl acetate (50:50 v/v) | | A | | | | |
| 39 | heptane:2-propanol (50:50 v/v) | I | I | | | | |
| 40 | heptane:tetrahydrofuran (50:50 v/v) | | | | | | |
| 41 | heptane:2-butanone (50:50 v/v) | A | A | | | | |
| 42 | cyclohexane:acetone (40:60 v/v) | | | | | | |
| 43 | cyclohexane:2-butanone (40:60 v/v) | | | | | | |
| 44 | MIBK (4-methyl-2-pentanone) | | | | | | |

| | | |
|---|---|---|
| 45 Ethyl Acetate (EtOAc) | | |
| 46 2-methyl-2-butanol | T | T |
| 47 nitromethane:1-propanol (40:60 v/v) | | |
| 48 dimethylcarbonate (DMC) | A1 | A1 |

| | | |
|---|---|---|
| A | Form IV | Non-solvated Form IV |
| B | Form V | Toluene solvate |
| C | Form VI | Hydrate |
| D | Form VII | IPE or IPE/Water solvate |
| E | Form VIII | Toluene/MIBK solvate |
| F | Form IX | Unstable Toluene solvate |
| G | Form X | MTBE/Water solvate |
| H | Form XI | Chloroform/IPA solvate |
| I | Form XII | IPA solvate (isostructural to Form XI) |
| J | Form I | Non-solvated Form I |
| K | Form XIII | Hydrate |
| L | Form XIV | Transient Non-solv. form (similar to Form IV) |
| M | Form XV | Cyclohexane solvate |
| N | Form XVI | Poorly crystalline Nitromethane solvate |
| O | Form XVII | 2-Methyl-2-Butanol solvate |
| P | Form XVIII | Chloroform/Water solvate |
| Q | Form II | Non-solvated Form II |
| R | Form XIX | Hydrate |
| S | Form XX | Hydrate (unstable) |
| T | Form XXI | 2-Methyl-2-Butanol solvate 2 (unstable) |
| U | Form XXII | IPE or IPE/VVater solvate 2 |
| V | Form XXIII | Cyclohexane/EtOAc solvate |
| W | Form XIV | IPE Solvate (unstable to desolvation) |
| X | Amorphous | |
| | No Solid | |

Notes:
1. Some extra peaks of unknown transient form observed. Some conversion to Form IV observed at ambient conditions.
2. Sample was a solution after 30 days of evaporation.
3. Sample was a solution after 11 days mixing.

Example 8: Description of the Obtained Crystal Forms of Mirdametinib

The following sections describe and summarize the physical properties of each of the crystal forms observed for mirdametinib.

Transient Non-Solvated Form XIV

The characterization data for Form XIV, a transient non-solvated form very similar to Form IV, are presented in FIG. 12A and FIG. 12B. PXRD and PLM analysis indicates that the material is crystalline. DSC analysis shows a single sharp endotherm with onset at about 111° C. (ΔH=85.6 J/g). TGA-IR analysis shows about 0.15% wt. loss to 150° C., indicating a non-solvated form. Form XIV was found to convert to Form IV within four days at ambient conditions. Form XIV was not scaled up to be used for further studies (e.g. relative stability studies).

Toluene Solvate Form V

The characterization data for Form V, a process-relevant toluene solvate, are presented in FIG. 3A and FIG. 3B. PXRD and PLM analysis indicates that the material is crystalline. DSC analysis shows two overlapping endotherms with onsets at about 77° C. (ΔH=44.3 J/g) and about 95° C. (ΔH=33.2 J/g). TGA-IR analysis shows about 2.7% wt. (0.15 eq) loss of toluene upon heating to 100° C. and about 4.7% wt. (0.26 eq) total loss of toluene upon heating to 185° C., indicating a solvated form. Form V was found to be stable at ambient conditions for ≥10 days. Form V was scaled up to be used for focused studies around the mirdametinib crystallization process.

Preparation of Form V

Mirdametinib (308.0 mg) was dissolved in 3.0 mL of methanol and the solution was filtered through a 0.2 μm PTFE filter. The solution was rapidly evaporated under reduced pressure (GeneVac®) overnight to yield amorphous material. Toluene (150 μL) and a stir disc was added to the amorphous product and the mixture was stirred at 25° C. for 35 min. Seeds (~1 mg) were added, and the sample was stirred at 25° C. for 23 hours. The damp solids were dried in a nitrogen flow chamber for 3 hours. The batch weight was about 212 mg, and the yield was about 69% wt. of Form V.

Form VIII (Toluene/MIBK Solvate)

The characterization data for Form VIII, a toluene/MIBK solvate, are presented FIG. 6A and FIG. 6B. PXRD and PLM analysis indicates that the material is crystalline. DSC analysis shows a broad endotherm with onset at about 81° C. (ΔH=67.1 J/g) followed by a small broad endotherm with onset at about 110° C. (ΔH=7.1 J/g). TGA-IR analysis shows about 3.3% wt. loss of toluene and MIBK upon heating to 112° C. and about 0.8% wt. additional loss of toluene and MIBK upon heating from 112 to 150° C., indicating a solvated form. Form VIII was stable at ambient conditions for ≥2 days. Form VIII was not scaled up for further studies (e.g., focused studies around the mirdametinib crystallization process).

Unstable Toluene Solvate Form IX

The characterization data for Form IX, an unstable toluene solvate, are presented in FIG. 7A and FIG. 7B. PXRD and PLM analysis indicates that the material is crystalline. DSC analysis shows a broad endotherm with onset at about 84° C. (ΔH=17.1 J/g), an endotherm at about 107° C. (ΔH=12.4 J/g), and a sharper endotherm with onset at about 114° C. (ΔH=39.6 J/g). TGA-IR analysis shows about 4.6% wt. loss of toluene upon heating to 128° C., indicating a solvated form. Form IX exhibited significant conversion toward Form IV after 20 hours at ambient conditions. Form IX was not scaled up for further studies (e.g. focused studies around the mirdametinib crystallization process).

Hydrate Form VI

The characterization data for Form VI, a hydrate, are presented in FIG. 4A and FIG. 4B. PXRD and PLM analysis indicates that the material is crystalline. DSC analysis shows three broad endotherms with onsets at about 41° C. ($\Delta H=11.4$ J/g), about 70° C. ($\Delta H=48.1$ J/g), and about 109° C. ($\Delta H=21.3$ J/g). TGA-IR analysis shows about 2.4% wt. (0.7 eq) loss of water upon heating to 125° C., indicating a hydrated form. Form VI was found to be stable for ≥2 weeks in solid-state at ambient conditions. Form VI was scaled up to be used for water activity studies between non-solvated Form IV and the stable hydrates.

Preparation of Form VI/Form IV Mixture

Mirdametinib (120.8 mg) was dissolved in 1.0 mL of methanol. The solution was filtered through a 0.2 μm PTFE filter and rapidly evaporated under reduced pressure (Gene-Vac®) overnight. Water (1.0 mL) and a stir disc were added to the dry solids, followed by seeds (~0.1 mg). The suspension was mixed at 25° C. for 24 hours, and the solids were isolated by vacuum-filtration. The batch weight was about 58 mg, and the yield was an about 48% wt. of a mixture of Form VI and Form IV.

Hydrate Form IX

The characterization data for Form IX, a hydrate, are presented in FIG. 7A and FIG. 7B. PXRD and PLM analysis indicates that the material is crystalline and contains some Form IV. DSC analysis shows two broad endotherms with onsets at about 55° C. ($\Delta H=66.8$ J/g) and about 109° C. ($\Delta H=25.5$ J/g). TGA-IR analysis shows about 3.1% wt. (0.9 eq) loss of water upon heating to 100° C., indicating a hydrated form. Form IX was observed only once (as phase-pure) during screening, and it was observed to slowly convert to Form IV in solid-state at ambient conditions. Form IX was not scaled up for further studies (e.g., water activity studies).

Hydrate Form XIX

The characterization data for Form XIX, a hydrate, are presented in FIG. 17A and FIG. 17B. PXRD and PLM analysis indicates that the material is crystalline. DSC analysis shows a broad endotherm with onset at about 69° C. ($\Delta H=28.5$ J/g), followed by an exotherm with onset at about 98° C. ($\Delta H=13.5$ J/g), and a sharp endotherm with onset at about 115° C. ($\Delta H=59.6$ J/g). TGA-IR analysis shows about 1.85% wt. (0.5 eq) loss of water upon heating to 92° C., indicating a hydrated form. Form XIX was found to be stable in a capped vial for ≥2 weeks. Form XIX was scaled up to be used for water activity studies between non-solvated Form IV and the stable hydrates.

Preparation of Form XIX

Mirdametinib (about 497 mg) was dissolved in 3.0 mL of water:MeOH (40:60 v/v) by mixing at 50° C. for 10 min. The solution was filtered hot through a 0.2 μm PTFE filter into a second vial at 50° C. The solution was rapidly cooled to −20° C., and seeds (1-2 mg) were added and dispersed by swirling. After 30 min., the product was a thick paste, so 1.0 mL more solvent was added, and the suspension cooled at −20° C. for 30 min. The solids in the cold suspension were isolated by vacuum-filtration, then allowed to air dry for 16 hours. The batch weight was about 278 mg, and the yield was about 56% wt. of Form XIX.

Hydrate Form XX

The characterization data for Form XX, a hydrate, are presented in FIG. 18A and FIG. 18B. PXRD and PLM analysis indicates that the material is crystalline. DSC analysis shows three broad endotherms with onsets at about 77° C. ($\Delta H=29.0$ J/g), about 92° C. ($\Delta H=9.8$ J/g) and about 110° C. ($\Delta H=6.8$ J/g). TGA-IR analysis shows about 2.6% wt. (0.7 eq) loss of mostly water with a small amount of acetonitrile upon heating to 126° C., indicating a hydrated form. TGA-IR analysis of a second less-crystalline sample of Form XX showed only water evolved upon heating. Form XX was found to convert to Form IV within 10 days at ambient conditions. Form XX was not scaled up for further studies (e.g., water activity studies).

Other Non-Process Related Solvates (Forms VII, X-XII, XV-XVIII, XXI-XXIV)

A summary of the non-process related solvates (Forms VII, X-XII, XV-XVIII, and XXI-XXIV) is shown in Table 2. The characterization data for these solvates are shown in FIGS. 5A-5B, 8A-8B, 9A-9B, 10A-10B, 13A-13B, 14A-14B, 15A-15B, 16A-16B, 19A-19B, 20A-20B, 21A-21B, and 22A-22B.

TABLE 2

Summary of Non-Process Solvates

| Form | Nature of Solvate | DSC Endotherm Onsets (approximate ° C.) | TGA-IR Data (Wt. Loss) |
|---|---|---|---|
| VII | IPE or IPE/water | 85, 110 | 5.2% isopropyl ether |
| X | MTBE/water | 89 (2 merged) | 2.9% MTBE and water |
| XI | Chloroform/IPA | 69, 104 | 7.6% chloroform and IPA |
| XII | IPA | 72, 109 | 8.5% IPA (low sample quantity) |
| XV | Cyclohexane | 104 | 3.8% (0.2 eq.) cyclohexane |
| XVI | Nitromethane (poorly crystalline) | 74, 102 (2 merged), 114 | 2.1% (0.2 eq.) nitromethane |
| XVII | 2-Methyl-2-Butanol | 89 | 2.7% (0.15 eq.) 2-methyl-2-butanol |
| XVIII | Likely Chloroform | 83 | 1.6% chloroform and water |
| XXI | 2-Methyl-2-Butanol (converts to Form IV) | 52 (overlap of two), 90 | 14.1% (0.9 eq.) 2-methyl-2-butanol |
| XXII | IPE or IPE/water | 65, 89, 102 | 13.8% isopropyl ether and water |
| XXIII | Cyclohexane/EtOAc | 81, 101 | 4.4% cyclohexane and EtOAc |
| XXIV | IPE or IPE/water | 104 (multiple overlapping endotherms) | 1.2% isopropyl ether and water |

PXRD, TGA, and DSC data for each form presented herein are shown in FIGS. 2A-21B, 3A-3B3, 4A-4B3, 5A-5B3, 6A-6B3, 7A-7, 8A-8, 9A-9, 10A-10B3, 11A-11B, 12A-12B, 13A-13B, 14A-14B, 15A-15B, 16A-16B, 17A-17B, 18A-18B, 19A-19B, 20A-20B, 21A-211B, 22A-22B, and 23A-23B.

Example 9: Water Activity Studies of Hydrates at 23° C.

Water activity studies of the stable hydrated Forms VI and XIX were conducted to determine their relative thermodynamic stabilities. The studies were conducted at 23° C. in various water/ethanol mixtures to provide water activities (aw) from 0.6-0.99. The water activity range includes the approximate water activity of the current final isolation step of the mirdametinib manufacturing process. Saturated suspensions were prepared by stirring an excess of mirdametinib in the test solvents for 16 hours. The suspensions were filtered and transferred onto mixtures containing equivalent amounts of Form VI and Form XIX.

The suspensions were stirred at the target temperatures, sampled at three and five days and analyzed by PXRD. The results are summarized below and show that all experiments produced Form IV. The hydrates may be kinetically favored at higher water activities.

Example 10: Drying of Certain Forms Via Vacuum Oven

Drying studies for certain forms were conducted overnight in a vacuum oven at 45° C. After drying, samples were equilibrated to RT for 10 min. and analyzed by PXRD at about 70% ambient lab humidity. The results are summarized below.
  Form V (Toluene Solvate): Remained unchanged.
  Form VI (Hydrate): Partially converted to Form A.
  Form XIII (Hydrate): Form XIII/Form IV mixture converted to Form IV.
  Form XIX (Hydrate): Remained unchanged.

Desolvation/dehydration studies of certain forms were conducted in a TGA pan with loose lid at a heating rate of 15° C./min from 25 to 100° C. with a 5 min. hold at 100° C. Samples were air-cooled to RT on the TGA and analyzed by PXRD if crystalline. The results are summarized below.
  Form V (Toluene Solvate): After cooling, observed sample to be molten and transparent dark amber in appearance (melted and solidified in molten, amorphous state, possible decomposition).
  Form VI (Hydrate): After cooling, observed sample to be molten and transparent dark amber in appearance (melted and solidified in molten, amorphous state, possible decomposition).
  Form XIX (Hydrate): After cooling, observed sample to be very slightly sticky, but solid particles (not melted). PXRD indicated Form I.

Example 11: Toluene-Spiked Slurry Studies

The process-relevant toluene solvate (Form V) was stirred in water:ethanol (1.1/0.5 v/v) overnight at RT with varying amounts of added toluene. The suspensions were filtered, and solids analyzed by PXRD. The results are summarized below.
  With no added toluene, Form V converted to phase-pure Form IV.
  With 0.5% added toluene (relative to mirdametinib weight), Form V converted to mostly Form IV with some lesser amount of Form V.
  With 1% and 2% added toluene, higher relative amounts of Form V were observed, but difficult to distinguish between 1% and 2% toluene, since PXRD data was qualitative and variable.

The results of the toluene-spiked slurry studies suggest that if crude mirdametinib from toluene/ethanol was the pure toluene solvate, controlling toluene levels going into the final crystallization would be critical. However, if the crude mirdametinib is mostly Form IV with lesser amounts of the toluene solvate, it may not be as critical to monitor toluene levels in the crude mirdametinib.

Example 12: Single Crystal X-Ray Diffraction Analysis of Form IV

A suitable single Form IV crystal was analyzed using a Bruker D8 Venture Photon II CPAD diffractometer equipped with a CuKα INCOATEC Imus micro-focus source (λ=1.54178 Å). The simulated PXRD pattern was calculated from the low temperature (100 K) structure and room temperature (298 K, 25° C.) unit cell parameters shown below. Unit cell at room temperature was initially determined by Difference Vectors method based on 235 reflections harvested from 151, 1° diffraction frames. Unit cell parameters were subsequently refined during data integration by Saint (Bruker (2020). SAINT. Data Reduction Software) and are based on 903 reflections recorded between 19.1 and 1.1 Å resolution. The simulated pattern was consistent with an experimental Form IV pattern as shown in FIG. 1A.

TABLE 3

Initially Determined Unit Cell Parameters at Room Temperature

| a[Å] | b[Å] | c[Å] | α[Å] | β[Å] | γ[Å] | V[Å3] |
|---|---|---|---|---|---|---|
| 27.080(2) | 27.080(2) | 4.6971(5) | 90 | 90 | 90 | 3444.5(8) |

TABLE 4

Form IV Crystal Data and Structure Refinement

| Crystal system | Tetragonal |
|---|---|
| Space group | $P4_1$ |
| a/Å | 26.9861(4) |
| b/Å | 26.9861(4) |
| c/Å | 4.66600(10) |
| α/° | 90 |
| β/° | 90 |
| γ/° | 90 |
| Volume/Å$^3$ | 3398.01(12) |
| Z | 8 |
| ρcalc g/cm$^3$ | 1.885 |
| μ/mm$^{-1}$ | 15.351 |
| F(000) | 1888 |

| | Formulation Composition | | | | | |
|---|---|---|---|---|---|---|
| | 1 mg | | 2 mg | | 5 mg | |
| Ingredient | % (w/w) | mg/cap | % (w/w) | mg/cap | % (w/w) | mg/cap |
| Mirdametinib[a] | 0.77 | 1 | 0.77 | 2 | 5.26 | 5 |
| Microcrystalline Cellulose[b] | 93.23 | 121.2 | 93.23 | 242.4 | 89.74 | 85.25 |
| Croscarmellose sodium | 5 | 6.5 | 5 | 13 | 5 | 4.75 |
| Magnesium Stearate | 1 | 1.3 | 1 | 2.6 | 0 | 0 |
| Total | 100 | 130 | 100 | 260 | 100 | 95 |
| Capsule Shells | | Size #3 HG capsules | | Size #1 HG capsules | | Size #2 HG capsules |

HG = Hard Gelatin
[a]Based on a theoretical potency of 1.000. Actual quantity may be adjusted based on the actual potency.
[b]Quantity of microcrystalline cellulose may be adjusted for slight potency changes of PD-0325901.

Example 14: Dispersible Tablets

| | Formulation Composition | | | |
|---|---|---|---|---|
| | 0.5 mg | | 1.0 mg | |
| Ingredient | % (w/w) | mg/tab | % (w/w) | mg/tab |
| Mirdametinib [a] | 0.75 | 0.50 | 0.75 | 1.00 [c] |
| Microcrystalline Cellulose [b] | 90.52 | 60.60 | 90.52 | 121.20 [c] |

-continued

| Ingredient | Formulation Composition | | | |
|---|---|---|---|---|
| | 0.5 mg % (w/w) | mg/tab | 1.0 mg % (w/w) | mg/tab |
| Croscarmellose sodium | 4.85 | 3.25 | 4.85 | 6.50 [c] |
| Grape flavor | 1.94 | 1.30 | 1.94 | 2.60 |
| Sucralose | 0.97 | 0.65 | 0.97 | 1.30 |
| Magnesium Stearate | 0.97 | 0.65 | 0.97 | 1.30 [c] |
| Total | 100.0 | 66.95 | 100.0 | 133.90 |

[a] Based on theoretical potency of 1.000. Quantity may be adjusted based on the actual potency.
[b] Quantity of microcrystalline cellulose may be adjusted for slight potency changes of mirdametinib
[c] Excipients are present at the same mg/unit as the 1 mg capsule All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific aspects thereof, it will be understood that invention is capable of further modifications and this application is intended to cover any variations, uses, or adaptations following, in general, the principles and including such departures from the present disclosure that come within known or customary practice within the art to which the invention pertains and can be applied to the essential features hereinbefore set forth, and follows in the scope of the claimed.

In addition to the various embodiments described herein, the present disclosure includes the following embodiments numbered E1 through E275. This list of embodiments is presented as an exemplary list and the application is not limited to these embodiments.

E1. A crystalline form of N—((R)-2,3-dihydroxypropoxy)-3,4-difluoro-2-(2-fluoro-4-iodo-phenylamino)-benzamide of Formula (I)

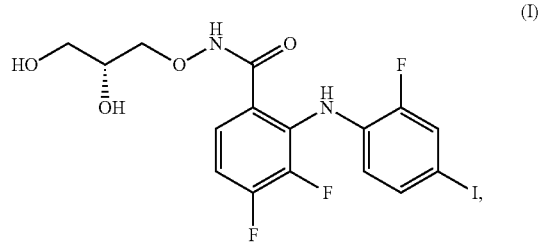 [SMILES: O=C(NOC[C@H](O)CO)c1ccc(F)c(F)c1Nc1ccc(I)cc1F]

(I)

selected from the group consisting of:
a crystalline form of N—((R)-2,3-dihydroxypropoxy)-3,4-difluoro-2-(2-fluoro-4-iodo-phenylamino)-benzamide characterized by an XRPD pattern having peaks at 5.4±0.2, 17.5±0.2, and 22.8±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 5.9±0.2, 7.2±0.2, and 21.2±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 5.3±0.2, 10.6±0.2, and 16.1±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 5.4±0.2, 10.7±0.2, and 18.7±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 6.7±0.2, 13.5±0.2, and 22.2±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 10.6±0.2, 19.6±0.2, and 24.8±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 6.9±0.2, and 10.1±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 10.1±0.2, 17.3±0.2, and 22.6±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 5.1±0.2, and 14.6±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 23.4±0.2, and 25.2±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 14.7±0.2, and 20.9±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 6.0±0.2, 17.1±0.2, and 20.6±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 5.9±0.2, 10.1±0.2, and 15.5±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 10.7±0.2, and 15.9±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 10.2±0.2, 11.6±0.2, and 20.0±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 7.8±0.2, 14.0±0.2, and 17.1±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 8.2±0.2, and 16.7±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 7.2±0.2, 21.7±0.2, and 29.1±0.2 degrees two theta;
a crystalline form of N—((R)-2,3-dihydroxypropoxy)-3,4-difluoro-2-(2-fluoro-4-iodo-phenylamino)-benzamide characterized by an XRPD pattern having peaks at 5.4±0.2, 9.7±0.2, and 10.7±0.2 degrees two theta; and a crystalline form of N—((R)-2,3-dihydroxypropoxy)-3,4-difluoro-2-(2-fluoro-4-iodo-phenylamino)-benzamide characterized by an XRPD pattern having peaks at 7.2±0.2, 20.6±0.2, and 23.0±0.2 degrees two theta.

E2. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks 5.4±0.2, 17.5±0.2, and 22.8±0.2 degrees two theta.

E3. The crystalline form of E2, wherein the crystalline form of N—((R)-2,3-dihydroxypropoxy)-3,4-difluoro-2-(2-fluoro-4-iodo-phenylamino)-benzamide is characterized by an XRPD pattern having peaks 5.4±0.2, 12.5±0.2, 17.5±0.2, and 22.8±0.2 degrees two theta.

E4. The crystalline form of E2 or E3, wherein the TGA exhibits that the crystalline form of N—((R)-2,3-dihydroxypropoxy)-3,4-difluoro-2-(2-fluoro-4-iodo-phenylamino)-benzamide loses about 2.7 wt % between about 35° C. and about 100° C.

E5. The crystalline form of any one of E2-E4, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 77° C.

E6. The crystalline form of any one of E2-E5, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 95° C.

E7. The crystalline form of any one of E2-E6, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 77° C. and a second endotherm onset at about 95° C.

E8. The crystalline form of any one of E2-E7, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 2A.

E9. The crystalline form of any one of E2-E8, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 2B; and/or
b) a DSC profile substantially as shown in FIG. 2B.

E10. The crystalline form of any one of E2-E9, wherein the crystalline form of N—((R)-2,3-dihydroxypropoxy)-3,4-difluoro-2-(2-fluoro-4-iodo-phenylamino)-benzamide is Form V.

E11. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.9±0.2, 7.2±0.2, and 21.2±0.2 degrees two theta.

E12. The crystalline form of E11, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.9±0.2, 7.2±0.2, 9.3±0.2, and 21.2±0.2 degrees two theta.

E13. The crystalline form of E11 or E12, wherein the TGA exhibits that the crystalline form of N—((R)-2,3-dihydroxypropoxy)-3,4-difluoro-2-(2-fluoro-4-iodo-phenylamino)-benzamide loses about 2.4 wt % between about 25° C. and about 125° C.

E14. The crystalline form of any one of E11-E13, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 41° C.

E15. The crystalline form of any one of E11-E14, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 70° C.

E16. The crystalline form of any one of E11-E15, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 109° C.

E17. The crystalline form of any one of E11-E16, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 41° C., a second endotherm onset at about 70° C., and a third endotherm onset at about 109° C.

E18. The crystalline form of E11-E17, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 3A.

E19. The crystalline form of E11-E18, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 3B; and/or
b) a DSC profile substantially as shown in FIG. 3B.

E20. The crystalline form of any one of E11-E19, wherein the crystalline form of N—((R)-2,3-dihydroxypropoxy)-3,4-difluoro-2-(2-fluoro-4-iodo-phenylamino)-benzamide is Form VI.

E21. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.3±0.2, 10.6±0.2, and 16.1±0.2 degrees two theta.

E22. The crystalline form of E21, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.3±0.2, 10.6±0.2, 13.9±0.2, and 16.1±0.2 degrees two theta.

E23. The crystalline form of E21 or E22, wherein the TGA exhibits that the crystalline form of N—((R)-2,3-dihydroxypropoxy)-3,4-difluoro-2-(2-fluoro-4-iodo-phenylamino)-benzamide loses about 5.2 wt % between about 40° C. and about 120° C.

E24. The crystalline form of any one of E21-E23, wherein the crystalline form of N—((R)-2,3-dihydroxypropoxy)-3,4-difluoro-2-(2-fluoro-4-iodo-phenylamino)-benzamide exhibits a DSC thermogram that an endotherm onset at about 85° C.

E25. The crystalline form of any one of E21-E24, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 110° C.

E26. The crystalline form of any one of E21-E25, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 85° C. and a second endotherm onset at about 110° C.

E27. The crystalline form of any one of E21-E26, wherein the crystalline form of N—((R)-2,3-dihydroxypropoxy)-3, 4-difluoro-2-(2-fluoro-4-iodo-phenylamino)-benzamide is characterized by an XRPD pattern substantially as shown in FIG. 4A.

E28. The crystalline form of any one of E21-E27, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 4B; and/or
b) a DSC profile substantially as shown in FIG. 4B.

E29. The crystalline form of any one of E21-E28, wherein the crystalline form of N—((R)-2,3-dihydroxypropoxy)-3,4-difluoro-2-(2-fluoro-4-iodo-phenylamino)-benzamide is Form VII.

E30. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.4±0.2, 10.7±0.2, and 18.7±0.2 degrees two theta.

E31. The crystalline form of E30, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.4±0.2, 10.7±0.2, 18.7±0.2, and 23.9±0.2 degrees two theta.

E32. The crystalline form of E30 or E31, wherein the TGA exhibits that the crystalline form of N—((R)-2,3-dihydroxypropoxy)-3,4-difluoro-2-(2-fluoro-4-iodo-phenylamino)-benzamide loses about 3.3 wt % between about 40° C. and about 112° C.

E33. The crystalline form of any one of E30-E32, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 81° C.

E34. The crystalline form of any one of E30-E33, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 110° C.

E35. The crystalline form of any one of E30-E34, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 81° C. and a second endotherm onset at about 110° C.

E36. The crystalline form of any one of E30-E35, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 5A.

E37. The crystalline form of any one of E30-E36, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 5B; and/or
b) a DSC profile substantially as shown in FIG. 5B.

E38. The crystalline form of any one of E30-E37, wherein the crystalline form of N—((R)-2,3-dihydroxypropoxy)-3,4-difluoro-2-(2-fluoro-4-iodo-phenylamino)-benzamide is Form VIII.

E39. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 6.7±0.2, 13.5±0.2, and 22.2±0.2 degrees two theta.

E40. The crystalline form of E39, wherein the crystalline form of N—((R)-2,3-dihydroxypropoxy)-3,4-difluoro-2-(2-fluoro-4-iodo-phenylamino)-benzamide is characterized by an XRPD pattern having peaks at 6.7±0.2, 8.0±0.2, 13.5±0.2, and 22.2±0.2 degrees two theta.

E41. The crystalline form of E39 or E40, wherein the TGA exhibits that the crystalline form of N—((R)-2,3-dihydroxypropoxy)-3,4-difluoro-2-(2-fluoro-4-iodo-phenylamino)-benzamide loses about 4.6 wt % between about 28° C. and about 128° C.

E42. The crystalline form of any one of E39-E41, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 84° C.

E43. The crystalline form of any one of E39-E42, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 107° C.

E44. The crystalline form of any one of E39-E43, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 114° C.

E45. The crystalline form of any one of E39-E44, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 84° C., a second endotherm onset at about 107° C., and a third endotherm onset at about 114° C.

E46. The crystalline form of any one of E39-E45, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 6A.

E47. The crystalline form of any one of E39-E46, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 6B; and/or
b) a DSC profile substantially as shown in FIG. 6B.

E48. The crystalline form of any one of E39-E47, wherein the crystalline form of N—((R)-2,3-dihydroxypropoxy)-3,4-difluoro-2-(2-fluoro-4-iodo-phenylamino)-benzamide is Form IX.

E49. The crystalline of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 10.6±0.2, 19.6±0.2, and 24.8±0.2 degrees two theta.

E50. The crystalline of E49, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 10.6±0.2, 19.6±0.2, and 24.8±0.2 degrees two theta.

E51. The crystalline form of E49 or E50, wherein the TGA exhibits that the crystalline form of N—((R)-2,3-dihydroxypropoxy)-3,4-difluoro-2-(2-fluoro-4-iodo-phenylamino)-benzamide loses about 2.9 wt % between about 40° C. and about 115° C.

E52. The crystalline form of any one of E49-E51, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 89° C.

E53. The crystalline form of any one of E49-E52, wherein the crystalline form of N—((R)-2,3-dihydroxypropoxy)-3, 4-difluoro-2-(2-fluoro-4-iodo-phenylamino)-benzamide is characterized by an XRPD pattern substantially as shown in FIG. 7A.

E54. The crystalline form of any one of E49-E53, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 7B; and/or
b) a DSC profile substantially as shown in FIG. 7B.

E55. The crystalline form of any one of E49-E54, wherein the crystalline form of N—((R)-2,3-dihydroxypropoxy)-3,4-difluoro-2-(2-fluoro-4-iodo-phenylamino)-benzamide is Form X.

E56. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 6.9±0.2, and 10.1±0.2 degrees two theta.

E57. The crystalline form of E56, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 6.9±0.2, 10.1±0.2, and 19.2±0.2 degrees two theta.

E58. The crystalline form of E56 or E57, wherein the TGA exhibits that the crystalline form of N—((R)-2,3-dihydroxypropoxy)-3,4-difluoro-2-(2-fluoro-4-iodo-phenylamino)-benzamide loses about 7.6 wt % between about 40° C. and about 175° C.

E59. The crystalline form of any one of E56-E58, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 69° C.

E60. The crystalline form of any one of E56-E59, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 104° C.

E61. The crystalline form of any one of E56-E60, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 69° C. and a second endotherm onset at about 104° C.

E62. The crystalline form of any one of E56-E61, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 8A.

E63. The crystalline form of any one of E56-E62, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 8B; and/or
b) a DSC profile substantially as shown in FIG. 8B.

E64. The crystalline form of any one of E56-E63, wherein the crystalline form of N—((R)-2,3-dihydroxypropoxy)-3,4-difluoro-2-(2-fluoro-4-iodo-phenylamino)-benzamide is Form XI.

E65. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 10.1±0.2, 17.3±0.2, and 22.6±0.2 degrees two theta.

E66. The crystalline form of E65, wherein the crystalline form of N—((R)-2,3-dihydroxypropoxy)-3,4-difluoro-2-(2-fluoro-4-iodo-phenylamino)-benzamide is characterized by an XRPD pattern having peaks at 10.1±0.2, 17.3±0.2, 21.5±0.2, and 22.6±0.2 degrees two theta.

E67. The crystalline form of E65 or E66, wherein the TGA exhibits that the crystalline form of N—((R)-2,3-dihydroxypropoxy)-3,4-difluoro-2-(2-fluoro-4-iodo-phenylamino)-benzamide loses about 8.5 wt % between about 40° C. and about 160° C.

E68. The crystalline form of any one of E65-E67, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 72° C.

E69. The crystalline form of any one of E65-E68, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 109° C.

E70. The crystalline form of any one of E65-E69, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 72° C. and a second endotherm onset at about 109° C.

E71. The crystalline form of any one of E65-E70, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 9A.

E72. The crystalline form of any one of E65-E71, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 9B; and/or
b) a DSC profile substantially as shown in FIG. 9B.

E73. The crystalline form of any one of E65-E72, wherein the crystalline form of N—((R)-2,3-dihydroxypropoxy)-3,4-difluoro-2-(2-fluoro-4-iodo-phenylamino)-benzamide is Form XII.

E74. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 5.1±0.2, and 14.6±0.2 degrees two theta.

E75. The crystalline form of E74 wherein the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 5.1±0.2, 6.4±0.2, and 14.6±0.2 degrees two theta.

E76. The crystalline form of E74 or E75, wherein the TGA exhibits that the crystalline form of N—((R)-2,3-dihydroxypropoxy)-3,4-difluoro-2-(2-fluoro-4-iodo-phenylamino)-benzamide loses about 3.1 wt % between about 20° C. and about 100° C.

E77. The crystalline form of any one of E74-E76, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 55° C.

E78. The crystalline form of any one of E74-E77, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 109° C.

E79. The crystalline form of any one of E74-E78, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 55° C. and a second endotherm onset at about 109° C.

E80. The crystalline form of any one of E74-E79, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 10A.

E81. The crystalline form of any one of E74-E80, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 10B; and/or
b) a DSC profile substantially as shown in FIG. 10B.

E82. The crystalline form of any one of E74-E81, wherein the crystalline form of N—((R)-2,3-dihydroxypropoxy)-3,4-difluoro-2-(2-fluoro-4-iodo-phenylamino)-benzamide is Form XIII.

E83. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 23.4±0.2, and 25.2±0.2 degrees two theta.

E84. The crystalline form of E83, wherein the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 23.4±0.2, 25.2±0.2, and 30.6±0.2 degrees two theta.

E85. The crystalline form of E83 or E84, wherein the TGA exhibits that the crystalline form of N—((R)-2,3-dihydroxypropoxy)-3,4-difluoro-2-(2-fluoro-4-iodo-phenylamino)-benzamide loses about 0.15 wt % between about 40° C. and about 150° C.

E86. The crystalline form of any one of E83-E85, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 111° C.

E87. The crystalline form of any one of E83-E86, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 11A.

E88. The crystalline form of any one of E83-E87, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 11B; and/or
b) a DSC profile substantially as shown in FIG. 11B.

E89. The crystalline form of any one of E83-E88, wherein the crystalline form of N—((R)-2,3-dihydroxypropoxy)-3,4-difluoro-2-(2-fluoro-4-iodo-phenylamino)-benzamide is Form XIV.

E90. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 14.7±0.2, and 20.9±0.2 degrees two theta.

E91. The crystalline form of E90, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 14.7±0.2, 20.9±0.2, and 26.6±0.2 degrees two theta.

E92. The crystalline form of E90 or E91, wherein the TGA exhibits that the crystalline form of N—((R)-2,3-dihydroxypropoxy)-3,4-difluoro-2-(2-fluoro-4-iodo-phenylamino)-benzamide loses about 3.8 wt % between about 40° C. and about 150° C.

E93. The crystalline form of any one of E90-E92, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 104° C.

E94. The crystalline form of any one of E90-E93, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 12A.

E95. The crystalline form of any one of E90-E94, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 12B; and/or
b) a DSC profile substantially as shown in FIG. 12B.

E96. The crystalline form of any one of E90-E95, wherein the crystalline form of N—((R)-2,3-dihydroxypropoxy)-3,4-difluoro-2-(2-fluoro-4-iodo-phenylamino)-benzamide is Form XV.

E97. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 6.0±0.2, 17.1±0.2, and 20.6±0.2 degrees two theta.

E98. The crystalline form of E97, wherein the crystalline form of N—((R)-2,3-dihydroxypropoxy)-3,4-difluoro-2-(2-fluoro-4-iodo-phenylamino)-benzamide is characterized by an XRPD pattern having peaks at 6.0±0.2, 12.8±0.2, 17.1±0.2, and 20.6±0.2 degrees two theta.

E99. The crystalline form of E97 or E98, wherein the TGA exhibits that the crystalline form of N—((R)-2,3-dihydroxypropoxy)-3,4-difluoro-2-(2-fluoro-4-iodo-phenylamino)-benzamide loses about 2.1 wt % between about 40° C. and about 150° C.

E100. The crystalline form of anyone of E97-E99, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 74° C.

E101. The crystalline form of anyone of E97-E100, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 102° C.

E102. The crystalline form of anyone of E97-E101, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 114° C.

E103. The crystalline form of anyone of E97-E102, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 74° C., a second endotherm onset at about 102° C., and a third endotherm onset at about 114° C.

E104. The crystalline form of anyone of E97-E103, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 13A.

E105. The crystalline form of anyone of E97-E104, wherein the crystalline form of N—((R)-2,3-dihydroxypropoxy)-3,4-difluoro-2-(2-fluoro-4-iodo-phenylamino)-benzamide is characterized by:

a) a TGA profile substantially as shown in FIG. 13B; and/or
b) a DSC profile substantially as shown in FIG. 13B.

E106. The crystalline form of anyone of E97-E105, wherein the crystalline form of N—((R)-2,3-dihydroxypropoxy)-3,4-difluoro-2-(2-fluoro-4-iodo-phenylamino)-benzamide is Form XVI.

E107. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.9±0.2, 10.1±0.2, and 15.5±0.2 degrees two theta.

E108. The crystalline form of E107, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.9±0.2, 10.1±0.2, 11.7±0.2, and 15.5±0.2 degrees two theta.

E109. The crystalline form of E107 or E108, wherein the TGA exhibits that the crystalline form of N—((R)-2,3-dihydroxypropoxy)-3,4-difluoro-2-(2-fluoro-4-iodo-phenylamino)-benzamide loses about 2.7 wt % between about 40° C. and about 100° C.

E110. The crystalline form of anyone of E107-E109, wherein crystalline form of N—((R)-2,3-dihydroxypropoxy)-3,4-difluoro-2-(2-fluoro-4-iodo-phenylamino)-benzamide exhibits a DSC thermogram that has an endotherm onset at about 89° C.

E111. The crystalline form of anyone of E107-E110, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 14A.

E112. The crystalline form of anyone of E107-E111, wherein the crystalline form of N—((R)-2,3-dihydroxypropoxy)-3,4-difluoro-2-(2-fluoro-4-iodo-phenylamino)-benzamide is characterized by:

a) a TGA profile substantially as shown in FIG. 14B; and/or
b) a DSC profile substantially as shown in FIG. 14B.

E113. The crystalline form of anyone of E107-E112, wherein the crystalline form of N—((R)-2,3-dihydroxypropoxy)-3,4-difluoro-2-(2-fluoro-4-iodo-phenylamino)-benzamide is Form XVII.

E114. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 10.7±0.2, and 15.9±0.2 degrees two theta.

E115. The crystalline form of E114, wherein the crystalline form of N—((R)-2,3-dihydroxypropoxy)-3,4-difluoro-2-(2-fluoro-4-iodo-phenylamino)-benzamide is characterized by an XRPD pattern having peaks at 4.6±0.2, 10.7±0.2, 15.9±0.2, and 19.6±0.2 degrees two theta.

E116. The crystalline form of E114 or E115, wherein the TGA exhibits that the crystalline form of N—((R)-2,3-dihydroxypropoxy)-3,4-difluoro-2-(2-fluoro-4-iodo-phenylamino)-benzamide loses about 1.6 wt % between about 30° C. and about 150° C.

E117. The crystalline form of anyone of E114-E116, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 83° C.

E118. The crystalline form of anyone of E114-E117, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 15A.

E119. The crystalline form of anyone of E114-E118, wherein the crystalline form of N—((R)-2,3-dihydroxypropoxy)-3,4-difluoro-2-(2-fluoro-4-iodo-phenylamino)-benzamide is characterized by:

a) a TGA profile substantially as shown in FIG. 15B; and/or
b) a DSC profile substantially as shown in FIG. 15B.

E120. The crystalline form of anyone of E114-E119, wherein the crystalline form of N—((R)-2,3-dihydroxypropoxy)-3,4-difluoro-2-(2-fluoro-4-iodo-phenylamino)-benzamide is Form XVIII.

E121. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 10.2±0.2, 11.6±0.2, and 20.0±0.2 degrees two theta.

E122. The crystalline form of E121, wherein the crystalline form of N—((R)-2,3-dihydroxypropoxy)-3,4-difluoro-2-(2-fluoro-4-iodo-phenylamino)-benzamide is characterized by an XRPD pattern having peaks at 10.2±0.2, 11.6±0.2, 17.1±0.2, and 20.0±0.2 degrees two theta.

E123. The crystalline form of E121 or E122, wherein the TGA exhibits that the crystalline form of N—((R)-2,3-dihydroxypropoxy)-3,4-difluoro-2-(2-fluoro-4-iodo-phenylamino)-benzamide loses about 1.85 wt % between about 23° C. and about 92° C.

E124. The crystalline form of anyone of E121-E123, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 69° C.

E125. The crystalline form of anyone of E121-E124, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 98° C.

E126. The crystalline form of anyone of E121-E125, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 115° C.

E127. The crystalline form of anyone of E121-E126, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 69° C., a second endotherm onset at about 98° C., and a third endotherm onset at about 115° C.

E128. The crystalline form of anyone of E121-E127, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 16A.

E129. The crystalline form of anyone of E121-E128, wherein the crystalline form of N—((R)-2,3-dihydroxypropoxy)-3,4-difluoro-2-(2-fluoro-4-iodo-phenylamino)-benzamide is characterized by:

a) a TGA profile substantially as shown in FIG. 16B; and/or
b) a DSC profile substantially as shown in FIG. 16B.

E130. The crystalline form of anyone of E121-E129, wherein the crystalline form of N—((R)-2,3-dihydroxypropoxy)-3,4-difluoro-2-(2-fluoro-4-iodo-phenylamino)-benzamide is Form XIX.

E131. The crystalline form of E1, wherein the crystalline form of N—((R)-2,3-dihydroxypropoxy)-3,4-difluoro-2-(2- fluoro-4-iodo-phenylamino)-benzamide is characterized by an XRPD pattern having peaks at 7.8±0.2, 14.0±0.2, and 17.1±0.2 degrees two theta.

E132. The crystalline form of E131, wherein the crystalline form of N—((R)-2,3-dihydroxypropoxy)-3,4-difluoro-2-(2-fluoro-4-iodo-phenylamino)-benzamide is characterized by an XRPD pattern having peaks at 7.8±0.2, 14.0±0.2, 15.6±0.2, and 17.1±0.2 degrees two theta.

E133. The crystalline form of E131 or E132, wherein the TGA exhibits that the crystalline form of N—((R)-2,3-dihydroxypropoxy)-3,4-difluoro-2-(2-fluoro-4-iodo-phenylamino)-benzamide loses about 2.6 wt % between about 29° C. and about 126° C.

E134. The crystalline form of anyone of E131-133, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 77° C.

E135. The crystalline form of anyone of E131-E134, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 92° C.

E136. The crystalline form of anyone of E131-E135, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 110° C.

E137. The crystalline form of anyone of E131-E136, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 77° C., a second endotherm onset at about 92° C., and a third endotherm onset at about 110° C.

E138. The crystalline form of anyone of E131-E137, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 17A.

E139. The crystalline form of anyone of E131-E138, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 17B; and/or
b) a DSC profile substantially as shown in FIG. 17B.

E140. The crystalline form of anyone of E131-E139, wherein the crystalline form of N—((R)-2,3-dihydroxypropoxy)-3,4-difluoro-2-(2-fluoro-4-iodo-phenylamino)-benzamide is Form XX.

E141. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 8.2±0.2, and 16.7±0.2 degrees two theta.

E142. The crystalline form of E141, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.5±0.2, 8.2±0.2, 16.7±0.2, and 17.7±0.2 degrees two theta.

E143. The crystalline form of E141 or E142, wherein the TGA exhibits that the crystalline form of N—((R)-2,3-dihydroxypropoxy)-3,4-difluoro-2-(2-fluoro-4-iodo-phenylamino)-benzamide loses about 14.1 wt % between about 30° C. and about 110° C.

E144. The crystalline form of anyone of E141-E143, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 52° C.

E145. The crystalline form of anyone of E141-E144, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 90° C.

E146. The crystalline form of anyone of E141-E145, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 52° C. and a second endotherm onset at about 90° C.

E147. The crystalline form of anyone of E141-E146, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 18A.

E148. The crystalline form of anyone of E141-E147, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 18B; and/or
b) a DSC profile substantially as shown in FIG. 18B.

E149. The crystalline form of anyone of E141-E148, wherein the crystalline form of N—((R)-2,3-dihydroxypropoxy)-3,4-difluoro-2-(2-fluoro-4-iodo-phenylamino)-benzamide is Form XXI.

E150. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 7.2±0.2, 21.7±0.2, and 29.1±0.2 degrees two theta.

E151. The crystalline form of E150, wherein the crystalline form of N—((R)-2,3-dihydroxypropoxy)-3,4-difluoro-2-(2-fluoro-4-iodo-phenylamino)-benzamide is characterized by an XRPD pattern having peaks at 7.2±0.2, 18.6±0.2, 21.7±0.2, and 29.1±0.2 degrees two theta.

E152. The crystalline form of E150 or E151, wherein the TGA exhibits that the crystalline form of N—((R)-2,3-dihydroxypropoxy)-3,4-difluoro-2-(2-fluoro-4-iodo-phenylamino)-benzamide loses about 13.8 wt % between about 26° C. and about 135° C.

E153. The crystalline form of anyone of E150-E152, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 65° C.

E154. The crystalline form of anyone of E150-E153, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 89° C.

E155. The crystalline form of anyone of E150-E154, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 102° C.

E156. The crystalline form of anyone of E150-E155, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 65° C., a second endotherm onset at about 89° C., and a third endotherm onset at about 102° C.

E157. The crystalline form of anyone of E150-E156, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 19A.

E158. The crystalline form of anyone of E150-E157, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 19B; and/or
b) a DSC profile substantially as shown in FIG. 19B.

E159. The crystalline form of anyone of E150-E158, wherein the crystalline form of N—((R)-2,3-dihydroxypropoxy)-3,4-difluoro-2-(2-fluoro-4-iodo-phenylamino)-benzamide is Form XXII.

E160. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.4±0.2, 9.7±0.2, and 10.7±0.2 degrees two theta.

E161. The crystalline form of E160, wherein the crystalline form of N—((R)-2,3-dihydroxypropoxy)-3,4-difluoro-2-(2-fluoro-4-iodo-phenylamino)-benzamide is characterized by an XRPD pattern having peaks at 5.4±0.2, 6.5±0.2, 9.7±0.2, and 10.7±0.2 degrees two theta.

E162. The crystalline form of E160 or E161, wherein the TGA exhibits that the crystalline form of N—((R)-2,3-dihydroxypropoxy)-3,4-difluoro-2-(2-fluoro-4-iodo-phenylamino)-benzamide loses about 4.4 wt % between about 27° C. and about 137° C.

E163. The crystalline form of anyone of E160-E162, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 81° C.

E164. The crystalline form of anyone of E160-E163, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 101° C.

E165. The crystalline form of anyone of E160-E164, wherein the crystalline form of N—((R)-2,3-dihydroxypropoxy)-3,4-difluoro-2-(2-fluoro-4-iodo-phenylamino)-benzamide exhibits a DSC thermogram that has a first endotherm onset at about 81° C. and a second endotherm onset at about 101° C.

E166. The crystalline form of anyone of E160-E165, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 20A.

E167. The crystalline form of anyone of E160-E166, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 20B; and/or
b) a DSC profile substantially as shown in FIG. 20B.

E168. The crystalline form of anyone of E160-E167, wherein the crystalline form of N—((R)-2,3-dihydroxypropoxy)-3,4-difluoro-2-(2-fluoro-4-iodo-phenylamino)-benzamide is Form XXIII.

E169. The crystalline form of E1, wherein the crystalline form of N—((R)-2,3-dihydroxypropoxy)-3,4-difluoro-2-(2-fluoro-4-iodo-phenylamino)-benzamide is characterized by an XRPD pattern having peaks at 7.2±0.2, 20.6±0.2, and 23.0±0.2 degrees two theta.

E170. The crystalline form of E169, wherein the crystalline form of N—((R)-2,3-dihydroxypropoxy)-3,4-difluoro-2-(2-fluoro-4-iodo-phenylamino)-benzamide is characterized by an XRPD pattern having peaks at 7.2±0.2, 9.5±0.2, 20.6±0.2, and 23.0±0.2 degrees two theta.

E171. The crystalline form of E169 or E170, wherein the TGA exhibits that the crystalline form of N—((R)-2,3-dihydroxypropoxy)-3,4-difluoro-2-(2-fluoro-4-iodo-phenylamino)-benzamide loses about 1.2 wt % between about 30° C. and about 119° C.

E172. The crystalline form of anyone of E169-E171, wherein the crystalline form of N—((R)-2,3-dihydroxypropoxy)-3,4-difluoro-2-(2-fluoro-4-iodo-phenylamino)-benzamide exhibits a DSC thermogram that has an endotherm onset at about 104° C.

E173. The crystalline form of anyone of E169-E172, wherein the crystalline form of N—((R)-2,3-dihydroxypropoxy)-3,4-difluoro-2-(2-fluoro-4-iodo-phenylamino)-benzamide is characterized by an XRPD pattern substantially as shown in FIG. 21A.

E174. The crystalline form of anyone of E169-E173, wherein the crystalline form of N—((R)-2,3-dihydroxypropoxy)-3,4-difluoro-2-(2-fluoro-4-iodo-phenylamino)-benzamide is characterized by:
a) a TGA profile substantially as shown in FIG. 21B; and/or
b) a DSC profile substantially as shown in FIG. 21B.

E175. The crystalline form of any one of E169-E174, wherein the crystal form of N—((R)-2,3-dihydroxypropoxy)-3,4-difluoro-2-(2-fluoro-4-iodo-phenylamino)-benzamide is Form XXIV.

E176. Amorphous solid of N—((R)-2,3-dihydroxypropoxy)-3,4-difluoro-2-(2-fluoro-4-iodo-phenylamino)-benzamide of Formula (I)

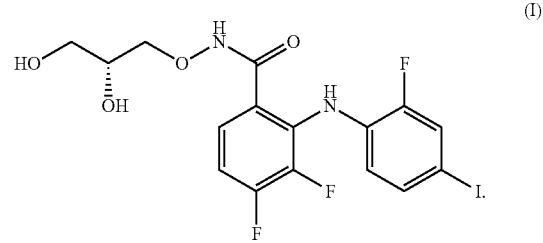 [SMILES: O=C(NOC[C@H](O)CO)c1ccc(F)c(F)c1Nc1ccc(I)cc1F]

(I)

E177. The amorphous solid of claim 176, wherein the amorphous solid of N—((R)-2,3-dihydroxypropoxy)-3,4-difluoro-2-(2-fluoro-4-iodo-phenylamino)-benzamide is characterized by an XRPD pattern substantially as shown in FIG. 22A.

E178. The amorphous solid of E176 or E177, wherein the amorphous solid of N—((R)-2,3-dihydroxypropoxy)-3,4-difluoro-2-(2-fluoro-4-iodo-phenylamino)-benzamide is characterized by:
a) a TGA profile substantially as shown in FIG. 22B; and/or
b) a DSC profile substantially as shown in FIG. 22B.

E179. A pharmaceutical composition comprising: the crystalline form of any one of claims 1-175 or the amorphous solid of any one of claims 176-178; and one or more pharmaceutically acceptable carriers.

E180. The pharmaceutical composition of E179, wherein the crystalline form or the amorphous solid comprises less than 10% by weight total of one or more other crystalline forms and/or amorphous solid.

E181. The pharmaceutical composition of E179, wherein the crystalline form or the amorphous solid comprises less than 5% by weight total of one or more other crystalline forms and/or amorphous solid.

E182. The pharmaceutical composition of E179, wherein the crystalline form or the amorphous solid comprises less than 2% by weight total of one or more other crystalline forms and/or amorphous solid.

E183. The pharmaceutical composition of E179, wherein the crystalline form or the amorphous solid comprises less than 1% by weight total of one or more other crystalline forms and/or amorphous solid.

E184. The pharmaceutical composition of E179, wherein the crystalline form or the amorphous solid comprises less than 0.5% by weight total of one or more other crystalline forms and/or amorphous solid.

E185. The pharmaceutical composition of E179, wherein the crystalline form or the amorphous solid comprises less than 0.1% by weight total of one or more other crystalline forms and/or amorphous solid.

E186. The pharmaceutical composition of anyone of E179-E185, wherein the pharmaceutical composition is for oral administration.

E187. The pharmaceutical composition of anyone of E179-E186, wherein the pharmaceutical composition is a solid dosage form.

E188. The pharmaceutical composition of anyone of E179-E187, wherein the pharmaceutical composition is a capsule, tablet, powder, granules, minitablet, or pellet.

E189. The pharmaceutical composition of E188, wherein the pharmaceutical composition is a capsule.

E190. The pharmaceutical composition of E189, wherein the capsule comprises about 1 mg of N—((R)-2,3-dihydroxypropoxy)-3,4-difluoro-2-(2-fluoro-4-iodo-phenylamino)-benzamide, wherein each component of the capsule is as follows:
 a) about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide;
 b) about 50 wt/wt % to about 98 wt/wt % of one or more diluents;
 c) about 1 wt/wt % to about 10 wt/wt % of one or more disintegrants;
 d) 0 wt/wt % to about 5 wt/wt % of one or more lubricants; and
 e) a gelatin capsule which encapsulates components a-d.

E191. The pharmaceutical composition of E189, wherein the capsule comprises about 2 mg of N—((R)-2,3-dihydroxypropoxy)-3,4-difluoro-2-(2-fluoro-4-iodo-phenylamino)-benzamide, wherein each component of the capsule is as follows:
 a) about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide;
 b) about 50 wt/wt % to about 98 wt/wt % of one or more diluents;
 c) about 1 wt/wt % to about 10 wt/wt % of one or more disintegrants;
 d) 0 wt/wt % to about 5 wt/wt % of one or more lubricants; and
 e) a gelatin capsule which encapsulates components a-d.

E192. The pharmaceutical composition of E189, wherein the capsule comprises about 5 mg of N—((R)-2,3-dihydroxypropoxy)-3,4-difluoro-2-(2-fluoro-4-iodo-phenylamino)-benzamide, wherein each component of the capsule is as follows:
 a) about 2.5 wt/wt % to about 7.0 wt/wt % of the crystalline form or the amorphous solid of N—((R)-2,3-dihydroxypropoxy)-3,4-difluoro-2-(2-fluoro-4-iodo-phenylamino)-benzamide;
 b) about 50 wt/wt % to about 98 wt/wt % of one or more diluents;
 c) about 1 wt/wt % to about 10 wt/wt % of one or more disintegrants; and
 d) a gelatin capsule which encapsulates components a-c.

E193. The pharmaceutical composition of any one of E190-E192, wherein at least one of the diluents is selected from the group consisting of microcrystalline cellulose, lactose, mannitol, sorbitol, xylitol, sucrose, pregelatinized starch, calcium sulfate, calcium carbonate, starch, and dibasic calcium phosphate.

E194. The pharmaceutical composition of E193, wherein at least one of the diluents is microcrystalline cellulose.

E195. The pharmaceutical composition of anyone of E190-E194, wherein at least one of the disintegrants is selected from the group consisting of croscarmellose sodium, sodium starch glycolate, crospovidone, microcrystalline cellulose, starch, pregelatinized starch, low substituted hydroxypropyl cellulose, and alginic acid.

E196. The pharmaceutical composition of E195, wherein at least one of the disintegrants is croscarmellose sodium.

E197. The pharmaceutical composition of anyone of E190-E196, wherein at least one of the lubricants is selected from the group consisting of magnesium stearate, sodium stearyl fumarate, glycerol dibehenate, stearic acid, hydrogenated vegetable oil, calcium stearate, zinc stearate, beeswax, colloidal silicon dioxide, and talc.

E198. The pharmaceutical composition of E197, wherein at least one of the lubricants is magnesium stearate.

E199. The pharmaceutical composition of E188, wherein the pharmaceutical composition is a tablet.

E200. The pharmaceutical composition of E199, wherein the tablet is a dispersible tablet.

E201. The pharmaceutical composition of E200, wherein the dispersible tablet comprises about 0.5 mg of N—((R)-2,3-dihydroxypropoxy)-3,4-difluoro-2-(2-fluoro-4-iodo-phenylamino)-benzamide, and wherein each component of the dispersible tablet is as follows:
 a. about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide;
 b. about 50 wt/wt % to about 98 wt/wt % of one or more diluents;
 c. about 1 wt/wt % to about 10 wt/wt % of one or more disintegrants;
 d. 0 wt/wt % to about 5 wt/wt % of one or more flavoring agents;
 e. 0 wt/wt % to about 5 wt/wt % of one or more sweeteners; and
 f. 0 wt/wt % to about 5 wt/wt % of one or more lubricants.

E202. The pharmaceutical composition of E200, wherein the dispersible tablet comprises about 1 mg of N—((R)-2,3-dihydroxypropoxy)-3,4-difluoro-2-(2-fluoro-4-iodo-phenylamino)-benzamide, and wherein each component of the dispersible tablet is as follows:
 a. about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide;
 b. about 50 wt/wt % to about 98 wt/wt % of one or more diluents;

c. about 1 wt/wt % to about 10 wt/wt % of one or more disintegrants;

d. 0 wt/wt % to about 5 wt/wt % of one or more flavoring agents;

e. 0 wt/wt % to about 5 wt/wt % of one or more sweeteners; and f. 0 wt/wt % to about 5 wt/wt % of one or more lubricants.

E203. The pharmaceutical composition of E201 or E202, wherein at least one of the diluents is selected from the group consisting of microcrystalline cellulose, lactose, mannitol, sorbitol, xylitol, sucrose, pregelatinized starch, calcium sulfate, calcium carbonate, starch, and dibasic calcium phosphate.

E204. The pharmaceutical composition of E203, wherein at least one of the diluents is microcrystalline cellulose.

E205. The pharmaceutical composition of anyone of E201-E204, wherein at least one of the disintegrants is selected from the group consisting of croscarmellose sodium, sodium starch glycolate, crospovidone, microcrystalline cellulose, starch, pregelatinized starch, low substituted hydroxypropyl cellulose, and alginic acid.

E206. The pharmaceutical composition of E205, wherein at least one of the disintegrants is croscarmellose sodium.

E207. The pharmaceutical composition of anyone of E201-E206, wherein at least one of the flavoring agents is selected from the group consisting of natural or synthetic flavors including but not limited to grape flavoring, bubble gum flavoring, caramel flavoring, orange flavoring, lemon flavoring, strawberry flavoring, raspberry flavoring, mint flavoring, peppermint flavoring, grapefruit flavoring, pineapple flavoring, pear flavoring, peach flavoring, vanilla flavoring, banana flavoring, or cherry flavoring.

E208. The pharmaceutical composition of E207, wherein at least one of the flavoring agents is grape flavoring.

E209. The pharmaceutical composition of anyone of E201-E208, wherein at least one sweetener of the dispersible tablet is selected from the group consisting of sucralose, acesulfame, saccharin, sucrose, xylitol, mannitol, sorbitol, glucose, fructose, and aspartame.

E210. The pharmaceutical composition of E209, wherein the sweetener is sucralose.

E211. The pharmaceutical composition of anyone of E201-E210, wherein at least one of the lubricants is selected from the group consisting of magnesium stearate, sodium stearyl fumarate, glycerol dibehenate, stearic acid, hydrogenated vegetable oil, calcium stearate, zinc stearate, beeswax, colloidal silicon dioxide, and talc.

E212. The pharmaceutical composition of E211, wherein at least one of the lubricants is magnesium stearate.

E213. The pharmaceutical composition of anyone of E199-E212, wherein the tablet is an orodispersible tablet.

E214. The pharmaceutical composition of E188, wherein the pharmaceutical composition is a powder.

E215. The pharmaceutical composition of E214, wherein the powder is a dispersible powder.

E216. The pharmaceutical composition of E215, wherein the dispersible powder comprises about 0.5 mg of N—((R)-2,3-dihydroxypropoxy)-3,4-difluoro-2-(2-fluoro-4-iodo-phenylamino)-benzamide, and wherein each component of the dispersible powder is as follows:

a. about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide;

b. about 50 wt/wt % to about 98 wt/wt % of one or more diluents;

c. about 1 wt/wt % to about 10 wt/wt % of one or more disintegrants;

d. 0 wt/wt % to about 5 wt/wt % of one or more flavoring agents;

e. 0 wt/wt % to about 5 wt/wt % of one or more sweeteners; and f. 0 wt/wt % to about 5 wt/wt % of one or more lubricants.

E217. The pharmaceutical composition of E215, wherein the dispersible powder comprises about 1 mg of N—((R)-2,3-dihydroxypropoxy)-3,4-difluoro-2-(2-fluoro-4-iodo-phenylamino)-benzamide, and wherein each component of the dispersible powder is as follows:

a. about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide;

b. about 50 wt/wt % to about 98 wt/wt % of one or more diluents;

c. about 1 wt/wt % to about 10 wt/wt % of one or more disintegrants;

d. 0 wt/wt % to about 5 wt/wt % of one or more flavoring agents;

e. 0 wt/wt % to about 5 wt/wt % of one or more sweeteners; and f. 0 wt/wt % to about 5 wt/wt % of one or more lubricants.

E218. The pharmaceutical composition of E216 or E217, wherein at least one of the diluents is selected from the group consisting of microcrystalline cellulose, lactose, mannitol, sorbitol, xylitol, sucrose, pregelatinized starch, calcium sulfate, calcium carbonate, starch, and dibasic calcium phosphate.

E219. The pharmaceutical composition of E218, wherein at least one of the diluents is microcrystalline cellulose.

E220. The pharmaceutical composition of any one of E216-E219, wherein at least one of the disintegrants is selected from the group consisting of croscarmellose sodium, sodium starch glycolate, crospovidone, microcrystalline cellulose, starch, pregelatinized starch, low substituted hydroxypropyl cellulose, and alginic acid.

E221. The pharmaceutical composition of E220, wherein at least one of the disintegrants is croscarmellose sodium.

E222. The pharmaceutical composition of anyone of E216-E221, wherein at least one of the flavoring agents is selected from the group consisting of natural or synthetic flavors including but not limited to grape flavoring, bubble gum flavoring, caramel flavoring, orange flavoring, lemon flavoring, strawberry flavoring, raspberry flavoring, mint flavoring, peppermint flavoring, grapefruit flavoring, pineapple flavoring, pear flavoring, peach flavoring, vanilla flavoring, banana flavoring, or cherry flavoring.

E223. The pharmaceutical composition of E222, wherein at least one of the flavoring agents is grape flavoring.

E224. The pharmaceutical composition of any one of E216-E223, wherein at least one sweetener of the dispersible powder is selected from the group consisting of sucralose, acesulfame, saccharin, sucrose, xylitol, mannitol, sorbitol, glucose, fructose, and aspartame.

E225. The pharmaceutical composition of E224, wherein the sweetener is sucralose.

E226. The pharmaceutical composition of any one of E216-E225, wherein at least one of the lubricants is selected from the group consisting of magnesium stearate, sodium stearyl fumarate, glycerol dibehenate, stearic acid, hydrogenated vegetable oil, calcium stearate, zinc stearate, beeswax, colloidal silicon dioxide, and talc.

E227. The pharmaceutical composition of E226, wherein at least one of the lubricants is magnesium stearate.

E228. The pharmaceutical composition of any one of E215-E227, wherein the powder is an orodispersible powder.

E229. The pharmaceutical composition of E188, wherein the pharmaceutical composition is granules.

E230. The pharmaceutical composition of E229, wherein the granules are dispersible granules.

E231. The pharmaceutical composition of E230, wherein the dispersible granules comprise about 0.5 mg of N—((R)-2,3-dihydroxypropoxy)-3,4-difluoro-2-(2-fluoro-4-iodo-phenylamino)-benzamide, and wherein each component of the dispersible granules is as follows:
  a. about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide;
  b. about 50 wt/wt % to about 98 wt/wt % of one or more diluents;
  c. about 1 wt/wt % to about 10 wt/wt % of one or more disintegrants;
  d. 0 wt/wt % to about 5 wt/wt % of one or more flavoring agents;
  e. 0 wt/wt % to about 5 wt/wt % of one or more sweeteners; and
  f. 0 wt/wt % to about 5 wt/wt % of one or more lubricants.

E232. The pharmaceutical composition of E230, wherein the dispersible granules comprise about 1 mg of N—((R)-2,3-dihydroxypropoxy)-3,4-difluoro-2-(2-fluoro-4-iodo-phenylamino)-benzamide, and wherein each component of the dispersible granules is as follows:
  a. about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide;
  b. about 50 wt/wt % to about 98 wt/wt % of one or more diluents;
  c. about 1 wt/wt % to about 10 wt/wt % of one or more disintegrants;
  d. 0 wt/wt % to about 5 wt/wt % of one or more flavoring agents;
  e. 0 wt/wt % to about 5 wt/wt % of one or more sweeteners; and
  f. 0 wt/wt % to about 5 wt/wt % of one or more lubricants.

E233. The pharmaceutical composition of E231 or E232, wherein at least one of the diluents is selected from the group consisting of microcrystalline cellulose, lactose, mannitol, sorbitol, xylitol, sucrose, pregelatinized starch, calcium sulfate, calcium carbonate, starch, and dibasic calcium phosphate.

E234. The pharmaceutical composition of E233, wherein at least one of the diluents is microcrystalline cellulose.

E235. The pharmaceutical composition of anyone of E231-E234, wherein at least one of the disintegrants is selected from the group consisting of croscarmellose sodium, sodium starch glycolate, crospovidone, microcrystalline cellulose, starch, pregelatinized starch, low substituted hydroxypropyl cellulose, and alginic acid.

E236. The pharmaceutical composition of E235, wherein at least one of the disintegrants is croscarmellose sodium.

E237. The pharmaceutical composition of anyone of E231-E236, wherein at least one of the flavoring agents is selected from the group consisting of natural or synthetic flavors including but not limited to grape flavoring, bubble gum flavoring, caramel flavoring, orange flavoring, lemon flavoring, strawberry flavoring, raspberry flavoring, mint flavoring, peppermint flavoring, grapefruit flavoring, pineapple flavoring, pear flavoring, peach flavoring, vanilla flavoring, banana flavoring, or cherry flavoring.

E238. The pharmaceutical composition of E237, wherein at least one of the flavoring agents is grape flavoring.

E239. The pharmaceutical composition of anyone of E231-E238, wherein at least one sweetener of the dispersible granules is selected from the group consisting of sucralose, acesulfame, saccharin, sucrose, xylitol, mannitol, sorbitol, glucose, fructose, and aspartame.

E240. The pharmaceutical composition of E239, wherein the sweetener is sucralose.

E241. The pharmaceutical composition of anyone of E231-E240, wherein at least one of the lubricants is selected from the group consisting of magnesium stearate, sodium stearyl fumarate, glycerol dibehenate, stearic acid, hydrogenated vegetable oil, calcium stearate, zinc stearate, beeswax, colloidal silicon dioxide, and talc.

E242. The pharmaceutical composition of E241, wherein at least one of the lubricants is magnesium stearate.

E243. The pharmaceutical composition of any one of E229-E242, wherein the granules are orodispersible granules.

E244. The pharmaceutical composition of E188, wherein the pharmaceutical composition is a minitablet.

E245. The pharmaceutical composition of E244, wherein the minitablets are dispersible minitablets.

E246. The pharmaceutical composition of E245, wherein the dispersible minitablets comprise about 0.5 mg of N—((R)-2,3-dihydroxypropoxy)-3,4-difluoro-2-(2-fluoro-4-iodo-phenylamino)-benzamide, and wherein each component of the dispersible minitablets is as follows:
  a. about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide;
  b. about 50 wt/wt % to about 98 wt/wt % of one or more diluents;
  c. about 1 wt/wt % to about 10 wt/wt % of one or more disintegrants;
  d. 0 wt/wt % to about 5 wt/wt % of one or more flavoring agents;
  e. 0 wt/wt % to about 5 wt/wt % of one or more sweeteners; and
  f. 0 wt/wt % to about 5 wt/wt % of one or more lubricants.

E247. The pharmaceutical composition of E245, wherein the dispersible minitablets comprise about 1 mg of N—((R)-2,3-dihydroxypropoxy)-3,4-difluoro-2-(2-fluoro-4-iodo-phenylamino)-benzamide, and wherein each component of the dispersible minitablets is as follows:
  a. about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide;
  b. about 50 wt/wt % to about 98 wt/wt % of one or more diluents;
  c. about 1 wt/wt % to about 10 wt/wt % of one or more disintegrants;
  d. 0 wt/wt % to about 5 wt/wt % of one or more flavoring agents;
  e. 0 wt/wt % to about 5 wt/wt % of one or more sweeteners; and
  f. 0 wt/wt % to about 5 wt/wt % of one or more lubricants.

E248. The pharmaceutical composition of E246 or E247, wherein at least one of the diluents is selected from the group consisting of microcrystalline cellulose, lactose, mannitol, sorbitol, xylitol, sucrose, pregelatinized starch, calcium sulfate, calcium carbonate, starch, and dibasic calcium phosphate.

E249. The pharmaceutical composition of E248, wherein at least one of the diluents is microcrystalline cellulose.

E250. The pharmaceutical composition of any one of E246-E249, wherein at least one of the disintegrants is selected from the group consisting of croscarmellose sodium, sodium starch glycolate, crospovidone, microcrystalline cellulose, starch, pregelatinized starch, low substituted hydroxypropyl cellulose, and alginic acid.

E251. The pharmaceutical composition of E250, wherein at least one of the disintegrants is croscarmellose sodium.

E252. The pharmaceutical composition of anyone of E246-E251, wherein at least one of the flavoring agents is selected from the group consisting of natural or synthetic flavors including but not limited to grape flavoring, bubble gum flavoring, caramel flavoring, orange flavoring, lemon flavoring, strawberry flavoring, raspberry flavoring, mint flavoring, peppermint flavoring, grapefruit flavoring, pineapple flavoring, pear flavoring, peach flavoring, vanilla flavoring, banana flavoring, or cherry flavoring.

E253. The pharmaceutical composition of E252, wherein at least one of the flavoring agents is grape flavoring.

E254. The pharmaceutical composition of any one of E246-E253, wherein at least one sweetener of the dispersible minitablets is selected from the group consisting of sucralose, acesulfame, saccharin, sucrose, xylitol, mannitol, sorbitol, glucose, fructose, and aspartame.

E255. The pharmaceutical composition of E254, wherein the sweetener is sucralose.

E256. The pharmaceutical composition of any one of E246-E255, wherein at least one of the lubricants is selected from the group consisting of magnesium stearate, sodium stearyl fumarate, glycerol dibehenate, stearic acid, hydrogenated vegetable oil, calcium stearate, zinc stearate, beeswax, colloidal silicon dioxide, and talc.

E257. The pharmaceutical composition of E256, wherein at least one of the lubricants is magnesium stearate.

E258. The pharmaceutical composition of any one of E244-E257, wherein the minitablets are orodispersible minitablets.

E259. The pharmaceutical composition of E188, wherein the pharmaceutical composition is a pellet.

E260. The pharmaceutical composition of E259, wherein the pellets are dispersible pellets.

E261. The pharmaceutical composition of E260, wherein the dispersible pellets comprise about 0.5 mg of N—((R)-2,3-dihydroxypropoxy)-3,4-difluoro-2-(2-fluoro-4-iodo-phenylamino)-benzamide, and wherein each component of the dispersible pellets is as follows:
  a. about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide;
  b. about 50 wt/wt % to about 98 wt/wt % of one or more diluents;
  c. about 1 wt/wt % to about 10 wt/wt % of one or more disintegrants;
  d. 0 wt/wt % to about 5 wt/wt % of one or more flavoring agents;
  e. 0 wt/wt % to about 5 wt/wt % of one or more sweeteners; and
  f. 0 wt/wt % to about 5 wt/wt % of one or more lubricants.

E262. The pharmaceutical composition of E260, wherein the dispersible pellets comprise about 1 mg of N—((R)-2,3-dihydroxypropoxy)-3,4-difluoro-2-(2-fluoro-4-iodo-phenylamino)-benzamide, and wherein each component of the dispersible pellets is as follows:
  a. about 0.1 wt/wt % to about 7 wt/wt % of the crystalline form or the amorphous solid of N—((R)-2,3-dihydroxypropoxy)-3,4-difluoro-2-(2-fluoro-4-iodo-phenylamino)-benzamide;
  b. about 50 wt/wt % to about 98 wt/wt % of one or more diluents;
  c. about 1 wt/wt % to about 10 wt/wt % of one or more disintegrants;
  d. 0 wt/wt % to about 5 wt/wt % of one or more flavoring agents;
  e. 0 wt/wt % to about 5 wt/wt % of one or more sweeteners; and
  f. 0 wt/wt % to about 5 wt/wt % of one or more lubricants.

E263. The pharmaceutical composition of E261 or E262, wherein at least one of the diluents is selected from the group consisting of microcrystalline cellulose, lactose, mannitol, sorbitol, xylitol, sucrose, pregelatinized starch, calcium sulfate, calcium carbonate, starch, and dibasic calcium phosphate.

E264. The pharmaceutical composition of E263, wherein at least one of the diluents is microcrystalline cellulose.

E265. The pharmaceutical composition of anyone of E261-E264, wherein at least one of the disintegrants is selected from the group consisting of croscarmellose sodium, sodium starch glycolate, crospovidone, microcrystalline cellulose, starch, pregelatinized starch, low substituted hydroxypropyl cellulose, and alginic acid.

E266. The pharmaceutical composition of E265, wherein at least one of the disintegrants is croscarmellose sodium.

E267. The pharmaceutical composition of anyone of E261-E266, wherein at least one of the flavoring agents is selected from the group consisting of natural or synthetic flavors including but not limited to grape flavoring, bubble gum flavoring, caramel flavoring, orange flavoring, lemon flavoring, strawberry flavoring, raspberry flavoring, mint flavoring, peppermint flavoring, grapefruit flavoring, pineapple flavoring, pear flavoring, peach flavoring, vanilla flavoring, banana flavoring, or cherry flavoring.

E268. The pharmaceutical composition of E267, wherein at least one of the flavoring agents is grape flavoring.

E269. The pharmaceutical composition of anyone of E261-E268, wherein at least one sweetener of the dispersible pellets is selected from the group consisting of sucralose, acesulfame, saccharin, sucrose, xylitol, mannitol, sorbitol, glucose, fructose, and aspartame.

E270. The pharmaceutical composition of E269, wherein the sweetener is sucralose.

E271. The pharmaceutical composition of anyone of E261-E270, wherein at least one of the lubricants is selected from the group consisting of magnesium stearate, sodium stearyl fumarate, glycerol dibehenate, stearic acid, hydrogenated vegetable oil, calcium stearate, zinc stearate, beeswax, colloidal silicon dioxide, and talc.

E272. The pharmaceutical composition of E271, wherein at least one of the lubricants is magnesium stearate.

E273. The pharmaceutical composition of any one of E259-E272, wherein the pellets are orodispersible pellets.

E274. A method of treating a tumor, cancer, or Rasopathy disorder comprising administering to a subject in need of such treatment the pharmaceutical composition of any one of E179-E273.

E275. The method of E274, wherein the tumor is a neurofibroma.

E276. The method of E274 or E275, wherein the tumor is a neurofibroma associated with Neurofibromatosis Type 1.

E277. The method of any one of claims E274-E276, wherein the tumor is selected from the group consisting of cutaneous neurofibroma, plexiform neurofibroma, optic pathway glioma, low grade glioma, high grade glioma, and malignant peripheral nerve sheath tumor.

E278. The method of E277, wherein the tumor is plexiform neurofibroma.

E279. The method of anyone of E274-E278, wherein the subject has been diagnosed with a Rasopathy disorder selected from the group consisting of neurofibromatosis type 1, neurofibromatosis type 2, cardio-facio-cutaneous syndrome, Costello syndrome, Legius syndrome, Noonan syndrome, and Noonan syndrome with multiple lentigines.

E280. The method of any one of E274-E279, wherein the cancer is selected from the group consisting of skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum.

E281. The method of E280, wherein the leukemia is selected from the group consisting of acute lymphocytic leukemia, acute myelogenous leukemia, chronic lymphocytic leukemia, and chronic myelogenous leukemia.

E282. The method of E280, wherein the lymphoma is selected from the group consisting of B-cell lymphoma, T-cell lymphoma, Burkitt's lymphoma, follicular lymphoma, mantle cell lymphoma, primary mediastinal B cell lymphoma, small lymphocytic lymphoma, and Waldenstrom macroglobulinemia.

E283. The method of E280, wherein the lung cancer is selected from the group consisting of lung adenocarcinoma, squamous non-small cell lung cancer, non-squamous non-small cell lung cancer, and small cell lung cancer.

E284. The method of anyone of E274-E283, wherein the subject bears a mutation or other aberration in one or more genes for which the mutation or other aberration causes a gain or loss of function characteristic of certain cancers, wherein the mutation or other aberration in one or more genes is a mutation or other aberration in one or more of KRAS, NRAS, HRAS, BRAF, MEK1, MEK2, RASA1, MAP2K4, NF1, or NF2.

E285. The method of any one of E274-E284, wherein the N—((R)-2,3-dihydroxypropoxy)-3,4-difluoro-2-(2-fluoro-4-iodo-phenylamino)-benzamide is administered in a total daily dose that does not exceed 20 mg.

E286. The method of any one of E274-E284, wherein the N—((R)-2,3-dihydroxypropoxy)-3,4-difluoro-2-(2-fluoro-4-iodo-phenylamino)-benzamide is administered in a total daily dose that does not exceed 10 mg.

E287. The method of any one of E274-E284, wherein the N—((R)-2,3-dihydroxypropoxy)-3,4-difluoro-2-(2-fluoro-4-iodo-phenylamino)-benzamide is administered in a total daily dose that does not exceed 8 mg.

E288. The method of any one of E274-E284, wherein the N—((R)-2,3-dihydroxypropoxy)-3,4-difluoro-2-(2-fluoro-4-iodo-phenylamino)-benzamide is administered in a total daily dose that does not exceed 6 mg.

E289. The method of any one of E274-E288, wherein the total daily dose of the N—((R)-2,3-dihydroxypropoxy)-3,4-difluoro-2-(2-fluoro-4-iodo-phenylamino)-benzamide is administered once daily.

E290. The method of E289, wherein the total daily dose of the N—((R)-2,3-dihydroxypropoxy)-3,4-difluoro-2-(2-fluoro-4-iodo-phenylamino)-benzamide is administered once daily at a dose of about 0.1 mg to about 20 mg.

E291. The method of E290, wherein the total daily dose of the N—((R)-2,3-dihydroxypropoxy)-3,4-difluoro-2-(2-fluoro-4-iodo-phenylamino)-benzamide is administered once daily at a dose of about 0.5 mg.

E292. The method of E290, wherein the total daily dose of the N—((R)-2,3-dihydroxypropoxy)-3,4-difluoro-2-(2-fluoro-4-iodo-phenylamino)-benzamide is administered once daily at a dose of about 1 mg.

E293. The method of E290, wherein the total daily dose of the N—((R)-2,3-dihydroxypropoxy)-3,4-difluoro-2-(2-fluoro-4-iodo-phenylamino)-benzamide is administered once daily at a dose of about 2 mg.

E294. The method of E290, wherein the total daily dose of the N—((R)-2,3-dihydroxypropoxy)-3,4-difluoro-2-(2-fluoro-4-iodo-phenylamino)-benzamide is administered once daily at a dose of about 4 mg.

E295. The method of E290, wherein the total daily dose of the N—((R)-2,3-dihydroxypropoxy)-3,4-difluoro-2-(2-fluoro-4-iodo-phenylamino)-benzamide is administered once daily at a dose of about 6 mg.

E296. The method of E290, wherein the total daily dose of the N—((R)-2,3-dihydroxypropoxy)-3,4-difluoro-2-(2-fluoro-4-iodo-phenylamino)-benzamide is administered once daily at a dose of about 8 mg.

E297. The method of E290, wherein the total daily dose of the N—((R)-2,3-dihydroxypropoxy)-3,4-difluoro-2-(2-fluoro-4-iodo-phenylamino)-benzamide is administered once daily at a dose of about 20 mg.

E298. The method of any one of E274-E288, wherein the total daily dose of the N—((R)-2,3-dihydroxypropoxy)-3,4-difluoro-2-(2-fluoro-4-iodo-phenylamino)-benzamide is administered two times daily.

E299. The method of E298, wherein the total daily dose of the N—((R)-2,3-dihydroxypropoxy)-3,4-difluoro-2-(2-fluoro-4-iodo-phenylamino)-benzamide is administered two times daily at a dose of about 0.1 mg to about 10 mg each.

E300. The method of E298, wherein the total daily dose of the N—((R)-2,3-dihydroxypropoxy)-3,4-difluoro-2-(2-fluoro-4-iodo-phenylamino)-benzamide is administered two times daily at a dose of about 0.5 mg each.

E301. The method of E298, wherein the total daily dose of the N—((R)-2,3-dihydroxypropoxy)-3,4-difluoro-2-(2-fluoro-4-iodo-phenylamino)-benzamide is administered two times daily at a dose of about 1 mg each.

E302. The method of E298, wherein the total daily dose of the N—((R)-2,3-dihydroxypropoxy)-3,4-difluoro-2-(2-fluoro-4-iodo-phenylamino)-benzamide is administered two times daily at a dose of about 2 mg each.

E303. The method of E298, wherein the total daily dose of the N—((R)-2,3-dihydroxypropoxy)-3,4-difluoro-2-(2-fluoro-4-iodo-phenylamino)-benzamide is administered two times daily at a dose of about 3 mg each.

E304. The method of E298, wherein the total daily dose of the N—((R)-2,3-dihydroxypropoxy)-3,4-difluoro-2-(2-fluoro-4-iodo-phenylamino)-benzamide is administered two times daily at a dose of about 4 mg each.

E305. The method of E298, wherein the total daily dose of the N—((R)-2,3-dihydroxypropoxy)-3,4-difluoro-2-(2-fluoro-4-iodo-phenylamino)-benzamide is administered two times daily at a dose of about 10 mg each.

E306. The method of any one of E274-E305, wherein an individual dose of the N—((R)-2,3-dihydroxypropoxy)-3,4-difluoro-2-(2-fluoro-4-iodo-phenylamino)-benzamide is administered as more than one capsule, more than one tablet, more than one dose of dispersible powder, more than one dose of granules, more than one dose of minitablets, more than one dose of pellets, or a combination thereof.

E307. The method of any one of E274-E306, wherein the pharmaceutical composition is a dispersible tablet, a dispersible powder, dispersible granules, dispersible minitablets, or dispersible pellets, and wherein the dispersible tablet, dispersible powder, dispersible granules, dispersible minitablets, or dispersible pellets is dispersed in a potable liquid prior to administration to the subject.

E308. The method of E307, wherein the subject experiences dysphagia caused by one or more of: disease of the nervous system, muscle weakening, developmental disability, stroke, injury, anatomical defect, cancer, treatment for cancer, allergic reaction, dementia, memory loss, or cognitive decline.

E309. The method of E307 or E308, wherein the subject is a pediatric subject.

E310. The method of anyone of E274-E309, wherein the N—((R)-2,3-dihydroxypropoxy)-3,4-difluoro-2-(2-fluoro-4-iodo-phenylamino)-benzamide is administered on a 28-day dosing cycle comprising: (a) 21 days in which the total daily dose is administered; and (b) 7 days in which no N—((R)-2,3-dihydroxypropoxy)-3,4-difluoro-2-(2-fluoro-4-iodo-phenylamino)-benzamide is administered.

E311. The method of anyone of E274-E309, wherein the N—((R)-2,3-dihydroxypropoxy)-3,4-difluoro-2-(2-fluoro-4-iodo-phenylamino)-benzamide is administered on a 28-day dosing cycle comprising: (a) 21 consecutive days in which the total daily dose is administered; followed by (b) 7 consecutive days in which no N—((R)-2,3-dihydroxypropoxy)-3,4-difluoro-2-(2-fluoro-4-iodo-phenylamino)-benzamide is administered.

E312. The method of any one of E274-E309, wherein the N—((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 days in which the total daily dose is administered and (ii) 2 days in which no N—((R)-2,3-dihydroxypropoxy)-3,4-difluoro-2-(2-fluoro-4-iodo-phenylamino)-benzamide; and (b) 7 days in which no N—((R)-2,3-dihydroxypropoxy)-3,4-difluoro-2-(2-fluoro-4-iodo-phenylamino)-benzamide is administered.

E313. The method of any one of E274-E309, wherein the N—((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 consecutive days in which the total daily dose is administered and (ii) 2 consecutive days in which no N—((R)-2,3-dihydroxypropoxy)-3,4-difluoro-2-(2-fluoro-4-iodo-phenylamino)-benzamide; followed by (b) 7 consecutive days in which no N—((R)-2,3-dihydroxypropoxy)-3,4-difluoro-2-(2-fluoro-4-iodo-phenylamino)-benzamide is administered.

E314. The method of anyone of E310-E313, wherein the 28-day dosing cycle is repeated up to a total of 24 consecutive 28-day dosing cycles.

E315. Use of the pharmaceutical composition of anyone of E179-E273 for the manufacture of a medicament for treating a tumor, cancer, or Rasopathy disorder.

E316. The use of E315, wherein the tumor is a neurofibroma.

E317. The use of E315 or E316, wherein the tumor is a neurofibroma associated with Neurofibromatosis Type 1.

E318. The use of any one of E315-E317, wherein the tumor is selected from the group consisting of cutaneous neurofibroma, plexiform neurofibroma, optic pathway glioma, low grade glioma, high grade glioma, and malignant peripheral nerve sheath tumor.

E319. The use of E318, wherein the tumor is plexiform neurofibroma.

E320. The use of anyone of E315-E319, wherein the subject has been diagnosed with a Rasopathy disorder selected from the group consisting of neurofibromatosis type 1, neurofibromatosis type 2, cardio-facio-cutaneous syndrome, Costello syndrome, Legius syndrome, Noonan syndrome, and Noonan syndrome with multiple lentigines.

E321. The use of anyone of E315-E320, wherein the cancer is selected from the group consisting of skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum.

E322. The use of E321, wherein the leukemia is selected from the group consisting of acute lymphocytic leukemia, acute myelogenous leukemia, chronic lymphocytic leukemia, and chronic myelogenous leukemia.

E323. The use of E321, wherein the lymphoma is selected from the group consisting of B-cell lymphoma, T-cell lymphoma, Burkitt's lymphoma, follicular lymphoma, mantle cell lymphoma, primary mediastinal B cell lymphoma, small lymphocytic lymphoma, and Waldenstrom macroglobulinemia.

E324. The use of E321, wherein the lung cancer is selected from the group consisting of lung adenocarcinoma, squamous non-small cell lung cancer, non-squamous non-small cell lung cancer, and small cell lung cancer.

E325. The use of anyone of E315-E324, wherein the subject bears a mutation or other aberration in one or more genes for which the mutation or other aberration causes a gain or loss of function characteristic of certain cancers, wherein the mutation or other aberration in one or more genes is a mutation or other aberration in one or more of KRAS, NRAS, HRAS, BRAF, MEK1, MEK2, RASA1, MAP2K4, NF1, or NF2.

E326. The use of anyone of E315-E325, wherein the N—((R)-2,3-dihydroxypropoxy)-3,4-difluoro-2-(2-fluoro-4-iodo-phenylamino)-benzamide is administered in a total daily dose that does not exceed 20 mg.

E327. The use of anyone of E315-E325, wherein the N—((R)-2,3-dihydroxypropoxy)-3,4-difluoro-2-(2-fluoro-4-iodo-phenylamino)-benzamide is administered in a total daily dose that does not exceed 10 mg.

E328. The use of anyone of E315-E325, wherein the N—((R)-2,3-dihydroxypropoxy)-3,4-difluoro-2-(2-fluoro-4-iodo-phenylamino)-benzamide is administered in a total daily dose that does not exceed 8 mg.

E329. The use of anyone of E315-E325, wherein the N—((R)-2,3-dihydroxypropoxy)-3,4-difluoro-2-(2-fluoro-4-iodo-phenylamino)-benzamide is administered in a total daily dose that does not exceed 6 mg.

E330. The use of any one of E315-E329, wherein the total daily dose of the N—((R)-2,3-dihydroxypropoxy)-3,4-difluoro-2-(2-fluoro-4-iodo-phenylamino)-benzamide is administered once daily.

E331. The use of E330, wherein the total daily dose of the N—((R)-2,3-dihydroxypropoxy)-3,4-difluoro-2-(2-fluoro-4-iodo-phenylamino)-benzamide is administered once daily at a dose of about 0.1 mg to about 20 mg.

E332. The use of E331, wherein the total daily dose of the N—((R)-2,3-dihydroxypropoxy)-3,4-difluoro-2-(2-fluoro-4-iodo-phenylamino)-benzamide is administered once daily at a dose of about 0.5 mg.

E333. The use of E331, wherein the total daily dose of the N—((R)-2,3-dihydroxypropoxy)-3,4-difluoro-2-(2-fluoro-4-iodo-phenylamino)-benzamide is administered once daily at a dose of about 1 mg.

E334. The use of E331, wherein the total daily dose of the N—((R)-2,3-dihydroxypropoxy)-3,4-difluoro-2-(2-fluoro-4-iodo-phenylamino)-benzamide is administered once daily at a dose of about 2 mg.

E335. The use of E331, wherein the total daily dose of the N—((R)-2,3-dihydroxypropoxy)-3,4-difluoro-2-(2-fluoro-4-iodo-phenylamino)-benzamide is administered once daily at a dose of about 4 mg.

E336. The use of E331, wherein the total daily dose of the N—((R)-2,3-dihydroxypropoxy)-3,4-difluoro-2-(2-fluoro-4-iodo-phenylamino)-benzamide is administered once daily at a dose of about 6 mg.

E337. The use of E331, wherein the total daily dose of the N—((R)-2,3-dihydroxypropoxy)-3,4-difluoro-2-(2-fluoro-4-iodo-phenylamino)-benzamide is administered once daily at a dose of about 8 mg.

E338. The use of E331, wherein the total daily dose of the N—((R)-2,3-dihydroxypropoxy)-3,4-difluoro-2-(2-fluoro-4-iodo-phenylamino)-benzamide is administered once daily at a dose of about 20 mg.

E339. The use of any one of E315-E329, wherein the total daily dose of the N—((R)-2,3-dihydroxypropoxy)-3,4-difluoro-2-(2-fluoro-4-iodo-phenylamino)-benzamide is administered two times daily.

E340. The use of E339, wherein the total daily dose of the N—((R)-2,3-dihydroxypropoxy)-3,4-difluoro-2-(2-fluoro-4-iodo-phenylamino)-benzamide is administered two times daily at a dose of about 0.1 mg to about 10 mg each.

E341. The use of E340, wherein the total daily dose of the N—((R)-2,3-dihydroxypropoxy)-3,4-difluoro-2-(2-fluoro-4-iodo-phenylamino)-benzamide is administered two times daily at a dose of about 0.5 mg each.

E342. The use of E340, wherein the total daily dose of the N—((R)-2,3-dihydroxypropoxy)-3,4-difluoro-2-(2-fluoro-4-iodo-phenylamino)-benzamide is administered two times daily at a dose of about 1 mg each.

E343. The use of E340, wherein the total daily dose of the N—((R)-2,3-dihydroxypropoxy)-3,4-difluoro-2-(2-fluoro-4-iodo-phenylamino)-benzamide is administered two times daily at a dose of about 2 mg each.

E344. The use of E340, wherein the total daily dose of the N—((R)-2,3-dihydroxypropoxy)-3,4-difluoro-2-(2-fluoro-4-iodo-phenylamino)-benzamide is administered two times daily at a dose of about 3 mg each.

E345. The use of E340, wherein the total daily dose of the N—((R)-2,3-dihydroxypropoxy)-3,4-difluoro-2-(2-fluoro-4-iodo-phenylamino)-benzamide is administered two times daily at a dose of about 4 mg each.

E346. The use of E340, wherein the total daily dose of the N—((R)-2,3-dihydroxypropoxy)-3,4-difluoro-2-(2-fluoro-4-iodo-phenylamino)-benzamide is administered two times daily at a dose of about 10 mg each.

E347. The use of any one of E315-E346, wherein an individual dose of the N—((R)-2,3-dihydroxypropoxy)-3,4-difluoro-2-(2-fluoro-4-iodo-phenylamino)-benzamide is administered as more than one capsule, more than one tablet, more than one dose of dispersible powder, more than one dose of granules, more than one dose of minitablets, more than one dose of pellets, or a combination thereof.

E348. The use of any one of E315-E347, wherein the pharmaceutical composition is a dispersible tablet, a dispersible powder, dispersible granules, a dispersible minitablet, or a dispersible pellet, and wherein the dispersible tablet, dispersible powder, dispersible granules, dispersible minitablets, or dispersible pellets is dispersed in a potable liquid prior to administration to the subject.

E349. The use of E348, wherein the subject experiences dysphagia caused by one or more of: disease of the nervous system, muscle weakening, developmental disability, stroke, injury, anatomical defect, cancer, treatment for cancer, allergic reaction, dementia, memory loss, or cognitive decline.

E350. The use of E348 or E349, wherein the subject is a pediatric subject.

E351. The use of anyone of E315-E350, wherein the N—((R)-2,3-dihydroxypropoxy)-3,4-difluoro-2-(2-fluoro-4-iodo-phenylamino)-benzamide is administered on a 28-day dosing cycle comprising: (a) 21 days in which the total daily dose is administered; and (b) 7 days in which no N—((R)-2,3-dihydroxypropoxy)-3,4-difluoro-2-(2-fluoro-4-iodo-phenylamino)-benzamide is administered.

E352. The use of anyone of E315-E350, wherein the N—((R)-2,3-dihydroxypropoxy)-3,4-difluoro-2-(2-fluoro-4-iodo-phenylamino)-benzamide is administered on a 28-day dosing cycle comprising: (a) 21 consecutive days in which the total daily dose is administered; followed by (b) 7 consecutive days in which no N—((R)-2,3-dihydroxypropoxy)-3,4-difluoro-2-(2-fluoro-4-iodo-phenylamino)-benzamide is administered.

E353. The use of anyone of E315-E350, wherein the N—((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 days in which the total daily dose is administered and (ii) 2 days in which no N—((R)-2,3-dihydroxypropoxy)-3,4-difluoro-2-(2-fluoro-4-iodo-phenylamino)-benzamide; and (b) 7 days in which no N—((R)-2,3-dihydroxypropoxy)-3,4-difluoro-2-(2-fluoro-4-iodo-phenylamino)-benzamide is administered.

E354. The use of anyone of E315-E350, wherein the N—((R)-2,3-dihydroxypropoxy)-3,4-difluoro-2-(2-fluoro-4-iodo-phenylamino)-benzamide is administered on a 28-day dosing cycle comprising: (a) three 7-day periods each comprising (i) 5 consecutive days in which the total daily dose is administered and (ii) 2 consecutive days in which no N—((R)-2,3-dihydroxypropoxy)-3,4-difluoro-2-(2-fluoro-4-iodo-phenylamino)-benzamide; followed by (b) 7 consecutive days in which no N—((R)-2,3-dihydroxypropoxy)-3,4-difluoro-2-(2-fluoro-4-iodo-phenylamino)-benzamide is administered.

E355. The use of anyone of E351-E354, wherein the 28-day dosing cycle is repeated up to a total of 24 consecutive 28-day dosing cycles.

E356. A method of producing N—((R)-2,3-dihydroxypropoxy)-3,4-difluoro-2-(2-fluoro-4-iodo-phenylamino)-benzamide of Formula (I)

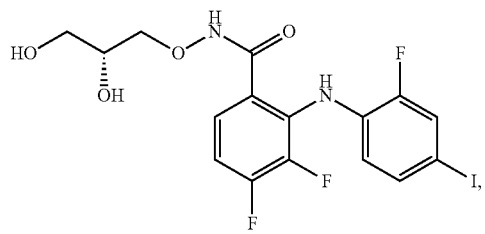

the method comprising reacting PD-0315209 (FIPFA) and PD-0337792 (IPGA) with a coupling reagent 1-propylphosphonic anhydride (T3P) to obtain 901 Acetonide as shown in Scheme 1:

Scheme 1

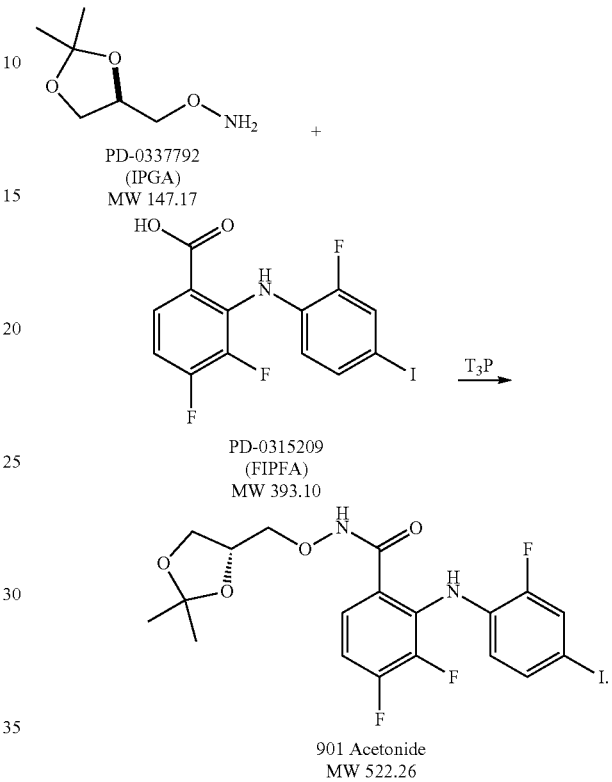

E357. The method of E356, wherein the 1-propylphosphonic anhydride is in solution.

E358. The method of E356 or E357, wherein the 1-propylphosphonic anhydride is provided as a solution in ethyl acetate.

E359. The method of E356, wherein the method of producing N—((R)-2,3-dihydroxypropoxy)-3,4-difluoro-2-(2-fluoro-4-iodo-phenylamino)-benzamide of Formula (I), comprises a) reacting PD-0315209 (FIPFA) and PD-0337792 (IPGA) with a coupling reagent that is 1-propylphosphonic anhydride (T3P) to obtain 901 Acetonide; and b) treating 901 Acetonide with acid to form N—((R)-2,3-dihydroxypropoxy)-3,4-difluoro-2-(2-fluoro-4-iodo-phenylamino)-benzamide as shown in Scheme II Scheme II

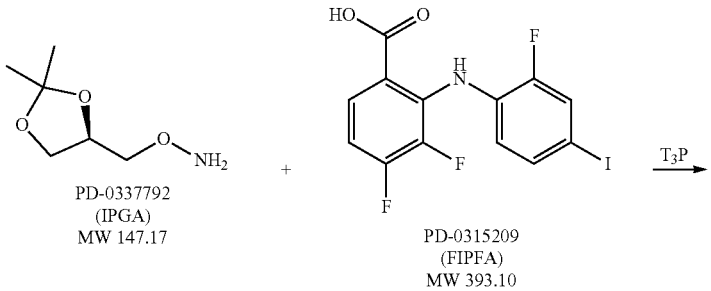

-continued

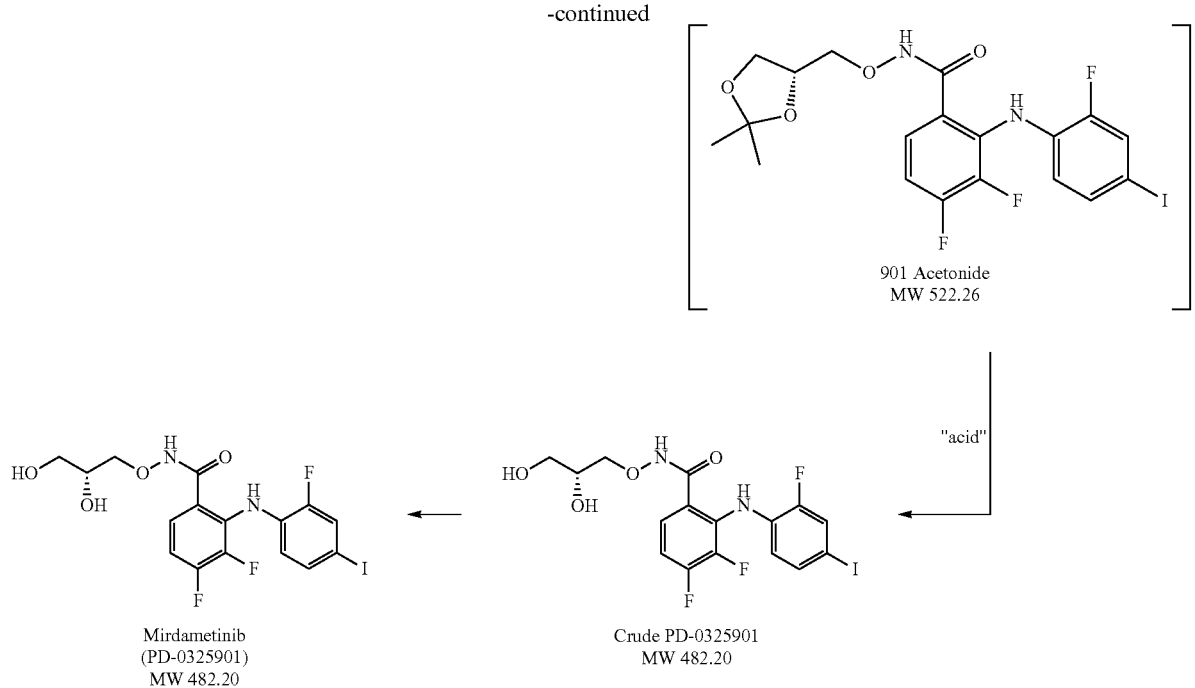

E360. The method of E356, wherein the method of producing N—((R)-2,3-dihydroxypropoxy)-3,4-difluoro-2-(2-fluoro-4-iodo-phenylamino)-benzamide of Formula (I)

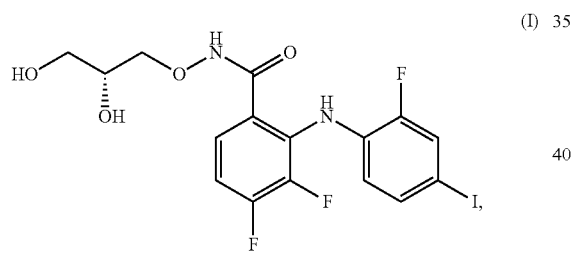

comprises:
reacting PD-0315209 (FIPFA) and PD-0337792 (PGA) with a coupling reagent to obtain 901 Acetonide; and
treating 901 Acetonide with acid to form N—((R)-2,3-dihydroxypropoxy)-3,4-difluoro-2-(2-fluoro-4-iodo-phenylamino)-benzamide according to Scheme III:

Scheme III

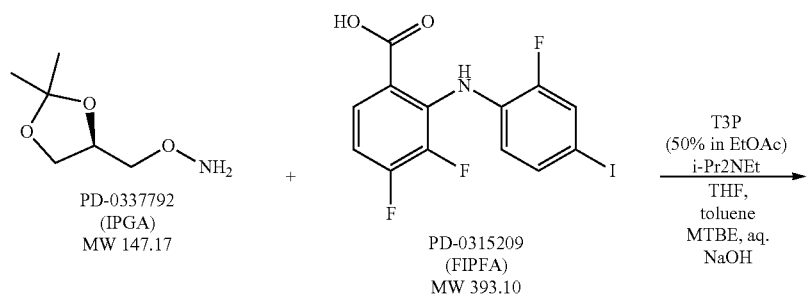

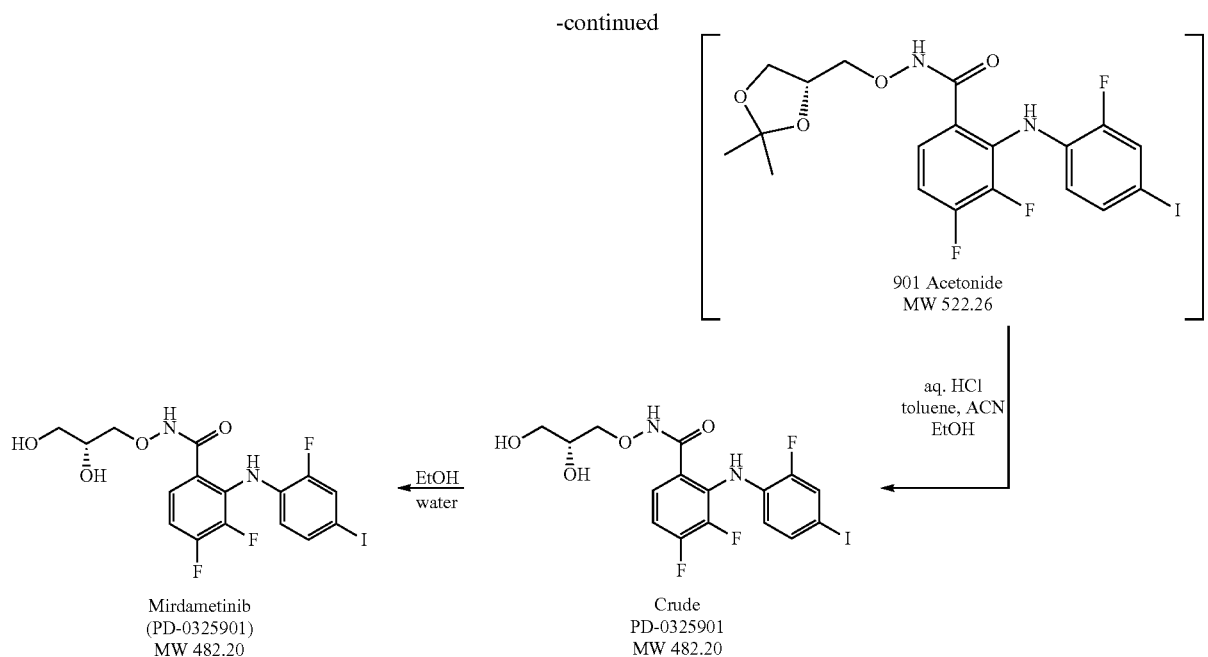

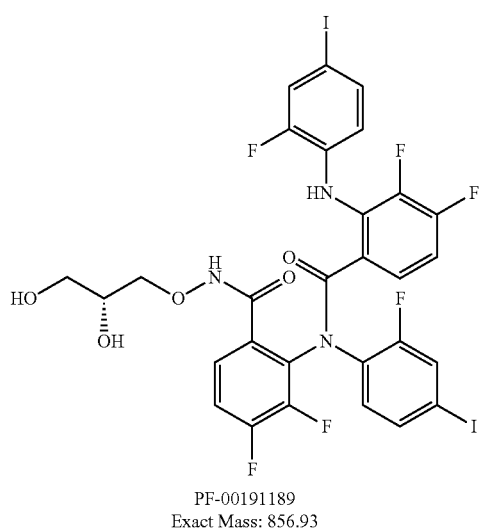 [SMILES: O=C(NOC[C@H](O)CO)c1ccc(F)c(F)c1N(C(=O)c1ccc(F)c(F)c1Nc1ccc(I)cc1F)c1ccc(I)cc1F]

E361. A crystalline composition that is essentially pure Form IV N—((R)-2,3-dihydroxypropoxy)-3,4-difluoro-2-(2-fluoro-4-iodo-phenylamino)-benzamide prepared by the method of any one of E356-E360.

E362. The crystalline composition of E361, wherein the crystalline composition contains ≤0.2% of dimeric impurity PF-00191189.

E363. The crystalline composition of E361 or E362, wherein the crystalline composition contains about 0.05% to about 0.19% by weight of dimeric impurity PF-00191189.

E364. The crystalline composition of anyone of E361-E363, wherein the crystalline composition contains no detectable amount of dimeric impurity PF-00191189.

What is claimed is:

1. A crystalline form of N—((R)-2,3-dihydroxypropoxy)-3,4-difluoro-2-(2-fluoro-4-iodo-phenylamino)-benzamide of Formula (I)

(I)

selected from the group consisting of:
  a) a crystalline form of N—((R)-2,3-dihydroxypropoxy)-3,4-difluoro-2-(2-fluoro-4-iodo-phenylamino)-benzamide characterized by an XRPD pattern having peaks at 5.4±0.2, 12.5±0.2, 17.5±0.2, and 22.8±0.2 degrees two theta;
  b) a crystalline form of N—((R)-2,3-dihydroxypropoxy)-3,4-difluoro-2-(2-fluoro-4-iodo-phenylamino)-benzamide characterized by an XRPD pattern having peaks at 5.9±0.2, 7.2±0.2, 9.3±0.2, and 21.2±0.2 degrees two theta;
  c) a crystalline form of N—((R)-2,3-dihydroxypropoxy)-3,4-difluoro-2-(2-fluoro-4-iodo-phenylamino)-benzamide characterized by an XRPD pattern having peaks at 5.3±0.2, 10.6±0.2, 13.9±0.2, and 16.1±0.2 degrees two theta;
  d) a crystalline form of N—((R)-2,3-dihydroxypropoxy)-3,4-difluoro-2-(2-fluoro-4-iodo-phenylamino)-benzamide characterized by an XRPD pattern having peaks at 5.4±0.2, 10.7±0.2, 18.7±0.2, and 23.9±0.2 degrees two theta;
  e) a crystalline form of N—((R)-2,3-dihydroxypropoxy)-3,4-difluoro-2-(2-fluoro-4-iodo-phenylamino)-benzamide characterized by an XRPD pattern having peaks at 6.7±0.2, 13.5±0.2, and 22.2±0.2 degrees two theta;
  f) a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 10.6±0.2, 19.6±0.2, and 24.8±0.2 degrees two theta;

g) a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 6.9±0.2, 10.1±0.2, and 19.2±0.2 degrees two theta;

h) a crystalline form of N—((R)-2,3-dihydroxypropoxy)-3,4-difluoro-2-(2-fluoro-4-iodo-phenylamino)-benzamide characterized by an XRPD pattern having peaks at 10.1±0.2, 17.3±0.2, 21.5±0.2, and 22.6±0.2 degrees two theta;

i) a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 5.1±0.2, 6.4±0.2, and 14.6±0.2 degrees two theta;

j) a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 23.4±0.2, and 25.2±0.2 degrees two theta;

k) a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 14.7±0.2, 20.9±0.2, and 26.6±0.2 degrees two theta;

l) a crystalline form of N—((R)-2,3-dihydroxypropoxy)-3,4-difluoro-2-(2-fluoro-4-iodo-phenylamino)-benzamide characterized by an XRPD pattern having peaks at 6.0±0.2, 12.8±0.2, 17.1±0.2, and 20.6±0.2 degrees two theta;

m) a crystalline form of N—((R)-2,3-dihydroxypropoxy)-3,4-difluoro-2-(2-fluoro-4-iodo-phenylamino)-benzamide characterized by an XRPD pattern having peaks at 5.9±0.2, 10.1±0.2, 11.7±0.2, and 15.5±0.2 degrees two theta;

n) a crystalline form of N—((R)-2,3-dihydroxypropoxy)-3,4-difluoro-2-(2-fluoro-4-iodo-phenylamino)-benzamide characterized by an XRPD pattern having peaks at 4.6±0.2, 10.7±0.2, 15.9±0.2, and 19.6±0.2 degrees two theta;

o) a crystalline form of N—((R)-2,3-dihydroxypropoxy)-3,4-difluoro-2-(2-fluoro-4-iodo-phenylamino)-benzamide characterized by an XRPD pattern having peaks at 10.2±0.2, 11.6±0.2, and 20.0±0.2 degrees two theta;

p) a crystalline form of N—((R)-2,3-dihydroxypropoxy)-3,4-difluoro-2-(2-fluoro-4-iodo-phenylamino)-benzamide characterized by an XRPD pattern having peaks at 7.8±0.2, 14.0±0.2, 15.6±0.2, and 17.1±0.2 degrees two theta;

q) a crystalline form of N—((R)-2,3-dihydroxypropoxy)-3,4-difluoro-2-(2-fluoro-4-iodo-phenylamino)-benzamide characterized by an XRPD pattern having peaks at 5.5±0.2, 8.2±0.2, 16.7±0.2, and 17.7±0.2 degrees two theta;

r) a crystalline form of N—((R)-2,3-dihydroxypropoxy)-3,4-difluoro-2-(2-fluoro-4-iodo-phenylamino)-benzamide characterized by an XRPD pattern having peaks at 7.2±0.2, 21.7±0.2, and 29.1±0.2 degrees two theta;

s) a crystalline form of N—((R)-2,3-dihydroxypropoxy)-3,4-difluoro-2-(2-fluoro-4-iodo-phenylamino)-benzamide characterized by an XRPD pattern having peaks at 5.4±0.2, 6.5±0.2, 9.7±0.2, and 10.7±0.2 degrees two theta; and t) a crystalline form of N—((R)-2,3-dihydroxypropoxy)-3,4-difluoro-2-(2-fluoro-4-iodo-phenylamino)-benzamide characterized by an XRPD pattern having peaks at 7.2±0.2, 20.6±0.2, and 23.0±0.2 degrees two theta.

2. Amorphous solid of N—((R)-2,3-dihydroxypropoxy)-3,4-difluoro-2-(2-fluoro-4-iodo-phenylamino)-benzamide of Formula (I)

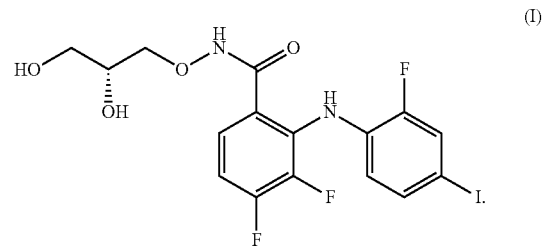 [SMILES: O=C(NOC[C@H](O)CO)c1ccc(F)c(F)c1Nc1ccc(I)cc1F]

3. A pharmaceutical composition comprising: the crystalline form of claim 1 or the amorphous solid of claim 2; and a pharmaceutically acceptable carrier.

4. The pharmaceutical composition of claim 3, wherein the crystalline form or the amorphous solid comprises less than 10% by weight total of one or more other crystalline forms and/or amorphous solid.

5. The pharmaceutical composition of claim 3, wherein the pharmaceutical composition is a capsule, tablet, powder, granules, minitablet, or pellet.

6. The pharmaceutical composition of claim 5, wherein the pharmaceutical composition is a tablet.

7. The pharmaceutical composition of claim 6, wherein the tablet is a dispersible tablet.

8. A method of producing N—((R)-2,3-dihydroxypropoxy)-3,4-difluoro-2-(2-fluoro-4-iodo-phenylamino)-benzamide of Formula (I)

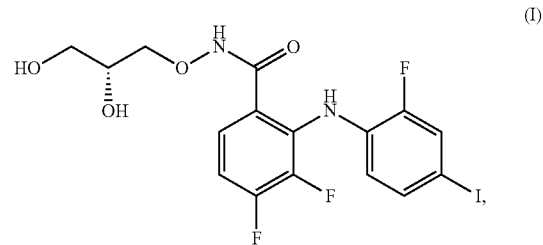 [SMILES: O=C(NOC[C@H](O)CO)c1ccc(F)c(F)c1Nc1ccc(I)cc1F]

the method comprising reacting PD-0315209 (FIPFA) and PD-0337792 (IPGA) with a coupling reagent 1-propylphosphonic anhydride (T3P) to obtain 901 Acetonide as shown in Scheme 1:

Scheme I

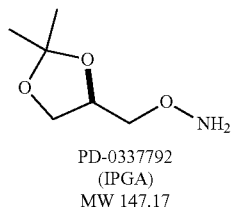

PD-0337792
(IPGA)
MW 147.17

+

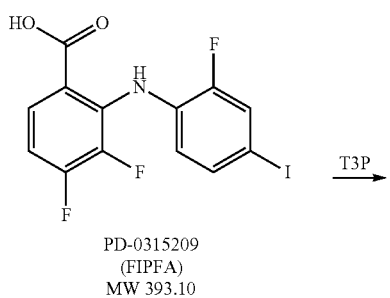

PD-0315209
(FIPFA)
MW 393.10

T3P →

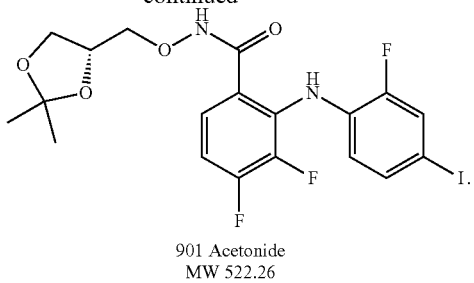

901 Acetonide
MW 522.26

9. The method of claim 8, wherein the 1-propylphosphonic anhydride is in solution.

10. The method of claim 9, wherein the 1-propylphosphonic anhydride is provided as a solution in ethyl acetate.

11. The method of claim 8, wherein the method of producing N—((R)-2,3-dihydroxypropoxy)-3,4-difluoro-2-(2-fluoro-4-iodo-phenylamino)-benzamide of Formula (I), comprises a) reacting PD-0315209 (FIPFA) and PD-0337792 (IPGA) with a coupling reagent that is 1-propylphosphonic anhydride (T3P) to obtain 901 Acetonide; and b) treating 901 Acetonide with acid to form N—((R)-2,3-dihydroxypropoxy)-3,4-difluoro-2-(2-fluoro-4-iodo-phenylamino)-benzamide as shown in Scheme II:

Scheme II

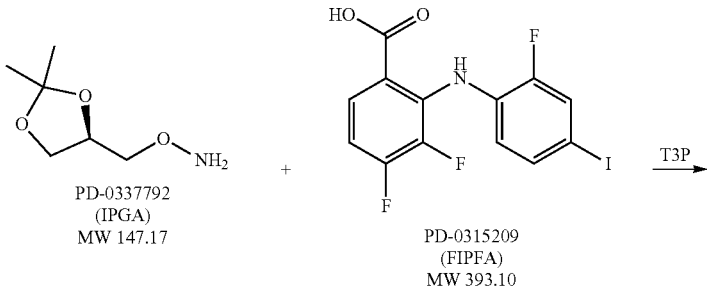 T3P →

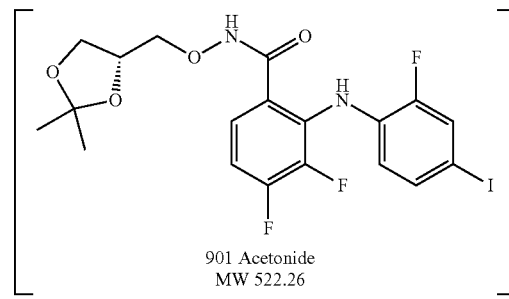

901 Acetonide
MW 522.26

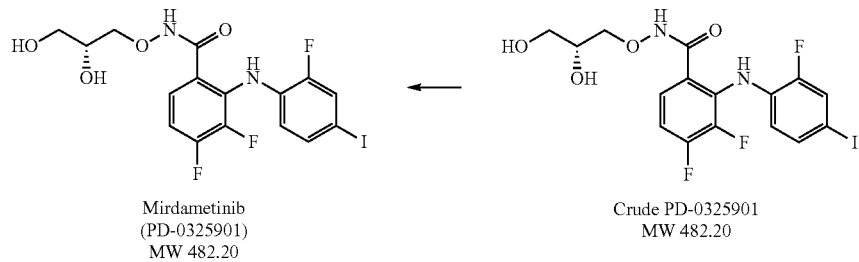
12. The method of claim 8, wherein the method of producing N—((R)-2,3-dihydroxypropoxy)-3,4-difluoro-2-(2-fluoro-4-iodo-phenylamino)-benzamide of Formula (I)
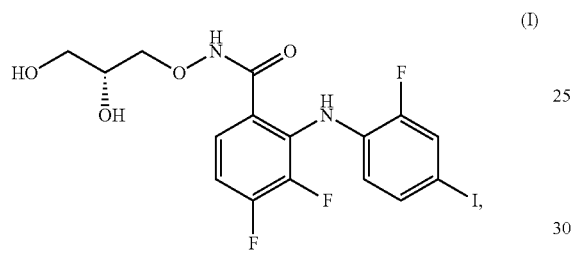
comprises:
a) reacting PD-0315209 (FIPFA) and PD-0337792 (IPGA) with a coupling reagent to obtain 901 Acetonide; and
b) treating 901 Acetonide with acid to form N—((R)-2,3-dihydroxypropoxy)-3,4-difluoro-2-(2-fluoro-4-iodo-phenylamino)-benzamide according to Scheme III:
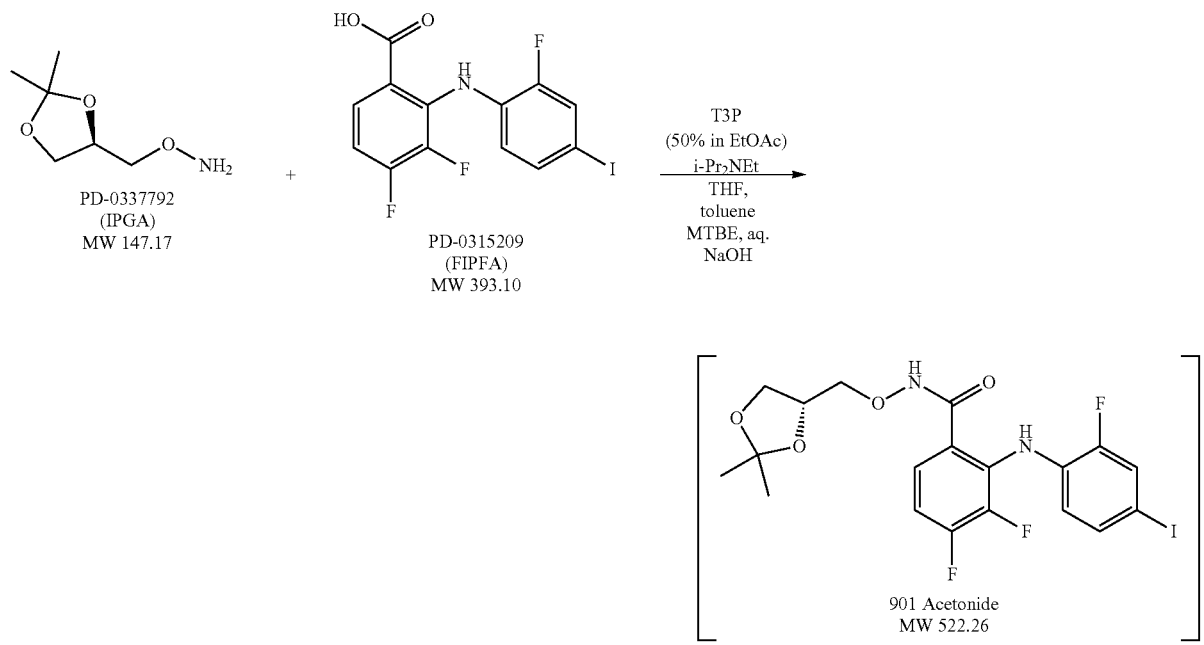

-continued

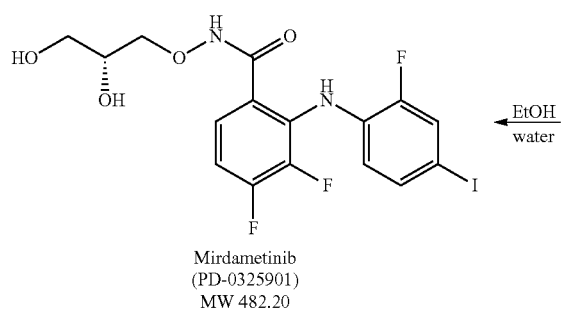

Mirdametinib
(PD-0325901)
MW 482.20

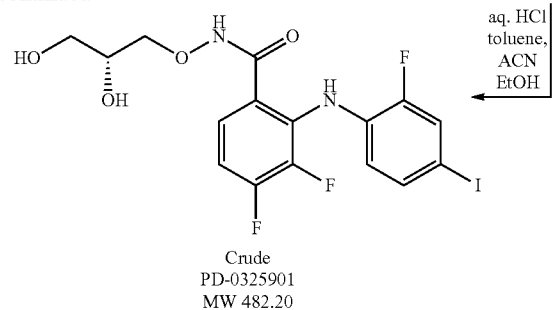

Crude
PD-0325901
MW 482.20

13. A crystalline composition that is essentially pure Form IV N—((R)-2,3-dihydroxypropoxy)-3,4-difluoro-2-(2-fluoro-4-iodo-phenylamino)-benzamide prepared by the method of claim 8.

14. The crystalline composition of claim 13, wherein the crystalline composition contains ≤0.2% of dimeric impurity PF-00191189

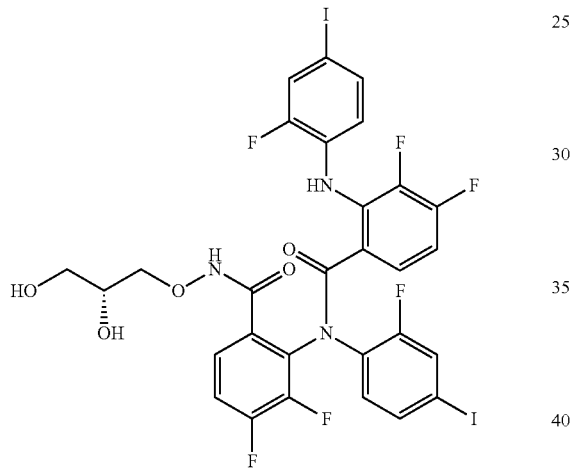

PF-00191189
Exact Mass: 856.93

15. A composition of N—((R)-2,3-dihydroxypropoxy)-3,4-difluoro-2-(2-fluoro-4-iodo-phenylamino)-benzamide prepared by the method of claim 8.

* * * * *